US006562792B1

(12) United States Patent
Brighty et al.

(10) Patent No.: US 6,562,792 B1
(45) Date of Patent: May 13, 2003

(54) HYGROMYCIN DERIVATIVES

(75) Inventors: Katherine E. Brighty, Groton, CT (US); Robert G. Linde, Old Lyme, CT (US); Takushi Kaneko, Guilford, CT (US); Matthew M. Hayward, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 62 days.

(21) Appl. No.: 09/693,118

(22) Filed: Oct. 20, 2000

Related U.S. Application Data

(60) Provisional application No. 60/162,581, filed on Oct. 29, 1999.

(51) Int. Cl.[7] ........................ A61K 31/70; C07H 15/00
(52) U.S. Cl. ........................ 514/25; 514/23; 536/16.8; 536/18.1; 536/17.9
(58) Field of Search ................ 536/16.8, 17.9, 536/18.1; 514/23, 25

(56) References Cited

U.S. PATENT DOCUMENTS 6,245,745 B1 * 6/2001 Hayward .................... 514/25

* cited by examiner

*Primary Examiner*—Elli Peseley
(74) *Attorney, Agent, or Firm*—Peter C. Richardson; Gregg C. Benson; Bryan C. Zielinski

(57) ABSTRACT

The present invention relates to compounds of the formula 1

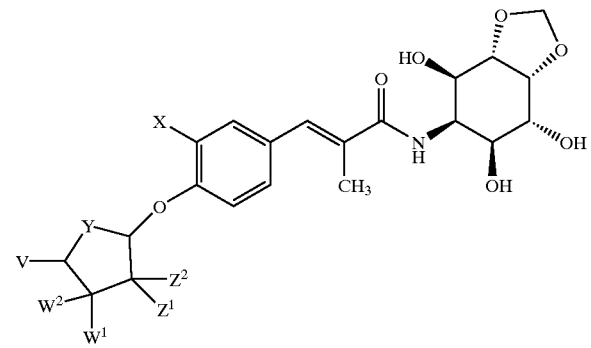

and to pharmaceutically acceptable salts, prodrugs and solvates thereof, wherein X, Y, V, $W^1$, $W^2$, $Z^1$ and $Z^2$ are as defined herein. The invention also relates to pharmaceutical compositions containing the above compounds and to methods of treating bacterial and protozoal infections in mammals by administering the above compounds.

20 Claims, No Drawings

HYGROMYCIN DERIVATIVES

This application claims the benefit of U.S. provisional application No. 60/162,581, filed Oct. 29, 1999.

BACKGROUND OF THE INVENTION

This invention relates to novel hygromycin derivatives that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Hygromycin A is a fermentation-derived natural product first isolated from *Streptomyces hygroscopicus* in 1953. As an antibiotic, hygromycin A possesses activity against human pathogens and is reported to possess potent in vitro activity against *Serpulina* (*Treponema*) *hyodysentetiae* which causes swine dysentery. Several references refer to semisynthetic modifications of hygromycin A, including the following: derivatization of the 5" ketone of hygromycin A to the 2,4-dinitrophenylhydrazone is referred to in K. Isono et al., *J. Antibiotics* 1957, 10, 21, and R. L. Mann and D. O. Woolf, *J. Amer Chem. Soc.* 1957, 79, 120. K. Isono et al., ibid., also refer to the thiosemicarbazone at 5"; reduction of the 5" ketone of hygromycin A to the 5" alcohol is referred to in R. L. Mann and D. O. Woolf, ibid., as well as in S. J. Hecker et al., *Bioorg. Med. Chem. Lett.* 1992, 2, 533 and S. J. Hecker et al., *Bioorg. Med. Chem. Lett.* 1993, 3, 295; furanose analogues are referred to in B. H. Jaynes et al., *Bioorg. Med. Chem. Lett.* 1993, 3, 1531, and B. H. Jaynes et al., *J. Antibiot.* 1992, 45, 1705; aromatic ring analogues are referred to in S. J. Hecker et al., *Bioorg. Med. Chem. Lett.* 1993, 3, 289, and C. B. Cooper et al., *Bioorg. Med. Chem. Lett.* 1997, 7, 1747; enamide analogues are referred to in S. J. Hecker et al., *Bioorg. Med. Chem. Lett.* 1992, 2, 533; aminocyclitol analogues are referred to in S. J. Hecker et al., *Bioorg. Med. Chem. Lett.* 1992, 2, 1015, and in S. J. Hecker et al., *Bioorg. Med. Chem. Lett.* 1992, 2, 1043. The hygromycin A derivatives of the present invention possess broad activity against both gram-negative and gram-positive bacteria and protozoa. WO 99/012941, published Sep. 14, 1999, refers to the treatment of bacterial infections by co-adminstering hygromycin and/or epihygromycin with a pyridone carboxylic acid antibacterial compound such as tosufloxacin, nalidixic acid, piromidic acid cinoxacin and/or enoxacin. Hygromycin derivatives are also described and claimed in U.S. provisional patent application Ser. No. 60/110,618 (filed Dec. 2, 1998), U.S. patent application Ser. No. 09/380,718 (filed Apr. 8, 1999), and PCT international patent application number PCT/IB99/00795 (filed May 13, 1999). The foregoing United States and PCT applications are incorporated herein by reference in their entirety.

SUMMARY OF THE INVENTION

The present invention relates to compounds of the formula

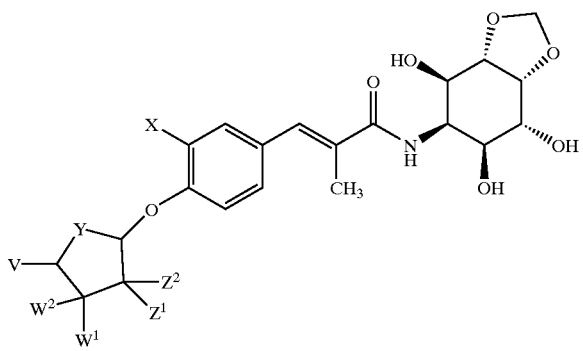

or a pharmaceutically acceptable salt, prodrug or solvate thereof, wherein:

X is H, F, OH, or $NH_2$;

Y is O or $CH_2$;

$Z^1$ is $R^3$ and $Z^2$ is $OR^{13}$; or $Z^1$ is H and $Z^2$ is $R^3$, $-NR^3R^4$, $-NR^3C(O)R^4$ or F;

or $Z^1$ and $Z^2$ are taken together to form $=O$ or $=NOR^3$;

$W^1$ is $R^3$ and $W^2$ is $OR^{13}$; or $W^1$ is H and $W^2$ is $R^3$, $-NR^3R^4$, $-NR^3C(O)R^4$, or F;

or $W^1$ and $W^2$ are taken together to form $=O$ or $=NOR^3$;

V is a group having the following structure

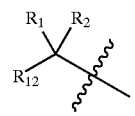

or V is $R^3OC(O)-$, $R^3R^4NC(O)-$ or $R^3O(R^4)NC(O)-$, in which groups $R^3$ and $R^4$ optionally can be taken together to form a 4 to 10 membered heterocyclic group which may be optionally substituted by 1 to 3 $R^6$ groups;

or V is a group having the following structure:

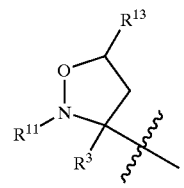

or V is a group of the structure

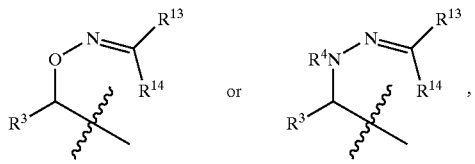

where both E and Z isomers are included;

or V is a carbon-linked 4 to 10 membered heterocyclic group, which may be optionally substituted by 1 to 3 $R^6$ groups;

$R^1$ is H and $R^2$ is $-NR^3R^4$, $-NR^4C(O)R^3$, $-OC(O)NR^3R^4$ or $-OR^3$;

or $R^1$ and $R^2$ are taken together to form O, =N—$OR^3$, or =C($R^5$)$X^1$—$X^2$—$R^8$, wherein:

$X^1$ is —$CR^9R^{10}$—, and $X^2$ is selected from —$CR^9R^{10}$—, —S(O)$_n$— wherein n is an integer from 0 to 2, —$NR^9$—, and O; where $X^2$ is —$NR^9$—, then $R^8$ and $R^9$ may be taken together to form a 5 to 12 membered heterocyclic group, which is optionally substituted by 1 to 3 $R^6$ groups; or $X^1$ and $X^2$ independently or together represent a bond with the proviso that if $X^1$ is a bond than $X^2$ is either a bond or —$CR^9R^{10}$—;

each $R^3$ is independently selected from H, $C_1$–$C_{10}$ alkyl, $C_2$–$C_{10}$ alkenyl, $C_2$–$C_{10}$ alkynyl, —$(CR^9R^{10})_t$ ($C_3$–$C_{10}$ cycloalkyl), —$(CR^9R^{10})_t(C_6$–$C_{10}$ aryl), and —$(CR^9R^{10})_t$(4 to 10 membered heterocyclic), wherein each t is independently an integer from 0 to 5, said alkyl, alkenyl and alkynyl groups optionally contain 1 or 2 hetero moieties selected from O, —S(O)$_j$— wherein j is an integer from 0 to 2, and —N($R^9$)— with the proviso that two O atoms, two S atoms, or an O and S atom are not attached directly to each other, and the proviso that an O atom, a S atom or a N atom are not attached directly to a triple bond or non-aromatic double bond; said cycloalkyl, aryl and heterocyclic $R^3$ groups are optionally fused to a benzene ring, a $C_5$–$C_8$ cycloalkyl group, or a 4 to 10 membered heterocyclic group; the —($CR^9R^{10}$)$_t$— moieties of the foregoing $R^3$ groups optionally include a carbon-carbon double or triple bond where t is an integer between 2 and 5; and the foregoing $R^3$ groups, except H but including any optional fused rings referred to above, are optionally substituted by 1 to 5 $R^6$ groups, and with the proviso that $R^3$ must be attached through a carbon atom unless $R^3$ is H;

each $R^4$ is independently H or $C_1$–$C_{10}$ alkyl;

$R^5$ is H or $C_1$–$C_6$ alkyl, wherein the foregoing $R^5$ alkyl group is optionally substituted by 1 or 2 $R^6$ groups each $R^6$ is independently selected from $C_1$–$C_{10}$ alkyl, $C_2$–$C_{10}$ alkenyl, $C_2$–$C_{10}$ alkynyl, $C_3$–$C_{10}$ cycloalkyl, oxo, halo, cyano, nitro, trifluoromethyl, difluoromethoxy, trifluoromethoxy, azido, —$OR^7$, —C(O)$R^7$, —C(O)$OR^7$, —$NR^9$C(O)$OR^{11}$, —OC(O)$R^7$, —$NR^9SO_2R^{11}$, —$SO_2NR^7R^9$, —$NR^9$C(O)$R^7$, —C(O)$NR^7R^9$, —$NR^7R^9$, —S(O)$_j$($CR^9R^{10}$)$_m$ ($C_6$–$C_{10}$ aryl), —S(O)$_j(C_1$–$C_6$ alkyl), wherein j is an integer from 0 to 2, —($CR^9R^{10}$)$_m(C_6$–$C_{10}$ aryl), —O($CR^9R^{10}$)$_m(C_6$–$C_{10}$ aryl), —$NR^9$($CR^9R^{10}$)$_m$ ($C_6$–$C_{10}$ aryl), and —($CR^9R^{10}$)$_m$(4 to 10 membered heterocyclic), wherein each m is independently an integer from 0 to 4; said alkyl, alkenyl and alkynyl groups optionally contain 1 or 2 hetero moieties selected from O, —S(O)$_j$— wherein j is an integer from 0 to 2, and —N($R^7$)— with the proviso that two O atoms, two S atoms, or an O and S atom are not attached directly to each other, and the proviso that an O atom, a S atom or a N atom are not attached directly to a triple bond or a non-aromatic double bond; said cycloalkyl, aryl and heterocyclic $R^6$ groups are optionally fused to a $C_6$–$C_{10}$ aryl group, a $C_5$–$C_8$ cycloalkyl group, or a 4 to 10 membered heterocyclic group; and said alkyl, cycloalkyl, aryl and heterocyclic R groups are optionally substituted by 1 to 5 substituents independently selected from oxo, halo, cyano, nitro, trifluoromethyl, difluoromethoxy, trifluoromethoxy, azido, —$NR^9SO_2R^{11}$, —$SO_2NR^7R^9$, —C(O)$R^7$, —C(O)$OR^7$, —OC(O)$R^7$, —$NR^9$C(O)$OR^{11}$, —$NR^9$C(O)$R^7$, —C(O)$NR^7R^9$, —$NR^7R^9$, —$OR^7$, $C_1$–$C_{10}$ alkyl, —($CR^9R^{10}$)$_m(C_6$–$C_{10}$ aryl), and —($CR^9R^{10}$)$_m$(4 to 10 membered heterocyclic), wherein each m is independently an integer ranging from 0 to 4;

each $R^7$ is independently selected from H, $C_1$–$C_{10}$ alkyl, $C_3$–$C_{10}$ cycloalkyl, —($CR^9R^{10}$)$_m(C_6$–$C_{10}$ aryl), and —($CR^9R^{10}$)$_m$(4 to 10 membered heterocyclic), wherein each m is independently an integer from 0 to 4; said alkyl group optionally includes 1 or 2 hetero moieties selected from O, —S(O)$_j$— wherein j is an integer ranging from 0 to 2, and —N($R^9$)— with the proviso that two O atoms, two S atoms, or an O and S atom are not attached directly to each other; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^7$ substituents, except H, are optionally substituted by 1 to 5 substituents independently selected from oxo, halo, cyano, nitro, trifluoromethyl, difluoromethoxy, trifluoromethoxy, azido, —C(O)$R^9$, —C(O)$OR^9$, —OC(O)$R^9$, —$NR^9$C(O)$R^{10}$, —C(O)$NR^9R^{10}$, —$NR^9R^{10}$, hydroxy, $C_1$–$C_6$ alkyl, and $C_1$–$C_6$ alkoxy, and with the proviso that $R^7$ must be attached through a carbon atom unless $R^7$ is H;

each $R^8$ is independently selected from $R^3$, —C(O)$R^3$, or —C(O)$NR^9R^3$, wherein $R^3$ is as defined above;

each $R^9$ and $R^{10}$ is independently H or $C_1$–$C_6$ alkyl; and, $R^{11}$ is selected from the substituents provided in the definition of $R^7$ except H.

$R^{12}$ is selected from the substituents provided in the definition of $R^3$, except that $R^{12}$ cannot be methyl if (a) X is OH, Y is O, $W^1$ is H, $W^2$ is α-OH, $Z^1$ is H, $Z^2$ is β-OH; or (b) if X is OH, Y is O, $W^1$ is H, $W^2$ is α-OH, $Z^1$ and $Z^2$ are both H; and with the proviso that $R^{12}$ must be attached through a carbon atom unless $R^{12}$ is H;

$R^{13}$ is defined as described for $R^3$; and, $R^{14}$ is H or $C_1$–$C_{10}$ alkyl, except that $R^{14}$ cannot be H when $R^{13}$ is H.

In a first preferred embodiment of the compound of formula 1:

V equals

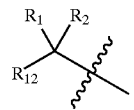

and the preferred configuration of the 1″ center is that of hygromycin A

In a second preferred embodiment of the compound of formula 1:

V is as indicated in the first preferred embodiment above, but $R^1$ and $R^2$ are taken together as =O or =$NOR^3$.

In a third preferred embodiment of the compound of formula 1:

the preferred groups as indicated for the second preferred embodiment, but:

$Z^1$ is $R^3$ and $Z^2$ is $OR^{13}$; or $Z^1$ is H and $Z^2$ is $R^3$, —$NR^3R^4$, —$NR^3$C(O)$R^4$, or F; and $W^1$ is $R^3$ and $W^2$ is $OR^{13}$; or $W^1$ is H and $W^2$ is $R^3$, —$NR^3R^4$, —$NR^3$C(O)$R^4$, or F; wherein each $R^3$ and $R^{13}$ are independently selected from H, $C_1$–$C_4$ alkyl, —($CR^9R^{10}$)$_t(C_3$–$C_{10}$ cycloalkyl), —($CR^9R^{10}$)$_t$ ($C_6$–$C_{10}$ aryl), and —$(CR^9R^{10})_t$(4 to 10 membered heterocyclic), wherein each t is independently an integer from 0 to 3, said alkyl group optionally contains 1 hetero moiety selected from O, —S(O)$_j$— wherein j is an integer from 0 to 2, and —N($R^9$)—, and the foregoing $R^3$ and $R^{13}$ groups, except H, are optionally substituted by 1 to 5 $R^6$ groups, and with the proviso that $R^3$ and $R^{13}$ must be attached through a carbon atom unless it is H; each $R^4$ is independently H or $C_1$–$C_4$ alkyl; each $R^6$ is independently selected from $C_1$–$C_4$ alkyl, oxo, halo, trifluoromethyl, difluoromethoxy, trifluoromethoxy, —$OR^7$, —C(O)$R^7$, —$NR^9$C(O)$OR^{11}$, —$NR^9$C(O)$R^7$, —C(O)$NR^7R^9$, —$NR^7R^9$; wherein $R^7$ and $R^9$ are H, $C_1$–$C_4$ alkyl; $R^{11}$ is $C_1$–$C_4$ alkyl.

$R^1$ and $R^2$ are taken together as =O or =$NOR^3$, wherein each $R^3$ is independently selected from $C_1$–$C_4$ alkyl, $C_3$–$C_8$ alkenyl, —$(CR^9R^{10})_t$($C_6$–$C_{10}$ aryl), and —$(CR^9R^{10})_t$(4 to 10 membered heterocyclic), wherein each t is independently an integer ranging from 0 to 3, said alkyl and alkenyl groups optionally contain 1 or 2 hetero moieties selected from O, —S(O)$_j$— wherein j is an integer ranging from 0 to 2 and —N($R^9$)—, with the proviso that two O atoms, two S atoms, or an O and S atom are not attached directly to each other, and the proviso that an O atom, a S atom or a N atom are not attached directly to a non-aromatic double bond; said aryl and heterocyclic $R^3$ groups are optionally fused to a benzene ring, a $C_5$–$C_8$ cycloalkyl group, or a 4 to 10 membered heterocyclic group; and the foregoing $R^3$ groups, including any optional fused rings referred to above, are optionally substituted by 1 to 5 $R^6$ groups, and with the proviso that $R^3$ must be attached through a carbon atom; $R^{12}$ is $C_1$–$C_4$ alkyl, and said alkyl group is optionally substituted by 1 to 3 $R^6$ groups, except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H; each $R^6$ is independently selected from $C_1$–$C_4$ alkyl, oxo, halo, trifluoromethyl, difluoromethoxy, trifluoromethoxy, —$OR^7$, —C(O)$R^7$, —$NR^9$C(O)$OR^{11}$, —$NR^9$SO$_2R^{11}$, —SO$_2NR^7R^9$, —$NR^9$C(O)$R^7$, —C(O)$NR^7R^9$, —$NR^7R^9$, —S(O)$_j$(CR$^9R^{10}$)$_m$($C_6$–$C_{10}$ aryl), —S(O)$_j$($C_1$–$C_6$ alkyl), wherein j is an integer ranging from 0 to 2, —$(CR^9R^{10})_m$($C_6$–$C_{10}$ aryl), —O$(CR^9R^{10})_m$($C_6$–$C_{10}$ aryl), —$NR^9$($CR^9R^{10})_m$($C_6$–$C_{10}$ aryl), and —$(CR^9R^{10})_m$(4 to 10 membered heterocyclic), wherein each m is independently an integer from 0 to 2; and said alkyl, cycloalkyl, aryl and heterocyclic $R^6$ groups are optionally substituted by 1 to 5 substituents independently selected from oxo, halo, trifluoromethyl, difluoromethoxy, trifluoromethoxy, —$NR^9$SO$_2R^{11}$, —C(O)$R^7$, —$NR^9$C(O)$OR^{11}$, —$NR^9$C(O)$R^7$, —C(O)$NR^7R^9$, —$NR^7R^9$, —$OR^7$, $C_1$–$C_4$ alkyl, —$(CR^9R^{10})_m$($C_6$–$C_{10}$ aryl), and —$(CR^9R^{10})_m$(4 to 10 membered heterocyclic), wherein each m is independently an integer from 0 to 2; $R^7$ is independently selected from H, $C_1$–$C_4$ alkyl, $C_3$–$C_6$ cycloalkyl, —$(CR^9R^{10})_m$($C_6$–$C_{10}$ aryl), and —$(CR^9R^{10})_m$(4 to 10 membered heterocyclic), wherein each m is independently an integer from 0 to 2; said alkyl group optionally includes 1 hetero moiety selected from O, —S(O)$_j$— wherein j is an integer from 0 to 2, and —N($R^9$)—; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^7$ substituents, except H, are optionally substituted by 1 to 5 substituents independently selected from oxo, halo, trifluoromethyl, difluoromethoxy, trifluoromethoxy, —C(O)$R^9$, —$NR^9$C(O)$R^{10}$, —C(O)$NR^9R^{10}$, —$NR^9R^{10}$, hydroxy, $C_1$–$C_4$ alkyl, and $C_1$–$C_4$ alkoxy, and with the proviso that $R^7$ must be attached through a carbon atom unless $R^7$ is H; $R^9$ and $R^{10}$ are independently H, $C_1$–$C_4$ alkyl; $R^{11}$ is selected from $R^7$ except H.

In a fourth preferred embodiment of the compound of formula 1:

the preferred groups as indicated for the third preferred embodiment, but:

X is F, H or OH;

Y is O;

$W^1$ is $R^3$, $w^2$ is $OR^{13}$; or $W^1$ is H, $W^2$ is $R^3$ or F; $Z^1$ is $R^3$, $Z^2$ is $OR^{13}$; or $Z^1$ is H, $Z^2$ is $R^3$ or F; wherein $R^3$ and $R^{13}$ are independently H, $C_1$–$C_4$ alkyl, and said alkyl groups are optionally substituted by 1 to 3 $R^6$ groups; wherein each $R^6$ is independently oxo, halo, trifluoromethyl, difluoromethoxy, trifluoromethoxy, —$OR^7$, —C(O)$R^7$, —$NR^9$C(O)$OR^{11}$, —$NR^9$C(O)$R^7$, —C(O)$NR^7R^9$, or —$NR^7R^9$; wherein $R^7$ and $R^9$ are H or $C_1$–$C_4$ alkyl; $R^{11}$ is $C_1$–$C_4$ alkyl;

$R^1$ and $R^2$ are taken together as =$NOR^3$, $R^3$ is —$(CR^9R^{10})_t$($C_6$–$C_{10}$ aryl), and —$(CR^9R^{10})_t$(4 to 10 membered heterocyclic), wherein each t is independently an integer from 0 to 3; the foregoing $R^3$ groups are optionally substituted by 1 to 5 $R^6$ groups, and with the proviso that $R^3$ must be attached through a carbon atom; $R^{12}$ is $C_1$–$C_4$ alkyl, and said alkyl group is optionally substituted by 1 to 3 $R^6$groups, except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H; wherein $R^6$ is $C_1$–$C_4$ alkyl, oxo, halo, trifluoromethyl, difluoromethoxy, trifluoromethoxy, —$OR^7$, —C(O)$R^7$, —$NR^9$C(O)$OR^{11}$, —$NR^9$C(O)$R^7$, —C(O)$NR^7R^9$, —$NR^7R^9$, —$(CR^9R^{10})_m$($C_6$–$C_{10}$ aryl), —O$(CR^9R^{10})_m$($C_6$–$C_{10}$ aryl), —$NR^9$($CR^9R^{10})_m$($C_6$–$C_{10}$ aryl), and —$(CR^9R^{10})_m$(4 to 10 membered heterocyclic), wherein each m is independently an integer from 0 to 2; said alkyl, aryl and heterocyclic $R^6$ groups are optionally substituted by 1 to 5 substituents independently selected from oxo, halo, trifluoromethyl, difluoromethoxy, trifluoromethoxy, —$NR^9$SO$_2R^{11}$, —C(O)$R^7$, —$NR^9$C(O)$OR^{11}$, —$NR^9$C(O)$R^7$, —C(O)$NR^7R^9$, —$NR^7R^9$, —$OR^7$, and $C_1$–$C_4$ alkyl;

$R^7$ is independently selected from H, $C_1$–$C_4$ alkyl, $C_3$–$C_6$ cycloalkyl, —$(CR^9R^{10})_m$($C_6$–$C_{10}$ aryl), and —$(CR^9R^{10})_m$(4 to 10 membered heterocyclic), wherein each m is independently an integer ranging from 0 to 2; the foregoing $R^7$ substituents, except H, are optionally substituted by 1 to 5 substituents independently selected from oxo, halo, trifluoromethyl, difluoromethoxy, trifluoromethoxy, —C(O)$R^9$, —$NR^9$C(O)$R^{10}$, —C(O)$NR^9R^{10}$, —$NR^9R^{10}$, hydroxy, $C_1$–$C_4$ alkyl, and $C_1$–$C_4$ alkoxy; each $R^9$ and $R^{10}$ are independently H or $C_1$–$C_4$ alkyl; $R^{11}$ is selected from $R^7$ except H.

In a fifth preferred embodiment of the compound of formula 1:
  the preferred groups as indicated for the fourth preferred embodiment, but:
    $Z^1$ is H, $Z^2$ is OH; or $Z^1$ is methyl, $Z^2$ is OH; or both $Z^1$ and $Z^2$ are H; or Z, is H, $Z^2$ is F;
    $W^1$ is H, $W^2$ is OH;
    $R^1$ and $R^2$ are taken together as =NOR$^3$, wherein $R^3$ is —(CR$^9$R$^{10}$)$_t$(C$_6$–C$_{10}$ aryl), and —(CR$^9$R$^{10}$)$_t$(4 to 10 membered heterocyclic), wherein each t is independently an integer ranging from 0 to 2, and the foregoing $R^3$ groups are optionally substituted by 1 to 5 $R^6$ groups; wherein $R^6$ is C$_1$–C$_4$ alkyl, oxo, halo, trifluoromethyl, difluoromethoxy, trifluoromethoxy, —OR$^7$, —C(O)R$^7$, —(CR$^9$R$^{10}$)$_m$(C$_6$–C$_{10}$ aryl), —O(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; said alkyl, aryl and heterocyclic $R^6$ groups are optionally substituted by 1 to 5 substituents independently selected from oxo, halo, trifluoromethyl, difluoromethoxy, trifluoromethoxy, —C(O)R$^7$, —NR$^9$C(O)OR$^{11}$, —NR$^9$C(O)R$^7$, —C(O)NR$^7$R$^9$, —OR$^7$, and C$_1$–C$_4$ alkyl;
    $R^7$ is independently selected from H, C$_1$–C$_4$ alkyl; the foregoing $R^7$ substituents, except H, are optionally substituted by 1 to 3 substituents independently selected from trifluoromethyl, —C(O)R$^9$, —NR$^9$C(O)R$^{11}$, —C(O)NR$^9$R$^{10}$, —NR$^9$R$^{10}$, hydroxy, and C$_1$–C$_4$ alkoxy; $R^9$ and $R^{10}$ are independently H, C$_1$–C$_4$ alkyl; $R^{11}$ is selected from $R^7$ except H; $R^{12}$ is C$_1$–C$_4$ alkyl except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H.

In a sixth preferred embodiment of the compound of formula 1:
  the preferred groups as indicated for the fifth preferred embodiment, but:
    $R^1$ and $R^2$ are taken together as =NOR$^3$, wherein $R^3$ is —(CR$^9$R$^{10}$)$_t$-phenyl, and —(CR$^9$R$^{10}$)$_t$(5 to 9 membered heterocyclic), where t is 0 or 1, and the foregoing $R^3$ groups are optionally substituted by 1 to 5 $R^6$ groups, wherein each $R^6$ is independently C$_1$–C$_4$ alkyl, halo, trifluoromethyl, and —(CR$^9$R$^{10}$)$_m$ (4 to 10 membered heterocyclic), wherein each m is independently an integer from 0 to 1; said heterocyclic $R^6$ groups are optionally substituted by 1 to 5 substituents independently selected from halo, trifluoromethyl, and C$_1$–C$_4$ alkyl; each $R^9$ and $R^{10}$ is independently H or C$_1$–C$_3$ alkyl.

In a seventh preferred embodiment of the compound of formula 1:

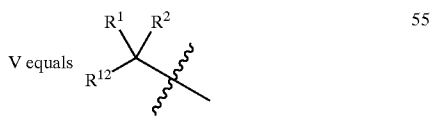

and $R^1$ and $R^2$ are taken together as =C(R$^5$)X$^1$—X$^2$—R$^8$ and the preferred configuration of the 1" center is that of hygromycin A.

In an eighth preferred embodiment of the compound of formula 1:
  the preferred groups as indicated for the seventh preferred embodiment, but:

$W^1$ is $R^3$, $W^2$ is OR$^{13}$; or $W^1$ is H, $W^2$ is $R^3$, NR$^3$R$^4$, NR$^3$C(O)R$^4$, or F; $Z^1$ is $R^3$, $Z^2$ is OR$^{13}$; or $Z^1$ is H, $Z^2$ is $R^3$, NR$^3$R$^4$, NR$^3$C(O)R$^4$, or F; wherein $R^3$ and $R^{13}$ are independently selected from H, C$_1$–C$_4$ alkyl, —(CR$^9$R$^{10}$)$_t$(C$_3$–C$_{10}$ cycloalkyl), —(CR$^9$R$^{10}$)$_t$(C$_6$–C$_{10}$ aryl), and —(CR$^9$R$^{10}$)$_t$(4 to 10 membered heterocyclic), wherein each t is independently an integer ranging from 0 to 3, said alkyl group optionally contains 1 hetero moiety selected from O, —S(O)$_j$— wherein j is an integer ranging from 0 to 2, and —N(R$^9$)—, and the foregoing $R^3$ and $R^{13}$ groups, except H, are optionally substituted by 1 to 5 $R^6$ groups, and with the proviso that $R^3$ and $R^{13}$ must be attached through a carbon atom unless it is H; each $R^4$ is independently H or C$_1$–C$_4$ alkyl; each $R^6$ is independently selected from C$_1$–C$_4$ alkyl, oxo, halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, and —NR$^7$R$^9$; wherein each $R^7$ and $R^9$ is independently H or C$_1$–C$_4$ alkyl; $R^{11}$ is C$_1$–C$_4$ alkyl;
$R^1$ and $R^2$ are taken together as =C(R$^5$)X$^1$—X$^2$—R$^8$; wherein X$^1$ is —CR$^9$R$^{10}$—, and X$^2$ is selected from —CR$^9$R$^{10}$—, —S(O)$_n$— wherein n is 0 to 2, —NR$^9$—, and O; where X$^2$ is —NR$^9$—, then $R^8$ and $R^9$ may be taken together to form a 5 to 12 membered heterocyclic, which is optionally substituted by 1 to 3 $R^6$ groups; X$^1$ and X$^2$ can also independently or together represent a bond with the proviso that if X$^1$ is a bond than X$^2$ must be either a bond or —CR$^9$R$^{10}$—;
and where $R^5$ is H or C$_1$–C$_6$ alkyl, wherein the foregoing $R^5$ alkyl group is optionally substituted by 1 or 2 $R^6$ groups:
and where each $R^8$ is independently selected from $R^3$, —C(O)R$^3$, or —C(O)NR$^9$R$^3$, with the additional proviso that an N and O atom, and an N and S atom are not attached directly to each other, wherein each $R^3$ is independently selected from C$_1$–C$_4$ alkyl, C$_3$–C$_8$ alkenyl, —(CR$^9$R$^{10}$)$_t$(C$_6$–C$_{10}$ aryl), and —(CR$^9$R$^{10}$)$_t$(4 to 10 membered heterocyclic), wherein each t is independently an integer ranging from 0 to 3, said alkyl or alkenyl group optionally contains 1 hetero moiety selected from O, —S(O)$_j$— wherein j is an integer ranging from 0 to 2, and —N(R$^9$)—, with the proviso that an O atom, a S atom or a N atom are not attached directly to a non-aromatic double bond; said aryl and heterocyclic $R^3$ groups are optionally fused to a benzene ring, a C$_5$–C$_8$ cycloalkyl group, or a 4 to 10 membered heterocyclic group; and the foregoing $R^3$ groups, including any optional fused rings referred to above, are optionally substituted by 1 to 5 $R^6$ groups, and with the proviso that $R^3$ must be attached through a carbon atom; $R^{12}$ is C$_1$–C$_4$ alkyl, and said alkyl group is optionally substituted by 1 to 3 $R^6$ groups, except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H; each $R^6$ is independently selected from C$_1$–C$_4$ alkyl, oxo, halo, trifluoromethyl, difluoromethoxy, trifluoromethoxy, —OR$^7$, —C(O)R$^7$, —NR$^9$C(O)OR$^{11}$, —NR$^9$SO$_2$R$^{11}$, —SO$_2$NR$^7$R$^9$, —NR$^9$C(O)R$^7$, —C(O)NR$^7$R$^9$, —NR$^7$R$^9$, —S(O)$_j$(CR$^9$R$^{10}$)$_m$(C$_6$–C$_{10}$ aryl), —S(O)$_j$(C$_1$–C$_6$ alkyl), wherein j is an integer ranging from 0 to 2, —(CR$^9$R$^{10}$)$_m$(C$_6$–C$_{10}$ aryl), —O(CR$^9$R$^{10}$)$_m$(C$_6$–C$_{10}$ aryl), —NR$^9$(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; and said alkyl, cycloalkyl, aryl and heterocyclic $R^6$ groups are optionally substituted by 1 to 5 substituents independently selected from oxo, halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, $C_1$–$C_4$ alkyl, —$(CR^9R^{10})_m$($C_6$–$C_{10}$ aryl), and —$(CR^9R^{10})_m$(4 to 10 membered heterocyclic), wherein each m is independently an integer ranging from 0 to 2; $R^7$ is independently selected from H, $C_1$–$C_4$ alkyl, $C_3$–$C_6$ cycloalkyl, —$(CR^9R^{10})_m$($C_6$–$C_{10}$ aryl), and —$(CR^9R^{10})_m$(4 to 10 membered heterocyclic), wherein each m is independently an integer ranging from 0 to 2; said alkyl group optionally includes 1 hetero moiety selected from O, —$S(O)_j$— wherein j is an integer ranging from 0 to 2, and —$N(R^9)$—; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^1$ substituents, except H, are optionally substituted by 1 to 5 substituents independently selected from oxo, halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy, and with the proviso that $R^7$ must be attached through a carbon atom unless $R^7$ is H; each $R^9$ and $R^{10}$ are independently H or $C_1$–$C_4$ alkyl; $R^{11}$ is selected from $R^7$ except H.

In a ninth preferred embodiment of the compound of formula 1:

the preferred groups as indicated for the eighth preferred embodiment, but:

X is F, H or OH;

Y is O;

$W^1$ is $R^3$, $W^2$ is $OR^{13}$; or $W^1$ is H, $W^2$ is $R^3$, $NR^3R^4$, or F; $Z^1$ is $R^3$, $Z^2$ is $OR^{13}$; or $Z^1$ is H, $Z^2$ is $R^3$, $NR^3R^4$, or F; wherein each $R^3$ and $R^{13}$ are independently H or $C_1$–$C_4$ alkyl, and said alkyl groups are optionally substituted by 1 to 3 $R^6$ groups; wherein each $R^6$ is independently oxo, halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, and —$NR^7R^9$; wherein each $R^7$ and $R^9$ is independently H or $C_1$–$C_4$ alkyl; $R^{11}$ is $C_1$–$C_4$ alkyl;

$R^1$ and $R^2$ are taken together as =$C(R^5)X^1$—$X^2$—$R^8$; wherein $X^1$ is —$CR^9R^{10}$—, and $X^2$ is selected from —$CR^9R^{10}$—, —$S(O)_n$— wherein n is 0 to 2, —$NR^9$—, and O; where $X^2$ is —$NR^9$—, then $R^8$ and $R^9$ may be taken together to form a 5 to 12 membered heterocyclic, which is optionally substituted by 1 to 3 $R^6$ groups; $X^1$ and $X^2$ can also independently or together represent a bond with the proviso that if $X^1$ is a bond than $X^2$ must be either a bond or —$CR^9R^{10}$—;

and where $R^5$ is H or $C_1$–$C_6$ alkyl, wherein the foregoing $R^5$ alkyl group is optionally substituted by 1 or 2 $R^6$ groups:

and where $R^8$ is $R^3$ wherein each $R^3$ is independently —$(CR^9R^{10})_t$($C_6$–$C_{10}$ aryl) or —$(CR^9R^{10})_t$(4 to 10 membered heterocyclic), wherein each t is independently an integer ranging from 0 to 3; the foregoing $R^3$ groups are optionally substituted by 1 to 5 $R^6$ groups, and with the proviso that $R^3$ must be attached through a carbon atom; $R^{12}$ is $C_1$–$C_4$ alkyl, and said alkyl group is optionally substituted by 1 to 3 $R^6$ groups, except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H; wherein each $R^6$ is independently $C_1$–$C_4$ alkyl, oxo, halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, —$NR^7R^9$, —$(CR^9R^{10})_m$($C_6$–$C_{10}$ aryl), —$O(CR^9R^{10})_m$($C_6$–$C_{10}$ aryl), —$NR^9(CR^9R^{10})_m$($C_6$–$C_{10}$ aryl), and —$(CR^9R^{10})_m$(4 to 10 membered heterocyclic), wherein each m is independently an integer ranging from 0 to 2; said alkyl, aryl and heterocyclic $R^6$ groups are optionally substituted by 1 to 5 substituents independently selected from oxo, halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, and $C_1$–$C_4$ alkyl;

each $R^7$ is independently selected from H, $C_1$–$C_4$ alkyl, $C_3$–$C_6$ cycloalkyl, —$(CR^9R^{10})_m$($C_6$–$C_{10}$ aryl), and —$(CR^9R^{10})_m$(4 to 10 membered heterocyclic), wherein each m is independently an integer ranging from 0 to 2; the foregoing $R^7$ substituents, except H, are optionally substituted by 1 to 5 substituents independently selected from oxo, halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy; each $R^9$ and $R^{10}$ are independently H or $C_1$–$C_4$ alkyl; $R^{11}$ is selected from $R^7$ except H.

In a tenth preferred embodiment of the compound of formula 1:

the preferred groups as indicated for the ninth preferred embodiment, but:

$Z^1$ is H, $Z^2$ is OH; or $Z^1$ is methyl, $Z^2$ is OH; or $Z^1$ is H, $Z^2$ is $NH_2$; or both $Z^1$ and $Z^2$ are H; or $Z^1$ is H, $Z^2$ is F;

$W^1$ is H, $W^2$ is OH;

$R^1$ and $R^2$ are taken together as =$C(R^5)X^1$—$X^2$—$R^8$; wherein $X^1$ is —$CH_2$—, and $X^2$ is selected from —$S(O)_n$— wherein n is 0 to 2, —$NR^9$—, and O; where $X^2$ is —$NR^9$—, then $R^8$ and $R^9$ may be taken together to form a 5 to 12 membered heterocyclic, which is optionally substituted by 1 to 3 $R^6$ groups;

and where $R^5$ is H or $C_1$–$C_6$ alkyl, wherein the foregoing $R^5$ alkyl group is optionally substituted by 1 or 2 $R^6$ groups:

and where $R^8$ is $R^3$, wherein $R^3$ is —$(CH_2)_t$($C_6$–$C_{10}$ aryl) or —$(CH_2)_t$(4 to 10 membered heterocyclic), wherein each t is independently an integer from 0 to 2, and the foregoing $R^3$ groups are optionally substituted by 1 to 5 $R^6$ groups; wherein each $R^6$ is independently $C_1$–$C_4$ alkyl, halo, trifluoromethyl, difluoromethoxy, trifluoromethoxy, —$OR^7$, —$C(O)R^7$, —$(CH_2)_m$($C_6$–$C_{10}$ aryl), —$O(CH_2)_m$($C_6$–$C_{10}$ aryl), and —$(CH_2)_m$(4 to 10 membered heterocyclic), wherein each m is independently an integer from 0 to 2; said alkyl, aryl and heterocyclic $R^6$ groups are optionally substituted by 1 to 5 substituents independently selected from oxo, halo, trifluoromethyl, difluoromethoxy, trifluoromethoxy, —$C(O)R^7$, —$NR^9C(O)OR^{11}$, —$NR^9C(O)R^7$, —$C(O)NR^7R^9$, —$OR^7$, and $C_1$–$C_4$ alkyl;

each $R^7$ is independently selected from H and $C_1$–$C_4$ alkyl; the foregoing $R^7$ substituents, except H, are optionally substituted by 1 to 3 substituents independently selected from oxo, trifluoromethyl, —$C(O)$ $R^9$, —$NR^9C(O)R^{10}$, —$C(O)NR^9R^{10}$, —$NR^9R^{10}$, hydroxy, and $C_1$–$C_4$ alkoxy; each $R^9$ and $R^{10}$ are independently H, $C_1$–$C_4$ alkyl; $R^{11}$ is selected from $R^7$ except H; $R^{12}$ is $C_1$–$C_4$ alkyl except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H.

In an eleventh preferred embodiment of the compound of formula 1:
  the preferred groups as indicated for the tenth preferred embodiment, but:
    $R^1$ and $R^2$ are taken together as =$C(R^5)X^1$—$X^2$—$R^8$; wherein $R^5$ is H, $X^1$ is —$CH_2$—, and $X^2$ is O, and wherein $R^8$ is $R^3$, wherein $R^3$ is phenyl or (5 to 6 membered heterocyclic), and the foregoing Re groups are optionally substituted by 1 to 5 $R^6$ groups, wherein each $R^6$ is independently selected from $C_1$–$C_4$ alkyl, halo, trifluoromethyl, and —$(CH_2)_m$(4 to 10 membered heterocyclic), wherein each m is independently an integer ranging from 0 to 1; said heterocyclic $R^6$ groups are optionally substituted by 1 to 5 substituents independently selected from halo, trifluoromethyl, and $C_1$–$C_4$ alkyl.

In a twelfth preferred embodiment of the compound of formula 1:
  the preferred groups as indicated for the first preferred embodiment, but:
    $R^1$ is H and $R^2$ is —$NR^3R^4$, —$NR^4C(O)R^3$, —$OC(O)NR^3R^4$ or —$OR^3$ and the preferred configuration of the 1" center is that of hygromycin A.

In a thirteenth preferred embodiment of the compound of formula 1:
  the preferred groups as indicated for the twelfth preferred embodiment, but:
    X is F, H or OH;
    Y is O;
    $W^1$ is $R^3$, $W^2$ is $OR^{13}$; or $W^1$ is H, $W^2$ is $R^3$ or F; $Z^1$ is $R^3$, $Z^2$ is $OR^{13}$; or $Z^1$ is H, $Z^2$ is $R^3$ or F; wherein each $R^3$ and $R^{13}$ are independently H or $C_1$–$C_4$ alkyl, and said alkyl groups are optionally substituted by 1 to 3 $R^6$ groups; wherein each $R^6$ is independently halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, or —$NR^7R^9$; wherein each $R^7$ and $R^9$ are independently H or $C_1$–$C_4$ alkyl; $R^{11}$ is $C_1$–$C_4$ alkyl;
    and in the substituent $R^2$, $R^3$ is independently selected from H, $C_1$–$C_{10}$ alkyl, —$(CR^9R^{10})_t(C_3$–$C_{10}$ cycloalkyl), —$(CR^9R^{10})_t(C_6$–$C_{10}$ aryl), and —$(CR^9R^{10})_t$(4 to 10 membered heterocyclic), wherein each t is independently an integer from 0 to 3, said alkyl group optionally contains 1 hetero moiety selected from O, —$S(O)_j$— wherein j is an integer ranging from 0 to 2, and —$N(R^9)$—; said cycloalkyl, aryl and heterocyclic $R^3$ groups are optionally fused to a benzene ring, a $C_5$–$C_8$ cycloalkyl group, or a 4 to 10 membered heterocyclic group; and the foregoing $R^3$ groups, except H but including any optional fused rings referred to above, are optionally substituted by 1 to 5 $R^6$ groups, and with the proviso that $R^3$ must be attached through a carbon atom unless $R^3$ is H; each $R^4$ is independently H or $C_1$–$C_6$ alkyl; each $R^6$ is independently $C_1$–$C_4$ alkyl, halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, —$NR^7R^9$, —$(CR^9R^{10})_m(C_6$–$C_{10}$ aryl), —$O(CR^9R^{10})_m(C_6$–$C_{10}$ aryl), —$NR^9(CR^9R^{10})_m(C_6$–$C_{10}$ aryl), and —$(CR^9R^{10})_m$(4 to 10 membered heterocyclic), wherein each m is independently an integer ranging from 0 to 2; said alkyl, aryl and heterocyclic $R^6$ groups are optionally substituted by 1 to 5 substituents independently selected from halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, and $C_1$–$C_4$ alkyl; each $R^7$ is independently selected from H, $C_1$–$C_4$ alkyl, $C_3$–$C_6$ cycloalkyl, —$(CR^9R^{10})_m(C_6$–$C_{10}$ aryl), and —$(CR^9R^{10})_m$(4 to 10 membered heterocyclic), wherein each m is independently an integer ranging from 0 to 2; the foregoing $R^7$ substituents, except H, are optionally substituted by 1 to 5 substituents independently selected from halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy; each $R^9$ and $R^{10}$ are independently H, $C_1$–$C_4$ alkyl; $R^{11}$ is selected from $R^7$ except H; $R^{12}$ is $C_1$–$C_4$ alkyl except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, Z is H.

In a fourteenth preferred embodiment of the compound of formula 1:
  V is $R^3OC(O)$, $R^3R^4NC(O)$ or $R^3O(R^4)NC(O)$ and the preferred configuration of the 1" center is that of hygromycin A.

In a fifteenth preferred embodiment of the compound of formula 1:
  the preferred groups as indicated for the fourteenth preferred embodiment, but:
    X is F, H or OH;
    Y is O;
    $W^1$ is $R^3$, $W^2$ is $OR^{13}$; or $W^1$ is H, $W^2$ is $R^3$ or F; $Z^1$ is $R^3$, $Z^2$ is $OR^{13}$; or Z is H, $Z^2$ is $R^3$ or F; wherein each $R^3$ and $R^{13}$ are independently H or $C_1$–$C_4$ alkyl, and said alkyl groups are optionally substituted by 1 to 3 $R^6$ groups; wherein each $R^6$ is independently halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, or —$NR^7R^9$; wherein each $R^7$ and $R^9$ are independently H or $C_1$–$C_4$ alkyl; $R^{11}$ is $C_1$–$C_4$ alkyl;
    within substituent V, $R^3$ is independently selected from H, $C_1$–$C_{10}$ alkyl, —$(CR^9R^{10})_t(C_3$–$C_{10}$ cycloalkyl), —$(CR^9R^{10})_t(C_6$–$C_{10}$ aryl), and —$(CR^9R^{10})_t$(4 to 10 membered heterocyclic), wherein each t is independently an integer ranging from 0 to 3, said alkyl group optionally contains 1 hetero moiety selected from O, —$S(O)_j$— wherein j is an integer ranging from 0 to 2, and —$N(R^9)$—; said cycloalkyl, aryl and heterocyclic $R^3$ groups are optionally fused to a benzene ring, a $C_5$–$C_8$ cycloalkyl group, or a 4 to 10 membered heterocyclic group; and the foregoing $R^3$ groups, except H but including any optional fused rings referred to above, are optionally substituted by 1 to 5 $R^6$ groups, and with the proviso that $R^3$ must be attached through a carbon atom unless $R^3$ is H; each $R^4$ is independently H or $C_1$–$C_6$ alkyl; each $R^6$ is independently $C_1$–$C_4$ alkyl, halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, —$NR^7R^9$, —$(CR^9R^{10})_m(C_6$–$C_{10}$ aryl), —$O(CR^9R^{10})_m(C_6$–$C_{10}$ aryl), —$NR^9(CR^9R^{10})_m$ ($C_6$–$C_{10}$ aryl), and —$(CR^9R^{10})_m$(4 to 10 membered heterocyclic), wherein each m is independently an integer ranging from 0 to 2; said alkyl, aryl and heterocyclic $R^6$ groups are optionally substituted by 1 to 5 substituents independently selected from halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, $C_1$–$C_4$ alkyl; $R^7$ is independently selected from H, $C_1$–$C_4$ alkyl, $C_3$–$C_6$ cycloalkyl, —$(CR^9R^{10})_m$($C_6$–$C_{10}$ aryl), and —$(CR^9R^{10})_m$(4 to 10 membered heterocyclic), wherein each m is independently an integer ranging from 0 to 2; the foregoing $R^7$ substituents, except H, are optionally substituted by 1 to 5 substituents independently selected from halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy; each $R^9$ and $R^{10}$ are independently H and $C_1$–$C_4$ alkyl; $R^{11}$ is selected from $R^7$ except H.

In a sixteenth preferred embodiment of the compound of formula 1:

V is a moiety of the structure

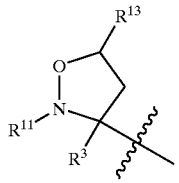

and the preferred configuration of the 1" center is that of hygromycin A.

In a seventeenth preferred embodiment of the compound of formula 1:

the preferred groups as indicated for the sixteenth preferred embodiment, but:
X is F, H or OH;
Y is O;
$W^1$ is $R^3$, $W^2$ is $OR^{13}$; or $W^1$ is H, $W^2$ is $R^3$ or F; $Z^1$ is $R^3$, $Z^2$ is $OR^{13}$; or $Z^1$ is H, $Z^2$ is $R^3$ or F; wherein each $R^3$ and $R^{13}$ are independently H or $C_1$–$C_4$ alkyl, and said alkyl groups are optionally substituted by 1 to 3 $R^6$ groups; wherein each $R^6$ is independently halo, trifluoromethyl, difluoromethoxy, trifluoromethoxy, —OR , —$C(O)R^7$, —$NR^9C(O)OR^{11}$, —$NR^9C(O)R^7$, —$C(O)NR^7R^9$, or —$NR^7R^9$; wherein each $R^7$ and $R^9$ is H or $C_1$–$C_4$ alkyl; $R^{11}$ is $C_1$–$C_4$ alkyl;
within the substituent V, $R^3$ is $C_1$–$C_6$ alkyl; each $R^{13}$ is independently selected from H, $C_1$–$C_{10}$ alkyl, —$(CR^9R^{10})_t$($C_3$–$C_{10}$ cycloalkyl), —$(CR^9R^{10})_t$($C_6$–$C_{10}$ aryl), and —$(CR^9R^{10})_t$(4 to 10 membered heterocyclic), wherein each t is independently an integer ranging from 0 to 3, said alkyl group optionally contains 1 hetero moiety selected from O, —$S(O)_j$— wherein j is an integer ranging from 0 to 2, and —$N(R^9)$—; said cycloalkyl, aryl and heterocyclic $R^3$ groups are optionally fused to a benzene ring, a $C_5$–$C_8$ cycloalkyl group, or a 4 to 10 membered heterocyclic group; and the foregoing $R^3$ groups, except H but including any optional fused rings referred to above, are optionally substituted by 1 to 5 $R^6$ groups, and with the proviso that $R^3$ must be attached through a carbon atom unless $R^3$ is H;

each $R^6$ is independently $C_1$–$C_4$ alkyl, halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, —$NR^7R^9$, —$(CR^9R^{10})_m$($C_6$–$C_{10}$ aryl), —$O(CR^9R^{10})_m$($C_6$–$C_{10}$ aryl), —$NR^9(CR^9R^{10})_m$($C_6$–$C_{10}$ aryl), and —$(CR^9R^{10})_m$(4 to 10 membered heterocyclic), wherein each m is independently an integer ranging from 0 to 2; said alkyl, aryl and heterocyclic $R^6$ groups are optionally substituted by 1 to 5 substituents independently selected from halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, and $C_1$–$C_4$ alkyl; each $R^7$ is independently selected from H, $C_1$–$C_4$ alkyl, $C_3$–$C_6$ cycloalkyl, —$(CR^9R^{10})_m$($C_6$–$C_{10}$ aryl), and —$(CR^9R^{10})_m$(4 to 10 membered heterocyclic), wherein each m is independently an integer ranging from 0 to 2; the foregoing $R^7$ substituents, except H, are optionally substituted by 1 to 5 substituents independently selected from halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy; each $R^9$ and $R^{10}$ are independently H or $C_1$–$C_4$ alkyl; $R^{11}$ is selected from $R^7$ except H.

In a eighteenth preferred embodiment of the compound of formula 1:

V is a group of the structure

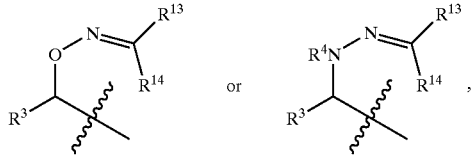

where both E and Z isomers are included and the preferred configuration of the 1" center is that of hygromycin A.

In a nineteenth preferred embodiment of the compound of formula 1:

the preferred groups as indicated for the eighteenth preferred embodiment, but:
X is F, H or OH;
Y is O;
$R^{13}$ is —$(CR^9R^{10})_t$($C_6$–$C_{10}$ aryl) or —$(CR^9R^{10})_t$(4 to 10 membered heterocyclic), wherein each t is independently an integer ranging from 0 to 2, and the foregoing $R^3$ groups are optionally substituted by 1 to 5 $R^6$ groups; wherein each $R^6$ is independently $C_1$–$C_4$ alkyl, oxo, halo, trifluoromethyl, difluoromethoxy, trifluoromethoxy, —$OR^7$, —$C(O)R^7$, $(CR^9R^{10})_m$($C_6$–$C_{10}$ aryl), —$O(CR^9R^{10})_m$ ($C_6$–$C_{10}$ aryl), or —$(CR^9R^{10})_m$(4 to 10 membered heterocyclic), wherein each m is independently an integer ranging from 0 to 2; said alkyl, aryl and heterocyclic $R^6$ groups are optionally substituted by 1 to 5 substituents independently selected from oxo, halo, trifluoromethyl, difluoromethoxy, trifluoromethoxy, —$C(O)R^7$, —$NR^9C(O)OR^{11}$, —$NR^9C(O)R^7$, —$C(O)NR^7R^9$, —$OR^7$, and $C_1$–$C_4$ alkyl; each $R^7$ is independently selected from H and $C_1$–$C_4$ alkyl; the foregoing $R^7$ substituents, except H, are optionally substituted by 1 to 3 substituents independently selected from trifluoromethyl, —$C(O)R^9$, —$NR^9C(O)R^{10}$, —$C(O)NR^9R^{10}$, —$NR^9R^{10}$, hydroxy, and $C_1$–$C_4$ alkoxy; each $R^9$ and $R^{10}$ are independently H or $C_1$–$C_4$ alkyl;

each $R^4$ and $R^{14}$ are independently selected from H and $C_1$–$C_4$ alkyl;

$R^3$ is $C_1$–$C_4$ alkyl, and said alkyl group is optionally substituted by 1 to 3 $R^6$ groups; each $R^6$ is independently selected from $C_1$–$C_4$ alkyl, oxo, halo, trifluoromethyl, difluoromethoxy, trifluoromethoxy, —$OR^7$, —$C(O)R^7$, —$NR^9C(O)OR^{11}$, —$NR^9SO_2R^{11}$, —$SO_2NR^7R^9$, —$NR^9C(O)R^7$, —$C(O)NR^7R^9$, —$NR^7R^9$, —$S(O)_j(CR^9R^{10})_m$ ($C_6$–$C_{10}$ aryl), —$S(O)_j(C_1$–$C_6$ alkyl), wherein j is an integer ranging from 0 to 2, —$(CR^9R^{10})_m(C_6$–$C_{10}$ aryl), —$O(CR^9R^{10})_m(C_6$–$C_{10}$ aryl), —$NR^9(CR^9R^{10})_m(C_6$–$C_{10}$ aryl), and —$(CR^9R^{10})_m$(4 to 10 membered heterocyclic), wherein each m is independently an integer ranging from 0 to 2; and said alkyl, cycloalkyl, aryl and heterocyclic $R^6$ groups are optionally substituted by 1 to 5 substituents independently selected from oxo, halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, $C_1$–$C_4$ alkyl, —$(CR^9R^{10})_m(C_6$–$C_{10}$ aryl), and —$(CR^9R^{10})_m$(4 to 10 membered heterocyclic), wherein each m is independently an integer ranging from 0 to 2; each $R^7$ is independently selected from H, $C_1$–$C_4$ alkyl, $C_3$–$C_6$ cycloalkyl, —$(CR^9R^{10})_m(C_6$–$C_{10}$ aryl), and —$(CR^9R^{10})_m$(4 to 10 membered heterocyclic), wherein each m is independently an integer ranging from 0 to 2; said alkyl group optionally includes 1 hetero moiety selected from O, —$S(O)_j$— wherein j is an integer ranging from 0 to 2, and —$N(R^9)$—; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^7$ substituents, except H, are optionally substituted by 1 to 5 substituents independently selected from oxo, halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy, and with the proviso that $R^7$ must be attached through a carbon atom unless $R^7$ is H; each $R^9$ and $R^{10}$ are independently H or $C_1$–$C_4$ alkyl.

In a twentieth preferred embodiment of the compound of formula 1:

V is a carbon-linked 4 to 10 membered heterocyclic group, which may be optionally substituted by 1 to 3 $R^6$ groups and the preferred configuration of the 1" center is that of hygromycin A.

Specific preferred compounds of formula 1 include those listed below as well as the pharmaceutically acceptable salts, solvates and prodrugs of the following compounds:

1. 3-(3-Fluoro-4-((2S,4S,5R)-4-hydroxy-5-(1-methoxyimino-2-phenoxy-ethyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 2. 3-(4-((2S,4S,5R)-5-(1-((E)-4-Fluoro-benzyloxyimino)-2-hydroxy-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 3. 3-(4-((2S,3S,4S,5R)-5-(5R-(3-Chloro-phenyl)-2,3-dimethyl-isoxazolidin-3-yl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo(1,3)dioxol-5-yl)-(2E)-acrylamide 4. (2S,3S,5S)-5-(2-Fluoro-4-(2-((3aS,4R,5R,6S,7R,7aR)-4,6,7-trihydroxy-hexahydro-benzo(1,3)dioxol-5-ylcarbamoyl)-propenyl)-phenoxy)-3-hydroxy-tetrahydro-furan-2-carboxylic acid benzyloxy-amide 5. 3-(4-((2S,4S,5R)-5-(((E)-2-Fluoro-4-chloro-benzyloxyimino)-methyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 6. (2S,3S,4S,5S)-3,4-Dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-propenyl)-phenoxy)-tetrahydro-furan-2-carboxylic acid benzyloxy-amide 7. (2S,3S,5S)-5-(2-Fluoro-4-(2-((3aS,4R,5R,6S,7R,7aR)-4,6,7-trihydroxy-hexahydro-benzo(1,3)dioxol-5-ylcarbamoyl)-propenyl)-phenoxy)-3-hydroxy-tetrahydro-furan-2-carboxylic acid benzylamide 8. 3-(4-((2R,4S,5S)-5-(1-((E)-2-Fluoro-4-chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 9. 3-(4-((2S,3S,5S)-5-(1-((E)-2,4-Dichloro-benzyloxyimino)-ethyl)-3-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 10. 3-(4-((2R,4S,5R)-5-(1-((E)-4-Fluoro-benzyloxyimino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 11. 3-(4-((2S,3S,5S)-5-(1-((E)-3,4-Difluoro-benzyloxyimino)-ethyl)-3-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 12. 3-(4-((2S,5S)-5-(1-((E)-2-Chloro-5-fluoro-benzyloxyimino)-ethyl)-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 13. 3-(4-((2R,4S,5R)-5-(1-((E)-2,4-Dichloro-5-fluoro-benzyloxyimino)-ethyl)-4-methoxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 14. 3-(4-((2S,3S,4S,5R)-3-Amino-5-(1-((E)-3-chloro-benzyloxyimino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 15. 3-(4-((2S,4S,5S)-5-(1-(3-Chloro-benzyloxy)-propyl)-4-hydroxy-tetrahydro-furan-2-yloxy)-3-fluoro-phenyl)-2-methyl-N-((3aS,4R,5R,6S,7R,7aR)-4,6,7-trihydroxy-3-(4-((2S,4R,5R)-5-(1-((E)-2-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 16. 3-(4-((2S,4S,5R)-5-(1-((E)-Benzo(1,3)dioxol-5-ylmethoxyimino)-ethyl)-4-hydroxy-tetrahydro-furan- 2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 17. 3-(4-((1R,3R,4R)-3-(1-((E)-Benzo(1,3)dioxol-5-ylmethoxyimino)-ethyl)-4-hydroxy-cyclopentyloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 18. 3-(4-((1R,3R,4R)-3-(((E)-Benzo(1,3)dioxol-5-ylmethoxyimino)-methyl)-4-hydroxy-cyclopentyloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 19. 3-(4-((2S,4S,5R)-5-(1-((E)-Benzo[1,3]dioxol-5-ylmethoxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 20. 3-(4-((2S,4S,5R)-5-(((E)-Benzo(1,3)dioxol-5-ylmethoxyimino)-methyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 21. 3-(4-((1R,2S,3R,4R)-4-(((E)-2,4-Dichloro-benzyloxyimino)-methyl)-2,3-dihydroxy-cyclopentyloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 22. 3-(4-((1S,3R,4R)-3-(1-((E)-2,3-Dichloro-5-fluoro-benzyloxyimino)-ethyl)-4-hydroxy-cyclopentyloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 23. 3-(4-((1R,2S,4R)-4-(1-((E)-3-Chloro-benzyloxyimino)-ethyl)-2-hydroxy-cyclopentyloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 24. 3-(4-((1S,3R)-3-(1-((E)-3,4-Difluoro-benzyloxyimino)-ethyl)-cyclopentyloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 25. 3-(4-((1R,2S,3R,4R)-4-(1-((E)-2-Fluoro-benzyloxyimino)-ethyl)-2,3-dihydroxy-cyclopentyloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 26. 3-(4-((2S,3S,4S,5S)-5-(1-(3-Chloro-benzylideneaminooxy)-ethyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 27. 3-(4-((2S,4S,5S)-5-(1-(1-(4-Fluoro-phenyl)-ethylideneaminooxy)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 28. 3-(4-((2S,4S,5S)-5-(1-(1-(2,4-Dichloro-phenyl)-ethylideneaminooxy)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 29. 3-(4-((2S,3S,4S,5R)-5-(2-(2,4-Dichloro-benzyl)-thiazol4-yl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 30. 3-(4-((2S,3S,4S,5R)-5-(3-(2,4-Dichloro-phenoxy)-1-hydroxymethyl-(E)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 31. 3-(4-((2S,4S,5R)-5-(3-(2,4-Dichloro-phenoxy)-1-hydroxymethyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 32. 3-(4-((1R,2S,3R,4S)-4-(3-(2,4-Dichloro-phenoxy)-(E)-propenyl)-2,3-dihydroxy-cyclopentyloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 33. 3-(4-((2S,3S,4S,5R)-5-(2-(2,4-Dichloro-benzyl)-3H-imidazol4-yl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 34. 3-(4-((2S,3S,4S,5R)-5-(6-Chloro-1H-benzoimidazol-2-yl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 35. 3-(4-((2S,3S,4S,5R)-5-(1-(N'-(2,4-Dichloro-benzylidene)-hydrazino)-ethyl)-3,4-dihydroxy-tetrahydro-furan-2-yioxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 36. 3-(4-((2S,3S,4S,5R)-5-(1-(N'-(2-Chloro-benzylidene)-hydrazino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 37. 3-(4-((2S,4S,5R)5-(1-(N'-(2-Chloro-5-fluoro-benzylidene)-hydrazino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 38. 3-(4-((2S,4S,5R)-5-(1-(N'-(3-Chloro-benzylidene)-hydrazino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 39. 3-(4-((2S,4S,5R)-5-(1-((E)-3-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 40. 3-(4-((2S,3R,4S,5R)-5-(1-((E)-2,3-Dichloro-5-fluoro-benzyloxyimino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 41. 3-(4-((2S,3R,4S,5R)-5-(1-((E)-3-Chloro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 42. 3-(4-((2S,4S,5R)-5-(1-((E)-4-Fluoro-benzyloxyimino)-propyl)-4-hydroxy-tetrahydro-furan- 42. ...2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
43. 3-(4-((2S,4S,5R)-5-((E)-1-Benzyloxyimino-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
44. 3-(4-((2S,3S,4R,5R)-5-(1-((E)-3-Chloro-benzyloxyimino)-ethyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
45. 3-(4-((2S,3S,4R,5R)-5-(1-((E)-3,4-Difluoro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
46. 3-(4-((2S,3R,4R,5R)-5-(1-((E)-3-Chloro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
47. 3-(3-Fluoro-4-((2S,4S,5R)-5-(1-((E)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
48. 3-(3-Amino-4-((2S,4S,5R)-5-(1-((E)-4-fluoro-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
49. 3-(4-((2S,4S,5R)-5-(3-(2,4-Dichloro-phenoxy)-1-methyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
50. 3-(3-Amino-4-((2S,4S,5R)-5-(3-(2-chloro-5-fluoro-phenoxy)-1-methyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
51. 3-(3-Amino-4-((2S,3R,4S,5R)-5-(1-((E)-2-chloro-benzyloxyimino)-ethyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
52. 3-(4-((2S,3R,4S,5R)-5-(3-(2-Fluoro-phenoxy)-1-methyl-(E)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
53. 3-(3-Amino-4-((2S,3R,4R,5R)-5-(3-(3-chloro-phenoxy)-1-methyl-(E)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
54. 3-(4-((2S,3R,4R,5R)-5-(1-((E)-3-Chloro-benzyloxyimino)-ethyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
55. 3-(3-Amino-4-((2S,3R,4R,5R)-5-(1-((E)-3-Chloro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
56. 3-(4-((2S,3R,4R,5R)-5-(3-(3,4-Difluoro-phenoxy)-1-methyl-(E)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
57. 3-(3-Amino-4-((2S,3R,4R,5R)-5-(3-(2-fluoro-4-chloro-phenoxy)-1-methyl-(E)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
58. 3-(4-((2S,4S,5R)-5-(1-((E)-4-Fluoro-benzyloxyimino)-propyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
59. 3-(3-Amino-4-((2S,4S,5R)-5-(1-((E)-2,4-dichloro-benzyloxyimino)-propyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
60. 3-(4-((2S,4S,5R)-5-(3-(3-Chloro-phenoxy)-1-ethyl-(E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
61. 3-(3-Amino-4-((2S,4S,5R)-5-(3-(2,3-dichloro-5-fluoro-phenoxy)-1-ethyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
62. 3-(3-Amino-4-((2S,4S,5R)-5-((E)-1-benzyloxyimino-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
63. 3-(3-Fluoro-4-((2S,4S,5R)-4-hydroxy-5-(1-methyl-3-phenoxy-(E)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
64. 3-(3-Amino-4-((2S,4S,5R)-4-hydroxy-5-(1-methyl-3-phenoxy-(E)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
65. 3-(4-((2S,3S,4R,5R)-5-(1-((E)-2-Chloro-5-fluoro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
66. 3-(3-Amino-4-((2S,3S,4R,5R)-5-(1-((E)-2-chloro-benzyloxyimino)-ethyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
67. 3-(4-((2S,3S,4R,5R)-5-(3-(3-Chloro-phenoxy)-1-methyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
68. 3-(3-Amino-4-((2S,3S,4R,5R)-5-(3-(2-fluoro-phenoxy)-1-methyl-(E)-propenyl)-3-fluoro-4-hydroxytetrahydro-furan-2-yloxy)-phenyl)-2-methyl-N-((3aS, 4R,5R,6S,7R,7aR)-4,6,7-trihydroxy-hexahydro-benzo (1,3)dioxol-5-yl)-(2E)-acrylamide
69. 3-(4-((2S,3S,4R,5R)-5-(1-((E)-4-Fluoro-benzyloxyimino)-propyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
70. 3-(4-((2S,3S,4R,5R)-5-(1-((E)-3-Chloro-benzyloxyimino)-propyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
71. 3-(4-((2S,3S,4R,5R)-5-(3-(3-Chloro-phenoxy)-1-ethyl-(E)-propenyl)-3-fluoro-4-hydroxy-tetrahydro-furan-2-yloxy)-3-fluoro-phenyl)-2-methyl-N-((3aS, 4R,5R,6S,7R,7aR)-4,6,7-trihydroxy-hexahydro-benzo (1,3)dioxol-5-yl)-(2E)-acrylamide
72. 3-(4-((2S,3S,4R,5R)-5-(3-(3-Chloro-phenoxy)-1-ethyl-(E)-propenyl)-3-fluoro-4-hydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide
73. 3-(4-((2S,3R,4R,5R)-5-(1-((E)-3,4-Difluoro-benzyloxyimino)-ethyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
74. 3-(3-Amino-4-((2S,3R,4R,5R)-5-(1-((E)-2,3-dichloro-5-fluoro-benzyloxyimino)-ethyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
75. 3-(4-((2S,3R,4R,5R)-5-(3-(2-Chloro-5-fluoro-phenoxy)-1-methyl-(E)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
76. 3-(3-Amino-4-((2S,3R,4R,5R)-5-(3-(2-fluoro-4-chloro-phenoxy)-1-methyl-(E)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
77. 3-(3-Amino-4-((2S,4S,5R)-5-(1-((E)-3-fluoro-4-morpholin-4-yl-benzyloxyimino)-ethyl)-4-hydroxy-tetrahydro-furan-2-yloxy)-phenyl)-2-methyl-N-((3aS, 4R,5R,6S,7R,7aR)-4,6,7-trihydroxy-hexahydro-benzo (1,3)dioxol-5-yl)-(2E)-acrylamide
78. 3-(3-Fluoro-4-((2S,4S,5R)-5-(3-(3-fluoro-4-morpholin-4-yl-phenoxy)-1-methyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
79. 3-(3-Amino-4-((2S,4S,5R)-5-(3-(3-fluoro-4-morpholin-4-y-phenoxy)-1-methyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
80. 3-(4-((2S,3S,4R,5R)-5-(1-((E)-4-Fluoro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
81. 3-(4-((2S,3S,4R,5R)-5-(1-((E)-2-Fluoro-benzyloxyimino)-ethyl)-3,4-dihydroxy-3-methyl-tetrahydro-furan-2-yloxy)-3-hydroxy-phenyl)-2-methyl-N-((3aS,4R 5R,6S,7R,7aR)-4,6,7-trihydroxy-hexahydro-benzo(1,3)dioxol-5-yl)-(2E)-acrylamide
82. 3-(3-Amino-4-((2S,3S,4R,5R)-5-(1-((E)-3-Chloro-benzyloxyimino)-ethyl)-3,4-dihydroxy-3-methyl-tetrahydro-furan-2-yloxy)-phenyl)-2-methyl-N-((3aS, 4R,5R,6S,7R,7aR)-4,6,7-trihydroxy-hexahydro-benzo (1,3)dioxol-5-yl)-(2E)-acrylamide
83. 3-(4-((2S,3S,4R,5R)-5-(3-(3-Chloro-phenoxy)-1-methyl-(E)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
84. 3-(3-Amino-4-((2S,3S,4R,5R)-5-(3-(3-chloro-phenoxy)-1-methyl-(E)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
85. 3-(4-((2S,3S,5S)-5-(1-((E)-2,4-Dichloro-benzyloxyimino)-ethyl)-3-fluoro-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3) dioxol-5-yl)-(2E)-acrylamide
86. 3-(4-((2S,3S,5S)-5-(3-(3,4-Difluoro-phenoxy)-1-methyl-(E)-propenyl)-3-fluoro-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3) dioxol-5-yl)-(2E)-acrylamide
87. 3-(4-((2S,3S,5S)-5-(1-((E)-2-Chloro-benzyloxyimino)-ethyl)-3-fluoro-tetrahydro-furan-2-yloxy)-3-fluoro-phenyl)-2-methyl-N-((3aS,4R,5R,6S, 7R,7aR)-4,6,7-trihydroxy-hexahydro-benzo(1,3) dioxol-5-yl)-(2E)-acrylamide
88. 3-(4-((2S,3S,5S)-5-(3-(2-Fluoro-phenoxy)-1-methyl-(E)-propenyl)-3-fluoro-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
89. 3-(4-((2S,3R,5S)-5-(1-((E)-2-Fluoro-4-chloro-benzyloxyimino)-ethyl)-3-fluoro-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3) dioxol-5-yl)-(2E)-acrylamide
90. 3-(4-((2S,3R,5S)-5-(3-(3-Chloro-phenoxy)-1-methyl-(E)-propenyl)-3-fluoro-tetrahydro-furan-2-yloxy)-3-hydroxy-phenyl)-2-methyl-N-((3aS,4R,5R,6S,7R, 7aR)-4,6,7-trihydroxy-hexahydro-benzo(1,3)dioxol-5-yl)-(2E)-acrylamide
91. 3-(4-((2S,3R,5S)-5-(1-((E)-2-Chloro-5-fluoro-benzyloxyimino)-ethyl)-3-fluoro-tetrahydro-furan-2-yloxy)-3-fluoro-phenyl)-2-methyl-N-((3aS,4R,5R,6S, 7R,7aR)-4,6,7-trihydroxy-hexahydro-benzo(1,3) dioxol-5-yl)-(2E)-acrylamide
92. 3-(4-((2S,3R,5S)-5-(3-(3-Chloro-phenoxy)-1-methyl-(E)-propenyl)-3-fluoro-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
93. 3-(4-((2S,3R,4R,5R)-5-(3-(3-Chloro-phenoxy)-1-methyl-(E)-propenyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
94. 3-(4-((2S,4S,5R)-5-(3-(3,4-Difluoro-phenoxy)-1-ethyl-(E)-propenyl)-4-hydroxy-tetrahydro-furan-2- yloxy)-3-fluoro-phenyl)-2-methyl-N-((3aS,4R,5R,6S, 7R,7aR)-4,6,7-trihydroxy-hexahydro-benzo(1,3) dioxol-5-yl)-(2E)-acrylamide
95. 3-(4-((2S,3S,4R,5R)-5-(3-(2-Chloro-5-fluoro-phenoxy)-1-methyl-(E)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
96. 3-(4-((2S,3S,4R,5R)-5-(3-(2-Fluoro-4-chloro-phenoxy)-1-methyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
97. 3-(4-((2S,3R,4R,5R)-5-(3-(2,4-Dichloro-phenoxy)-1-methyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
98. 3-(4-((2S,4S,5R)-5-(3-(3-Chloro-phenoxy)-1-methyl-(Z)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
99. 3-(3-Amino-4-((2S,4S,5R)-5-(3-(2-chloro-phenoxy)-1-methyl-(Z)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
100. 3-(4-((2S,3R,4S,5R)-5-(3-(2-Fluoro-phenoxy)-1-methyl-(Z)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3) dioxol-5-yl)-(2E)-acrylamide
101. 3-(3-Amino-4-((2S,3R,4S,5R)-5-(3-(3-chloro-phenoxy)-1-methyl-(Z)-propenyl)-3,4-dihydroxy-tetrahydro-furan-2-yloxy)-phenyl)-2-methyl-N-((3aS, 4R,5R,6S,7R,7aR)-4,6,7-trihydroxy-hexahydro-benzo (1,3)dioxol-5-yl)-(2E)-acrylamide
102. 3-(4-((2S,3R,4R,5R)-5-(3-(3,4-Difluoro-phenoxy)-1-methyl-(Z)-propenyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
103. 3-(4-((2S,3R,4R,5R)-5-(3-(4-Fluoro-phenoxy)-1-methyl-(Z)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
104. 3-(3-Amino-4-((2S,3R,4R,5R)-5-(3-(2-fluoro-4-chloro-phenoxy)-1-methyl-(Z)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
105. 3-(4-((2S,4S,5R)-5-(3-(3-Chloro-phenoxy)-1-ethyl-(Z)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
106. 3-(4-((2S,4S,5R)-5-(3-(2,3-Dichloro-5-fluoro-phenoxy)-1-ethyl-(Z)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
107. 3-(3-Amino-4-((2S,4S,5R)-5-(3-(2-fluoro-phenoxy)-1-ethyl-(Z)-propenyl)-4-hydroxy-tetrahydro-furan-2-yloxy)-phenyl)-2-methyl-N-((3aS, 4R,5R,6S,7R,7aR)-4,6,7-trihydroxy-hexahydro-benzo (1,3)dioxol-5-yl)-(2E)-acrylamide
108. 3-(3-Fluoro-4-((2S,4S,5R)-4-hydroxy-5-(1-methyl-3-phenoxy-(Z)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
109. 3-(3-Amino-4-((2S,4S,5R)-4-hydroxy-5-(1-methyl-3-phenoxy-(Z)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
110. 3-(4-((2S,3S,4R,5R)-5-(3-(2-Chloro-5-fluoro-phenoxy)-1-methyl-(Z)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
111. 3-(4-((2S,3S,4R,5R)-5-(3-(3-Chloro-phenoxy)-1-methyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
112. 3-(3-Amino-4-((2S,3S,4R,5R)-5-(3-(2,4-dichloro-phenoxy)-1-methyl-(Z)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
113. 3-(4-((2S,3S,4R,5R)-5-(3-(3,4-Difluoro-phenoxy)-1-ethyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
114. 3-(4-((2S,3S,4R,5R)-5-(3-(2-Chloro-phenoxy)-1-ethyl-(Z)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
115. 3-(4-((2S,3S,4R,5R)-5-(3-(2-Fluoro-4-chloro-phenoxy)-1-ethyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
116. 3-(4-((2S,3R,4R,5R)-5-(3-(3-Chloro-phenoxy)-1-methyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
117. 3-(4-((2S,3R,4R,5R)-5-(3-(3-Chloro-phenoxy)-1-methyl-(Z)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
118. 3-(3-Amino-4-((2S,3R,4R,5R)-5-(3-(2,4-dichloro-phenoxy)-1-methyl-(Z)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
119. 3-(3-Fluoro-4-((2S,4S,5R)-5-(3-((E)-3-fluoro-4-morpholin-4-yl-phenoxy)-1-methyl-(Z)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
120. 3-(3-Amino-4-((2S,4S,5R)-5-(3-((E)-3-fluoro-4-morpholin-4-yl-phenoxy)-1-methyl-(Z)-propenyl)-4- hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
121. 3-(4-((2S,3R,4S,5R)-3-Amino-5-(1-((E)-3,4-difluoro-benzyloxyimino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
122. 3-(4-((2S,3S,4R,5R)-5-(3-(3-Chloro-phenoxy)-1-methyl-(Z)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
123. 3-(3-Amino-4-((2S,3S,4R,5R)-5-(3-(4-fluoro-phenoxy)-1-methyl-(Z)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
124. 3-(4-((2S,3S,4S,5R)-5-(1-((E)-2-Fluoro-benzyloxyimino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
125. 3-(3-Amino-4-((2S,3S,4S,5R)-5-(1-((E)-2-chloro-5-fluoro-benzyloxyimino)-ethyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
126. 3-(4-((2S,3S,4S,5R)-5-(3-(3-Chloro-phenoxy)-1-methyl-(E)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
127. 3-(3-Amino-4-((2S,3S,4S,5R)-5-(3-(2,4-dichloro-phenoxy)-1-methyl-(E)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
128. 3-(4-((2S,3S,4S,5R)-5-(3-(2-Fluoro-4-chloro-phenoxy)-1-methyl-(Z)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
129. 3-(3-Amino-4-((2S,3S,4S,5R)-5-(3-(3,4-difluoro-phenoxy)-1-methyl-(Z)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
130. 3-(4-((2S,3S,4S,5R)-5-(5S-(3-Chloro-phenyl)-2,3-dimethyl-isoxazolidin-3-yl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
131. 3-(4-((2S,4S,5R)-5-(1-((Z)-2-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
132. 3-(4-((2S,3R,4S,5R)-5-(1-((Z)-2,4-Dichloro-5-fluoro-benzyloxyimino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
133. 3-(4-((2S,3R,4S,5R)-5-(1-((Z)-2-Chloro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
134. 3-(4-((2S,4S,5R)-5-(1-((Z)-3,4-Difluoro-benzyloxyimino)-propyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
135. 3-(4-((2S,4S,5R)-5-((Z)-1-Benzyloxyimino-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
136. 3-(4-((2S,3S,4R,5R)-5-(1-((Z)-2-Fluoro-benzyloxyimino)-ethyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
137. 3-(4-((2S,3S,4R,5R)-5-(1-((Z)-2,4-Dichloro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
138. 3-(4-((2S,3R,4R,5R)-5-(1-((Z)-2,4-Dichloro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
139. 3-(3-Fluoro-4-((2S,4S,5R)-5-(1-((Z)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
140. 3-(3-Amino-4-((2S,4S,5R)-5-(1-((Z)-2-fluoro-4-chloro-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
141. 3-(4-((2S,3R,4R,5R)-5-(1-((Z)-2-Chloro-benzyloxyimino)-ethyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
142. 3-(3-Amino-4-((2S,3R,4R,5R)-5-(1-((Z)-2-chloro-5-fluoro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
143. 3-(4-((2S,4S,5R)-5-(1-((Z)-3-Chloro-benzyloxyimino)-propyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide
144. 3-(3-Amino-4-((2S,4S,5R)-5-(1-((Z)-3-Chloro-benzyloxyimino)-propyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide
145. 3-(4-((2S,3S,4R,5R)-5-(1-((Z)-2-Chloro-benzyloxyimino)-propyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide
146. 3-(4-((2S,3S,4R,5R)-5-(1-((Z)-3-Chloro-benzyloxyimino)-propyl)-3-fluoro-4-hydroxytetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 147. 3-(3-Amino-4-((2S,4S,5R)-5-(1-((Z)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 148. 3-(4-((2S,3S,4R,5R)-5-(1-((Z)-2,4-Dichloro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 149. 3-(3-Amino-4-((2S,3S,4R,5R)-5-(1-((Z)-2-fluoro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 150. 3-(4-((2S,4S,5R)-5-(1-((E)-3,4-Difluoro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide.

151. 3-(4-((2S,4R,5R)-5-(1-((E)-3-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 152. 3-(4-((2S,4R,5R)-5-(3-(2,4-Dichloro-phenoxy)-1-methyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 153. 3-(3-Fluoro-4-((2S,4R,5R)-4-hydroxy-5-(1-((E)-4-piperidin-1-yl-benzyloxyimino)-ethyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 154. 3-(4-((2S,4R,5R)-5-(1-((E)-3-Chloro-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 155. 3-(3-Fluoro-4-((2S,4R,5R)-4-hydroxy-5-(1-((E)-4-morpholin-4-yl-benzyloxyimino)-ethyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 156. 3-(4-((2S,3S,4R,5R)-5-(1-((E)-3-Chloro-benzyloxyimino)-ethyl)-3,4-dihydroxy-tetrahydro-furan-2-yloxy)-phenyl)-2-methyl-N-(4,6,7-trihydroxy-hexahydro-benzo[1,3]dioxol-5-yl)-(2E)-acrylamide 157. 3-(3-Fluoro-4-((2S,4R,5R)-5-(1-((E)-3-fluoro-4-piperidin-1-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide Additional preferred compounds of formula 1, which are more preferred than those referred to above, include those listed below as well as the pharmaceutically acceptable salts, solvates and prodrugs of the following compounds:

1. 3-(4-((2S,4S,5R)-5-(1-((E)-3-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 2. 3-(4-((2S,3R,4S,5R)-5-(1-((E)-2,3-Dichloro-5-fluoro-benzyloxyimino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 3. 3-(4-((2S,3R,4S,5R)-5-(1-((E)-3-Chloro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 4. 3-(4-((2S,4S,5R)-5-(1-((E)-4-Fluoro-benzyloxyimino)-propyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 5. 3-(4-((2S,4S,5R)-5-((E)-1-Benzyloxyimino-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 6. 3-(4-((2S,3S,4R,5R)-5-(1-((E)-3-Chloro-benzyloxyimino)-ethyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 7. 3-(4-((2S,3S,4R,5R)-5-(1-((E)-3,4-Difluoro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 8. 3-(4-((2S,3R,4R,5R)-5-(1-((E)-3-Chloro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 9. 3-(3-Fluoro-4-((2S,4S,5R)-5-(1-((E)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 10. 3-(3-Amino-4-((2S,4S,5R)-5-(1-((E)-4-fluoro-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 11. 3-(4-((2S,4S,5R)-5-(3-(2,4-Dichloro-phenoxy)-1-methyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 12. 3-(3-Amino-4-((2S,4S,5R)-5-(3-(2-chloro-5-fluoro-phenoxy)-1-methyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 13. 3-(3-Amino-4-((2S,3R,4S,5R)-5-(1-((E)-2-chloro-benzyloxyimino)-ethyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 14. 3-(4-((2S,3R,4S,5R)-5-(3-(2-Fluoro-phenoxy)-1-methyl-(E)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 15. 3-(3-Amino-4-((2S,3R,4R,5R)-5-(3-(3-chloro-phenoxy)-1-methyl-(E)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 16. 3-(4-((2S,3R,4R,5R)-5-(1-((E)-2-Fluoro-benzyloxyimino)-ethyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 17. 3-(3-Amino-4-((2S,3R,4R,5R)-5-(1-((E)-3-Chloro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 18. 3-(4-((2S,3R,4R,5R)-5-(3-(3,4-Difluoro-phenoxy)-1-methyl-(E)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 19. 3-(3-Amino-4-((2S,3R,4R,5R)-5-(3-(2-fluoro-4-chloro-phenoxy)-1-methyl-(E)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 20. 3-(4-((2S,4S,5R)-5-(1-((E)-4-Fluoro-benzyloxyimino)-propyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 21. 3-(3-Amino-4-((2S,4S,5R)-5-(1-((E)-2,4-dichloro-benzyloxyimino)-propyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 22. 3-(4-((2S,4S,5R)-5-(3-(3-Chloro-phenoxy)-1-ethyl-(E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 23. 3-(3-Amino-4-((2S,4S,5R)-5-(3-(2,3-dichloro-5-fluoro-phenoxy)-1-ethyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 24. 3-(3-Amino-4-((2S,4S,5R)-5-((E)-1-benzyloxyimino-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 25. 3-(3-Fluoro-4-((2S,4S,5R)-4-hydroxy-5-(1-methyl-3-phenoxy-(E)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 26. 3-(3-Amino-4-((2S,4S,5R)-4-hydroxy-5-(1-methyl-3-phenoxy-(E)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 27. 3-(4-((2S,3S,4R,5R)-5-(1-((E)-2-Chloro-5-fluoro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 28. 3-(3-Amino-4-((2S,3S,4R,5R)-5-(1-((E)-2-chloro-benzyloxyimino)-ethyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 29. 3-(4-((2S,3S,4R,5R)-5-(3-(3-Chloro-phenoxy)-1-methyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 30. 3-(3-Amino-4-((2S,3S,4R,5R)-5-(3-(2-fluoro-phenoxy)-1-methyl-(E)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 31. 3-(4-((2S,3S,4R,5R)-5-(1-((E)-4-Fluoro-benzyloxyimino)-propyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 32. 3-(4-((2S,3S,4R,5R)-5-(1-((E)-3-Chloro-benzyloxyimino)-propyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 33. 3-(4-((2S,3S,4R,5R)-5-(3-(3-Chloro-phenoxy)-1-ethyl-(E)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 34. 3-(4-((2S,3S,4R,5R)-5-(3-(3-Chloro-phenoxy)-1-ethyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 35. 3-(4-((2S,3R,4R,5R)-5-(1-((E)-3,4-Difluoro-benzyloxyimino)-ethyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 36. 3-(3-Amino-4-((2S,3R,4R,5R)-5-(1-((E)-2,3-dichloro-5-fluoro-benzyloxyimino)-ethyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 37. 3-(4-((2S,3R,4R,5R)-5-(3-(2-Chloro-5-fluoro-phenoxy)-1-methyl-(E)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 38. 3-(3-Amino-4-((2S,3R,4R,5R)-5-(3-(2-fluoro-4-chloro-phenoxy)-1-methyl-(E)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 39. 3-(3-Amino-4-((2S,4S,5R)-5-(1-((E)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 40. 3-(3-Fluoro-4-((2S,4S,5R)-5-(3-(3-fluoro-4-morpholin-4-yl-phenoxy)-1-methyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 41. 3-(3-Amino-4-((2S,4S,5R)-5-(3-(3-fluoro-4-morpholin-4-yl-phenoxy)-1-methyl-(E)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 42. 3-(4-((2S,3S,4R,5R)-5-(1-((E)-4-Fluoro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 43. 3-(4-((2S,3S,4R,5R)-5-(1-((E)-3-Chloro-benzyloxyimino)-ethyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 44. 3-(3-Amino-4-((2S,3S,4R,5R)-5-(1-((E)-3-Chloro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 45. 3-(4-((2S,3S,4R,5R)-5-(3-(3-Chloro-phenoxy)-1-methyl-(E)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 46. 3-(3-Amino-4-((2S,3S,4R,5R)-5-(3-(3-chloro-phenoxy)-1-methyl-(E)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 47. 3-(4-((2S,3S,5S)-5-(1-((E)-2,4-Dichloro-benzyloxyimino)-ethyl)-3-fluoro-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 48. 3-(4-((2S,3S,5S)-5-(3-(3,4-Difluoro-phenoxy)-1-methyl-(E)-propenyl)-3-fluoro-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 49. 3-(4-((2S,3S,5S)-5-(1-((E)-2-Chloro-benzyloxyimino)-ethyl)-3-fluoro-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 50. 3-(4-((2S,3S,5S)-5-(3-(2-Fluoro-phenoxy)-1-methyl-(E)-propenyl)-3-fluoro-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 51. 3-(4-((2S,3R,5S)-5-(1-((E)-2-Fluoro-4-chloro-benzyloxyimino)-ethyl)-3-fluoro-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 52. 3-(4-((2S,3R,5S)-5-(3-(3-Chloro-phenoxy)-1-methyl-(E)-propenyl)-3-fluoro-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 53. 3-(4-((2S,3R,5S)-5-(1-((E)-2-Chloro-5-fluoro-benzyloxyimino)-ethyl)-3-fluoro-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 54. 3-(4-((2S,3R,5S)-5-(3-(3-Chloro-phenoxy)-1-methyl-(E)-propenyl)-3-fluoro-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 55. 3-(4-((2S,3R,4R,5R)-5-(3-(3-Chloro-phenoxy)-1-methyl-(E)-propenyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 56. 3-(4-((2S,4S,5R)-5-(3-(3,4-Difluoro-phenoxy)-1-ethyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 57. 3-(4-((2S,3S,4R,5R)-5-(3-(2-Chloro-5-fluoro-phenoxy)-1-methyl-(E)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 58. 3-(4-((2S,3S,4R,5R)-5-(3-(2-Fluoro-4-chloro-phenoxy)-1-methyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 59. 3-(4-((2S,3R,4R,5R)-5-(3-(2,4-Dichloro-phenoxy)-1-methyl-(E)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 60. 3-(4-((2S,4S,5R)-5-(3-(3-Chloro-phenoxy)-1-methyl-(Z)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 61. 3-(3-Amino-4-((2S,4S,5R)-5-(3-(2-chloro-phenoxy)-1-methyl-(Z)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 62. 3-(4-((2S,3R,4S,5R)-5-(3-(2-Fluoro-phenoxy)-1-methyl-(Z)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 63. 3-(3-Amino-4-((2S,3R,4S,5R)-5-(3-(3-chloro-phenoxy)-1-methyl-(Z)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 64. 3-(4-((2S,3R,4R,5R)-5-(3-(3,4-Difluoro-phenoxy)-1-methyl-(Z)-propenyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 65. 3-(4-((2S,3R,4R,5R)-5-(3-(4-Fluoro-phenoxy)-1-methyl-(Z)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 66. 3-(3-Amino-4-((2S,3R,4R,5R)-5-(3-(2-fluoro-4-chloro-phenoxy)-1-methyl-(Z)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 67. 3-(4-((2S,4S,5R)-5-(3-(3-Chloro-phenoxy)-1-ethyl-(Z)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 68. 3-(4-((2S,4S,5R)-5-(3-(2,3-Dichloro-5-fluoro-phenoxy)-1-ethyl-(Z)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 69. 3-(3-Amino-4-((2S,4S,5R)-5-(3-(2-fluoro-phenoxy)-1-ethyl-(Z)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 70. 3-(3-Fluoro-4-((2S,4S,5R)-4-hydroxy-5-(1-methyl-3-phenoxy-(Z)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 71. 3-(3-Amino-4-((2S,4S,5R)-4-hydroxy-5-(1-methyl-3-phenoxy-(Z)-propenyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 72. 3-(4-((2S,3S,4R,5R)-5-(3-(2-Chloro-5-fluoro-phenoxy)-1-methyl-(Z)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 73. 3-(4-((2S,3S,4R,5R)-5-(3-(3-Chloro-phenoxy)-1-methyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 74. 3-(3-Amino-4-((2S,3S,4R,5R)-5-(3-(2,4-dichloro-phenoxy)-1-methyl-(Z)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 75. 3-(4-((2S,3S,4R,5R)-5-(3-(3,4-Difluoro-phenoxy)-1-ethyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 76. 3-(4-((2S,3S,4R,5R)-5-(3-(2-Chloro-phenoxy)-1-ethyl-(Z)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 77. 3-(4-((2S,3S,4R,5R)-5-(3-(2-Fluoro-4-chloro-phenoxy)-1-ethyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 78. 3-(4-((2S,3R,4R,5R)-5-(3-(3-Chloro-phenoxy)-1-methyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 79. 3-(4-((2S,3R,4R,5R)-5-(3-(3-Chloro-phenoxy)-1-methyl-(Z)-propenyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 80. 3-(3-Amino-4-((2S,3R,4R,5R)-5-(3-(2,4-dichloro-phenoxy)-1-methyl-(Z)-propenyl)-3-fluoro-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 81. 3-(3-Fluoro-4-((2S,4S,5R)-5-(3-((E)-3-fluoro-4-morpholin-4-yl-phenoxy)-1-methyl-(Z)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 82. 3-(3-Amino-4-((2S,4S,5R)-5-(3-((E)-3-fluoro-4-morpholin-4-yl-phenoxy)-1-methyl-(Z)-propenyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 83. 3-(4-((2S,3R,4S,5R)-3-Amino-5-(1-((E)-3,4-difluoro-benzyloxyimino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 84. 3-(4-((2S,3S,4R,5R)-5-(3-(3-Chloro-phenoxy)-1-methyl-(Z)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 85. 3-(3-Amino-4-((2S,3S,4R,5R)-5-(3-(4-fluoro-phenoxy)-1-methyl-(Z)-propenyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 86. 3-(4-((2S,3S,4S,5R)-5-(1-((E)-2-Fluoro-benzyloxyimino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 87. 3-(3-Amino-4-((2S,3S,4S,5R)-5-(1-((E)-2-chloro-5-fluoro-benzyloxyimino)-ethyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 88. 3-(4-((2S,3S,4S,5R)-5-(3-(3-Chloro-phenoxy)-1-methyl-(E)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 89. 3-(3-Amino-4-((2S,3S,4S,5R)-5-(3-(2,4-dichloro-phenoxy)-1-methyl-(E)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 90. 3-(4-((2S,3S,4S,5R)-5-(3-(2-Fluoro-4-chloro-phenoxy)-1-methyl-(Z)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 91. 3-(3-Amino-4-((2S,3S,4S,5R)-5-(3-(3,4-difluoro-phenoxy)-1-methyl-(Z)-propenyl)-3,4-dihydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 92. 3-(4-((2S,4S,5R)-5-(1-((Z)-2-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 93. 3-(4-((2S,3R,4S,5R)-5-(1-((Z)-2,4-Dichloro-5-fluoro-benzyloxyimino)-ethyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 94. 3-(4-((2S,3R,4S,5R)-5-(1-((Z)-2-Chloro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 95. 3-(4-((2S,4S,5R)-5-(1-((Z)-3,4-Difluoro-benzyloxyimino)-propyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 96. 3-(4-((2S,4S,5R)-5-((Z)-1-Benzyloxyimino-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 97. 3-(4-((2S,3S,4R,5R)-5-(1-((Z)-2-Fluoro-benzyloxyimino)-ethyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 98. 3-(4-((2S,3S,4R,5R)-5-(1-((Z)-2,4-Dichloro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 99. 3-(4-((2S,3R,4R,5R)-5-(1-((Z)-2,4-Dichloro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 100. 3-(3-Fluoro-4-((2S,4S,5R)-5-(1-((Z)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 101. 3-(3-Amino-4-((2S,4S,5R)-5-(1-((Z)-2-fluoro-4-chloro-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 102. 3-(4-((2S,3R,4R,5R)-5-(1-((Z)-2-Chloro-benzyloxyimino)-ethyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 103. 3-(3-Amino-4-((2S,3R,4R,5R)-5-(1-((Z)-2-chloro-5-fluoro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 104. 3-(4-((2S,4S,5R)-5-(1-((Z)-3-Chloro-benzyloxyimino)-propyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 105. 3-(3-Amino-4-((2S,4S,5R)-5-(1-((Z)-3-Chloro-benzyloxyimino)-propyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 106. 3-(4-((2S,3S,4R,5R)-5-(1-((Z)-2-Chloro-benzyloxyimino)-propyl)-3-fluoro-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 107. 3-(4-((2S,3S,4R,5R)-5-(1-((Z)-3-Chloro-benzyloxyimino)-propyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide 108. 3-(3-Amino-4-((2S,4S,5R)-5-(1-((Z)-3-fluoro-4-morpholin-4-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 109. 3-(4-((2S,3S,4R,5R)-5-(1-((Z)-2,4-Dichloro-benzyloxyimino)-ethyl)-3,4-dihydroxy-3-methyl-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 110. 3-(3-Amino-4-((2S,3S,4R,5R)-5-(1-((Z)-2-fluoro-benzyloxyimino)-ethyl)-3,4-dihydroxy-3-methyl-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 111. 3-(4-((2S,4S,5R)-5-(1-((E)-3,4-Difluoro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 112. 3-(4-((2S,4R,5R)-5-(1-((E)-3-Chloro-benzyloxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 113. 3-(4-((2S,4R,5R)-5-(3-(2,4-Dichloro-phenoxy)-1-methyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide 114. 3-(4-((2S,4R,5R)-5-(1-((E)-3-Chloro-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 115. 3-(3-Fluoro-4-((2S,4R,5R)-4-hydroxy-5-(1-((E)-4-morpholin-4-yl-benzyloxyimino)-ethyl)-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide 116. 3-(3-Fluoro-4-((2S,4R,5R)-5-(1-((E)-3-fluoro-4-piperidin-1-yl-benzyloxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula 1, a prodrug thereof or a pharmaceutically acceptable salt thereof, and a pharmaceutically acceptable carrier.

The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula 1, a prodrug thereof or a pharmaceutically acceptable salt thereof, in combination with a beta-lactam, quinolone, tetracycline, streptogramin, aminoglycoside, glycopeptide, macrolide or oxazolidinone antibiotic; or in combination with a compound which inhibits bacterial or protozoal efflux or degradation of a compound according to formula 1.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula 1, a prodrug thereof or a pharmaceutically acceptable salt thereof.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula 1, a prodrug thereof or a pharmaceutically acceptable salt thereof, in combination or co-administered with a beta-lactam, quinolone, tetracycline, streptogramin, aminoglycoside, glycopeptide, macrolide or oxazolidinone antibiotic; or in combination with a compound which inhibits bacterial or protozoal efflux or degradation of a compound according to formula 1.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or Peptostreptococcus spp.; pharyngitis, rheumatic fever, and glomerulonephritis related to infection by *Streptococcus pyogenes,* Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chiamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus,* coagulase-negative staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum,* Clostridium spp., or *Bartonella henselae*; uncomplicated acute urinary tract infections related to infection by *Staphylococcus aureus,* coagulase-negative staphylococcal species, or Enterococcus spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chiamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis or cardiovascular disease related to infection by *Helicobacter pylori* or *Chiamydia pneumoniae.* Bacterial infections and protozoal infections, and disorders related to such infections, which may be treated or prevented in animals include the following: bovine respiratory disease related to infection by *P. haemolytica, P. multocida, Mycoplasma bovis,* or Bordetella spp.; cow enteric disease related to infection by protozoa (i.e., coccidia, cryptosporidia, etc.); dairy cow mastitis related to infection by *S. aureus, Strep uberis, Streptococcus agalactiae, Streptococcus dysgalactiae,* Corynebacterium, or Enterococcus spp.; swine respiratory disease related to infection by *A. pleuro., P. multocida,* or Mycoplasma spp.; swine enteric disease related to infection by *Lawsonia intracellularis,* Salmonella, or *Serpulina hyodysinteriae*; cow footrot related to infection by Fusobacterium spp; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); skin and soft tissue infections in dogs and cats related to infection by *S. epidermidis, S. intermedius,* coagulase neg. Staphylococcus or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The compounds of the present invention may be active against the bacteria and protozoa, and associated conditions, referred to above, or specific strains of the bacteria and protozoa referred to above.

The term "halo", as used herein, unless otherwise indicated, includes fluoro, chloro, bromo or iodo. Preferred halo groups are fluoro and chloro.

The term "alkyl", as used herein, unless otherwise indicated, includes saturated monovalent hydrocarbon radicals having straight, cyclic or branched moieties. It is understood that for said alkyl group to include cyclic moieties it must contain at least three carbon atoms.

The term "alkenyl", as used herein, unless otherwise indicated, includes alkyl groups, as defined above, having at least one carbon-carbon double bond.

The term "alkynyl", as used herein, unless otherwise indicated, includes alkyl groups, as defined above, having at least one carbon-carbon triple bond.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached). The terms "5 to 12 membered heterocyclic", "5 to 6 membered heterocyclic", and other uses of "heterocyclic", correspond to the above definition with an appropriate number of ring members.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations of the —$OR^3$ group connected to the nitrogen where $R^1$ and $R^2$ are taken together as an oxime moiety of the formula =N—$OR^3$. The invention also includes both E and Z configurations of the $R^5$ and $X^1$—$X^2$—$R^8$ groups connected to cargon where $R^1$ and $R^2$ are taken together as =C($R^5$)$X^1$—$X^2$—$R^8$. The compounds of formula 1 may also exist as tautomers. This invention relates to the use of all such tautomers and mixtures thereof.

The subject invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, omithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem* 1996, 39, 10. Free amines can also be derivatized as amides, sulfonamides or phosphonamides. All of these prodrug moieties may incorporate groups including but not limited to ether, amine and carboxylic acid functionalities.

Selective introduction of prodrug side chains can be carried out on the hydroxy groups of the hygromycin A core molecule. For instance, exhaustive silylation of the six hydroxy groups of hygromycin A can be carried out, for instance with tert-butyl dimethylsilyl chloride. Subjection of the hexasilyl derivative to the action of potassium carbonate in methanol at room temperature selectively removes the phenolic silyl group, allowing further selective modification at that position. In another example, incomplete silylation of hygromycin A provides the pentasilyl derivative in which the C-2" hydroxy group of the furanose ring is free. Selective acylation, alkylation, etc. can be carried out on this derivative to provide prodrug attachment at C-2", followed by elaboration to the compounds of formula 1.

Selective introduction of prodrug side chains onto the Fragment C moiety may be carried out by functionalizing Fragment C (Scheme 1) prior to coupling with fragments B and A, or by utilizing selective protection strategies after assembly of the three fragments.

Selective introduction of prodrug side chains onto the hydroxyl groups of the inositol sugar can be carried out through total synthesis of the inositol (Fragment A in Scheme 1). Adaptation of the chemistry published by Chida (*J. Org. Chem.*, 1991, 56, 2976), Arjona (*Tetrahedron Lett.*, 1995, 36, 1319 and Dudash (Dissertation, Stanford Univ., 1998, Diss. Abstr. Int., B, 1998, 59, 2754) allows selective addition of a prodrug onto the hydroxyl group of choice through use of selectively protected intermediates described in these reports. The inositol derivative bearing the prodrug is then appended to fragments B and C as described below.

DETAILED DESCRIPTION OF THE INVENTION

The preparation of the compounds of the present invention is described and illustrated below.

Preparation of the compounds of formula 1 can most flexibly be carried out through assembly of Fragments A, B and C as outlined below. Alternatively, many of the compounds of formula 1 can be prepared from the natural product hygromycin A, as described in later sections. In the procedures provided below, certain abbreviations well known to those skilled in the art are used. For instance, "h" refers to hour(s), "min" refers to minute(s), and "rt" refers to room temperature.

Scheme 1
Preparation of Fragment A

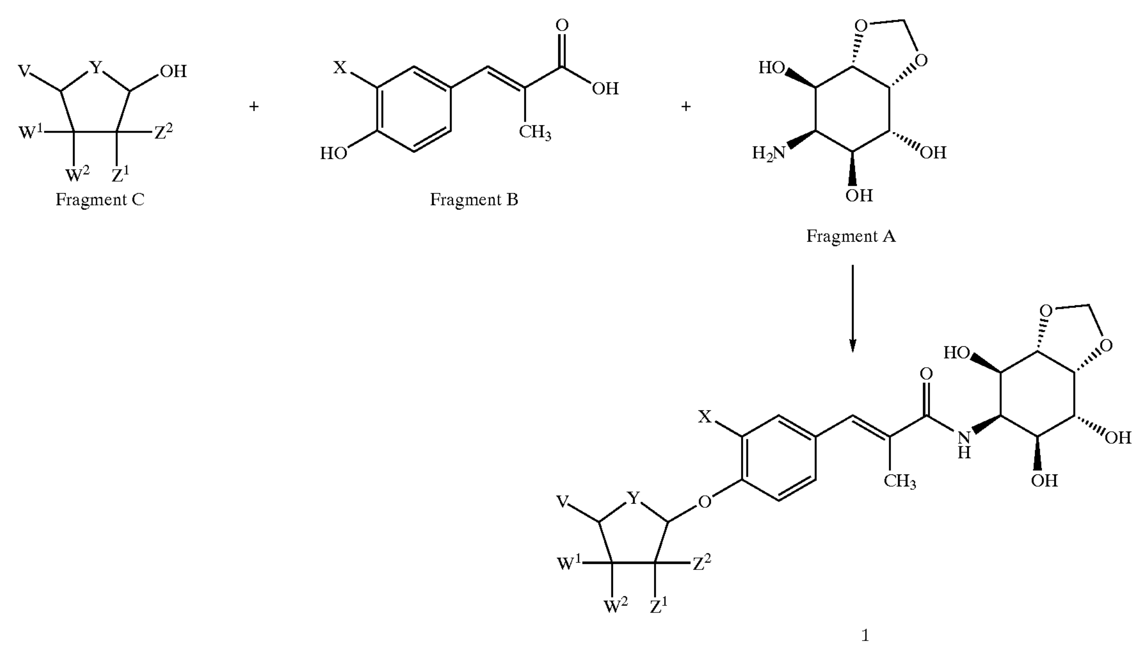

1

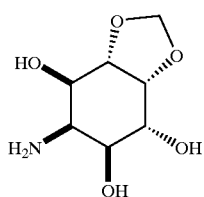

2

(1aS,3aR,4R,5S,6R,7R)-6-Amino-hexahydro-benzo[1,3]
dioxole-4,5,7-triol can be prepared from hygromycin A
(*Agric. Biol. Chem.* 1978, 42, 279 or *J. Org. Chem.* 1991, 56,
2976) with the former being the preferred method.

Preparation of Fragment C

In the following description, compounds may contain $R^3$, $R^{12}$ or $R^{13}$ groups that may not be compatible with functionalization of C-2, C-3 or C-4. Functional groups within $R^3$, $R^{12}$ or $R^{13}$ that are not compatible with chemistry carried out at C-2, C-3 or C-4, or during subsequent chemistry, can be protected prior to C-2, C-3 or C-4 manipulation. For example, an alcohol might be protected as an ether (benzyl, allyl or silyl) or ester (benzoate, pivaloate or acetate) and subsequently deprotected at an appropriate time. If $Z^1$ and $Z^2$ are taken together to form a ketone (as in compound 4), or an $R^3$, $R^{12}$ or $R^{13}$ within $Z^1$, $Z^2$, $W^1$ or $W^2$ contains a ketone, it may be necessary to protect it, for instance as a dimethyl ketal through the use of methanol and catalytic acid such as camphorsulfonic acid or p-toluenesulfonic acid (p-TsOH). Deprotection of the ketal can be carried out concomitantly with the cleavage of the anomeric methyl acetal to generate the hydroxyl group at C-1. Alternatively, a ketone may be masked as its protected alcohol, which can then be regenerated by deprotection and oxidation, for example under Swern conditions (*J. Org. Chem.*, 1976, 41, 3329). An amine might be protected as its 9-fluorenylmethoxycarbonyl-(FMOC), benzyloxycarbonyl-(CBZ) or tert-butoxycarbonyl carbamate (BOC) (see *Protective Groups in Organic Synthesis*, T. Greene and P. Wuts, Ed., John Wiley & Sons Ltd., New York, 1991 or *Protecting Groups*, P. Kocienski, Ed., Thieme Medical Publishers, New York, 1994) and subsequently deprotected at an appropriate time. It might also be advantageous to introduce said groups at a later stage by utilizing an intermediate that may, at an appropriate time, be further elaborated to the desired $R^3$, $R^{12}$ or $R^{13}$. Acids, carbonyl-linked amides and esters may be generated after C-2, C-3 or C4 elaboration from a protected primary alcohol, which is unmasked by deprotection and elaborated by double oxidation, for example Swern conditions followed by action of potassium permanganate (*Tetrahedron Lett.*, 1986, 27, 4537 and *J. Am. Chem. Soc.*, 1987, 109, 7575), or sodium chlorite (*J. Org. Chem.*, 1986, 51, 567 and *J. Am. Chem. Soc.*, 1997, 119, 7974) to the carboxylic acid. This may then coupled with the appropriate alcohol or amine, for instance by the action of dicyclohexylcarbodiimide (DCC), to produce the desired ester or amide. An N-linked amide or sulfonamide may be carried through as an amine, protected as above, which is then deprotected and acylated or sulfonylated. N-linked amides and sulfonamides and amines may alternatively be introduced by displacement of a leaving group. For example, a protected alcohol may be deprotected and the resulting alcohol transformed into the mesylate, for instance through the action of methanesulfonyl chloride and triethylamine ($NEt_3$) (*J. Org. Chem.*, 1970, 35, 3195). The mesylate is then displaced by azide, for example using sodium azide in N,N-dimethylformamide (DMF) and the azide reduced to the primary amine using for instance triphenylphosphine followed by aqueous hydrolysis. Acylation may then provide the corresponding amide. Sulfur containing moieties may also be introduced in this fashion, for example, by the displacement of the aforementioned mesylate with the appropriate thiolate or protected thiolate, followed if necessary by oxidation of the sulfur to the sulfoxide or sulfone.

Fragment C can be prepared by first functionalizing at the C-2 and C-3 positions, followed by elaboration of the substituent at C-4. Functionalization of the C-2 position may be carried out first, as described below, to generate intermediate 3 (TBDPS=tert-butyldiphenylsilyl), where $Z^1$ and $Z^2$ are as described in formula 1, or are present as a precursor, protected precursor or protected form of $Z^1$ and $Z^2$.

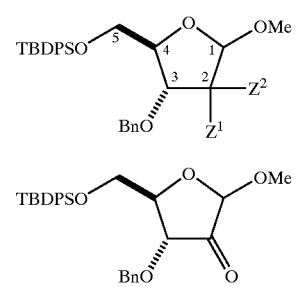

3

4

Compound 4 (Bn=benzyl), where $Z^1$ and $Z^2$ are taken together to form =O may be prepared from available starting material 5 (*Tetrahedron*, 1995, 51, 871).

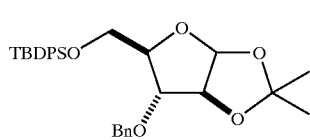

5

For instance, selective removal of the 1,2-acetonide and methyl ketal formation may be achieved with the action of trifluoroacetic acid (TFA) in tetrahydrofuran/methanol (see precedent: *J. Org. Chem.*, 1986, 51, 789) or alternatively by a two step procedure. For example, acetal cleavage may be achieved with the action of TFA in tetrahydrofuran/water (*J. Org. Chem.*, 1986, 51, 789) followed by ketal formation using methanol in the presence of acid (*J. Am. Chem. Soc.*, 1954, 76, 3598 and *J. Org. Chem.*, 1984, 49, 4564). The resulting methyl ketal, 6, may be oxidized, for example under Swern (*J. Org. Chem.*, 1976, 41, 3329) or Dess-Martin (*J. Org. Chem.*, 1983, 48, 4155) conditions, to lead to compound 4.

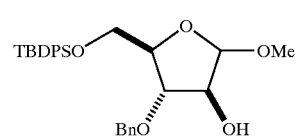

6

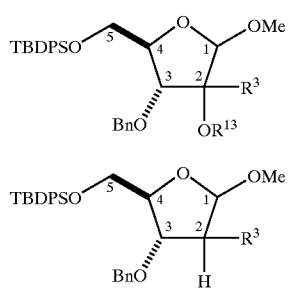

7

8

Compounds 7 and 8 may be prepared from either 6 or 4.

For example, compound 7, with $R^{13}$=H and $R^3$ as defined but not H, may be prepared by addition of an organometallic reagent $R^3M$, for example Grignard, organolithium or organocerium reagents (*Tetrahedron Lett.*, 1984 25, 4233) to 4 in a solvent such as tetrahydrofuran (THF), dioxane or $Et_2O$ at a temperature ranging from −78° C. to 25° C. These reagents may be prepared from the corresponding halide, $R^3$-halide, using standard procedures (see *Organometallics In Synthesis; A Manual*, M. Schlosser, Ed., John Wiley & Sons Ltd., New York, 1994). This addition will generate both C-2 diastereomers, which may be separated using chromatography.

Compound 7 with $R^{13}$ as defined and $R^3$=H may be prepared from 6 by reaction of the alkoxide of 6, generated with a strong base such as sodium hydride or potassium carbonate, with halide-$R^3$ in a polar aprotic solvent, such as THF or DMF at a temperature ranging from 0° C. to 25° C. To generate the α-$OR^3$ one may first react 6 in a Mitsunobu reaction with dialkylazodicarboxylate, wherein the alkyl group is preferably ethyl, propyl, isopropyl, or tert-butyl; 4-nitrobenzoic acid and triphenylphosphine in a suitable organic solvent such as THF, $Et_2O$ or dioxane at a temperature ranging from 0° C. to 65° C., preferably from 0° C. to 25° C. (*Bull. Chem. Soc. Jpn.*, 1967, 40, 2380). Hydrolysis of the resultant ester, with an alkali base such as lithium hydroxide or sodium hydroxide, in a solvent mixture containing water, methanol and tetrahydrofuran at a temperature ranging from 0° C. to 25° C., will lead to the desired 2-α-OH diastereomer which may be subsequently alkylated as above.

Compound 7, with $R^{13}$ as defined but not H and $R^3$ as defined but not H, may be prepared by further reaction of compound 7 wherein $R^{13}$ is as defined and $R^3$ is H, prepared as described above. The 2-OH may be alkylated by reaction of the alkoxide, generated with a strong base such as sodium hydride or potassium carbonate, with halide-$R^3$ in a polar aprotic solvent, such as tetrahydrofuran or dimethylformamide at a temperature ranging from 0° C. to 25° C.

Compound 8 may be prepared by organometallic addition, for example Grignard or organocerium addition (*Tetrahedron Lett.*, 1984 25, 4233) of the appropriate $R^3$ reagent to 4. The resulting mixture of diastereomers may be separated and the C-2-OH removed by Barton-McCombie deoxygenation (*J. Chem. Soc. Perkin I*, 1975, 1574). Compound 8 may also be prepared by addition of said organometallic to the C-2-iodide formed from 6 in an aprotic solvent, such as ethyl ether or tetrahydrofuran, at temperatures from −78° C. to 0° C., preferably from −78° C. to −25° C. The aforementioned iodide may be formed by reaction of 6 with iodine, imidazole and triphenylphosphine in a solvent such as toluene at a temperature ranging from 0° C. to 25° C. (*J. Am. Chem. Soc.*, 1998, 120, 7647).

Compound 8, where $R^3$ is —$CH_2O$—X and X falls under the definition of $R^3$, may alternatively be prepared from 4 via formation of the C-2-methylene (i.e. $Z^1$ and $Z^2$ are taken together to form =$CH_2$), which may be accomplished following the precedent in *J. Org. Chem.*, 1995, 60, 7298, followed by hydroboration (*Org. React.*, 1963, 13, 1 and *Tetrahedron*, 1981, 37, 3547) and finally alkylation, as above Compound 8, where $R^3$ is H, may be prepared from Barton-McCombie deoxygenation (*J. Chem. Soc. Perkin I*, 1975, 1574) of 6. Alternatively, 8 may be prepared from commercially available 1-O-methyl-2-deoxy-D-ribose. For example, selective silylation with tert-butyl diphenylsilyl chloride (TBDPSCl) of the C-5-OH may be accomplished by reaction of the ribose in a solvent such as DMF or dichloromethane with tert-butyl diphenylsilyl chloride in the presence of an amine base, such as pyridine or triethylamine at a temperature ranging from 0° C. to 25° C. The addition of catalytic dimethylaminopyridine may be advantageous. Benzylation of C-3 OH may be accomplished by subsequent reaction of the C-3-alkoxide, generated by the action of a strong base such as potassium tert-butoxide or sodium hydride, in a solvent such as DMF or THF with benzyl bromide.

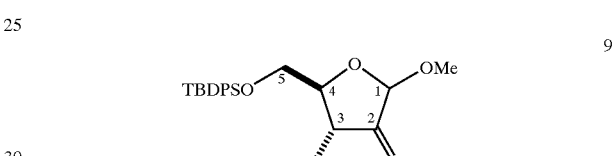

9

Compound 9, where $Z^1$ and $Z^2$ are taken together to form an oxime of the formula =$NOR^3$, wherein $R^3$ is as defined above, may be prepared by treating compound 4 with a hydroxylamine of the formula $R^3ONH_2$, using the free base or salt of the hydroxylamine, preferably the free base of the hydroxylamine. The reaction is carried out in an inert solvent, such as methanol, with addition of base, such as $K_2CO_3$, if the salt, for instance the HCl salt, of the hydroxylamine is used, at a temperature ranging from about 0° C. to 65° C., preferably from 0° C. to 25° C. The hydroxylamine of formula $R^3ONH_2$ may be prepared using one or more procedures disclosed in *Bioconj. Chem.*, 990, 2, 96, *J. Pharm. Sci.*, 1969, 58, 138 or *Chem. Pharm. Bull.*, 1967,15, 345.

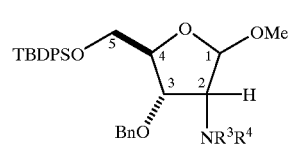

10

Compound 10, where $Z^1$ is H and Z is $NR^3R^4$, wherein $R^3$ and $R^4$ are as defined above, may be synthesized by reductive amination at the C-2 ketone site of the compound of formula 4. Combination of $R^4NH_2$ and the compound of formula 4 in an inert solvent such as methanol or ethanol and treatment with a reducing agent such as sodium borohydride ($NaBH_4$), sodium triacetoxyborohydride ($NaBH(OAc)_3$), or sodium cyanoborohydride ($NaCNBH_3$) at a temperature ranging from 0° C. to 25° C. provides the product with $R^3$=H. To introduce $R^3$ groups wherein $R^3$ is $RCH_2$— or RR'CH—, and R' and R are any of the moieties in the definition of $R^3$ that may be attached through a methylene or methine group, a reductive alkylation can be carried out with an appropriate aldehyde or ketone of the formula RC(O)H or RC(O)R' as described above. An Eschweiler-Clark reaction may be used to introduce a methyl group as the $R^3$ substituent (*Org. React.*, 1949, 5, 301). Both C-2 diastereomers are available using this chemistry.

11

[Structure: TBDPSO-CH2 on tetrahydrofuran with OMe at C1, H and NR³C(O)R⁴ at C2, BnO at C3]

To provide an amide group such as in compound 11, where $Z^1$ is H and $Z^2$ is $NR^3C(O)R^4$, an amine of the formula —$NHR^3$ may be introduced as described above and then an acyl moiety of the formula —$C(O)R^4$ may be introduced by treating the intermediate with an activated form of the carboxylic acid, such as $R^4COCl$ or $R^4C(O)OC(O)R^4$, or by using an amide coupling agent such as 2-ethoxy-1-ethoxycarbonyl-1,2-dihydroquinoline (EEDQ), 1,1'-carbonyl-diimidazole (CDI), or a carbodiimide such as DCC in a solvent such as dichloromethane, DMF or chloroform at a temperature ranging from 0° C. to 25° C. Both C-2 diastereomers are available using this chemistry. Compounds of formula 11 wherein $R^3$ is H and $R^4$ is as defined above, may be prepared through use of the primary amine derived from reductive amination of the compound of formula 4 with an ammonia equivalent, for instance through the use of ammonium acetate and sodium cyanoborohydride or sodium triacetoxyborohydride. Alternatively, this primary amine can be prepared via the corresponding azide: (1) the C-2 alcohol of compound 6 is transformed into the mesylate, for instance through the action of methanesulfonyl chloride and triethylamine in a solvent such as dichloromethane at a temperature ranging from 0° C. to 25° C.; 2) the mesylate is displaced by azide, for example using sodium azide in DMF at a temperature ranging from 0° C. to 90° C., preferably from 60° C. to 90° C.; and 3) the azide is reduced to the primary amine using for instance triphenylphosphine at a temperature from 25° C. to 60° C., followed by aqueous hydrolysis. Reaction of the resultant primary amine with an activated form of $R^4C(O)OH$, for instance $R^4C(O)Cl$ or $R^4C(O)OC(O)R^4$, provides the corresponding amide. Alternatively, amide coupling reagents can be used with $R^4C(O)OH$, such as 1-(3-dimethylaminopropyl)-3-ethyl-carbodiimide (EDC), diethyl phosphoryl cyanide (DEPC), DCC, CDI or EEDQ. To incorporate an $R^3$ group other than H, the amide referred to above may be alkylated. The alkylation may be carried out with a base and an alkylating agent, such as sodium hydride and an appropriate bromide of the formula $R^3$—Br.

12

[Structure: TBDPSO-CH2 tetrahydrofuran with OMe at C1, H and F at C2, BnO at C3]

Compound 12 may be prepared from available starting material 13 (*Chem. Ber.* 1979, 112, 1689).

13

[Structure: Ph3C-O-CH2 tetrahydrofuran with OMe at C1, OH at C2, BnO at C3]

For instance, diethylaminosulfur trifluoride (DAST) reaction of 13 in a solvent such as dichloromethane or THF at a temperature ranging from 0° C. to 65° C. (*Tetrahedron Lett.*, 1991, 32, 5963) provides the C-2-F intermediate. Removal of the trityl group using mild acid, for example p-toluenesulfonic acid in MeOH (*Tetrahedron Lett.*, 1981, 22, 1299), followed by silylation of the resultant primary alcohol with TBDPS-Cl, for example in dichloromethane or DMF in the presence of an amine base such as triethylamine at a temperature ranging from 0° C. to 25° C., may be used to complete the preparation of 12. The other C-2 diastereomer may be obtained by first inverting the C-2-OH of 13 by Mitsunobu inversion as described previously for compound 6.

14

[Structure: TBDPSO-CH2 tetrahydrofuran with OMe at C1, Z1 and Z2 at C2, BnO at C3]

Compound 14 may be prepared from the C4 isomer 15 (*J. Am. Chem. Soc.*, 1987, 109, 2205), using chemistry described for the preparation of compound 3.

15

[Structure: TBDPSO bicyclic with BnO and acetonide]

16

[Structure: TBDPSO-CH2 tetrahydrofuran with OMe at C1, $Z^1$ and $Z^2$ at C2, $W^1$ and $W^2$ at C3]

Functionalization of the C-3 position can be carried out on the substrates described above, such that the desired moieties are installed at both the C-2 and C-3 positions to generate intermediate 16, where $W^1$, $W^2$, $Z^1$ and $Z^2$ are as described in formula 1, or are present as their precursors, protected precursors, or protected derivatives.

17

[Structure: TBDPSO-CH2 tetrahydrofuran with OMe at C1, $Z^1$ and $Z^2$ at C2, ketone (=O) at C3]

Compound 17 may be prepared from compound 3.

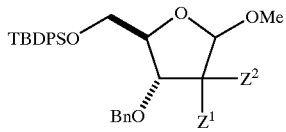
3

Removal of the benzyl group from 3 can be carried out by hydrogenation, for instance with hydrogen gas and a catalyst such as palladium on carbon, or by use of a hydrogen transfer agent such as cyclohexadiene and palladium on carbon, in a solvent such as THF, dioxane or methanol at a temperature ranging from 0° C. to 25° C. to provide alcohol 18. Oxidation of 18 by the methods cited for conversion of 6 to 4 generates 17.

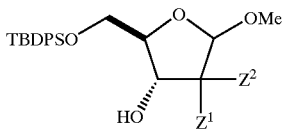
18

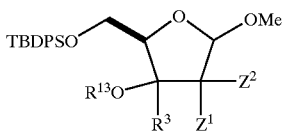
19

Compound 19 can be prepared from 17 and 18 using the chemistry described for synthesis of compound 7.

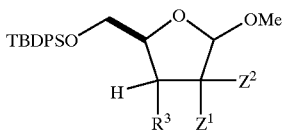
20

Compound 20 can be prepared from 17 using the chemistry described for synthesis of compound 8. Compound 20 wherein $R^3$ is H can be alternatively derived from known starting material 21 (*Acta Chem. Scand., Ser. B.*, 1981, 35, 155) by protection of the primary alcohol as its TBDPS ether as described for compound 8, and elaboration of the hydroxy group at C-2 as described for compounds 4, 7, 8, 9, 10, 11, and 12 above.

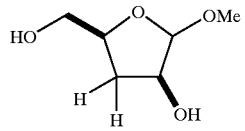
21

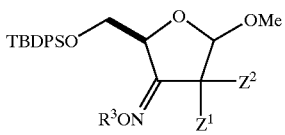
22

Compound 22 can be synthesized from 17 as described for preparation of compound

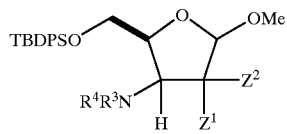
23

Compound 23 can be prepared from compound 17 as described for 10.

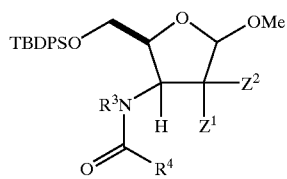
24

Compound 24 can be prepared from 17 or 18 using the chemistry described for 11.

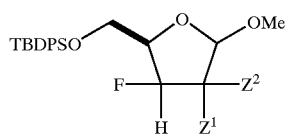
25

Compound 25 can be prepared from 3 through removal of the TBDPS ether, for instance with a fluoride source such as tetra-n-butyl ammonium fluoride (TBAF) in a solvent such as THF at a temperature ranging from 0° C. to 25° C., and installation of a trityl protecting group on the primary alcohol through use of, for instance, trityl chloride and pyridine in dichloromethane at a temperature ranging from 0° C. to 25° C. Debenzylation as described for conversion of 3 to 18 is then followed by the elaboration described for compound 12 above.

Where $Z^1$ is H and $Z^2$ is H, compound 16 can also be prepared by elaboration of 26, available from tert-butyldiphenylsilyl ether formation on the primary alcohol of the commercially available diol, by carrying out the chemistry described above.

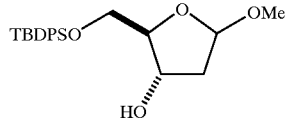
26

Compound 27, where $W^1$, $W^2$, $Z^1$ and $Z^2$ are each H in compound 16, is available from a literature procedure (*J. Org. Chem.*, 1997, 62, 1501).

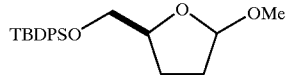
27

-continued

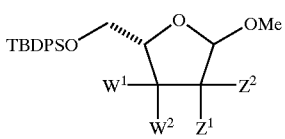

28

Compound 28, wherein the substituent at the C4 position is in the α-orientation, can be prepared from 14, using the chemistry described above for its isomer 3.

At this stage, the tert-butyidiphenylsilyloxymethyl substituent at the C4 position of intermediates 16 can be modified to provide key intermediates for introduction of V, as defined in the compound of formula 1. These compounds are then used to prepare 29, wherein V is as described in the compound of formula 1.

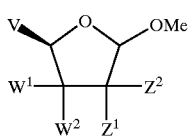

29

Removal of the tert-butyidiphenylsilyl protecting group from 16 can be carried out by treatment with a fluoride source such as TBAF in a solvent such as THF at a temperature ranging from 0° C. to 25° C., to provide primary alcohol 30. Swern or Dess-Martin oxidation of 30 gives aldehyde 31, which can be further oxidized through the action of potassium permanganate (*Tetrahedron Lett.*, 1986, 27, 4537 and *J. Am. Chem. Soc.*, 1987, 109, 7575) or sodium chlorite (*J. Org. Chem.* 1989, 54, 4100) to provide carboxylic acid 32.

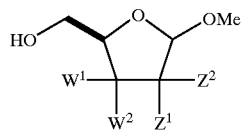

30

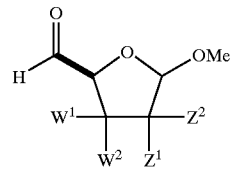

31

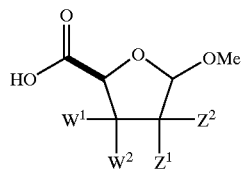

32

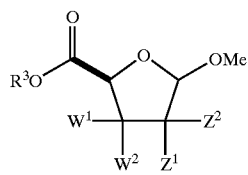

33

Compound 33 can be prepared from compound 32 through esterification with alcohol $R^3OH$. Reaction of $R^3OH$ and 32 in the presence of a coupling agent such as EDC, DEPC, DCC, CDI or EEDQ in a solvent such as dichloromethane, DMF or chloroform at a temperature ranging from 0° C. to 25° C. provides compound 33.

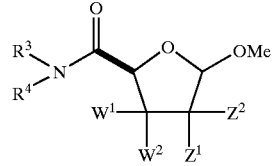

34

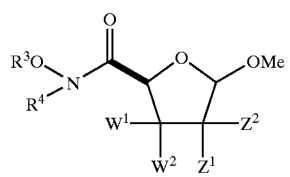

35

Compounds 34 and 35 can be prepared from compound 32 through amide formation with amine $R^3R^4NH$ or hydroxylamine $(R^3O)R^4NH$. Reaction of $R^3R^4NH$ or $(R^3O)R^4NH$ and 32 in the presence of coupling agent such as EDC, DEPC, DCC, CDI or EEDQ in a solvent such as dichloromethane, DMF or chloroform at a temperature ranging from 0° C. to 25° C., yields compounds 34 and 35.

Alternatively, 34 and 35 may be synthesized through reaction of $R^3NH_2$ or $R^3ONH_2$ with 32 in the presence of a coupling agent such as EDC, DEPC, DCC, CDI or EEDQ in a solvent such as dichloromethane, DMF or chloroform at a temperature ranging from 0° C. to 25° C. to generate an amide or hydroxamate. For compounds where $R^4$ does not equal H, $R^4$ may then be introduced via reaction of this intermediate amide or hydroxamate with a base such as sodium hydride or potassium t-butoxide and an alkylating agent $R^4$—L in a solvent such as THF or dioxane at a temperature ranging from 0° C. to 65° C., wherein L is a leaving group such as bromide, iodide or mesylate.

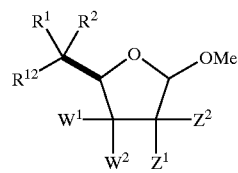

36

Compound 36, where

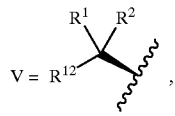

may be prepared from 30, 31 and 32.

$R^{12}$, where $R^{12}$ is not equal to H, can be introduced through organometallic addition of the appropriate $R^{12}$ moiety to aldehyde 31, providing alcohol 37, through use of for example the Grignard, organolithium or organocerium reagent (*Tetrahedron Lett.*, 1984 25, 4233). These reagents may be prepared from the corresponding halide, $R^{12}$-halide, using standard procedures (see *Organometallics In Synthesis; A Manual*, M. Schlosser, Ed., John Wiley & Sons Ltd., New York, 1994). This addition will generate both C-5 diastereomers, which may be separated using chromatography.

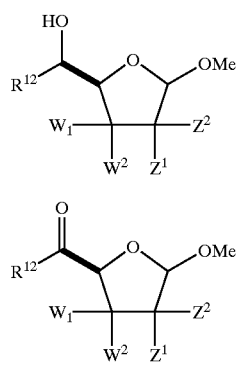

Ketone 38 is available through Swern or Dess-Martin oxidation of 37. Alternatively, carboxylic acid 32 can be transformed to its Weinreb amide through reaction with N,O-dimethylhydroxylamine and DCC or CDI in a solvent such as dichloromethane at a temperature ranging from 0° C. to 25° C. (*Tetrahedron Lett.*, 1981, 22, 39). Reaction of the Weinreb amide with an organometallic reagent derived from halide-$R^{12}$, as described above, also generates 38.

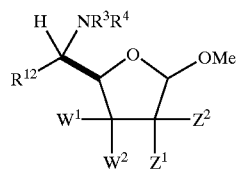

Compound 39 can be synthesized by reductive amination at the ketone functionality of compound 38. Combination of $R^4NH_2$ and 38 in an inert solvent and treatment with a reducing agent such as $NaBH_4$, $NaBH(OAc)_3$ or $NaCNBH_3$ provides the product with $R^3$=H. To introduce $R^3$ groups wherein $R^3$ is $RCH_2$— or RR'CH—, and R' and R are any of the moieties in the definition of $R^3$ that may be attached through a methylene or methine group, a reductive alkylation can be carried out with an appropriate aldehyde or ketone of the formula RC(O)H or RC(O)R'. An Eschweiler-Clark reaction may be used to introduce a methyl group as the $R^3$ substituent. If $R^{12}$=H, these compounds may be prepared from compound 31 in similar fashion.

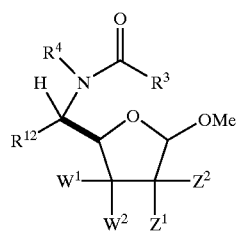

For preparation of compounds 40, an amine of the formula —$NHR^4$ may be introduced as described above and then an acyl moiety of the formula —$C(O)R^3$ may be introduced by treating the amine intermediate with an activated form of the carboxylic acid, such as $R^3COCl$ or $R^3C(O)OC(O)R^3$, or by reacting the amine intermediate with a carboxylic acid $R^3COOH$ and an amide coupling agent such as EDC, DEPC, DCC, CDI or EEDQ in a solvent such as dichloromethane DMF or chloroform at a temperature ranging from 0° C. to 25° C. Alternatively, compounds 40, wherein $R^4$ is H and $R^3$ is as defined above, may be prepared through use of the primary amine derived from reductive amination of 38 with an ammonia equivalent, for instance through the use of ammonium acetate and sodium cyanoborohydride or sodium triacetoxyborohydride. This primary amine can also be prepared via the corresponding azide: alcohol 37 can be transformed into the mesylate, for instance through the action of methanesulfonyl chloride and triethylamine; the mesylate is displaced by azide, for example using sodium azide in N,N-dimethylformamide (DMF); and the azide is reduced to the primary amine, using for instance triphenylphosphine followed by aqueous hydrolysis.

Reaction of the primary amine with an activated form of $R^3C(O)OH$, for instance $R^3C(O)Cl$ or $R^3C(O)OC(O)R^3$, provides the corresponding amide. Alternatively, amide coupling reagents, such as EDC, DEPC, DCC, CDI or EEDQ in a solvent such as dichloromethane DMF or chloroform can be used with $R^3C(O)OH$ at a temperature ranging from 0° C. to 25° C. To incorporate an $R^4$ group other than H, the amide referred to above may be alkylated. The alkylation may be carried out with a base and an alkylating agent, such as sodium hydride and an appropriate bromide of the formula $R^4$—Br. If $R^{12}$ is H, compounds 40 may be prepared from either compound 30 or 31.

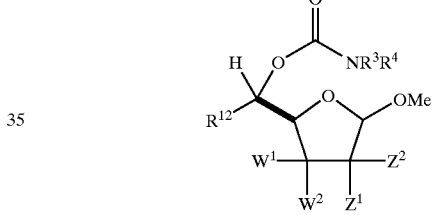

Compounds 41 may be prepared by reacting compound 37 with isocyanate $R^3NCO$ in toluene at temperatures from 40° C. to 110° C., preferably 50–80° C. Addition of 4-dimethylaminopyridine and triethylamine to the reaction may be advantageous. The product of this reaction, which has $R^4$ equal to H, may be alkylated to give $R^4$ equal to $C_1$–$C_{10}$ alkyl through use of a base such as sodium hydride and an alkylating agent such as a bromide of the formula $R^4$—Br in a solvent such as THF or dioxane at a temperature ranging from 0° C. to 65° C. If $R^{12}$=H, compounds 41 may be prepared from compound 30.

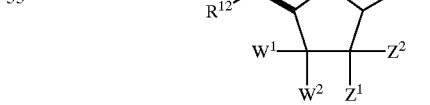

Compounds 42 can be prepared through alkylation of compound 37 with $R^3$—L, wherein L is a leaving group such as Cl, Br or methanesulfonate, in the presence of a base, such as sodium hydride or potassium tert-butoxide in a solvent such as THF or dioxane at a temperature ranging from 0° C. to 65° C. Compounds of formula 42 where $R^3$ is an aromatic or heterocyclic moiety may be prepared via a Mitsunobu reaction, wherein compound 37 is subjected to reaction with R³OH, mediated by triphenylphosphine and diethyl azodicarboxylate (D. L. Hughes, *Org. Reactions*, 1992, 42, 335). Alternatively, wherein R³ is an aromatic or heterocyclic moiety, the alcohol of 37 can be transformed into a leaving group, for instance the bromide or mesylate derivative. The leaving group can then be displaced by R³OH using a base such as sodium hydride, potassium tert-butoxide or potassium carbonate in a solvent such as THF or dioxane at a temperature ranging from 0° C. to 65° C. If $R^{12}$=H, compounds 42 may be prepared from compound 30.

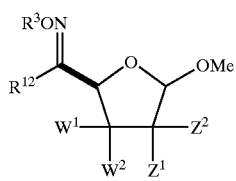

43

Compounds 43 wherein $R^{12}$ is not H can be prepared by treating ketone 38 with a hydroxylamine of the formula R³ONH₂, using the same conditions described for the preparation of 9. If $R^{12}$=H, compounds 43 may be prepared in the same manner from compound 31.

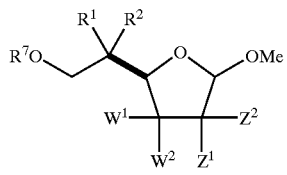

44

Compound 44, where $R^{12}$ can be written as R⁷OCH₂, can be prepared from compound 38 where $R^{12}$=Me, through reaction with triethylamine and trimethylsilyl triflate (TMSOTf) in an aprotic solvent, preferably dichloromethane, at temperatures between –40° C. and 0° C., preferably –30° C. to –15° C., to generate enol ether 45. Reaction of compound 45 with m-chloroperbenzoic acid (mCPBA), in a solvent such as dichloromethane or chloroform at temperatures between 10° C. and 40° C., followed by an acidic workup, using for instance 0.2 N HCl in THF or dioxane at temperatures between 10° C. and 40° C., yields α-hydroxy ketone 46. Alkylation of the hydroxyl group in 46 with a base such as sodium hydride or potassium t-butoxide and halide-R⁷, where halide is Br or I, in a solvent such as THF or dimethylsulfoxide (DMSO) at temperatures between 10° C. and 40° C., provides compound 47. For aromatic and heteroaromatic R⁷, a Mitsunobu reaction may be carried out with R⁷—OH, triphenylphosphine and dialkyl azodicarboxylate. Alternatively, the hydroxyl group of 46 can be converted into a leaving group such as the mesylate and displaced with R⁷—OH, under the influence of a base such as sodium hydride or potassium t-butoxide; this reaction can be carried out in an aprotic solvent such as THF or dioxane at temperatures ranging from 20° C. to 50° C. Further manipulation, as described above for 38, generates compound 44. Alternatively, the carbonyl at C-5 of 46 may be protected, for instance as its dioxolanyl ketal, and R⁷ introduced, followed by deprotection and introduction of R¹ and R². In another route, protection of the primary alcohol at the 6-position of 46, for instance as its tert-butyl dimethyl silyl ether or acetate, can be followed by introduction of R¹ and R², followed by regeneration of the primary alcohol and introduction of R⁷.

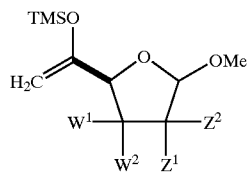

45

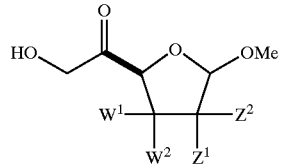

46

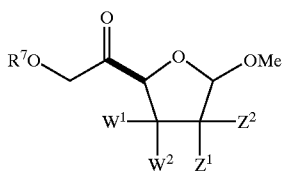

47

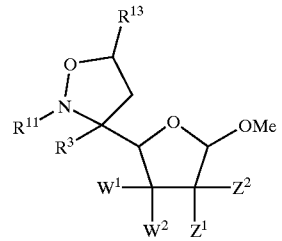

48

Compound 48 can be prepared from aldehyde 31 through organometallic addition of R³—M followed by oxidation, as described for $R^{12}$ in preparation of 36, to give 49. Reaction of compound 49 with $R^{11}$—NHOH provides nitrone 50. The reaction is carried out in an inert solvent, such as methanol, ethanol or pyridine, with addition of base, such as NaOAc, Na₂CO₃ or K₂CO₃, if the salt, for instance the HCl salt, of the hydroxylamine is used, at a temperature ranging from about 0° C. to 65° C., preferably from 0° C. to 25° C. Cycloaddition with $R^{13}$—HC=CH₂ provides compound 48. The cycloaddition reaction is carried out in an inert solvent such as benzene or toluene, at a temperature ranging from 50° C. to 110° C., preferably from 80° C. to 110° C.

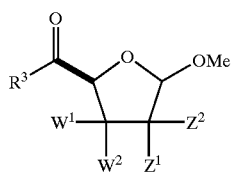

49

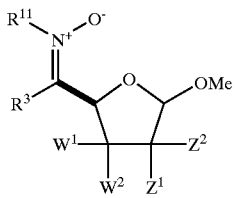

50

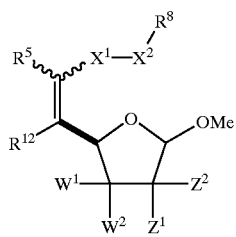

51

Compounds 51 can be prepared from ketone 38 utilizing the Wittig (*Chem. Rev.*, 1989, 89, 863 and *Chem. Soc. Rev.*, 1988, 17, 1), Horner-Wadsworth-Emmons (*J. Am. Chem. Soc.*, 1961, 83, 1733 and *Chem. Rev.*, 1974, 79, 87) or Peterson olefination (*Org. React.*, 1990, 38, 1) reactions via reaction with $Ph_3P$—$CH(R^5)X^1$—$X^2$—$R^8$, $(EtO)_2P(O)$—$CH(R^5)X^1$—$X^2$—$R^8$ or $(CH_3)_3Si$—$CH(R^5)X^1$—$X^2$—$R^8$, respectively. These reagents are generally commercially available but may be alternatively prepared by those skilled in the art. For example, Wittig reagents may be prepared from L—$CH(R^5)X^1$—$X^2$—$R^8$, where L is a halide (see above Wittig reference for relevant procedures), Horner-Wadsworth-Emmons reagents may be made from the same precursor using an Arbuzov-Michaelis reaction (*Chem. Rev.*, 1984, 45, 577) and finally, Peterson reagents made be made from the same precursor following the precedents in the *Org. React.* reference above. Functionalities contained within $W^1$, $W^2$, $Z^1$ or $Z^2$ that may be incompatible with this chemistry may either be protected as described previously or installed after functionalization at C-4.

Alternatively, these compounds may be made via the following chemistry:

For example, the compound of formula 51 where $R^5$ is defined as above, $X^1$ is $CR^9R^{10}$, $X^2$ is O and $R^8$ is H may be prepared through the corresponding α,β-unsaturated ester intermediates derived from Wittig, Horner-Emmons or Peterson olefination of the C5 ketone of 38. For instance, when $CR^9R^{10}$ is $CH_2$, (carbethoxymethylene)triphenylphosphorane or (carbethoxyethylidene)triphenylphosphorane can be reacted with ketone 38 in an aprotic solvent, such as toluene or diethyl ether, to provide the unsaturated ethyl ester. This compound may then be reduced, for instance with diisobutyl aluminum hydride in an aprotic solvent, such as toluene or diethyl ether at a temperature ranging from −78° C. to 25° C., to produce the desired allyl alcohol.

The compound of formula 51 where $R^5$ is defined as above, $X^1$ is a bond, $X^2$ is a bond and $R^8$ is —$C(O)OR^3$ or $C(O)NR^9R^3$ wherein $R^3$ and $R^9$ are defined above, may be prepared first by hydrolysis of the above unsaturated ethyl ester, for example with sodium hydroxide or lithium hydroxide in a solvent mixture containing water and some organic solvent such as tetrahydrofuran and then by esterification, with HO—$R^3$, or amidation, with $HNR^9R^3$ using standard coupling reagents such as EDC, DEPC, DCC, CDI or EEDQ in a solvent such as dichloromethane, DMF or chloroform at a temperature ranging from 0° C. to 25° C.

The compound of formula 51 where $R^5$ is defined as above, $X^1$ is $CH_2$, $X^2$ is O and $R^8$ is —$C(O)R^3$, wherein $R^3$ is defined above, may be prepared via acylation of allyl alcohol described above; for example by treatment of said alcohol with L—$C(O)R^3$, wherein L is a leaving group such as Cl, Br or N-hydroxysuccinimide (NHS) ester, in the presence of a base, such as sodium hydride, triethylamine or potassium tert-butoxide in a solvent such as THF or dioxane at a temperature ranging from 0° C. to 65° C.

The compound of formula 51 where $R^5$ is defined as above, $X^1$ is $CH_2$, $X^2$ is O and $R^8$ is equal to $R^3$, may be prepared via alkylation of allyl alcohol described above; for example by treatment of said alcohol with L—$R^3$, wherein L is a leaving group such as Cl, Br or mesylate, in the presence of a base, such as sodium hydride, triethylamine or potassium tert-butoxide in a solvent such as THF or dioxane at a temperature ranging from 0° C. to 65° C.

The compound of formula 51 where $R^5$ is defined as above, $X^1$ is $CH_2$, $X^2$ is O or S, and where $R^8$ is —$(CH_2)_m$—$(C_6$–$C_{10}$ aryl), wherein "m" is 0, may also be prepared via a Mitsunobu reaction. The allyl alcohol, prepared as described above, is subjected to Mitsunobu reaction with HO—$(CH_2)_m(C_6$–$C_{10}$ aryl), or HS—$(CH_2)_mC_6$–$C_{10}$ aryl), mediated by triphenylphosphine and diethyl azodicarboxylate as described in *Org. Reactions*, 1992, 42, 335. The resulting thioether may be oxidized, for instance with m-CPBA to get to the compound where $X^2$ is $SO_2$.

The compound of formula 51 where $R^5$ is defined as above, $X^1$ is $CH_2$, $X^2$ is O and $R^8$ is —$C(O)NR^9R^3$, may be prepared by reacting allyl alcohol, prepared as described above, with isocyanate $OCNR^3$ in toluene at temperatures from 40° C. to 110° C., preferably 50° C. to 80° C. Addition of dimethylaminopyridine and triethylamine to the reaction may be advantageous. The $R^9$ group may be subsequently added via alkylation of carbamate with $R^9$—L, where L is a leaving group such as Cl, Br or N-hydroxysuccinimide (NHS) ester, in the presence of a base, such as sodium hydride, triethylamine, n-butyl lithium or potassium tert-butoxide (see *J. Het. Chem.*, 1988, 25, 148 or *Synthesis*, 1985, 856).

The compound of formula 51 where $R^5$ is defined as above, $X^1$ is $CH_2$, $X^2$ is $NR^9$ and $R^8$ is defined as above, with the proviso that nitrogen is not adjacent to a carbonyl functionality, may be prepared via reduction amination of the aldehyde, prepared by the oxidation of the allyl alcohol above: (1) the allyl alcohol may be oxidized, for example using Swern conditions as described in *Org. Reactions*, 1990, 39, 297, (2) and combined with $HNR^9R^8$ in an inert solvent and then (3) treated with a reducing agent such as $NaBH_4$, $NaBH(OAc)_3$, or $NaCNBH_3$. $R^9$ may be introduced as part of $HNR^9R^8$ in step (2) or introduced after step (3), wherein $H_2NR^8$ was used, via alkylation, for instance with a base such as sodium hydride or potassium tert-butoxide and an alkylating agent such as $R^9$—L where is L is Br, Cl or methanesulfonate in a solvent such as THF or dioxane at a temperature ranging from 0° C. to 65° C.

The compound of formula 51 where $R^5$ is defined above, $X^1$ is $CH_2$ and where $X^2$ is $NR^9$ and $X^2$ and $R^8$ are taken together as described above may be prepared by the reaction of $HX^2R^8$ with the derived allyl mesylate in the presence of an amine base, such as triethylamine or pyridine. The allyl mesylate may be prepared by the reaction of the allyl alcohol described above with methanesulfonyl chloride in the presence of an amine base, such as triethylamine or pyridine.

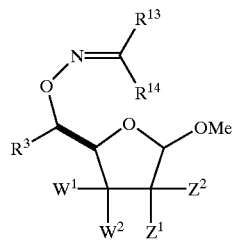

52

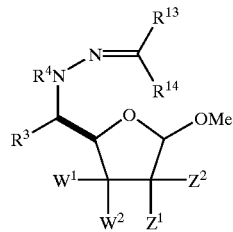

56

Compound 52 can be prepared from compound 49. Reduction with sodium borohydride provides alcohol 53. Conversion of 53 to the phthalimide derivative 54 can be carried out through a Mitsunobu reaction (*Synthesis*, 1981, 1) or via formation of the triflate from 53 through reaction with trifluoromethanesulfonyl chloride and dimethylaminopyridine in an aprotic solvent such as dichloromethane, followed by displacement with N-hydroxyphthalimide at a temperature ranging from 0° C. to 25° C. Cleavage of the phthalimide group by treatment with hydrazine or aqueous methylamine yields the corresponding hydroxylamine 55, which can be transformed to 52 by reaction with an aldehyde or ketone $R^{13}C(O)R^{14}$ in nonprotic solvent such as tetrahydrofuran. If $W^1$ and $W^2$ or $Z^1$ and $Z^2$ are taken together to form a ketone, it may be necessary to protect it, for instance as a dimethyl ketal through the use of methanol and catalytic acid such as camphorsulfonic acid or p-TsOH. Deprotection of the ketal can be carried out concomitantly with the cleavage of the anomeric methyl acetal to generate the hydroxyl group at C-1. Alternatively, a ketone may be masked as its protected alcohol, which can then be regenerated by deprotection and oxidation, for example under Swern conditions.

Compound 56 is prepared from ketone 49. Reaction with t-butoxycarbonyl-hydrazine provides compound 57, which can be hydrogenated to yield compound 58 (*J. Org. Chem.*, 1976, 41, 3805). Removal of the BOC group with TFA or dry HCl in absolute ethanol gives the hydrazine 59 (*J. Org. Chem.*, 1976, 41, 3805), which can be condensed with aldehyde or ketone $R^{13}C(O)R^{14}$ in an inert solvent such as tetrahydrofuran or methanol to provide compound 56. When $R^4$ is not H, N1-substituted t-butoxycarbonyl-hydrazine, which can be prepared by alkylation of t-butoxycarbonyl-hydrazine (*J. Org. Chem.*, 1965, 30, 321), can be employed in the reaction with ketone 49. If $W^1$ and $W^2$ or $Z^1$ and $Z^2$ are taken together to form a ketone, it may be necessary to protect it, for instance as a dimethyl ketal through the use of methanol and catalytic acid such as camphorsulfonic acid or p-TsOH. Deprotection of the ketal can be carried out concomitantly with the cleavage of the anomeric methyl acetal to generate the hydroxyl group at C-1. Alternatively, a ketone may be masked as its protected alcohol, which can then be regenerated by deprotection and oxidation, for example under Swern conditions.

53

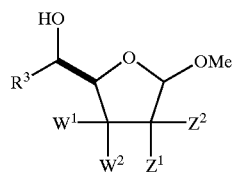

54

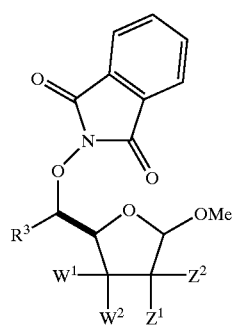

55

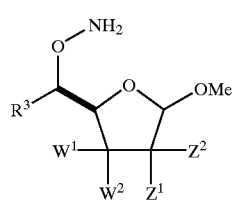

57

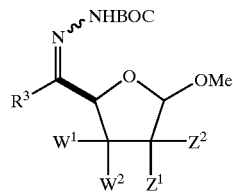

58

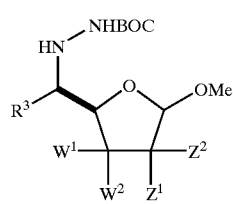

59

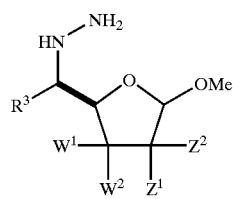

60

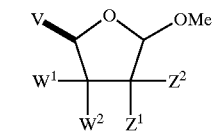

Compound 60, where V is a carbon-linked heterocycle as described for the compound of formula 1, may be prepared from 61, which in turn may be prepared from 49, wherein $R^3$ is R$^{15}$CH$_2$— and R$^{15}$ is any of the moieties in the definition of R$^3$ that may be attached through a methylene group. For example, reaction of 49 with triethylamine and trimethylsilyl triflate in an aprotic solvent, preferably dichloromethane, at temperatures between 0° C. and −40° C., preferably −15° C. to −30° C., and then reaction of the resultant silyl enol ether with N-bromosuccinimide and a base such as sodium hydrogen carbonate in a solvent such as THF or dioxane at a temperature ranging from 0° C. to 30° C., may lead to α-bromo ketone 61.

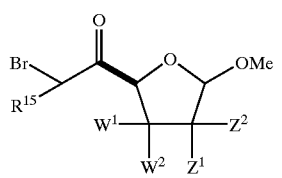

61

Compound 62, where G is O, S or N and t is an integer between 0–3, may be prepared by reaction of 61 with a thioamide, amide or amidine following the precedent of *J. Het. Chem.*, 1991, 28, 907, *J. Org. Chem.*, 1990, 55, 1479 and *Synth. Commun.*, 1979, 9, respectively. Thioamide, amide or amidine starting materials are generally commercially available.

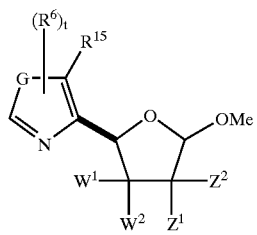

62

To prepare fused heterocycles a variety of chemistries may be utilized depended on the desired product. For example, one may react 61 with a 2-aminopyridine to produce 63 based on the precedent in *J. Het. Chem.*, 1989, 26, 293. One may react 61 with a thioxodihydropyridine to produce 64 based on the precedent in *Tetrahedron*, 1978, 34. One may react 61 with an aminophenol to produce 65 based on the precedent in *Synth. Comm.*, 1987, 17, 341. One may react 61 with an aniline to produce 66 or a phenylenediamine to produce 67 based on the precedents in *Aust. J. Chem.*, 1980, 33 and *J. Chem. Soc.*, 1953, 485, 487, respectively. One may react 61 with a benzaldehyde to produce 68 based on the precedent in *Synthesis*, 1990, 253.

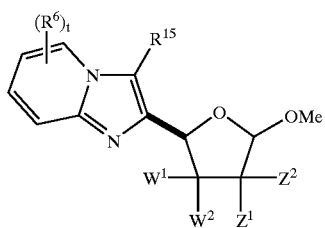

63

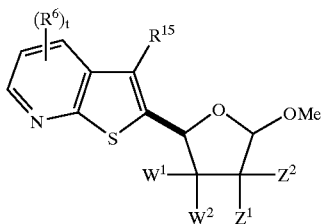

64

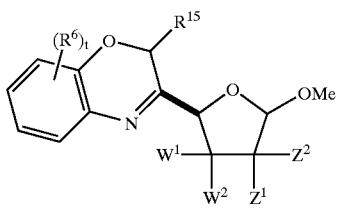

65

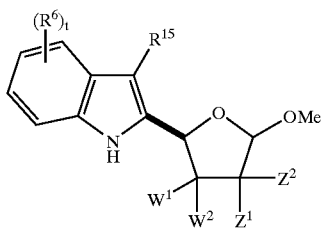

66

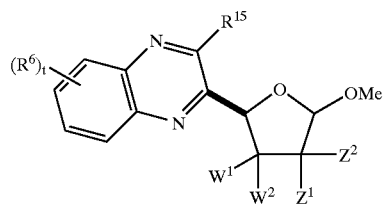

67

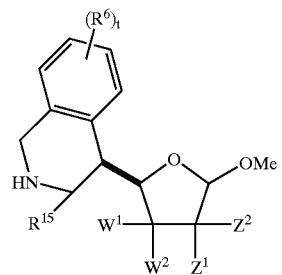

68

Similar modifications to those described above can be carried out on 28, the C-4 isomer of 16, to provide 69, with opposite stereochemistry at C-4. V, W$^1$, W$^2$, Z$^1$ and Z$^2$ of compound 69 are as described for the compound of formula 1.

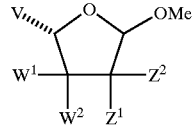

69

Fragment C

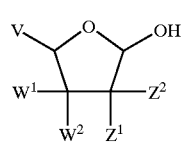

Fragment C is prepared by removal of the C-1 methyl acetal from compounds 29 or 69. This can be carried out via treatment with aqueous trifluoroacetic acid, and provides a hydroxy group at C-1 for attachment to fragment B.

Compounds wherein Y is $CH_2$ can be made using the chemistry below.

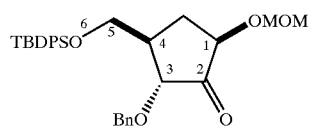
70

Compound 70 may be prepared from available starting material 71 (*Bull. Chem. Soc. Jpn.*, 1987, 60, 3673).

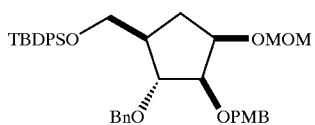
71

For instance, selective removal of the p-methoxybenzyl ether can be carried out with ceric ammonium nitrate or 2,3-dichloro-5,6-dicyano-1,4-benzoquinone (DDQ) in a mixture of organic and aqueous solvents at a temperature ranging from 0° C. to 65° C., preferably from 0° C. to 25° C. The resulting alcohol, 72, may be oxidized, for example under Swern (*J. Org. Chem.*, 1976, 41, 3329) or Dess-Martin (*J. Org. Chem.*, 1983, 48, 4155) conditions, to lead to compound 70.

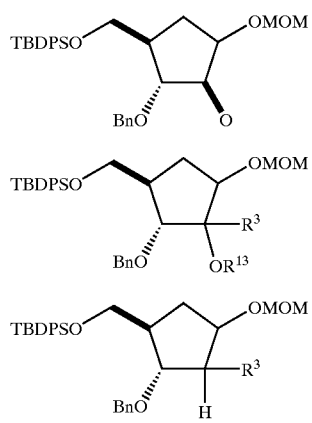

Compounds 73 and 74 may be prepared from either 72 or 70 using the methods described for the preparation of 7 and 8.

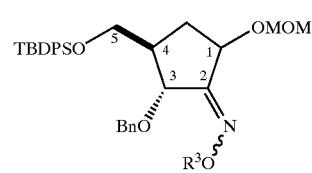
75

Compound 75, where $Z^1$ and $Z^2$ are taken together to form an oxime of the formula $=NOR^3$, wherein $R^3$ is as defined above, may be prepared by the methods described for the preparation of 9.

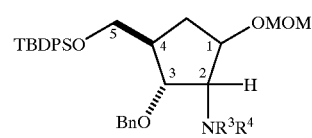
76

Compound 76, wherein $R^3$ and $R^4$ are as defined above, may be synthesized by reductive amination at the C-2 ketone site of the compound of formula 70 using the methods described for the preparation of 10. Both C-2 diastereomers are available using this chemistry.

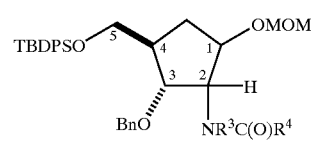
77

Compounds of the formula 77 can be prepared by the methods described for the preparation of 11.

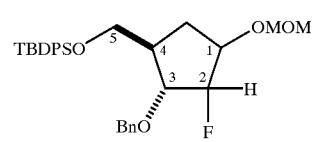
78

Compound 78, may be prepared from available starting material 79 which in turn can be prepared from 72.

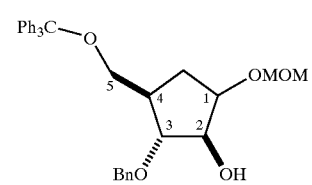
79

For instance, the TBDPS group can be removed using tetrabutylammonium fluoride (TBAF) in a solvent such as THF at a temperature ranging from 0° C. to 65° C., preferably from 0° C. to 25° C. The resultant alcohol can be converted to 79 by treatment with triphenylmethyl chloride and a base such as triethylamine in an organic solvent such as dichloromethane, dichloroethane, DMF or chloroform at a temperature ranging from 0° C. to 65° C., preferably from 0° C. to 25° C. Treatment of 79 with diethylaminosulfur trifluoride (DAST) (*Tetrahedron Lett.*, 1991, 32, 5963) provides the C-2-F intermediate. Removal of the trityl group using mild acid, for example p-toluenesulfonic acid in MeOH (*Tetrahedron Lett.*, 1981, 22, 1299), followed by silylation of the resultant primary alcohol with TBDPS-Cl, for example in dichloromethane or DMF in the presence of an amine base, may be used to complete the preparation of 78. The other C-2 diastereomer may be obtained by first inverting the C-2-OH of 79 by Mitsunobu inversion as described previously for compound 6.

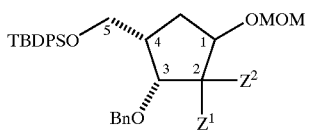

80

Compound 80 may be prepared from available starting material 81 which can prepared from L-glucose using chemistry described in the preparation of 71 (*Bull. Chem. Soc. Jpn.*, 1987, 60, 3673). Compound 82 can be obtained by Mitsunobu inversion of the C-3-OH followed by treatment of the alcohol with benzyl bromide and a suitable strong base such as sodium hydride or potassium carbonate in a polar aprotic solvent, such as tetrahydrofuran or dimethylformamide at a temperature ranging from 0° C. to 65° C., preferably from 0° C. to 25° C.

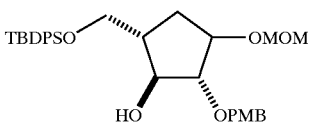

81

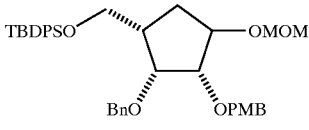

82

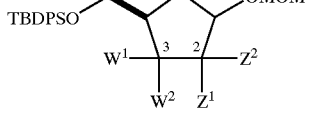

83

Functionalization of the C-3 position can be carried out on the substrates described above, such that the desired moieties are installed at both the C-2 and C-3 positions to generate intermediate 83, where $W^1$, $W^2$, $Z^1$ and $Z^2$ are as described in formula 1, or are present as their precursors, protected precursors, or protected derivatives.

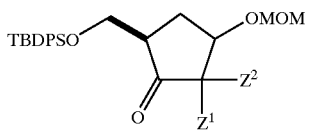

84

Compounds 84 may be prepared from compound 85, which represents compounds 70, 73, 74, 75, 76, 77, and 78 described above.

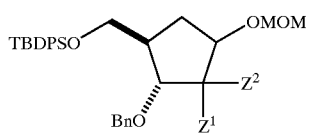

85

Removal of the benzyl group from 85 can be carried out by hydrogenation, for instance with hydrogen gas and a catalyst such as palladium on carbon, or by use of a hydrogen transfer agent such as cyclohexadiene and palladium on carbon in a solvent such as THF or methanol at a temperature ranging from 0° C. to 25° C., to provide alcohol 86. Oxidation of 86 by the methods cited for 72 above generates 84.

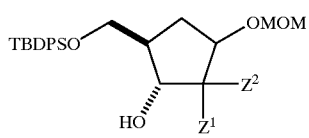

86

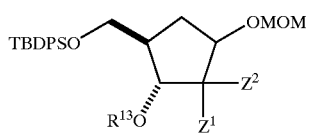

87

Compounds 87 can be prepared from 84 and 86 using the chemistry described for synthesis of 73.

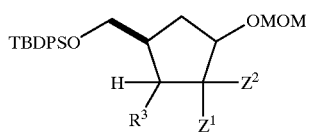

88

Compounds 88 can be prepared from 84 using the chemistry described for synthesis of 74. Compounds 88 wherein $R^3$ is H can be obtained by the removal of the 3-OH of compound 86 by Barton-McCombie deoxygenation (*J. Chem. Soc. Perkin I*, 1975, 1574). Compound 83 where $W^1$, $W^2$, $Z^1$ and $Z^2$ are each H, can be accessed by elaboration of 89 (*Chem. Ber.*, 1988, 121, 485), through tert-butyldiphenylsilyl ether formation on the primary alcohol, followed by introduction of a MOM group on the C-1 hydroxyl group.

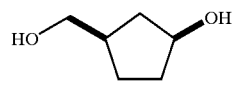

89

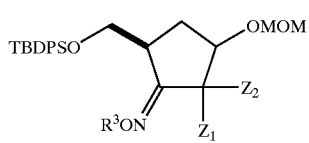

90

Compounds 90 can be synthesized from 84 as described for preparation of compound 75.

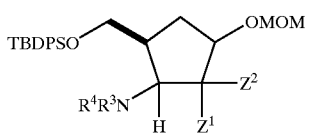
91

Compounds 91 can be prepared from compound 84 as described for 76.

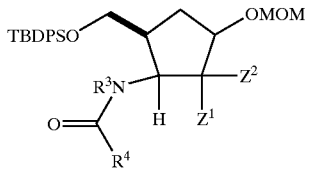
92

Compounds 92 can be prepared from 84 or 86 using the chemistry described for 77.

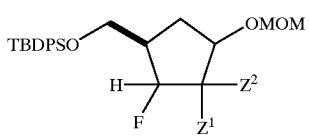
93

Compounds 93 can be prepared from 85 through removal of the TBDPS ether, for instance with a fluoride source such as TBAF in a solvent such as THF at a temperature ranging from 0° C. to 25° C., and installation of a trityl protecting group on the primary alcohol through use of, for instance, trityl chloride and pyridine in a solvent such as dichloromethane at a temperature ranging from 0° C. to 25° C. Debenzylation as described for 85 is then followed by the elaboration described for preparation of compound 78 above.

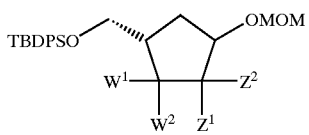
94

Compound 94, wherein the substituent at the C-4 position is in the α-orientation, can be prepared from 80, using the chemistry described above for its isomer 85.

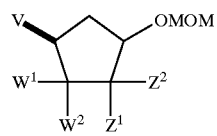
95

At this stage, the tert-butyldiphenylsilyloxymethyl substituent at the C-4 position of intermediates 83 can be modified to provide key intermediates for introduction of V, as defined in the compound of formula 1. These compounds are then used to prepare compound 95, wherein V is as described in the compound of formula 1. These compounds are prepared from 83 using the chemistry described for compounds 29–68.

Similar modifications to those described above can be carried out on 94, the C-4 isomer of 83, to provide 96, with opposite stereochemistry at C-4. V, $W^1$, $W^2$, $Z^1$ and $Z^2$ of compound 96 are as described for the compound of formula 1.

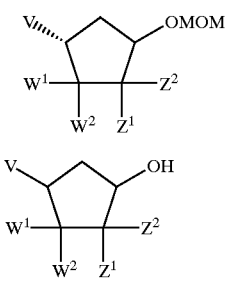
96

Fragment C

Fragment C is prepared by removal of the C-1 methoxymethyl ether from compounds 95 or 96. This can be carried out via treatment with aqueous trifluoroacetic acid, and provides a hydroxy group at C-1 for attachment to fragment B.

Preparation of Fragment B and Coupling to Fragments A and C

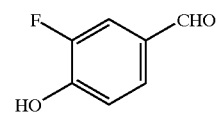
97

Compound 97 can be prepared by treatment of 3-fluoro-4-methoxybenzaldeyde with $BBr_3$, $BI_3$ or TMSI, preferably $BBr_3$, in a solvent such as dichloromethane at a temperature ranging from 0° C. to 65° C., preferably from 0° C. to 25° C.

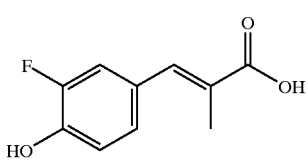
98

Compound 98 can be prepared by treatment of 97 with $Ph_3P=C(CH_3)CO_2Et$ in a solvent such as dichloromethane. The resultant ester can then be hydrolyzed with hydroxide as its lithium, sodium or potassium salt, preferably a 5–10 fold excess of the lithium salt in a mixture of organic solvents such as methanol, THF, $Et_2O$, dioxane and water preferably in a mixture of 3 THF:2methanol:1 water at a temperature ranging from 0° C. to 65° C., preferably from 0° C. to 25° C.

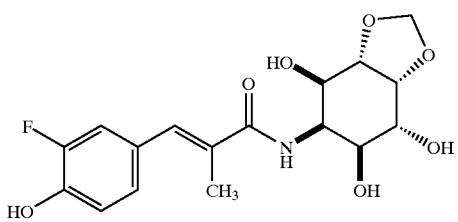
99

Compound 99 can be prepared by treatment of a solution of compounds of the formula 2 and 98 with an appropriate acid coupling reagent such as DCC, EDCI, BOPCI, PYBROP or 2-ethoxy-1-ethoxylcarbonyl-1,2-dihydroxyquinoline (EEDQ) in a polar aprotic solvent such as DMSO or DMF, preferably DMF, at a temperature ranging from 0° C. to 65° C. preferably from 25° C. to 65° C.

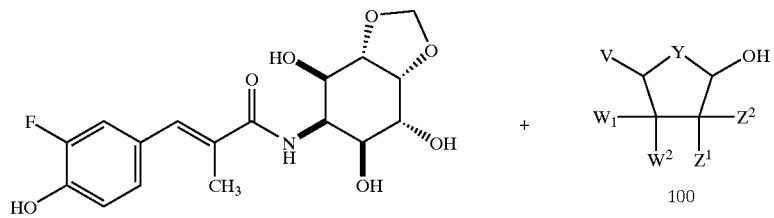

99 + 100

↓

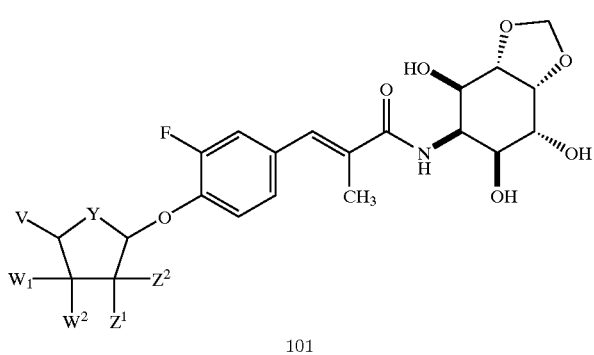

101

Compounds of the formula 101 can be prepared by treatment of compound 100 with dialkylazodicarboxylate, wherein alkyl is preferably ethyl, propyl, isopropyl, or tert-butyl; and triphenylphosphine or triphenylphosphine attached to a suitable polymer support; in a suitable organic solvent such as THF, Et$_2$O, dioxane at a temperature ranging from 0° C. to 65° C., preferably from 0° C. to 25° C.

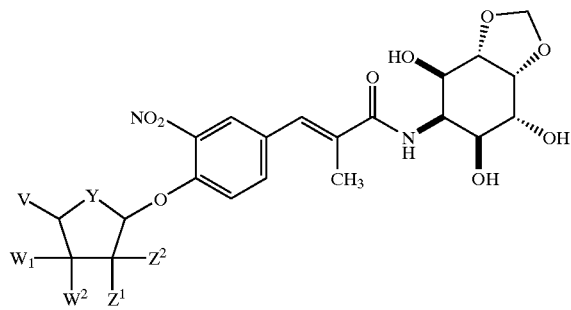

102

Compound 102 can be prepared from 4-hydroxy-3-nitrobenzaldehyde using the scheme outlined for the synthesis of compound 101.

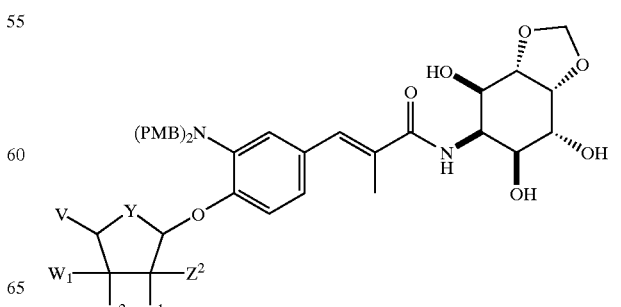

103

The compound of the formula 103 can be prepared by selective reduction of the aromatic nitro group using hydrogenation over Pd/C (*Chem. Pharm. Bull.*, 1997, 45, 1984). Alternatively compound of the formula 103 can be prepared from 104 by treatment with trifluoroacetic acid.

104

-continued

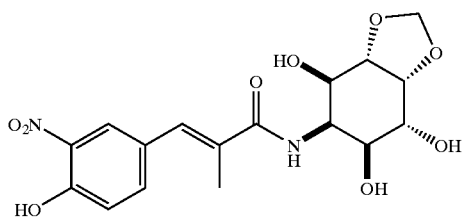
105

Compound of the formula 104 can be obtained from compound 105 which was prepared using the scheme outlined for 101. Reduction of the nitro group using Pd/C as above is followed by protection of the amine as its bis-4-methoxybenzyl ether. Coupling with 100 as described above can provide 104.

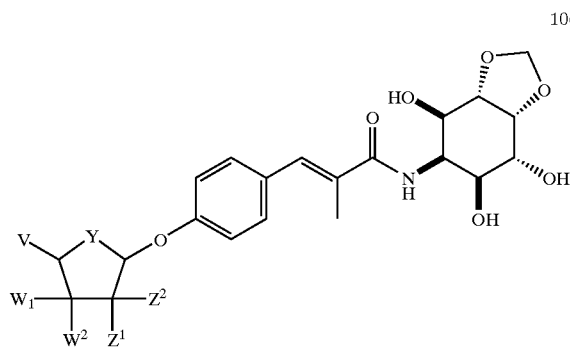
106

The compound of the formula 106 can be prepared from 4-hydroxybenzaldehyde using the scheme outlined for the synthesis of compound 101.

Alternatively, through coupling of fragments B and A to Fragment C wherein Y, $W^1$, $W^2$, $Z^1$ and $Z^2$ are as defined in the compound of formula 1 and V equals $R^3C(O)$, as in compound 49, compound 107 may be prepared. Reduction of the 5"-ketone or aldehyde to the alcohol at that position may be carried out through the action of sodium borohydride in methanol. Modification of 108, the ketone or aldehyde or their derived alcohols, can then be carried out as described above for 37, 38 and 49 to prepare compounds of the formula 1 wherein

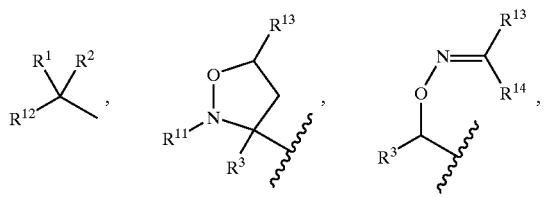

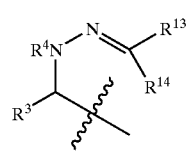

or a carbon-linked heterocyclic group as defined for formula 1.

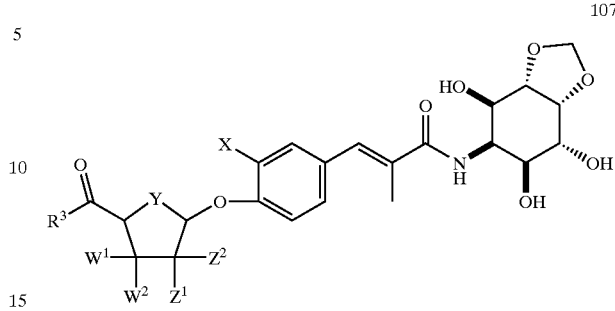
107

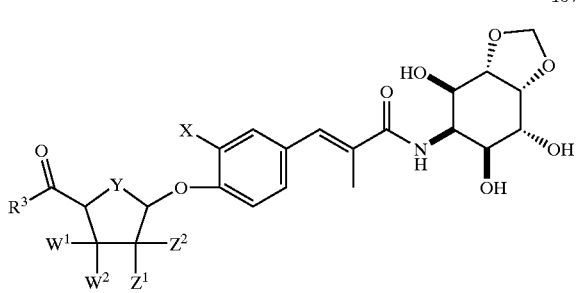
A = O; H, OH
108

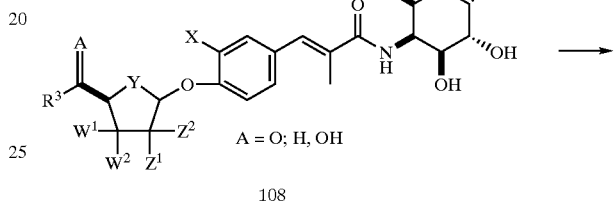

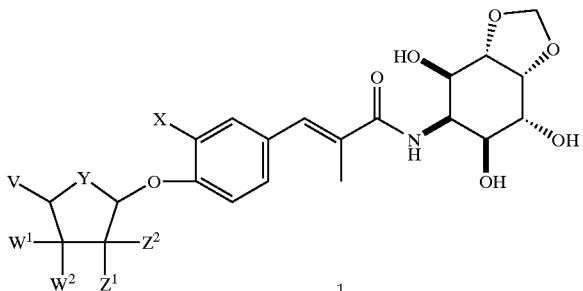
1

Compound 107 (preferentially where $R^3$=Me) may also be transformed into compounds of the formula 1 wherein V=$R^3$OC(O), $R^3R^4$NC(O) or ($R^3$O)$R^4$NC(O). Protection of labile functional groups in 107 is effected first. For instance, hydroxyl groups may be protected as their TBDMS ethers, for instance through treatment with >10 equivalents tert-butyldimethylsilyl chloride (TBDMSCl) and >10 equivalents of imidazole in DMF at a temperature of 60° C. to 90° C. The ketone 109 is then converted to its trimethylsilyl enol ether 110 via treatment with TMS triflate and triethylamine, followed by reaction with meta-chloroperoxybenzoic acid and acidic workup, which provides α-hydroxy ketone 111, as described for conversion of 38 to 46. Lead tetraacetate (Pb(OAc)$_4$) in benzene, at a temperature of 10° C. to 40° C. then converts compound 111 to carboxylic acid 112. Using the chemistry described for transformation of 32 to 33, 34 and 35, followed by deprotection if necessary, 112 can be converted to compounds of the formula 1 wherein V=$R^3$OC(O), $R^3R^4$NC(O) or ($R^3$O)$R^4$NC(O). Remaining TBDMS protecting groups can be removed by treatment with a fluoride source such as tetrabutyl ammonium fluoride in tetrahydrofuran or HF in pyridine and tetrahydrofuran at temperatures ranging from 10° C. to 40° C.

Preparation from Hygromycin A

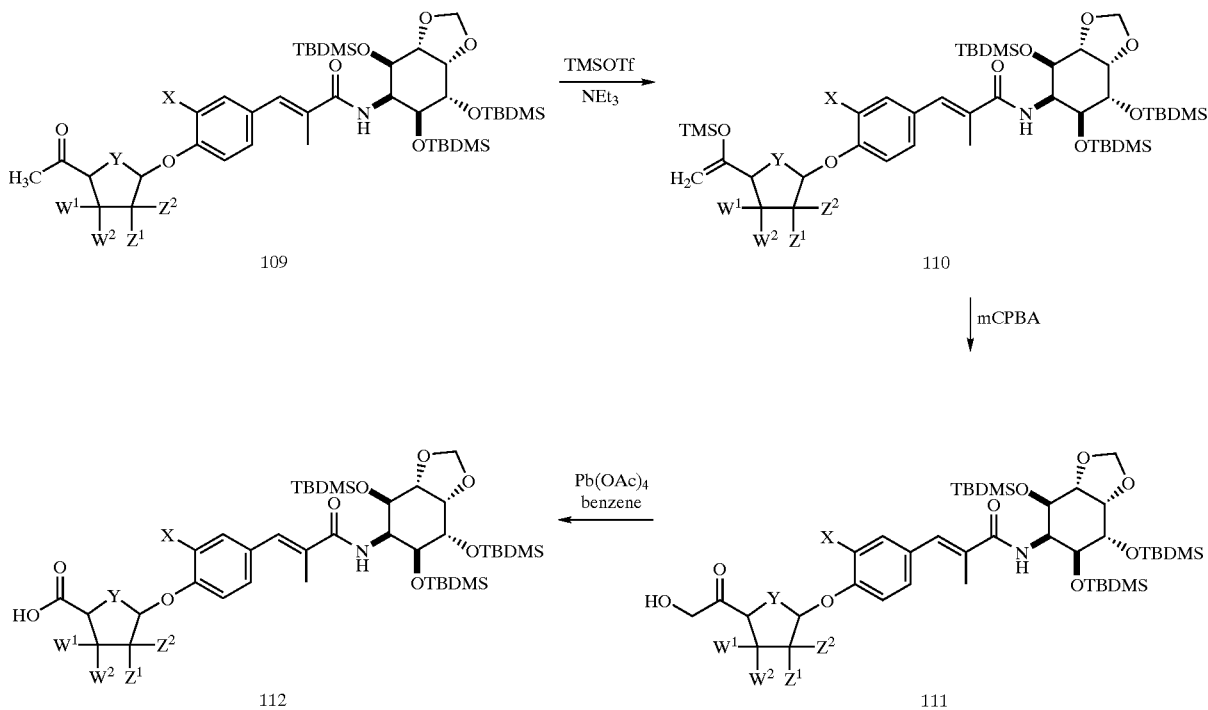

Alternatively, some of the compounds of formula 1 can be prepared from the natural product hygromycin. For example, the phenolic hydroxyl group of hygromycin can be removed to generate an analogue of the natural product wherein the substituent identified as X in the compound of formula 1 is H in the following manner. Compound 114 can be prepared by treatment of the corresponding compound 113 (hygromycin A) with trifluoromethanesulfonyl anhydride or N-diphenyltrifluoromethanesulfonyl amide in the presence of an amine base such as triethylamine in a solvent such as DMF or a mixture of DMF and dichloromethane at a temperature ranging from 0° C. to 65° C., preferably from 0° C. to 25° C. Treatment of compound 114 with Pd(PPh$_3$)$_4$ in DMF at a temperature ranging from 0° C. to 65° C., preferably from 0° C. to 25° C. can provide compound of the formula 115 (ref).

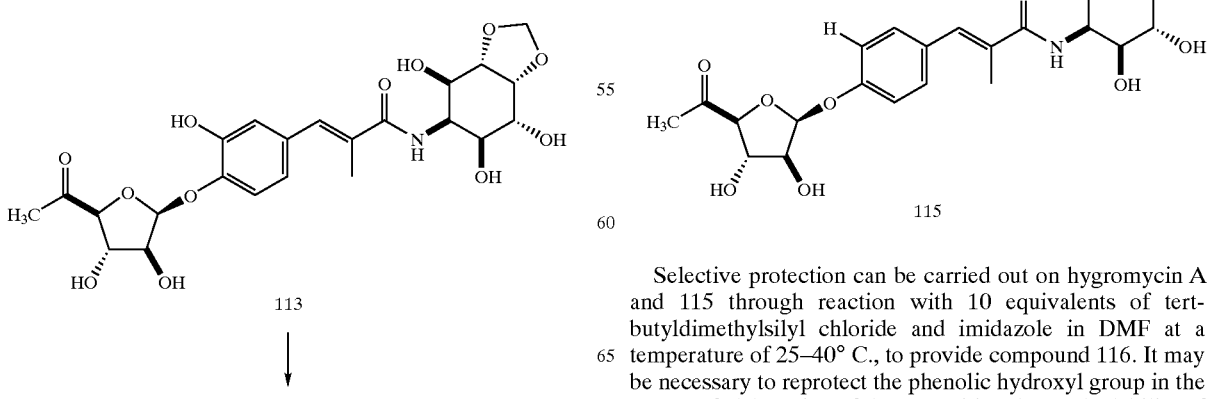

Selective protection can be carried out on hygromycin A and 115 through reaction with 10 equivalents of tert-butyldimethylsilyl chloride and imidazole in DMF at a temperature of 25–40° C., to provide compound 116. It may be necessary to reprotect the phenolic hydroxyl group in the course of elaboration of the 2″ position due to the lability of the TBDMS ether at this position. An ally group, for instance, can be introduced through reaction with ally bromide and potassium carbonate. Removal of the allyl group may be carried out at a later stage, for instance through use of iridium-mediated isomerization and subsequent hydrolysis (*J. Antibiotics*, 1992, 45, 1705) or through the use of palladium chemistry (*Tetrahedron Lett.*, 1994, 35, 4349 and *Synthesis*, 1996, 755).

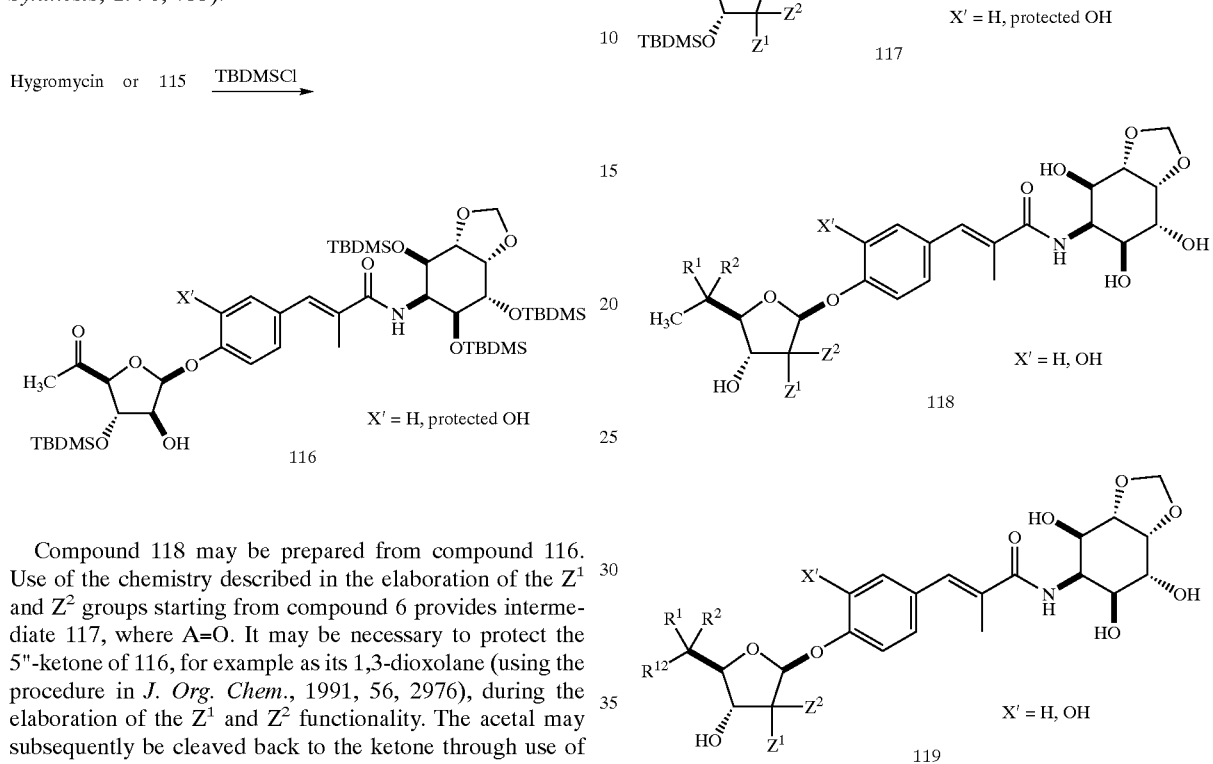

Compound 118 may be prepared from compound 116. Use of the chemistry described in the elaboration of the $Z^1$ and $Z^2$ groups starting from compound 6 provides intermediate 117, where A=O. It may be necessary to protect the 5"-ketone of 116, for example as its 1,3-dioxolane (using the procedure in *J. Org. Chem.*, 1991, 56, 2976), during the elaboration of the $Z^1$ and $Z^2$ functionality. The acetal may subsequently be cleaved back to the ketone through use of TFA and water (*J. Org. Chem.*, 1991, 56, 2976); it may be necessary to re-introduce the TBDMS groups at this point, if protection of the hydroxy functions is required for subsequent chemistry. Use of other protecting groups, such as acetyl, allyl, benzyl, and p-methoxybenzyl, may be advantageous, depending on the chemistry carried out at 2", 5" and elsewhere in the molecule, in this and subsequent preparations. Reduction of the 5"-ketone to the alcohol at that position may be carried out through the action of sodium borohydride in methanol. Modification of 117, the ketone or its derived alcohol, can then be carried out as described above for 37 and 38. Removal of the TBDMS protecting groups can be carried out by treatment with HF in pyridine, to generate 118.

Compounds 119 may be prepared from persilylated derivatives 117 or 120, which is prepared from hygromycin or compound 115 through treatment with 12 equivalents tert-butyldimethylsilyl chloride and 12 equivalents of imidazole in DMF at a temperature of 60–90° C., preferably 75–85° C. Formation of trimethylsilyl enol ether 121 via treatment with TMS triflate and triethylamine is followed by reaction with meta-chloroperoxybenzoic acid. Acidic workup leads to α-hydroxy ketone 122. Lead tetraacetate in benzene converts compound 122 to carboxylic acid 123, in a sequence analogous to that described for conversion of 109 to 112.

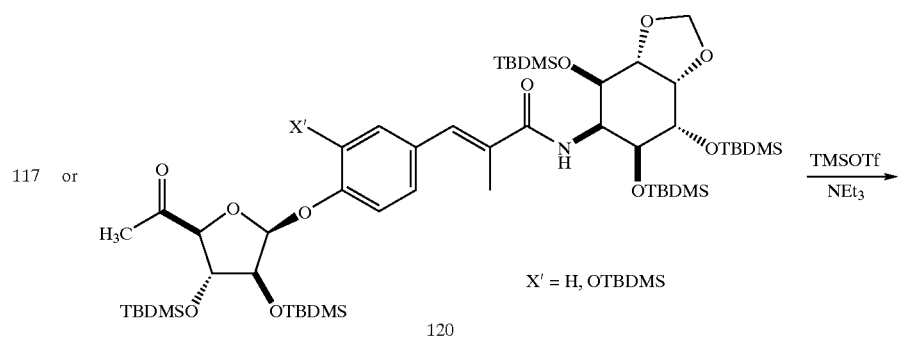

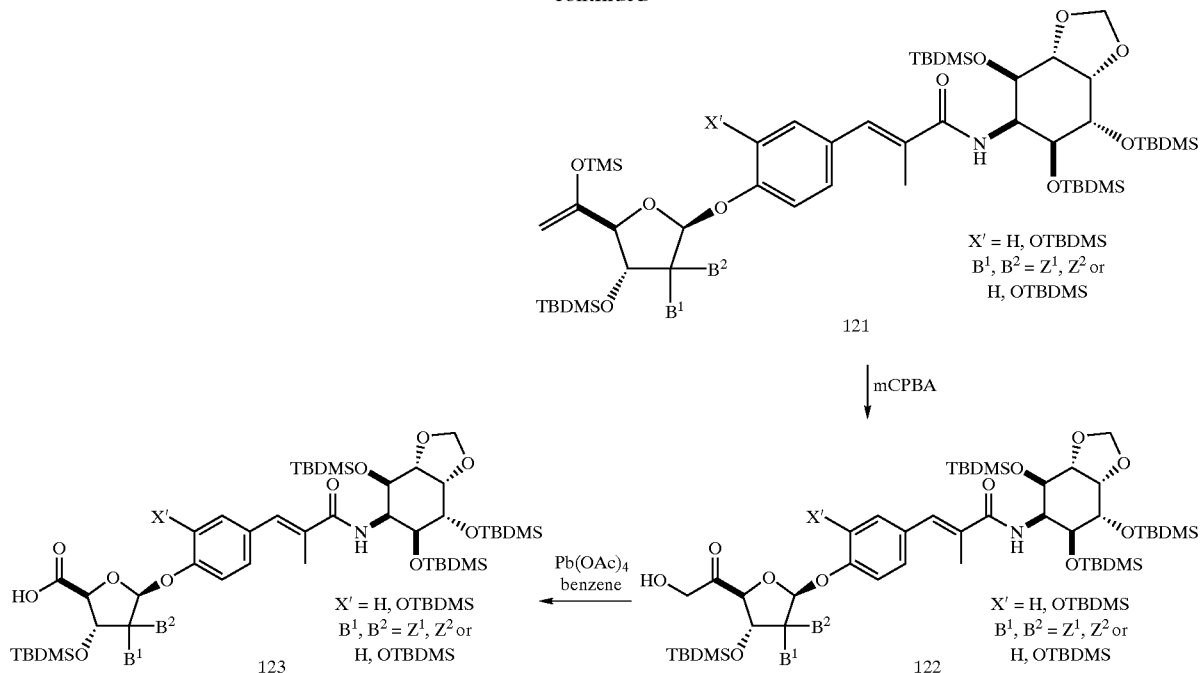

121

Similar treatment of 122 with lead tetraacetate in methanol provides the methyl ester at 5", which can be reduced with lithium borohydride to provide alcohol 124.

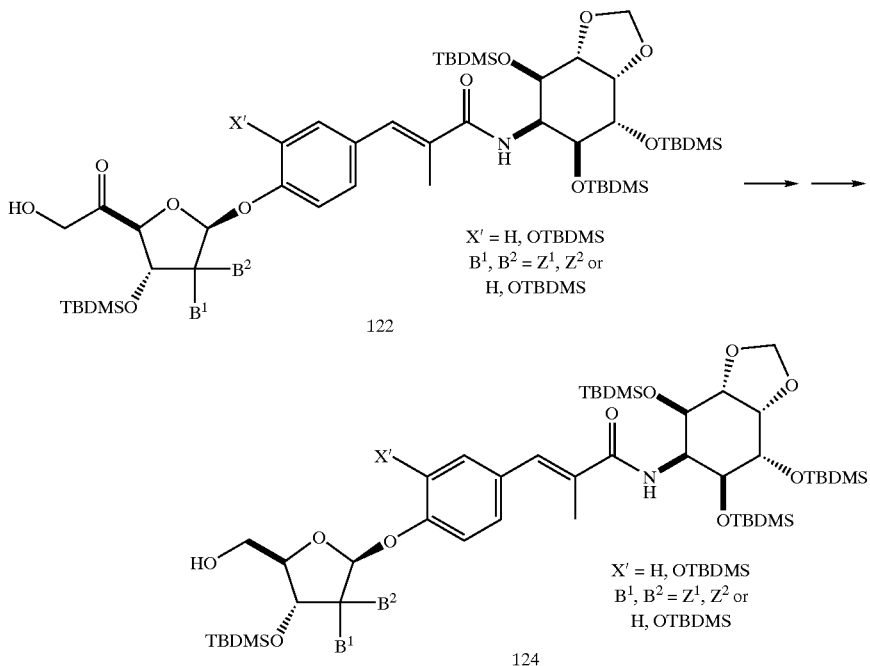

Modification of 123 and 124 as described above for 32 and 30 serves to install $R^1$, $R^2$ and $R^{12}$, as described for the compound of formula 1. It may be necessary to reprotect the phenolic hydroxyl group in the course of this elaboration due to the lability of the TBDMS ether at this position. An allyl group, for instance, can be introduced through reaction with allyl bromide and potassium carbonate. Removal of the allyl group may be carried out at a later stage, for instance through use of iridium-mediated isomerization and subsequent hydrolysis (*J. Antibiotics*, 1992, 45, 1705) or through the use of palladium chemistry (*Tetrahedron Lett.*, 1994, 35, 4349 and *Synthesis*, 1996, 755). Final deprotection of the TBDMS groups can then be carried out by treatment with fluoride ion, for instance reaction with hydrogen fluoride in pyridine, to generate compounds 119.

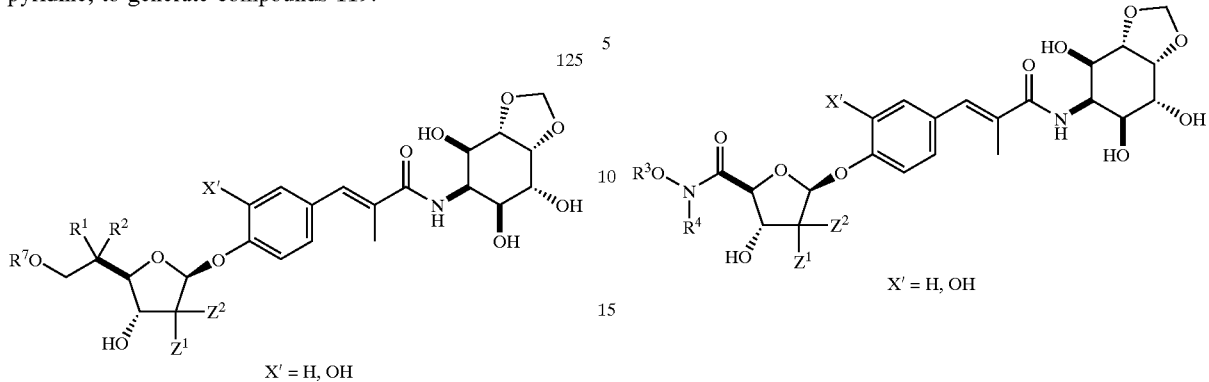

Compounds 125, where $R^{12}$ can be written as $R^7O(CH_2)$—, may be prepared using compounds 122, through use of the chemistry described for conversion of 46 to 47. It may be necessary to protect the phenolic hydroxy group, as for instance an allyl ether, during the base-mediated transformations. Further manipulation, as described above for 117, generates compound 125.

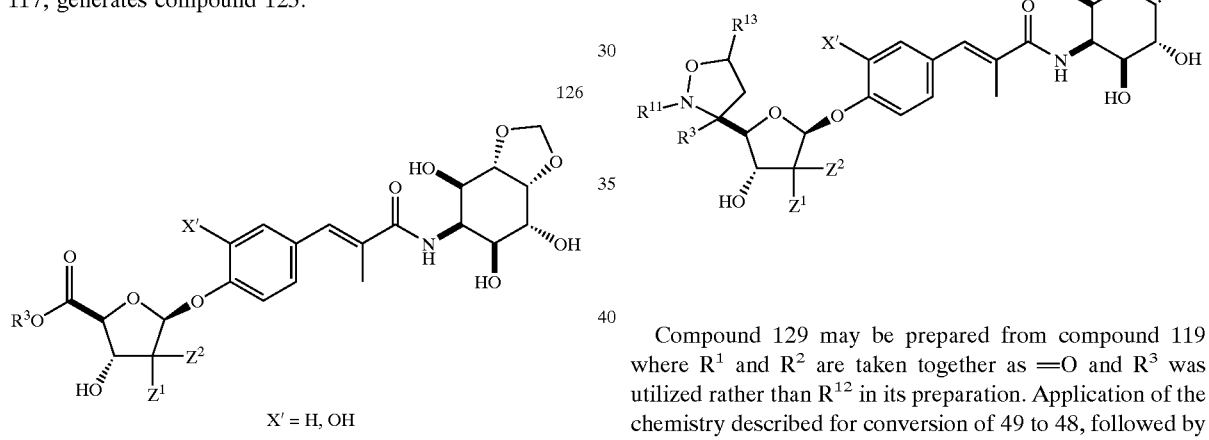

Compound 126 may be prepared from 123 by condensation with $R^3OH$ as described for 33, followed by deprotection.

Compounds 127 and 128 may be prepared in similar fashion from 123, by further elaboration to the amide or hydroxamate as described for 34 and 35, followed by deprotection.

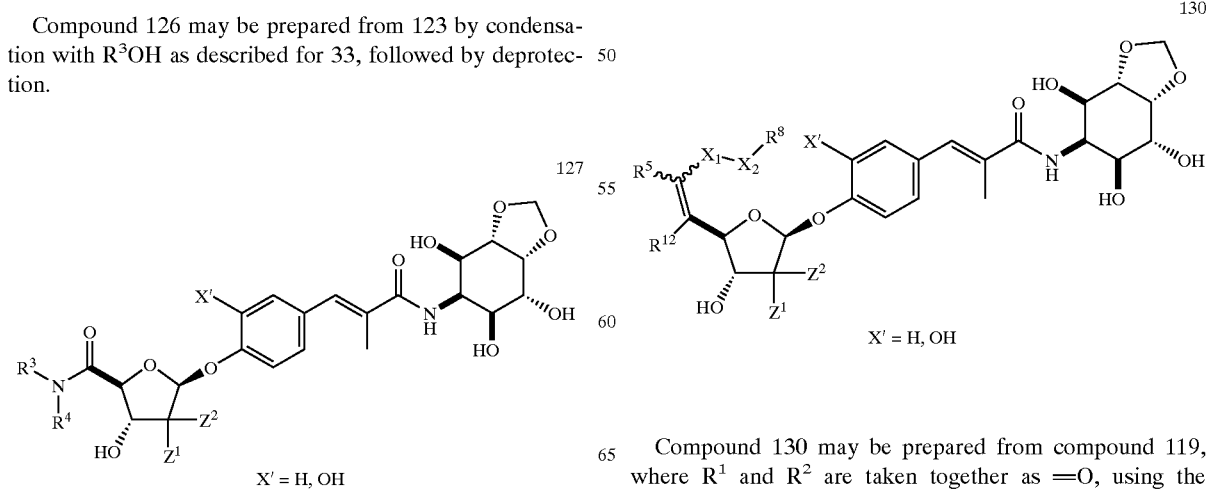

Compound 129 may be prepared from compound 119 where $R^1$ and $R^2$ are taken together as =O and $R^3$ was utilized rather than $R^{12}$ in its preparation. Application of the chemistry described for conversion of 49 to 48, followed by appropriate deprotection, provides 129.

Compound 130 may be prepared from compound 119, where $R^1$ and $R^2$ are taken together as =O, using the chemistry described for the preparation of compound 51.

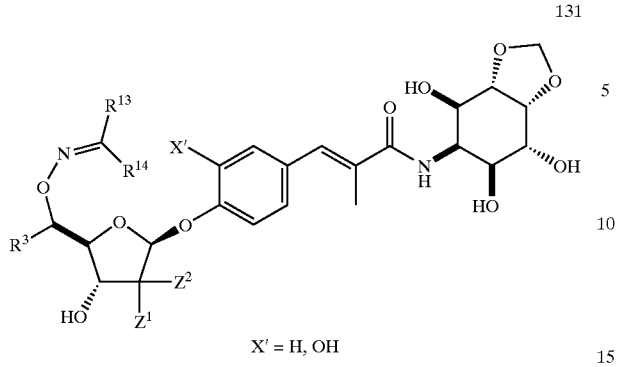

131

X' = H, OH

Compound 131 may be prepared from ketone 119, where $R^1$ is H and $R^2$ is OH, by the method described for preparation of 52.

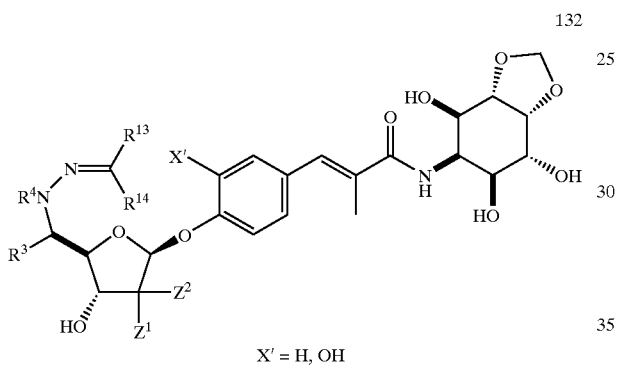

132

X' = H, OH

Compound 132 may be prepared from ketone 119, where $R^1$ and $R^2$ are taken together as =O, by the method described for preparation of 56.

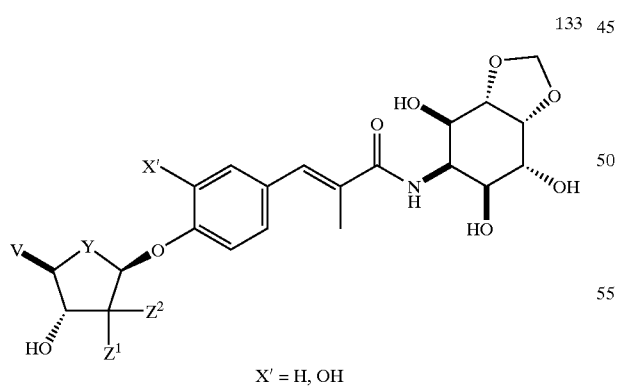

133

X' = H, OH

Compound 133, where V is a carbon-linked heterocycle, as described for the compound of formula 1, may be prepared from ketone 119, where $R^1$ and $R^2$ are taken together as =O, $R^{12}$ is $R^{15}CH_2$— and $R^{15}$ is any of the moieties in the definition of $R^{12}$ that may be attached through a methylene group. Synthesis of 133 is carried out by the method described for preparation of compound 60, where V is a carbon-linked heterocycle, as described for the compound of formula 1.

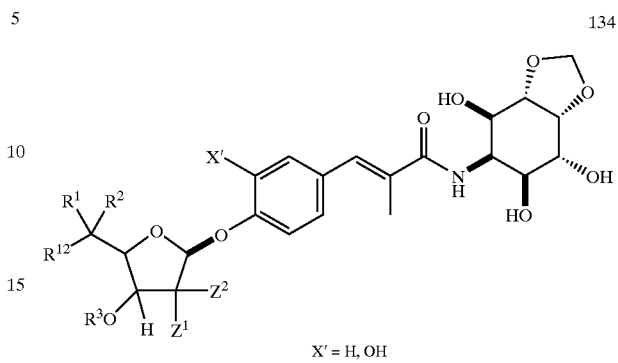

134

X' = H, OH

Compound 134 may be prepared from 117, where A is O. Treatment with potassium carbonate and $R^3OH$ at a temperature of 10° C. to 40° C. provides 135; an allyl protecting group may be introduced on the phenolic OH of 135 wherein X'=OH, if needed for further chemistry. Compound 134 may then be prepared using the chemistry described for elaboration of compound 117.

135

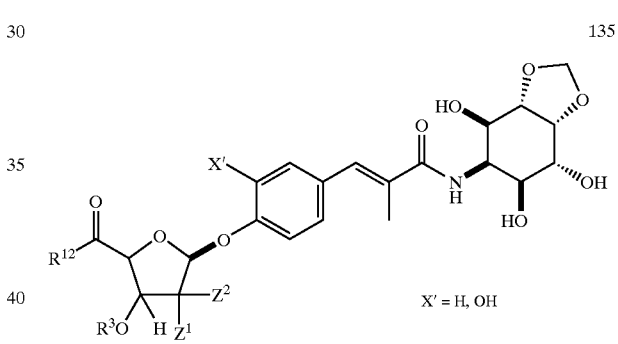

X' = H, OH

136

X' = H, OH

Compounds of the formula 136 may be prepared from 119, where $R^1$ and $R^2$ are taken together as =O, through conversion to 137 by the method of Jaynes (*Bioorg. Med. Chem. Lett.*, 1993, 3, 1531). Conversion of the hydroxyl groups of 137 to their allyl, silyl, benzyl or p-methoxybenzyl ethers can be followed by conversion of 137 to 136 by the chemistry described for elaboration of 117.

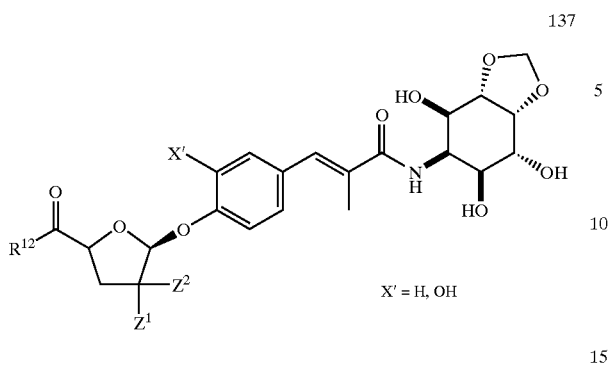

137

X' = H, OH

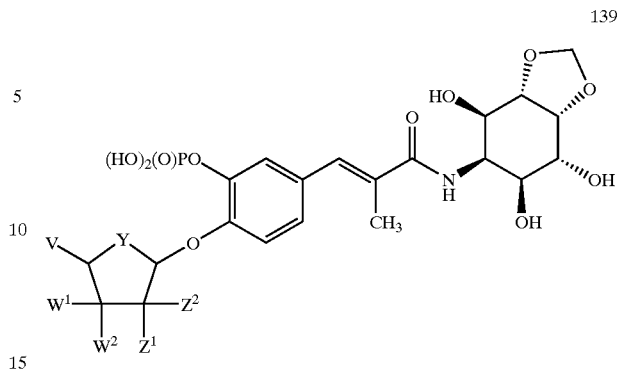

139

Representative prodrugs of the compounds of formula 1 may be prepared using the following chemistry:

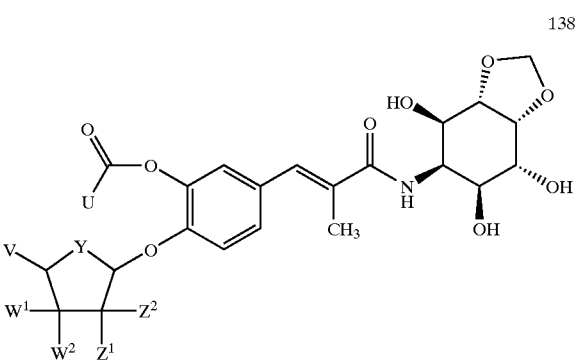

138

The compound of formula 1 in which X=OH is converted to the corresponding compound of formula 138, where UC(O)O— comprises an ester prodrug as described in the description of the invention, by reacting 1, in the presence of a base, such as sodium hydride or potassium hydride, with (a) an anhydride compound of the formula, (UC(O))$_2$O, or (b) an acylating agent of the formula, UC(O)L, wherein L is a leaving group such as a halide. If UC(O)— is an amino acid or polypeptide derivative, the amino group can be protected with a CBZ group or t-BOC group (see *Protective Groups in Organic Synthesis*, T. Greene and P. Wuts, Ed., John Wiley & Sons Ltd., New York, 1991). The reaction is stirred in an aprotic solvent, such as tetrahydrofuran, at a temperature range between about −20° C. to about 50° C., preferably between −20° C. and 10° C. If V, W$^1$, W$^2$, Z$^1$ or Z$^2$ contains a reactive group toward the reagents used in this transformation, it is necessary to protect such a group prior to this transformation and deprotect at the appropriate time. For example, a primary or secondary amino group might be protected as its 9-fluorenylmethoxy, benzyloxycarbonyl or tert-butoxycarbonyl carbamate. A carboxylic acid can be protected as an ester (see *Protective Groups in Organic Synthesis*, T. Greene and P. Wuts, Ed., John Wiley & Sons Ltd., New York, 1991 or *Protecting Groups*, P. Kocienski, Ed., Thieme Medical Publishers, New York, 1994).

The compound of formula 1 in which X is OH is converted to the corresponding compound of formula 139 by reacting 1, in the presence of a base, such as sodium hydride or potassium hydride, with (a) a compound of the formula, ((PhCH$_2$O)$_2$PO)$_2$O, or (b) a phosphorylating agent of the formula, (PhCH$_2$O)$_2$P(O)L, wherein L is chloro or bromo. The reaction is stirred in an aprotic solvent, such as tetrahydrofuran, at a temperature range between about −20° C. to about 50° C., preferably about −20° C. and 10° C. The resulting product is then treated with excess cyclohexadiene and Pd/C in ethanol at room temperature to provide a compound of structure 139. Its alkaline metal salts or alkaline earth metal salts can be prepared by treating 139 in an aqueous solution with, for example, NaOH or Ca(OH)$_2$. If V, W$^1$, W$^2$, Z$^1$ or Z$^2$ contains a reactive group toward the reagents used in this transformation, it is necessary to protect such a group prior to this transformation and deprotect at the appropriate time, as described for the preparation of compound 138.

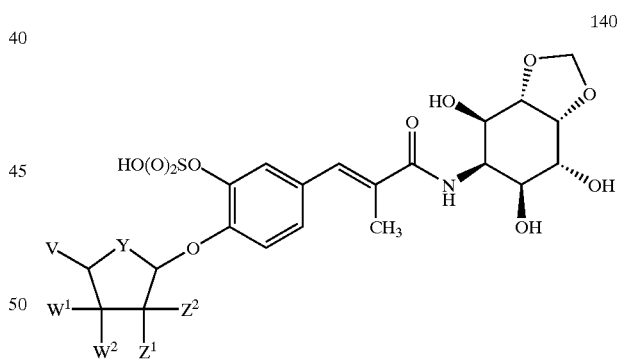

140

The compound of formula 1 in which X=OH is converted to the corresponding compound of formula 140 by reacting 1, in the presence of a base, such as sodium hydride or potassium hydride, with sulfur trioxide-DMF complex or sulfer trioxide-pyridine complex (*J. Chem. Soc., Perkin Trans.* 1. 1990, 1739). The reaction is stirred in an aprotic solvent, such as tetrahydrofuran, at a temperature range between about −20° C. to about 50° C., preferably between −15° C. to 15° C. Its alkaline metal salts or alkaline earth metal salts can be prepared by treating 140 in an aqueous solution with, for example, NaOH or Ca(OH)$_2$. If V, W$^1$, W$^2$, Z$^1$ or Z$^2$ contains a reactive group toward the reagents used in this transformation, it is necessary to protect such a group prior to this transformation and deprotect at the appropriate time, as described for the preparation of compound 138.

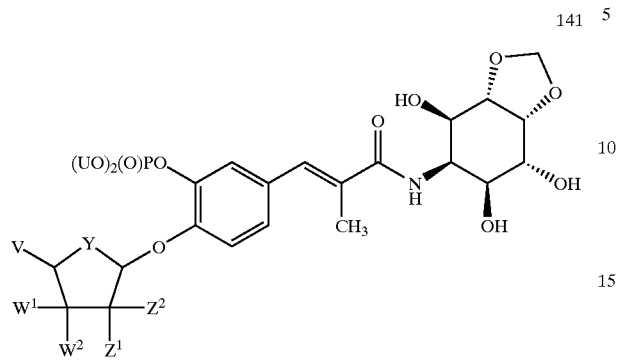

141

The compound of formula 1 in which X is OH is converted to the corresponding compound of formula 141, wherein (UO)$_2$P(O)O— comprises a phosphate prodrug as described in the description of the invention, by reacting 1, in the presence of a base, such as sodium hydride or potassium hydride, with (a) a compound of the formula, ((UO)$_2$PO)$_2$O, or (b) a phosphorylating agent of the formula, (UO)$_2$P(O)$_2$L, wherein L is chloro or bromo. The reaction is stirred in an aprotic solvent, such as tetrahydrofuran, at a temperature range between about –20° C. to about 50° C., preferably between –10° C. to 20° C. If V, W$^1$, W$^2$, Z$^1$ or Z$^2$ contains a reactive group toward the reagents used in this transformation, it is necessary to protect such a group prior to this transformation and deprotect at the appropriate time.

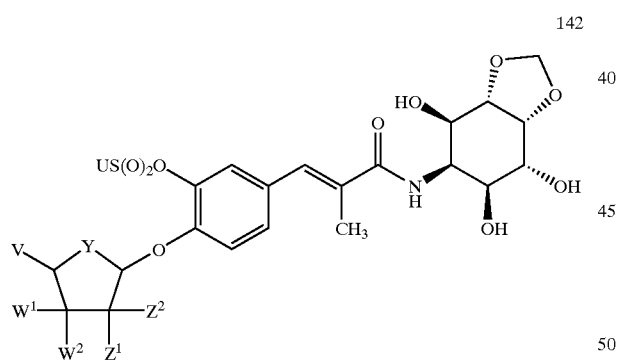

142

The compound of formula 1 is converted to the corresponding compound of formula 142, wherein US(O)$_2$O— is a sulfonate prodrug as described in the detailed description of the invention, by reacting 1, in the presence of a base, such as sodium hydride or potassium hydride, with a compound of the formula, (US(O)$_2$)$_2$O, or (b) US(O)$_2$L, wherein L is chloro or bromo. The reaction is stirred in an aprotic solvent, such as tetrahydrofuran, at a temperature range between about –20° C. to about 50° C., preferably between –10° C. to 20° C. If V, W$^1$, W$^2$, Z$^1$ or Z$^2$ contains a reactive group toward the reagents used in this transformation, it is necessary to protect such a group prior to this transformation and deprotect at the appropriate time.

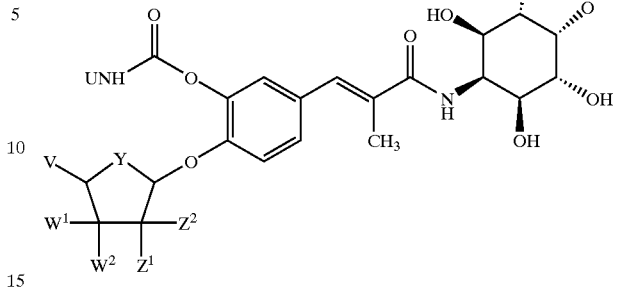

143

The compound of formula 1 where X is OH is converted to the corresponding compound of formula 143, wherein UNHC(O)O— is a carbamate prodrug as described in the detailed description of the invention, by reacting 1, in the presence of a base, such as sodium hydride or potassium hydride, with a compound of the formula, UN=C=O. The reaction is stirred in an aprotic solvent, such as tetrahydrofuran, at a temperature range between about –20° C. to about 50° C., preferably between 0° C. to 30° C. If U is H, a reagent of the formula ClSO$_2$N=C=O can be used, followed by treatment with water. If V, W$^1$, W$^2$, Z$^1$ or Z$^2$ contains a reactive group toward the reagents used in this transformation, it is necessary to protect such a group prior to this transformation and deprotect at the appropriate time.

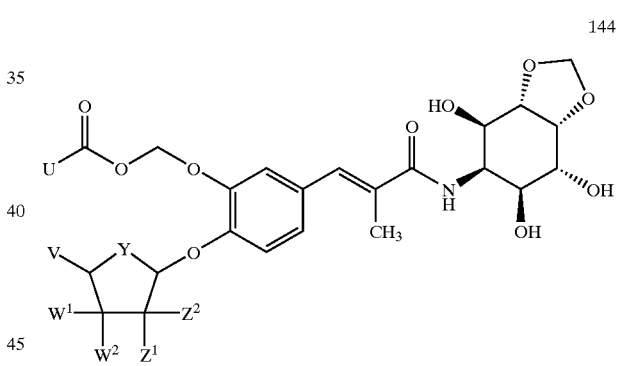

144

The compound of formula 1 in which X=OH is converted to the corresponding compound of formula 144, wherein UC(O)OCH$_2$O— is an (acyloxy)methyl ether as described in the detailed description of the invention, by reacting 1, in the presence of a base, such as sodium hydride or potassium hydride, with an acylating agent of the formula, UC(O)—OCH$_2$O—L (*J. Med. Chem.*, 1996, 39, 10). U may also be an N-protected amino acid residue or a polypeptide chain of two or more (e.g., two, three, or four) amino acid residues. For protection of the amino group a CBZ group or t-BOC group can be utilized (see *Protective Groups in Organic Synthesis*, T. Greene and P. Wuts, Ed., John Wiley & Sons Ltd., New York, 1991). The reaction is stirred in an aprotic solvent, such as tetrahydrofuran, at a temperature range between about –20° C. to about 50° C., preferably between –10° C. to 20° C. If V, W$^1$, W$^2$, Z$^1$ or Z$^2$ contains a reactive group toward the reagents used in this transformation, it is necessary to protect such a group prior to this transformation and deprotect at the appropriate time.

145

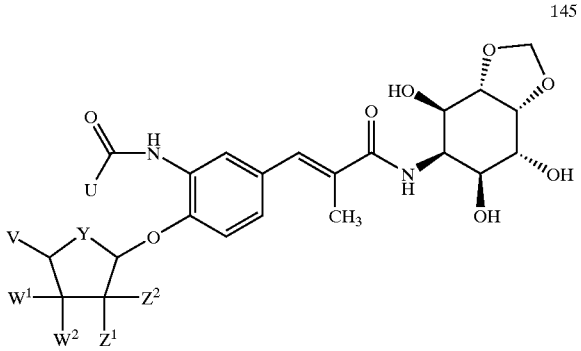

The compound of formula 1 in which X=NH$_2$ (compound 103) is converted to the corresponding compound of formula 145, wherein UC(O)NH— is an amide prodrug as described in the detailed description of the invention, by reacting 1, in the presence of excess base, such as triethylamine or pyridine, with (a) an anhydride compound of the formula, (UC(O))$_2$O, or (b) an acylating agent of the formula, UC(O)L, wherein L is chloro, bromo or imidazole. UC(O)— may also be an N-protected amino acid residue or a polypeptide chain of two or more (e.g., two, three, or four) amino acid residues. For protection of the amino group a CBZ group or t-BOC group can be utilized (see *Protective Groups in Organic Synthesis*, T. Greene and P. Wuts, Ed., John Wiley & Sons Ltd., New York, 1991). The reaction is stirred in an aprotic solvent, such as tetrahydrofuran, at a temperature range between about −20° C. to about 50° C., preferably about −10° C. to 20° C. The same transformation can be effected by treating a compound of structure 1 with a carboxylic acid of formula UC(O)OH in the presence of a coupling agent such as DCC, EDCI, or EEDQ. If V, W$^1$, W$^2$, Z$^1$ or Z$^2$ contains a reactive group toward the reagents used in this transformation, it is necessary to protect such a group prior to this transformation and deprotect at the appropriate time.

146

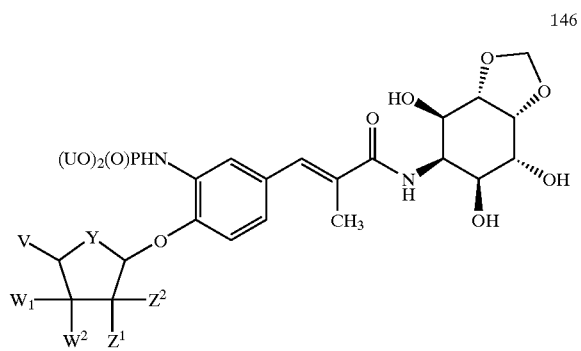

The compound of formula 1 in which X=NH$_2$ (compound 103) is converted to the corresponding compound of formula 146, wherein (UO)$_2$PONH— is a phosphoramide prodrug as described in the detailed description of the inventio, by reacting 1, in the presence of excess base, such as triethylamine or pyridine, with (a) a compound of the formula, ((UO)$_2$PO)$_2$O, or (b) a phosphorylating agent of the formula, (UO)$_2$P(O)L, wherein L is chloro or bromo. The same transformation may be effected by treating the compound of structure 1 where X=NH$_2$ with a reagent of formula (UO)$_2$P(O)OH in the presence of a coupling agent such as DCC or EDCI. If V, W$^1$, W$^2$, Z$^1$ or Z$^2$ contains a reactive group toward the reagents used in this transformation, it is necessary to protect such a group prior to this transformation and deprotect at the appropriate time. For example, a primary or secondary amino group might be protected as its 9-fluorenylmethyl, benzyloxycarbonyl or tert-butoxycarbonyl carbamate. A carboxylic acid can be protected as an ester (see *Protective Groups in Organic Synthesis*, T. Greene and P. Wuts, Ed., John Wiley & Sons Ltd., New York, 1991 or *Protecting Groups*, P. Kocienski, Ed., Thieme Medical Publishers, New York, 1994).

147

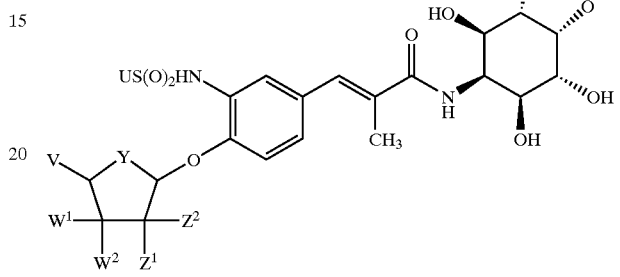

The compound of formula 1 in which X=NH$_2$ (compound 103) is converted to the corresponding compound of formula 147, wherein US(O)$_2$NH— is a sulfonamide prodrug as described in the detailed description of the invention, by reacting 1, in the presence of excess base, such as triethylamine or pyridine, with a compound of the formula, (US(O)$_2$)$_2$O, or (b) US(O)$_2$L, wherein L is chloro or bromo. The reaction is stirred in an aprotic solvent, such as tetrahydrofuran, at a temperature range between about −20° C. to about 50° C., preferably between −10° C. to 20° C. If V, W$^1$, W$^2$, Z$^1$ or Z$^2$ contains a reactive group toward the reagents used in this transformation, it is necessary to protect such a group prior to this transformation and deprotect at the appropriate time.

148

The compound of formula 1 where X=NH$_2$ is converted to the corresponding compound of formula 148, wherein UOC(O)NH— is a carbamate prodrug as described in the detailed description of the invention, by reacting 1, in the presence of excess base, such as triethylamine or pyridine, with chloroformate UOC(O)Cl. The reaction is stirred in an aprotic solvent, such as tetrahydrofuran, at a temperature range between about −20° C. to about 50° C., preferably between −10° C. to 20° C. If V, W$^1$, W$^2$, Z$^1$ or Z$^2$ contains a reactive group toward the reagents used in this transformation, it is necessary to protect such a group prior to this transformation and deprotect at the appropriate time.

149

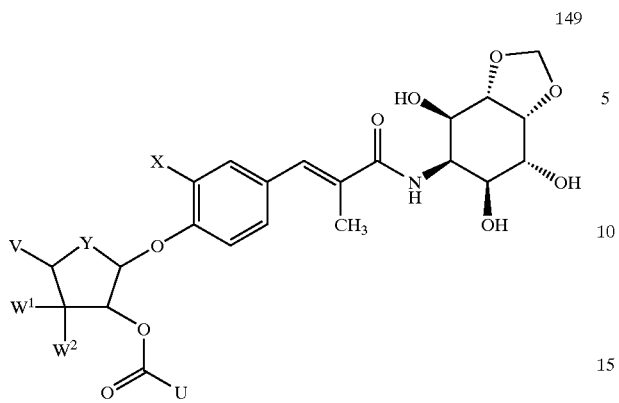

151

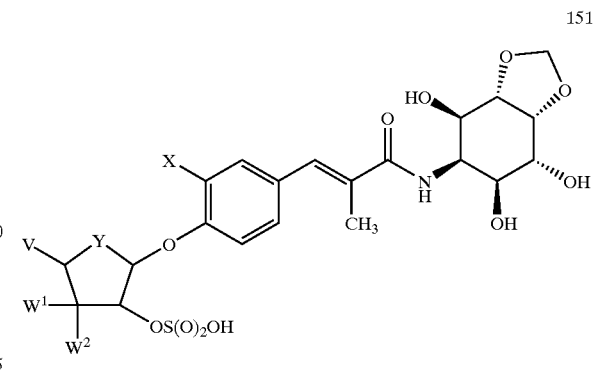

Compound 149, wherein UC(O)O— is an ester prodrug as described in the detailed description of the invention, may be prepared from compound 116 where X is H or protected OH. Conditions similar to those used in the preparation of 145 can be employed. Alternatively, compound 149 may be prepared from compounds 29, 69, 95 or 96 where $Z^1$ is H and $Z^2$ is OH. Introduction of the prodrug moiety using conditions similar to those described for preparation of 145 provides the functionalized furanose, which may be elaborated as described in earlier sections to provide 149. If V, $W^1$ or $W^2$ contains a reactive group toward the reagents used in this transformation, it is necessary to protect such a group prior to this transformation and deprotect at the appropriate time.

Compound 151 may be prepared from compound 116 where X is H or protected OH. The conditions similar to the preparation of 140 can be employed. Alternatively, compound 151 may be prepared from compounds 29, 69, 95 or 96 where $Z^1$ is H and $Z^2$ is OH. Introduction of the prodrug moiety using conditions similar to those described for preparation of 151 provides the functionalized furanose, which may be elaborated as described in earlier sections to provide 151. If V, $W^1$ or $W^2$ contains a reactive group toward the reagents used in this transformation, it is necessary to protect such a group prior to this transformation and deprotect at the appropriate time.

150

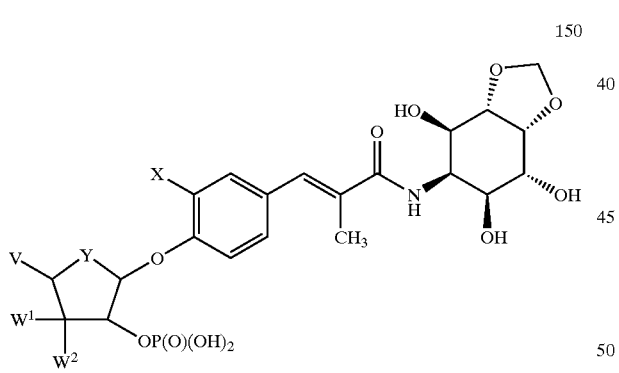

152

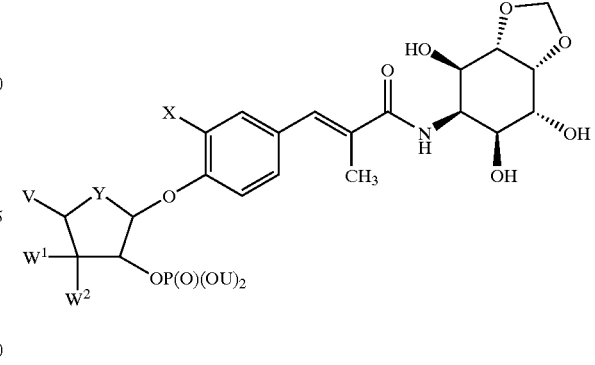

Compound 150 may be prepared from compound 116 where X is H or protected OH. Conditions similar to those used for the preparation of 139 can be employed. Alternatively, compound 150 may be prepared from compounds 29, 69, 95 or 96 where $Z^1$ is H and $Z^2$ is OH. Introduction of the prodrug moiety using conditions similar to those described for preparation of 139 provides the functionalized furanose, which may be elaborated as described in earlier sections to provide 150. If V, $W^1$ or $W^2$ contains a reactive group toward the reagents used in this transformation, it is necessary to protect such a group prior to this transformation and deprotect at the appropriate time.

Compound 152, wherein $(UO)_2P(O)O$— is a phosphate prodrug as defined in the description of the invention, may be prepared from compound 116 where X is H or protected OH. Conditions similar to the preparation of 141 can be employed. Alternatively, compound 152 may be prepared from compounds 29, 69, 95 or 96 where $Z^1$ is H and $Z^2$ is OH. Introduction of the prodrug moiety using conditions similar to those described for preparation of 141 provides the functionalized furanose, which may be elaborated as described in earlier sections to provide 152. If V, $W^1$ or $W^2$ contains a reactive group toward the reagents used in this transformation, it is necessary to protect such a group prior to this transformation and deprotect at the appropriate time.

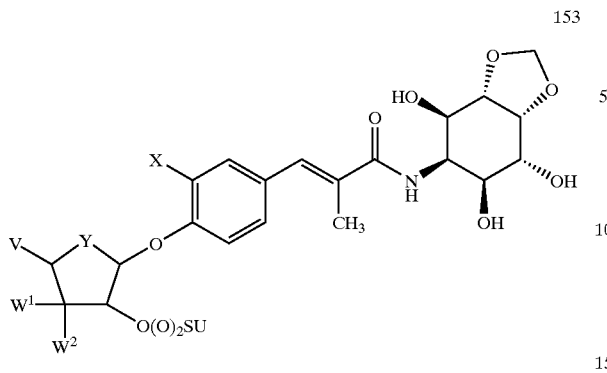

153

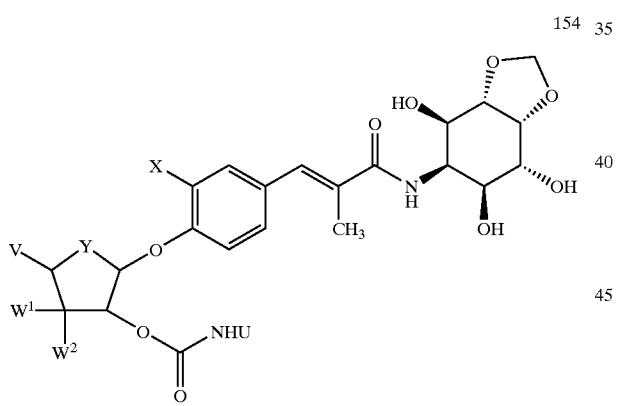

154

Compound 153, wherein US(O)₂O— is a sulfonate prodrug as described in the detailed description of the invention, may be prepared from compound 116 where X is H or protected OH. Conditions similar to the preparation of 142 can be employed. Alternatively, compound 153 may be prepared from compounds 29, 69, 95 or 96 where $Z^1$ is H and $Z^2$ is OH. Introduction of the prodrug moiety using conditions similar to those described for preparation of 142 provides the functionalized furanose, which may be elaborated as described in earlier sections to provide 153. If V, $W^1$ or $W^2$ contains a reactive group toward the reagents used in this transformation, it is necessary to protect such a group prior to this transformation and deprotect at the appropriate time.

Compound 154, wherein UNHC(O)O— is a carbamate prodrug as described in the detailed description of the invention, may be prepared from compound 116 where X is H or protected OH. Conditions similar to those used in the preparation of 143 can be employed. Alternatively, compound 154 may be prepared from compounds 29, 69, 95 or 96 where $Z^1$ is H and $Z^2$ is OH. Introduction of the prodrug moiety using conditions similar to those described for preparation of 143 provides the functionalized furanose, which may be elaborated as described in earlier sections to provide 154. If V, $W^1$ or $W^2$ contains a reactive group toward the reagents used in this transformation, it is necessary to protect such a group prior to this transformation and deprotect at the appropriate time.

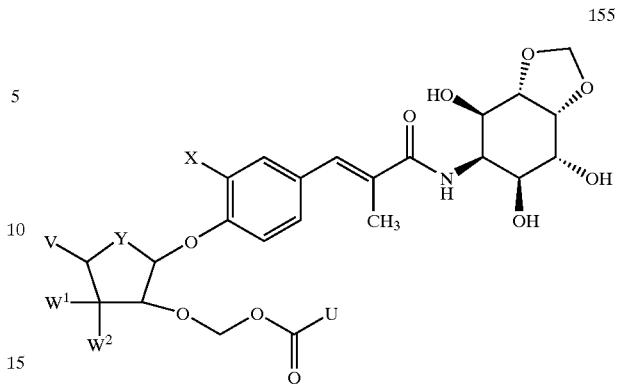

155

Compound 155, wherein UC(O)OCH₂O— is an acyloxymethyl prodrug as described in the detailed description of the invention, may be prepared from compound 116 where X is H or protected OH. Conditions similar to those used in the preparation of 143 can be employed. Alternatively, compound 155 may be prepared from compounds 29, 69, 95 or 96 where $Z^1$ is H and $Z^2$ is OH. Introduction of the prodrug moiety using conditions similar to those described for preparation of 143 provides the functionalized furanose, which may be elaborated as described in earlier sections to provide 155. If V, $W^1$ or $W^2$ contains a reactive group toward the reagents used in this transformation, it is necessary to protect such a group prior to this transformation and deprotect at the appropriate time.

Similarly, intermediates 18, 19, 26, 81, 86, 87 or 29, 69, 95, 96 where $W^1$ is H and $W^2$ is OH can be derivatized to incorporate an appropriate group and subsequently elaborated into the corresponding prodrugs modified at C3' (at $W^1$ or $W^2$). Intermediates 21, 30, 37, 42, and 44 can be derivatized to incorporate an appropriate group and subsequently elaborated into the corresponding prodrugs modified at V.

When V, $W^1$, $W^2$, $Z^1$ or $Z^2$ contains a primary or secondary amino group, it can be converted to a prodrug using the procedures described for compounds 145, 146, 147 and 148.

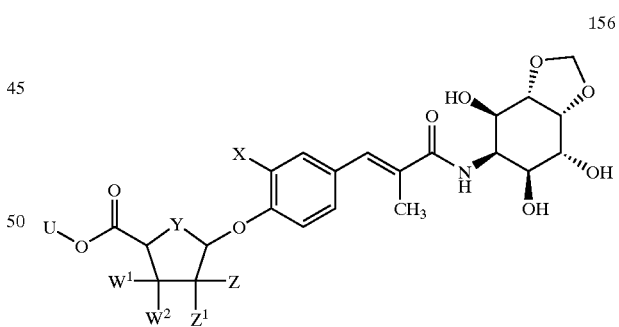

156

Compound 156, wherein UOC(O)— is an ester prodrug as described in the detailed description of the invention, may be prepared from compounds 112 and 123. Reaction of alcohol UOH with 112 or 123 in the presence of a coupling reagent such as DCC, EDCI, or EEDQ in dichloromethane or DMF at temperature ranging from 0° C. to 25° C. provides compound 156. Alternatively, U—L where L is chloro or bromo can be treated with 112 or 123 in the presence of Na₂CO₃ or K₂CO₃ in DMF (*Chem. Pharm. Bull.*, 1984, 2241). In the case where X, $W^1$, $W^2$, $Z^1$ or $Z^2$ contains a reactive group under the conditions employed for this transformation, it needs to be protected prior to this transformation and deprotected at the appropriate time (see *Protective Groups in Organic Synthesis*, T. Greene and P. Wuts, Ed., John Wiley & Sons Ltd., New York, 1991 or Protecting Groups, P. Kocienski, Ed., Thieme Medical Publishers, New York, 1994). Alternatively, intermediate 32 can be derivatized to incorporate the U group and be elaborated into compound 156 following the chemistry described in the earlier section.

The compounds of the present invention have asymmetric carbon atoms. Compounds having a mixture of isomers at one or more centers will exist as diastereomeric mixtures, which can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case, stoichiometric quantities of reagents are preferably employed in order to ensure completeness of reaction and maximum yields of the desired final product.

The antibacterial activity of the compounds of the present invention against bacterial pathogens is demonstrated by the compound's ability to inhibit growth of defined strains of pathogens.

Assay

The assay, described below, employs conventional methodology and interpretation criteria and is designed to provide direction for chemical modifications that may lead to compounds with antibacterial activity against susceptible and drug-resistant organisms including, but not limited to, beta-lactam, macrolide and vancomycin resistance. In the assay, a panel of bacterial strains is assembled to include a variety of target pathogenic species, including representatives of antibiotic resistant bacteria. Use of this panel enables the chemical structure/activity relationship to be determined with respect to potency and spectrum of activity. The assay is performed in microliter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

The activity of the compounds of the present invention also may be assessed in accord with Steers replicator technique which is a standard in vitro bacterial testing method described by Steers et al., *Antibiotics and Chemotherapy* 1959, 9, 307.

The in vivo activity of the compounds of the present invention can be determined by conventional animal protection studies well known to those skilled in the art, usually carried out in rodents.

According to one in vivo model, compounds are evaluated for efficacy in mouse models of acute bacterial infection. An example of one such in vivo system is provided as follows. Mice (CF1 mixed sex mice; 18–20 g) are allotted to cages upon their arrival, and allowed to acclimate 1-2 days before being placed in a study. The acute infection is produced by intraperitoneal inoculation of bacteria (*Staphylococcus aureus* strain 01A1095) suspended in 5% sterile hog gastric mucin. The inoculum is prepared by: growing the culture overnight at 37° C. on blood agar, harvesting the resulting surface growth with sterile brain heart infusion broth, and adjusting this suspension to a turbidity that when diluted 1:10 into 5% sterile hog gastric mucin would produce 100% lethality.

Mice (10 per group) are treated subcutaneously, at 0.5 hour and 4 hours after challenge. Appropriate non-treated (infected but not treated) and positive (vancomycin or minocycline, etc.) controls are included in each study. Percent survival is recorded after a 4-day observation period; the $PD_{50}$ (mg/kg/dose calculated to protect 50% of infected animals) is determined by the probit method.

The compounds of the present invention, and the pharmaceutically acceptable salts hereof (hereinafter "the active compounds"), may be administered through oral, parenteral, opical, or rectal routes in the treatment of bacterial and protozoal infections. In general, these compounds are most desirably administered in dosages ranging from about 0.2 mg per kg body eight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 3 mg/kg/day to about 60 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous ethanol or propylene glycol may be employed. Use of a cyclodextrin derivative such as β-cyclodextrin sulfobutyl ether, sodium salt (see U.S. Pat. No. 5,134,127) may also be advantageous. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is further described and exemplified in the preparations and examples described below. In the preparations and examples, "rt" means room or ambient temperature which is a temperature within the range of about 20–25° C.

Experimental procedures

Experimental Procedures For Examples

In cases where final purification was effected using silica gel chromatography with an eluant system containing more than 10% methanol, the chromatographed product was taken up in 89:10:1 chloroform: methanol: concentrated ammonium hydroxide and filtered, or dissolved in methanol and passed through a 0.45 $\mu$M filter. Removal of solvent in vacuo provided the final product.

Purifications were generally carried out by silica gel chromatography. When crude products were insoluble in the chloroform/methanol eluant system, they were generally preadsorbed onto silica gel through addition of dry silica gel to a methanol solution of the product, followed by complete removal of solvent. When crude products were insoluble in the ethyl acetate/hexanes eluant system, they could be loaded as solutions in dichloromethane. Column elution in many cases was run as a step gradient.

Preparation of Hydroxylamine Reagents for Synthesis of Oxime Ethers

The hydroxylamine reagents employed were either commercially available (generally as an acid salt), or prepared from the corresponding alcohol or halide via the methods outlined below:

1) Preparation of Phthalimide-protected Hydroxylamines:

From the alcohol:

A Mitsunobu reaction with diethyl azodicarboxylate and triphenylphosphine was used to couple N-hydroxyphthalimide and the alcohol starting material (*Synthesis*, 1976, 682).

From the bromide or chloride:

Reaction of N-hydroxyphthalimide (1 equivalent) with the halide starting material (1.2–2 equivalents) was carried out in DMSO solution, using potassium carbonate (0.6–2 equivalents) as base. The reactions were carried out at room temperature, generally by stirring overnight. Pouring the reaction mixture into cold water provided a precipitate, which was filtered to give the phthalimide-protected hydroxylamine. In many cases, this material was directly deprotected; silica gel chromatography can also be employed, using ethyl acetate-hexane mixtures, to purify the phthalimide-protected hydroxylamine.

2) Removal of the Phthalimide Protecting Group to Provide the Hydroxylamine:

Deprotection of the phthalimide-protected hydroxylamine was effected by reaction with hydrazine hydrate (1–2 equivalents) in ethanol solution, at temperatures ranging from room temperature to reflux, for periods ranging from 30 minutes to overnight. The reaction mixture was filtered, and the filtrate concentrated. This crude product can be taken to the next step as is, or can be further purified. Mixing the crude product with chloroform, removing solids by filtration and removal of solvent from the filtrate removes additional phthalhydrazide. Alternatively, the crude product was dissolved in 1N hydrochloric acid, and washed with ether or ethyl acetate. The aqueous layer was basified with saturated potassium carbonate solution and extracted with ether or ethyl acetate. Drying of the final organic layers and removal of solvent provided the hydroxylamine product. N-Methyl-O-benzylhydroxylamine was prepared according to the procedure reported in *J. Org. Chem.*, 1981, 46, 5438.

Preparation of Example 1–6

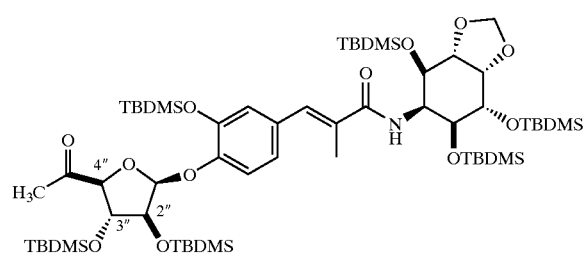

A solution of hygromycin A, tert-butyldimethylsilyl chloride (12 equivalents), and imidazole (12 equivalents) in DMF (hygromycin concentration 0.25 M) was stirred at 80° C. for 20 hours. After removal of the DMF under reduced pressure, the resulting residue was diluted with water and extracted with diethyl ether. The combined ether extracts were washed with water, then saturated sodium chloride solution, dried over sodium sulfate, filtered, and concentrated. The crude product was purified by silica gel chromatography, eluting with 10% ethyl acetate/ hexanes.

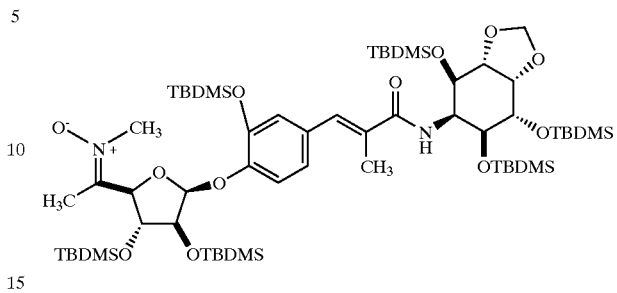

Compound A1 was dissolved in ethanol (0.1 M) and treated with methylhydroxylamine hydrochloride (1.5 equivalents) and sodium acetate (2.5 equivalents). The reaction mixture was stirred at room temperature for 18 hours, then poured into water. This mixture was treated with saturated sodium bicarbonate solution until the pH rose to 8, then extracted with chloroform. The combined organic layers were dried over magnesium sulfate and concentrated to provide A2.

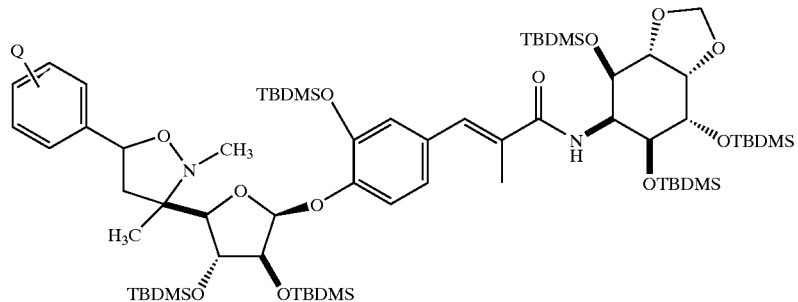

A solution of A2 in toluene (0.15–0.18 M) was treated with the appropriate styrene (3 equivalents) and the reaction mixture heated at reflux for 18–72 hours, until thin layer chromatography indicated that most of the starting material had been consumed. Removal of solvent in vacuo and purification by silica gel chromatography using 3–15% ethyl acetate in hexane provided the product A3. In some cases, both diastereomers around the phenyl group could be isolated.

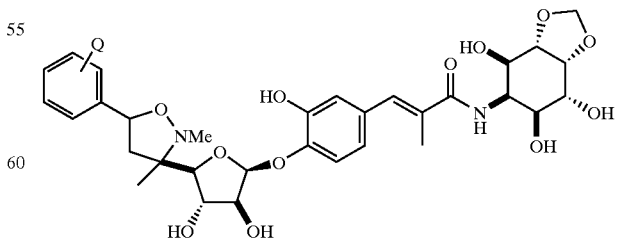

A solution of A3 in tetrahydrofuran (0.1 M) was treated with two volumes of an 8:2:1 mixture of tetrahydrofuran- :pyridine:70% HF in pyridine, and allowed to stir at room temperature for one to four days, until tlc indicated the reaction had substantially progressed. Solid sodium bicarbonate was added, giving a thick slurry, which was diluted with ethyl acetate and treated with additional sodium bicarbonate until gas evolution had ceased. The mixture was filtered, and the filtrate concentrated and purified by silica gel chromatography (eluant: 3–20% methanol in chloroform) to provide the compounds of Examples 1–6.

Preparation of Examples 7–11

A5

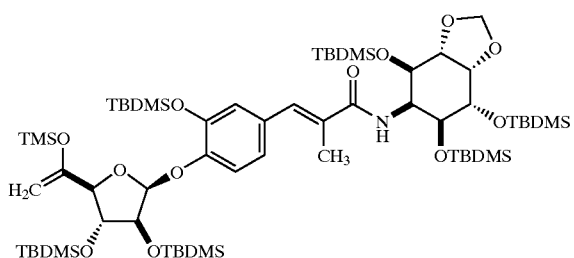

A solution of persilyl hygromycin A1 was dissolved in methylene chloride (0.06 M), treated with triethylamine and cooled to –50° C. Trimethylsilyl triflate (10 equivalents) was added dropwise over 15 minutes. After 5 hours, the reaction was quenched by addition of saturated ammonium chloride solution. The organic layer was concentrated in vacuo, and the residue was dissolved in ethyl acetate, washed with water, dried over sodium sulfate and concentrated in vacuo to provide crude A5, which was used without further purification.

A6

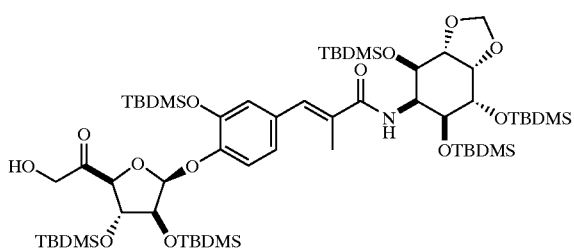

A solution of A5 in dichloromethane (0.1 M) was treated with m-chloroperbenzoic acid (1.1 equivalents) and allowed to stir at room temperature for 24 hours. The solvent was removed in vacuo, and the residue was dissolved in THF (0.2 M), and treated with hydrochloric acid (0.2 N, equal volume). After 4.5 hours at room temperature, the reaction was treated with saturated sodium bicarbonate solution, and concentrated in vacuo. The aqueous layer was extracted with ethyl acetate, and the combined organic layers were dried over sodium sulfate, filtered and concentrated to provide crude A6. Purification was carried out by silica gel chromatography (eluant: 3–10% ethyl acetate in hexanes).

A7

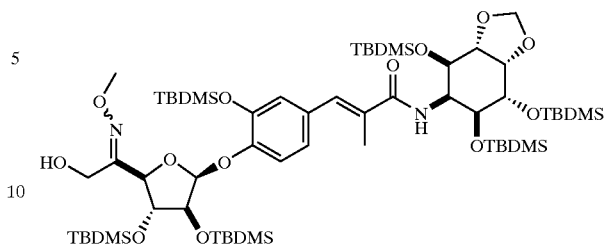

A solution of compound A6 in methanol (0.04 M) was treated with N-methyl hydroxylamine hydrochloride (2.3 eq.) and potassium carbonate (1.0 eq.) and allowed to react at room temperature for 18 hours. The solvent was removed in vacuo and the residue purified by silica gel chromatography (eluant: 5% 1–20% ethyl acetate in hexanes). Product A7 was obtained as a mixture of E and Z isomers around the oxime ether.

A8

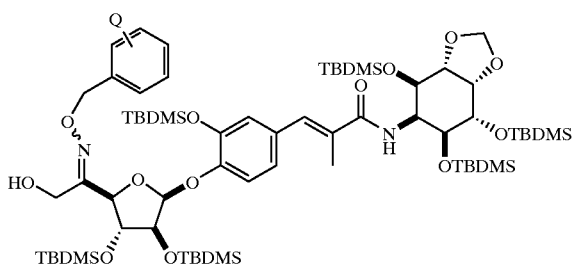

A solution of A6 in methanol (0.05–0.1M) was treated with the benzyl hydroxylamine (2 eq.) and allowed to stir at room temperature for 18–72 hours. In some cases, triethylamine hydrochloride (1.1 eq.) was used in the reaction. The solvent was removed in vacuo, and the crude material (a mixture of E and Z isomers around the oxime ether) was purified by silica gel chromatography (eluant, 5%–15% ethyl acetate in hexanes).

A9

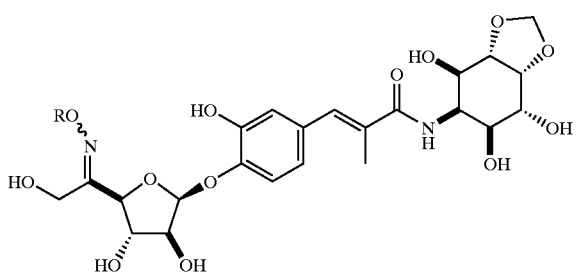

Removal of the silyl protecting groups from compound A7 and A8 was carried out by treating a solution of A7 or A8 in THF with pyridine and 70% HF in pyridine such that the final concentration of substrate was 0.01 M, and the solvent composition was 8:2:1 tetrahydrofuran:pyridine:70% HF in pyridine. The reaction mixture was stirred at room temperature for up to 5 days, until tlc indicated that the reaction had substantially progressed to product. In some cases, the reaction mixture was heated at 45° C. for 4.5 hours, then at room temperature for 48 hours. Solid sodium bicarbonate was added, and the mixture was filtered. Concentration of the filtrate gave crude product, which was purified by silica gel chromatography (eluant 3–10% methanol in chloroform). Product A9 was obtained as a mixture of E and Z isomers around the oxime ether.

Preparation of Example 12

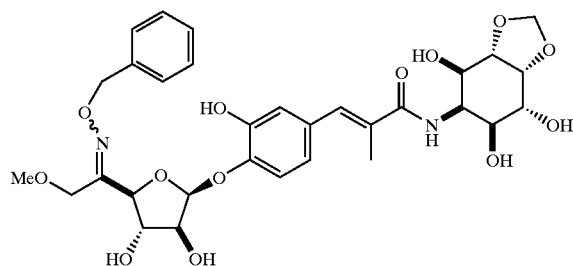

A10

Compound A6 was converted to its benzyl oxime ether by the procedure described for preparation of A8. This oxime ether was dissolved in THF (0.1 M) and treated with sodium hydride (1.2 eq.), followed by addition of methyl iodide (4 eq.). The reaction was allowed to stir for 18 hours at room temperature. Saturated aqueous ammonium chloride was added to the reaction, and volatiles were removed in vacuo. The aqueous mixture was extracted with chloroform, and the combined organic layers were dried over sodium sulfate, filtered and concentrated in vacuo. Purification was effected via silica gel chromatography, eluting with 5% to 6% ethyl acetate in hexanes. Removal of the silyl groups was carried out as described for preparation of A9, to provide the compound of Example 12.

Preparation of Examples 13–15

A solution of A7 (0.1–0.5 M) and the phenol reagent (2.7 eq.) in toluene was treated with triphenylphosphine (2.7 eq.) and diethyl azodicarboxylate (2.5 eq.). After 18 hours, the reaction was diluted with ethyl acetate and washed with phosphate buffer (pH 7). The aqueous layer was extracted with ethyl acetate and the combined organic layers were washed with saturated sodium chloride solution and dried over magnesium sulfate. Removal of solvent in vacuo gave a crude product which was purified by column chromatography (1% to 20% ethyl acetate in hexanes) to provide the α-phenoxy oxime ether.

Removal of the silyl protecting groups was carried out by treating a solution of the protected a-phenoxy oxime ether in THF with pyridine and 70% HF in pyridine such that the final concentration of substrate was 0.01 M, and the solvent composition was 8:1:1 tetrahydrofuran:pyridine:70% HF in pyridine. The reaction was allowed to stir at room temperature for 18 hours. Solid sodium bicarbonate was added, giving a thick slurry, which was diluted with ethyl acetate and treated with additional sodium bicarbonate until gas evolution had ceased. The mixture was filtered, and the filtrate concentrated and purified by silica gel chromatography (eluant: 3–10% methanol in chloroform) to provide the compounds of Examples 13–15 as a mixture of E and Z isomers around the oxime ether.

Preparation of Examples 16–22

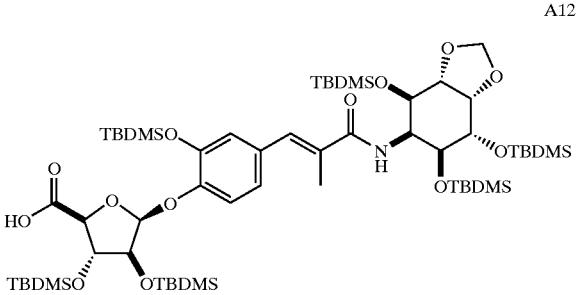

A12

Compound A6 was dissolved in benzene (0.05 M) and treated with water (2 eq) and lead tetraacetate (1.0 eq.). After 2 hours at room temperature, water was added to the reaction, and the mixture was extracted with ethyl acetate. The combined organic layers were washed with saturated sodium chloride solution, dried over sodium sulfate, filtered and concentrated in vacuo. This material can be used directly in further reactions, or be purified by silica gel chromatography (eluant: 5% to 10%, then 75% ethyl acetate in hexanes).

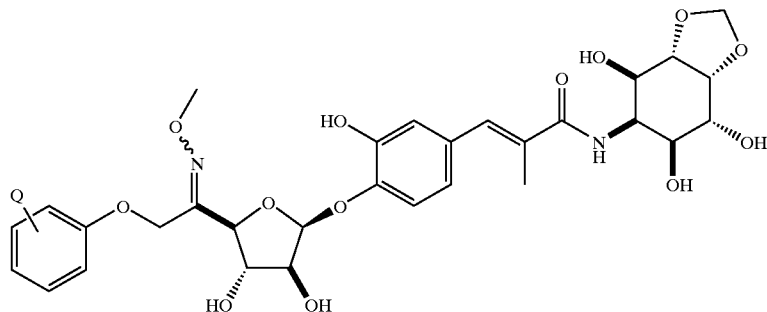

A11

A13

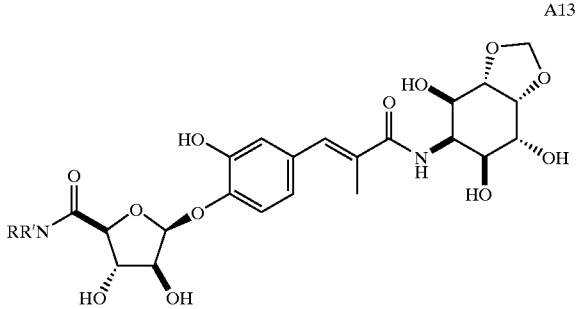

Compound A12 was dissolved in methylene chloride (0.1–0.15 M) and treated with the appropriate amine or hydroxylamine (1.1–1.5 eq.), 1-hydroxybenzotriazole (2 eq.) and 30 triethylamine (1 eq.). After addition of EDC (1 eq), the reaction was allowed to stir for 4–24 hours at room temperature. The reaction was then quenched by addition of water; the layers were separated and the aqueous layer was extracted with additional methylene chloride. The combined organic layers were dried over sodium sulfate and concentrated in vacuo to provide the crude product. Purification was effected by silica gel chromatography (6%–13% ethyl acetate in hexanes) to provide the persilylated amide or hydroxamate.

Removal of the silyl protecting groups was carried out using the same procedure as above for preparation of compound A4, to provide the compounds of Examples 16–22.

Preparation of Examples 23–25

A14

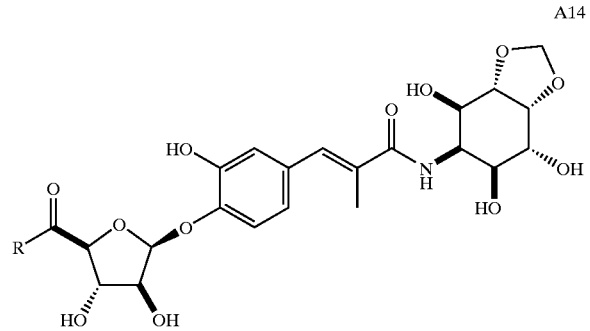

Compound A12 was dissolved in THF (0.2 M) and treated with carbonyl diimidazole (3 eq.). After 1 hour at room temperature, an equal volume of methylene chloride was added, followed by triethylamine (10 eq.) and N,O-dimethylhydroxylamine hydrochloride (5 eq.). The reaction was allowed to stir at ambient temperature for 1.5 hours, then poured into water and extracted with ethyl acetate. The combined organic layers were washed with brine, dried over sodium sulfate, filtered and concentrated in vacuo to give crude Weinreb amide. Purification was carried out by silica gel chromatography (eluant: 10% ethyl acetate in hexanes).

The Weinreb amide was dissolved in THF (0.4–0.8 M), cooled to 0° C., and treated with the appropriate Grignard reagent or organolithium reagent (1–6 eq.). The reaction mixture was allowed to warm to room temperature. After 34 hours the reaction mixture was poured into 0.01–0.1 N aqueous HCl and extracted with ethyl acetate. The combined organic layers were washed with saturated sodium chloride solution, dried over sodium sulfate, filtered and concentrated to provide the crude ketone. Purification was carried out by silica gel chromatography (eluant: 7%–10% ethyl acetate in hexanes).

Removal of the silyl protecting groups was carried out by dissolving the ketone product in tetrahydrofuran (0.1 M) and treating it with 2–5 volumes of an 8:1:1 mixture of tetrahydrofuran:pyridine:70% HF in pyridine. The reaction was allowed to stir at room temperature for one to four days, until tlc indicated the reaction had substantially progressed. Solid sodium bicarbonate was added, giving a thick slurry, which was diluted with methanol and filtered. Concentration of the filtrate gave a residue which was purified by silica gel chromatography (eluant: 5%–15% methanol in chloroform) to provide the compounds of Examples 23–25.

Preparation of Examples 26–31

A15

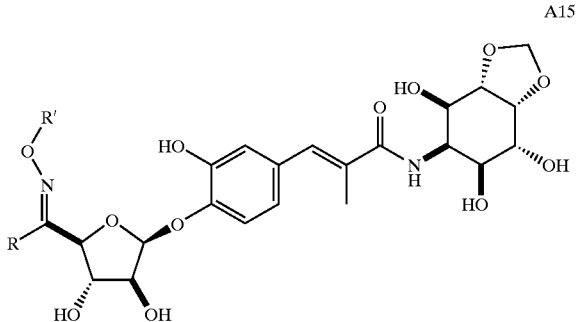

Ketone A14 was dissolved in methanol (0.02–0.1 M), treated with the appropriate hydroxylamine (3 eq.) and stirred at room temperature for 18 hours. In the case of the p-fluorophenyl ketone, the reaction was carried out at 50° C. for 10 hours. The reaction was then adsorbed onto silica gel and purified by silica gel chromatography (eluant 5–15% methanol in chloroform), to provide in some cases both E and Z oxime ether isomers of the compounds of Examples 26–31.

Preparation of Examples 32–36

A16

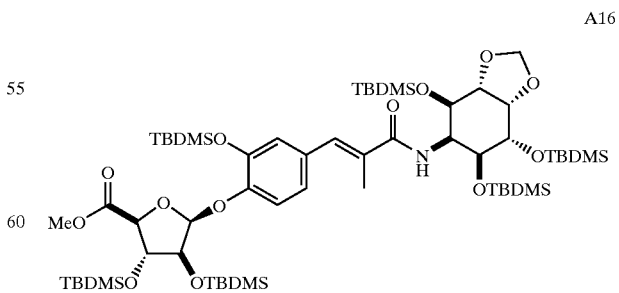

Compound A6 was dissolved in 2:1 benzene:methanol (0.1 M) and treated with lead tetraacetate (1.5 eq.). After 2 hours at 0° C., saturated sodium bicarbonate solution was added to the reaction. The mixture was filtered and volatiles removed in vacuo. The remaining aqueous mixture was extracted with chloroform, and the combined organic layers were dried over sodium sulfate. Filtration and concentration in vacuo provided A16, which was used without purification.

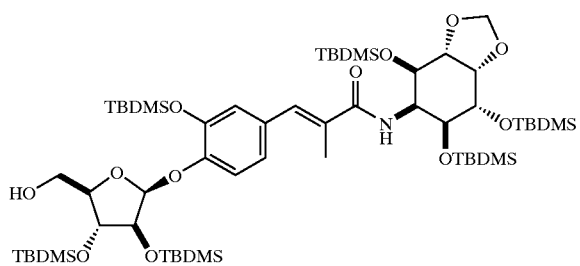

A17

A solution of compound A16 in THF (0.1 M) was cooled to 0° C. and treated with a solution of lithium borohydride in THF (2.0 M, 5 eq.). The reaction was allowed to warm to room temperature. After 48 hours, the reaction was poured into saturated aqueous ammonium chloride solution and extracted with methylene chloride. The combined organic layers were dried over sodium sulfate, filtered and concentrated in vacuo. Purification by silica gel chromatography (eluant: 15% ethyl acetate in hexanes) provided compound A17.

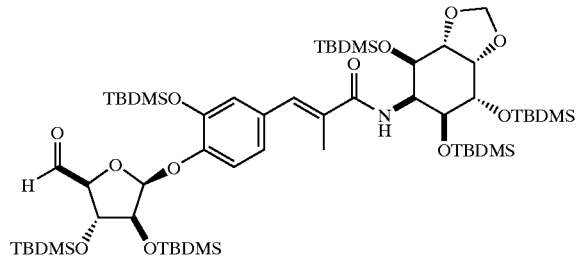

A18

A solution of oxalyl chloride (2 eq.) in methylene chloride (0.15 M) was cooled to −78° C., treated with DMSO (4 eq) in methylene chloride (4.2 M), and allowed to stir for 5 minutes. Compound A17 (1 eq.) in methylene chloride (0.2 M) was added dropwise at −78° C. over 5 minutes. The reaction was stirred an additional 25 minutes at −78° C., then treated with triethylamine (10 eq), ad allowed to warm to room temperature. After 40 minutes, the reaction was poured into water and extracted with methylene chloride. The combined organic layers were washed with saturated sodium chloride solution, dried over sodium sulfate, filtered and concentrated. Purification was carried out via silica gel chromatography (eluant: 10% ethyl acetate in hexanes) to provide compound A18.

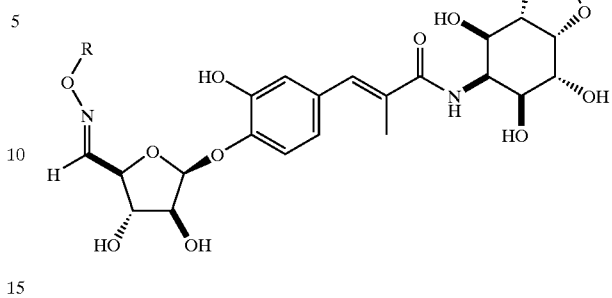

A19

A solution of compound A18 in methanol (0.06–0.15 M) was treated with the appropriate hydroxylamine reagent (2 eq) and triethylamine hydrochloride (1 eq) and stirred at 45–50° C. for 2–10 hours. Removal of solvent and purification of the residue by silica gel chromatography (eluant 12%–15% ethyl acetate in hexanes) gave the persilylated oxime ether. The silyl groups were removed via subjection of this intermediate in tetrahydrofuran (0.1 M) to 2–4 volumes of 8:2:1 tetrahydrofuran:pyridine:70% HF in pyridine. The reaction was allowed to stir at room temperature for 4 days. In some cases, the reaction was heated at 45–50° C. for 10 hours, then allowed to stir at room temperature for 8 hours. Solid sodium bicarbonate was added, and the mixture was diluted with THF and methanol and filtered. Purification via silica gel chromatography (eluant: 5%–15% methanol in chloroform) provided the compounds of Examples 32–36 as a mixture of isomers around the oxime ether.

Preparation of Example 37

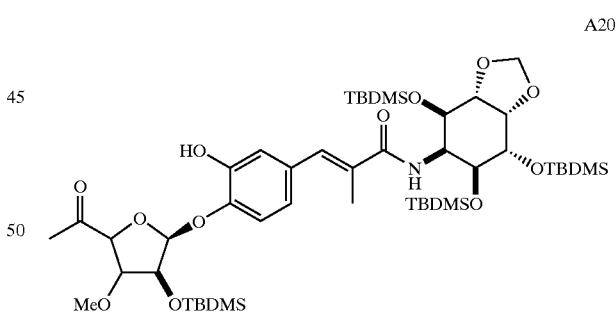

A20

A solution of compound A1 in methanol (0.1M) was treated with potassium carbonate (1.1 eq.). After 24 hours at room temperature, the reaction was concentrated in vacuo, and the residue taken up in phosphate buffer (pH 7). The aqueous mixture was extracted with ethyl acetate, and the combined organic layers were dried over sodium sulfate and evaporated to dryness. Purification was effected via silica gel chromatography (eluant 20% ethyl acetate in hexanes) to provide compound A20 as a minor product and predominantly one isomer.

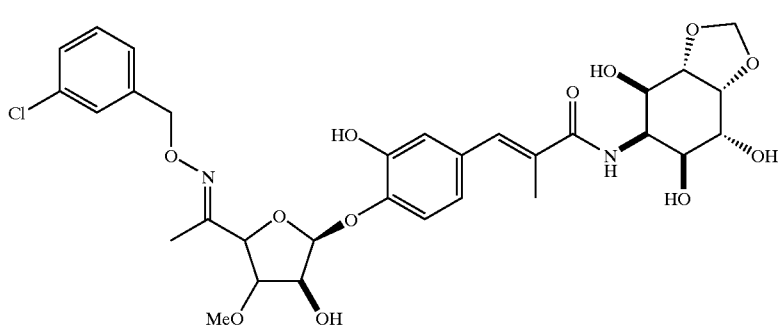

A21

A solution of A20 in methanol (0.15 M) was treated with O-(3-chlorobenzyl)hydroxylamine (1.2 eq.) and allowed to stir at room temperature for 4 days. The solvent was removed in vacuo, and the crude material was purified by silica gel chromatography (eluant, 8% ethyl acetate in hexanes) to provide the silylated benzyl oxime ether. Removal of the silyl groups was carried out as described for preparation of compound A9. The compound of Example 37 was obtained as predominantly one isomer.

Preparation of Examples 38 and 39

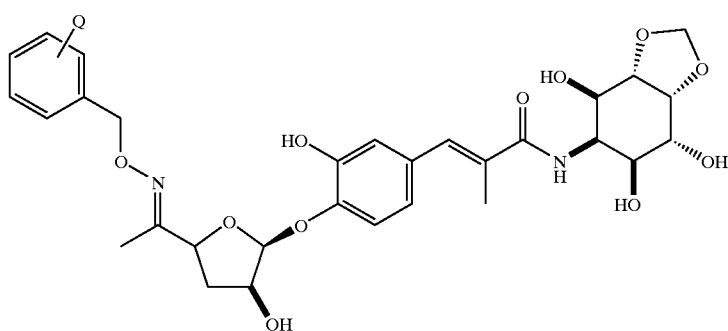

A22

3"-Deoxy hygromycin A, as a mixture of isomers at C-4", was prepared according to the method described in *Bioorg. & Medicinal Chem. Lett.*, 1993, 3, 1531. Oxime ether formation was carried out as described in the preparation of compound A8, except that 3 equivalents of the hydroxylamine were used. The compounds of Examples 38 and 39 were obtained as E and Z isomers around the oxime center, and as a mixture of isomers at CA4".

Preparation of Example 40

A solution of A6 (1 eq.) and imidazole (4.9 eq.) in dimethylformamide (0.1 M) was treated with tert-butyidimethylsilyl chloride (4.9 eq.) at 60° C. and allowed to stir for 2.5 hours. The reaction was cooled to room temperature, diluted with 1:1 hexanes:ether and washed with pH 7.0 phosphate buffer solution (0.05 M), water and finally saturated sodium chloride solution. The organic layer was dried over magnesium sulfate, filtered and concentrated to provide crude A23. The crude product was purified by silica gel chromatography, eluting with a step gradient of 2.5% ethyl acetate in hexanes to 20% ethyl acetate in hexanes.

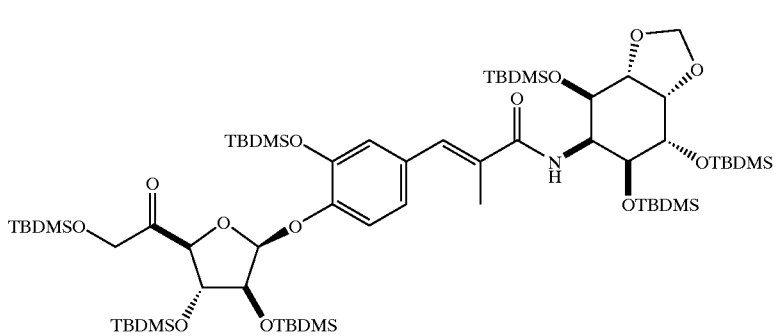

A23

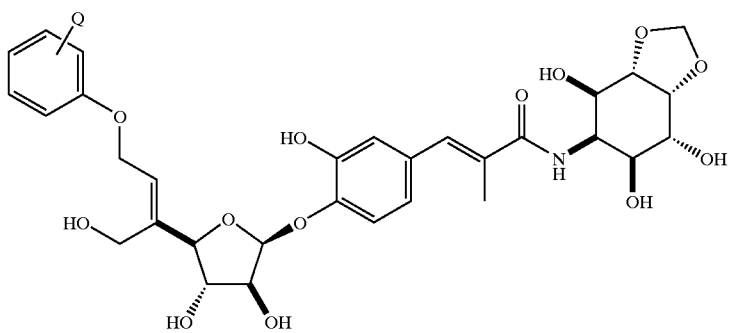

A24

A solution of ethyl (trimethylsilyl)acetate (4 eq.) in THF (roughly 0.4 M in ethyl (trimethylsilyl)acetate) at −78° C. was treated with lithium diisopropylamide (3.5 eq.). After 30 minutes a solution of A23 (1 eq.) in THF (roughly 0.5 M) was added. After 15 minutes the reaction was diluted with ethyl acetate and saturated ammonium chloride solution. The organic layer was washed with saturated ammonium chloride solution, then saturated sodium chloride solution, dried over magnesium sulfate, filtered and concentrated.

A solution of this crude ethyl ester (1 eq.) in dichloromethane (roughly 0.1M) at −78° C. was treated with diisobutyl aluminum hydride (8 eq.). After treatment with saturated Rochelle's salt and warming to room temperature the reaction was diluted with dichloromethane, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes to provide pure E allylic alcohol.

Silylated hygromycin allyl alcohol (1 eq.) in toluene (roughly 0.03 M) was treated with the appropiate phenol (3–5 eq.), triphenylphosphine (3–5 eq.) and diethyl azodicarboxylate (3–5 eq). After completion (roughly 30 minutes to 2 hours) the reactions were diluted with ethyl acetate and 0.05 M pH 7.0 phosphate buffer solution. The organic layer was washed with saturated sodium chloride solution, dried over magnesium sulfate, filtered, and concentrated.

Deprotection by the following method provided Example 40:

The silyl groups were removed by treatment of a solution of polysilylated hygromycin A derivative in THF (roughly 0.1M) with a solution of HF.pyridine/pyridine/THF for 20 to 50 hours at room temperature. The reactions were diluted with ethyl acetate, treated with solid NaHCO$_3$, filtered, concentrated and purified by silica gel chromatography, eluting with a step gradient of 5% methanol in dichloromethane to of 33% methanol in dichloromethane.

Preparation of Examples 41–43

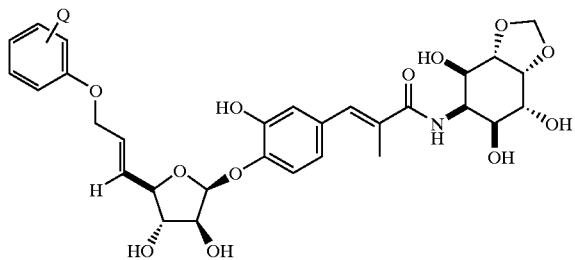

A25

A solution of A18 (1 eq.) and carboethoxymethylene triphenylphosphorane (2.5 eq.) in dimethylformamide (roughly 0.5 M) was allowed to stir at 50° C. for 15 hours and allowed to cool to room temperature. The reaction was diluted with hexanes and diethyl ether (roughly 1:1), washed with water, then saturated sodium chloride solution, dried over magnesium sulfate, filtered and concentrated.

A solution of the crude ethyl ester (1 eq.) in dichloromethane (roughly 0.1M) at −78° C. was treated with diisobutyl aluminum hydride (5 eq.). After treatment with saturated Rochelle's salt and warming to room temperature the reaction was diluted with dichloromethane, washed with pH 7.0 phosphate buffer solution (0.05 M), saturated ammonium chloride, saturated sodium chloride, and then dried over magnesium sulfate, filtered, and concentrated. The crude product was purified by silica gel chromatography, eluting with a step gradient of 5% ethyl acetate in hexanes to 20% ethyl acetate in hexanes to provide pure E allylic alcohol.

Silylated hygromycin allyl alcohol (1 eq.) in toluene (roughly 0.03 M) was treated with the appropiate phenol (3–5 eq.), triphenylphosphine (3–5 eq.) and diethyl azodicarboxylate (3–5 eq). After completion (roughly 30 minutes to 2 hours) the reactions were diluted with ethyl acetate and 0.05 M pH 7.0 phosphate buffer solution. The organic layers were washed with saturated sodium chloride solution, dried over magnesium sulfate, filtered, and concentrated.

The crude allyl ethers were deprotected and purified by the method used in preparation of compound A24, to provide the compounds of Examples 41–43.

Preparation of Example 44

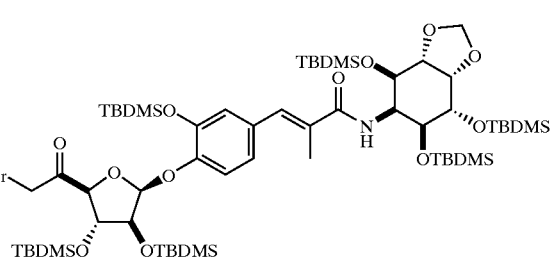

A26

A solution of A5 (1 eq.) and sodium bicarbonate (2.3 eq.) in tetrahydrofuran (0.1 M) at 4° C. was treated with N-bromosuccinimide (2 eq.) in tetrahydrofuran (0.5 M). After 30 minutes the reaction was diluted with ethyl acetate and washed with saturated ammonium chloride, water and saturated sodium chloride and then filtered, concentrated to afford A26.

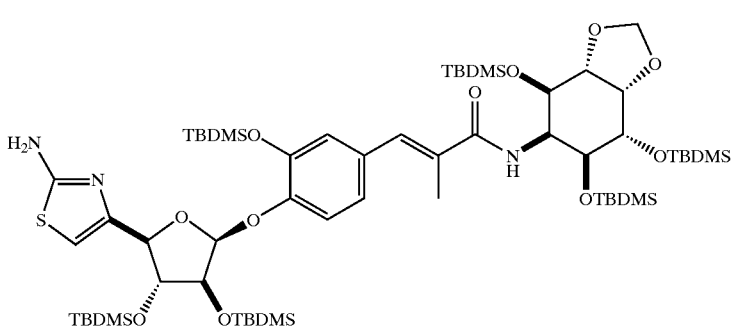

A27

A solution of A26 (1 eq.) in dimethylformamide (0.1 M) at 4° C. was treated with thiourea (2.2 eq.). After completion (1.5 hours) the reaction was diluted with hexanes and diethyl ether (roughly 1:1), washed with pH 7.0 phosphate buffer solution (0.05 M), saturated ammonium chloride, saturated sodium chloride, and then dried over magnesium sulfate, filtered, and concentrated. The crude product was purified by silica gel chromatography, eluting with a step gradient of 10% ethyl acetate in hexanes to 50% ethyl acetate in hexanes.

A solution of A27 (1 eq.) in toluene (0.05 M) at 70° C. was treated with the appropriate benzaldehyde (2–3 eq.). After 15–20 hours the reaction was concentrated, taken up in 3:1 methanol:dichloromethane (0.025 M) and treated with sodium borohydride (5 eq.). After 15 to 30 minutes the reaction was diluted with dichloromethane and water. Hydrochloric acid (1M) was added until the pH of the aqueous layer was 7. The layers were separated and the organic layer washed with water and saturated sodium chloride and then filtered, concentrated. Crude benzyl ami-

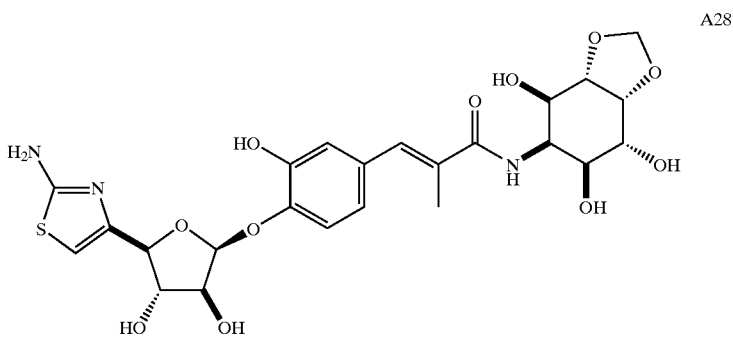

A28

Compound A27 was deprotected and purified by the method used in preparation of compound A24, to afford A28, the compound of Example 44.

nothiazole was deprotected and purified by the method used in preparation of compound A24, to afford A29, the compounds of Examples 45–47.

Preparation of Examples 45–47

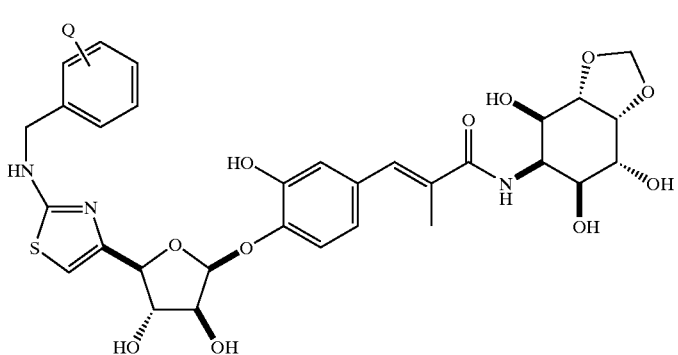

A29

Preparation of Example 49

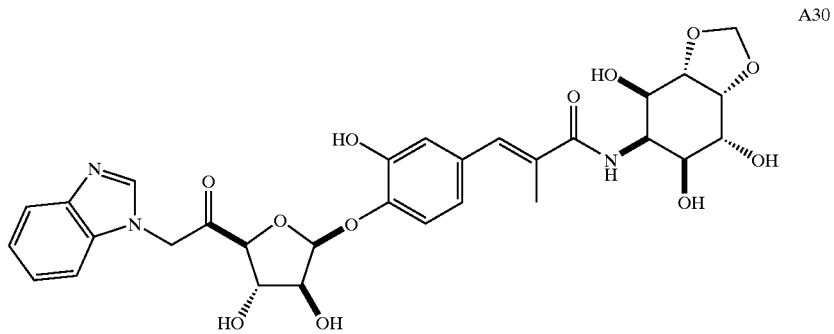

To a solution of A26 (1 eq.) in 9:1 toluene:dimethylformamide (0.1 M) was added benzimidazole (2.2 eq.). After 18 hours the reaction was diluted with hexanes and diethyl ether (roughly 1:1), washed with saturated ammonium chloride, saturated sodium chloride, and then dried over magnesium sulfate, filtered, and concentrated. The crude product was purified by silica gel chromatography, eluting with a step gradient of 10% ethyl acetate in hexanes to 33% ethyl acetate in hexanes.

Protected A30 was deprotected and purified by the method used in preparation of compound A24, to afford A30, the compound of Example 48.

Preparation of Example 49

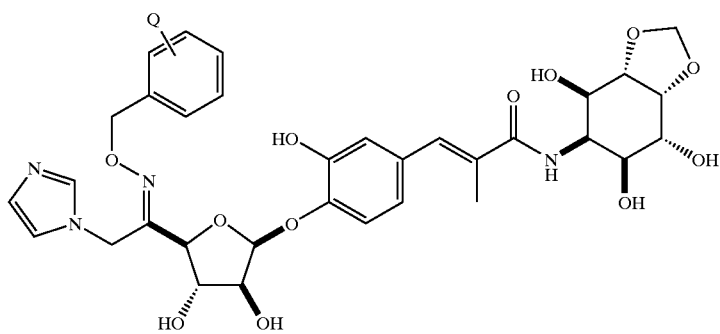

To a solution of A26 (1 eq.) in toluene (0.1 M) was added imidazole (1.3 eq.). After 16 hours the reaction was diluted with ethyl acetate, washed with pH 7.0 phosphate buffer solution (0.05 M), saturated sodium chloride and then dried over magnesium sulfate, filtered, and concentrated.

Crude ketone was converted to oxime via the chemistry described in preparation of the p-fluorophenyl compound A15, until tlc showed the reaction was substantially complete, and deprotected and purified by the method used in preparation of compound A24, to afford A31, the compound of Example 49.

Preparation of Example 50

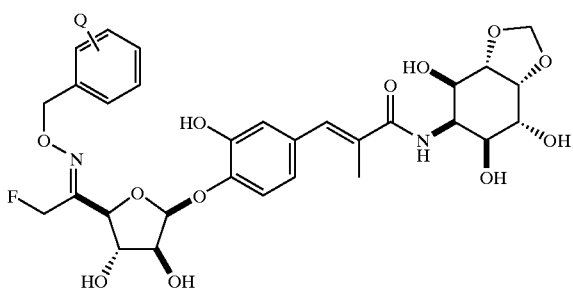

To a solution of A26 (1 eq.) in dimethylformamide (0.1 M) was added [1-(chloromethyl)4-fluoro-1,4-diazoniabicyclo[2.2.2]octane bis(tetrafluoro-borate) (5 eq.). After 15 hours the reaction was diluted with hexanes and diethyl ether (roughly 1:1), washed with water, saturated sodium chloride and then dried over magnesium sulfate, filtered, and concentrated. The crude product was purified by silica gel chromatography, eluting with a step gradient of 5% ethyl acetate in hexanes to 20% ethyl acetate in hexanes.

Crude ketone was converted to oxime via the chemistry described in preparation of the p-fluorophenyl compound A15, until tlc showed the reaction was substantially complete, then deprotected and purified by the method used in preparation of compound A24, to afford A32, the compound of Example 50.

Preparation of Example 51

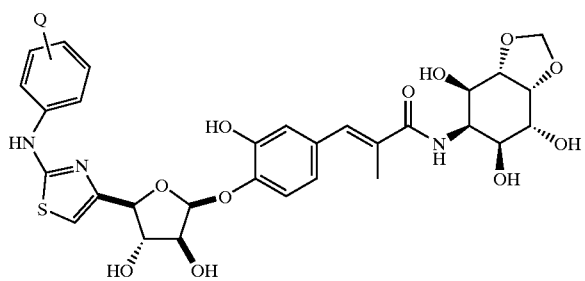

A33

To a solution of A26 (1 eq.) in tetrahydrofuran (~0.2 M) was added hydrochloric acid (0.2 N)(1000 eq.). After 1 hour the reaction was diluted with ethyl acetate and washed with saturated sodium bicarbonate solution, pH 7.0 phosphate buffer solution (0.05 M) and dried over magnesium sulfate. After filtration and concentration the crude phenol was purified by silica gel chromatography, eluting with a step gradient of 5% ethyl acetate in hexanes to 33% ethyl acetate in hexanes.

A solution of the above bromoketone (1 eq.) in dimethylformamide (0.1 M) at 4° C. was treated with the appropriate 1-(phenyl)-2-thiourea (6 eq.). After completion (1 hour) the reaction was diluted with hexanes and diethyl ether (roughly 1:1), washed with pH 7.0 phosphate buffer solution (0.05 M), saturated sodium chloride and then dried over magnesium sulfate, filtered, and concentrated. The crude product was purified by silica gel chromatography, eluting with a step gradient of 5% ethyl acetate in hexanes to 33% ethyl acetate in hexanes.

Protected aminothiazole was deprotected and purified by the method used in preparation of compound A24, to afford A33, the compound of Example 51.

Preparation of Example 52

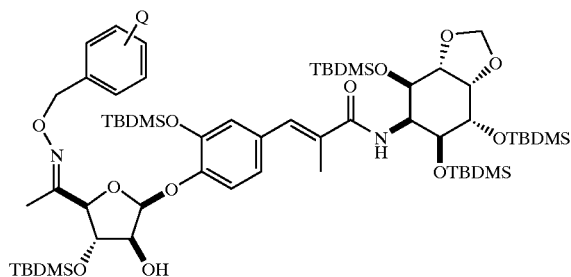

A34

A solution of hygromycin A (1 eq.) in dimethylformamide (0.1 M) was treated with imidazole (10 eq.) and tert-butyldimethylsilyl chloride (10 eq) at 35° C. for 15 hours. The reaction was poured into water and extracted with ethyl acetate. The combined extracts were dried over magnesium sulfate and concentrated. The product was obtained after chromatography eluting with a step gradient of 5% ethyl acetate in hexanes to of 15% ethyl acetate in hexanes.

The appropriate oxime was introduced using the chemistry described in preparation of the p-fluorophenyl compound A15, until tlc showed the reaction was substantially complete, to afford A34.

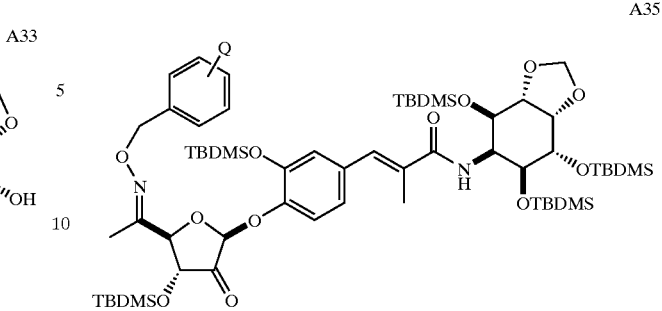

A35

A solution of A34 (1 eq.) in dichloromethane (0.1 M) was treated with Dess-Martin periodinane (2.6 eq.). After 7 hours the reaction was diluted with dichloromethane and washed with saturated sodium bicarbonate solution and brine. The organic layer was dried with magnesium sulfate, filtered and evaporated to afford A35.

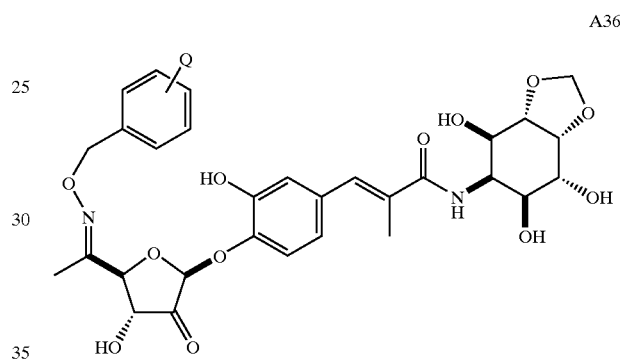

A36

Protected ketone, A35, was deprotected and purified by the method used in preparation of compound A24, to afford A36, the compound of Example 52.

Preparation of Example 53

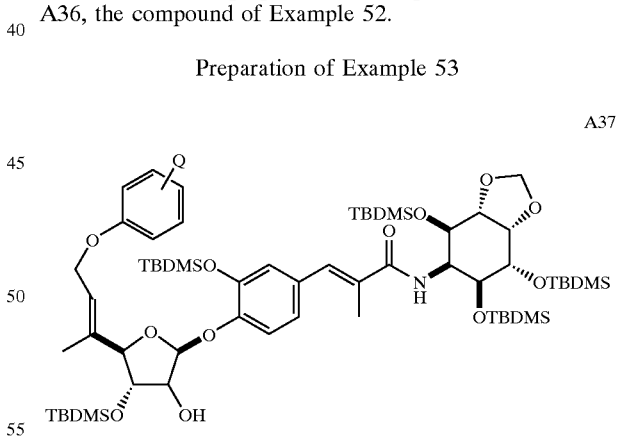

A37

A solution of hygromycin A (1 eq.) in dimethylformamide (0.1 M) was treated with imidazole (10 eq.) and tert-butyldimethylsilyl chloride (10 eq) at 35° C. for 15 hours. The reaction was poured into water and extracted with ethyl acetate. The combined extracts were dried over magnesium sulfate and concentrated. The product was obtained after chromatography eluting with a step gradient of 5% ethyl acetate in hexanes to of 15% ethyl acetate in hexanes.

The appropriate allyl ether was introduced using the method described for preparation of A25, to afford A37.

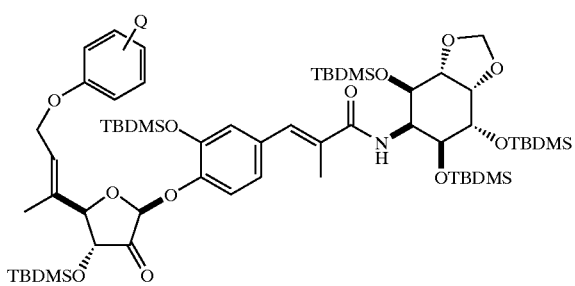

A38

A solution of A37 (1 eq.) in dichloromethane (0.1 M) was treated with Dess-Martin periodinane (2.6 eq.). After 7 hours the reaction was diluted with dichloromethane and washed with saturated sodium bicarbonate solution and brine. The organic layer was dried with magnesium sulfate, filtered and evaporated to afford A38.

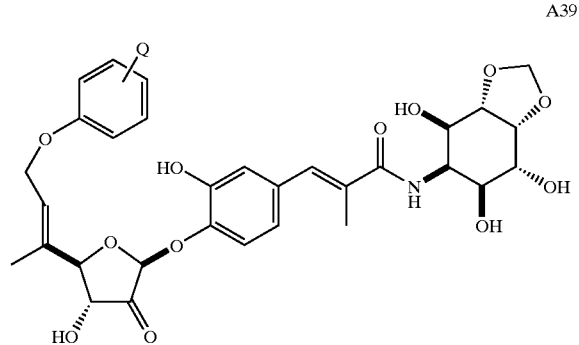

A39

Protected ketone, A38, was deprotected and purified by the method used in preparation of compound A24, to afford A39, the compound of Example 53.

Preparation of Examples 54–56

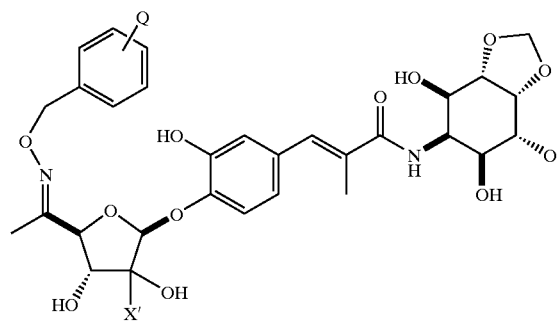

A40

To a solution of A35 (1 eq.) in tetrahydrofuran (0.05 M) at −15° C. was added the appropriate Grignard reagent (3–5 eq.) and the reactions were allowed to slowly warm to room temperature. After 10–20 hours the reactions were diluted with ethyl acetate, washed with pH 7.0 phosphate buffer solution (0.05 M) and saturated sodium chloride and then dried over magnesium sulfate, filtered, and concentrated. The crude products were purified by silica gel chromatography, eluting with a step gradient of 5% ethyl acetate in hexanes to 20% ethyl acetate in hexanes.

Protected adducts, of undefined stereochemistry at C2″, were deprotected and purified by the method used in preparation of compound A24, to afford A40, the compounds of Examples 54–56.

Preparation of Example 57

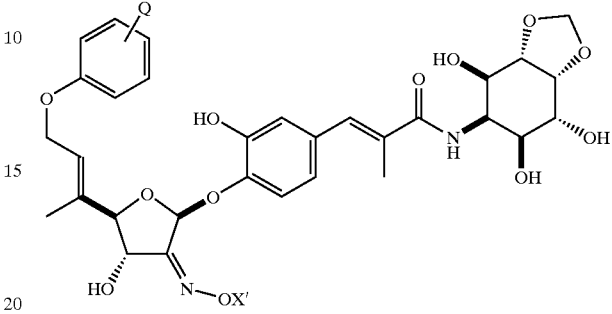

A41

To a solution of A39 (1 eq.) in methanol (0.025 M) was added the appropriate hydroxylamine (2.5 eq.) and the reaction warmed to 50° C. After 20–30 hours the reaction was concentrated and was purified by silica gel chromatography, eluting with a step gradient of 5% methanol in dichloromethane to 20% methanol in dichloromethane to afford A41, the compound of Example 57.

Preparation of Example 58

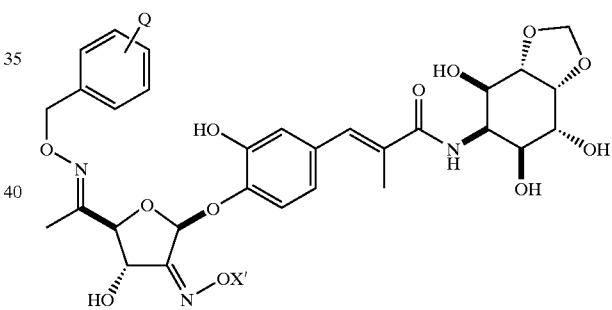

A42

Compound A42 was prepared from A36 using the chemistry described for preparation of A41.

Preparation of Example 59

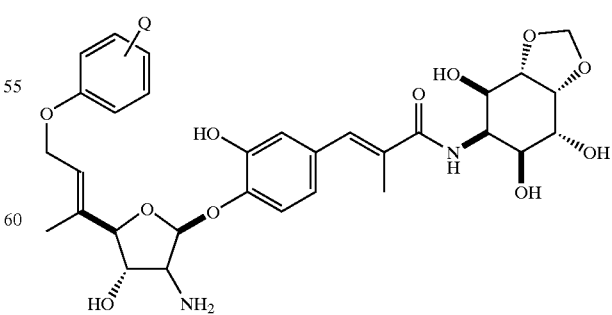

A43

To a solution of A41 (where X′=H, 1 eq.) in methanol (0.05 M) was added ammonium acetate (15 eq.) followed by the slow addition of titanium tetrachloride (2.5 eq.). After 10 minutes the reaction was neutralized with sodium bicarbonate, filtered and concentrated. The crude imine was taken up in methanol (0.05 M) and sodium borohydride (5.7 eq.) was added. After 10 minutes the reaction was acidified to pH 2 with hydrochloric acid (1 N). After 5 minutes the reaction was brought to pH 10 with sodium hydroxide (1 M) and concentrated and purified by silica gel chromatography, eluting with a step gradient of 5% methanol in dichloromethane to 20% methanol in dichloromethane to afford A43 with undefined C2" stereochemistry.

Preparation of Examples 60–61

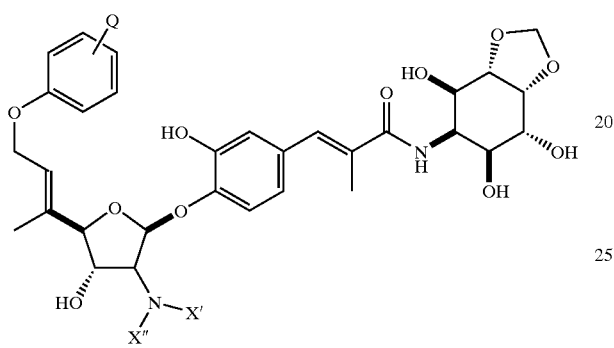

A44

To a solution of A39 (1 eq.) in methanol (0.03 M) was added the appropriate amine (8–10 eq.) followed by sodium cyanoborohydride (2.5 eq.). After 15–20 hours the reactions were acidified to pH 2 with hydrochloric acid (1 N). After 5 minutes the reactions were neutralized with sodium hydroxide (1 M) and concentrated and purified by silica gel chromatography, eluting with a step gradient of 2.5% methanol in dichloromethane to 10% methanol in dichloromethane to afford the compounds represented by A44 with undefined C2" stereochemistry.

Preparation of Examples 62, and 67–80

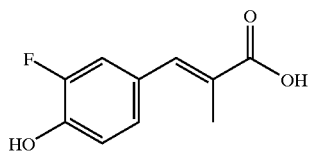

A45

4-Methoxy-3-fluorobenzaldehyde in dichloromethane (0.16 M) was treated with BBr$_3$ (1.5 eq.) and stirred for 9–10 hours. The reaction was quenched by the addition of excess methanol and the mixture was warmed to 70° C. for 30 minutes. After concentration the residue was dissolved in Et$_2$O, washed with water and brine, and concentrated. The resultant hydroxyaldehyde in dichloromethane (0.13 M) was treated with carbethoxy-ethylidenetriphenylphosphorane (1.2 eq) for about 15 hours. The reaction mixture was concentrated and chromatographed using a gradient from hexane to 15% ethyl acetate in hexane. This ester was hydrolyzed using LiOH (7 eq.) in a solution of 3THF:2methanol:1water (0.05 M) at a temperature of 60° C. overnight. The reaction was quenched by the addition of 1N HCl and the product A45 was isolated by extraction with ethyl acetate.

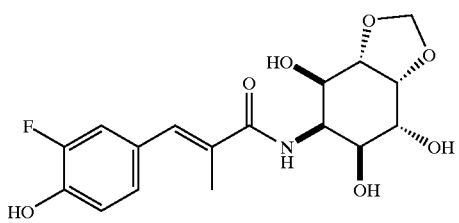

A46

Compound of the formula A46 was prepared by heating a mixture of inositol 2 (Scheme 1, Fragment A) (2 eq) and compound A45 with EEDQ (1.2 eq.) in DMF (0.1 M) to 60° C. for 3 hours and stirring at room temperature overnight. Concentration of the reaction mixture and chromatography using a step gradient of 5% to 20% methanol in chloroform provided A46.

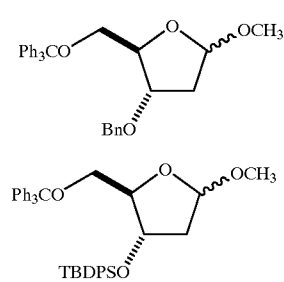

A47

A47.1

Compound A47 was prepared by treatment of the corresponding secondary alcohol (1 eq.) (*J. Org. Chem.*, 1995, 60, 202) with benzyl bromide (1.5 eq.) and sodium hydride (2 eq.) in THF (0.1 M) and stirring overnight. The reaction was quenched with water and extracted with ethyl acetate. Concentration and chromatography with 5–10% ethyl acetate in hexanes provided A47.

Alternatively, compound A47.1 was prepared by treatment of the same secondary alcohol with tert-butyldiphenyl silyl chloride (1.2 eq.) and imidazole (1.5 eq) in DMF at room temperature for 12–18 h. The reaction was quenched with water and extracted with methylene chloride. The combined organics were washed with brine and dried over MgSO$_4$ and concentrated. The residue was purified using a step gradient of 5% to 10% ethyl acetate in hexanes to provide A47.1.

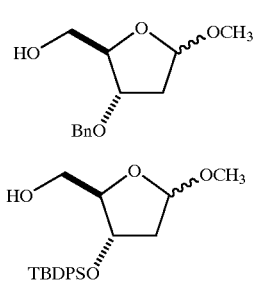

A48

A48.1

Compound A48 was prepared by treatment of A47 in methanol (0.1 M) with 0.5% HCl in methanol for 1.5 hours. The reaction mixture was quenched with Ag$_2$CO$_3$, filtered and concentrated. Product A48 was obtained after chromatography with a step gradient of 15% to 35% ethyl acetate in hexanes. Compound A48.1 was prepared in an analogous manner and isolated upon chromatography using a step gradient of 5% to 20% ethyl acetate in hexanes.

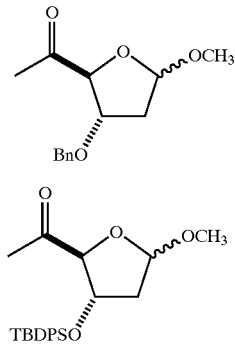

A49

A49.1

Compound A49 was prepared by adding A48 to a mixture of oxalyl chloride (2 eq.) and DMSO (4 eq.) in methylene chloride at −78° C. (substrate concentration, 0.05 M). After 1 hour, triethylamine (8 eq.) was added and the reaction warmed to room temperature. Water was added and the crude aldehyde was obtained by extraction with ether and concentration. A solution of this aldehyde in THF (0.05 M) was treated with methyl magnesium bromide (2 eq.) at −78° C. The reaction was quenched with sodium bicarbonate, extracted with $Et_2O$ and concentrated to provide a mixture of alcohols. Compound A49 was prepared by adding that mixture of alcohols to a mixture of oxalyl chloride (2 eq.) and DMSO (4 eq.) in methylene chloride at −78° C. (substrate concentration, 0.05 M). After 1 hour, triethylamine (8 eq.) was added and the reaction warmed to room temperature. Water was added and A49 was obtained by extraction with ether, concentration and chromatography using a step gradient of 10% to 20% ethyl acetate in hexanes. Compound A49.1 was prepared in an analogous fashion and obtained upon chromatography using a step gradient of 10% to 20% ethyl acetate in hexanes.

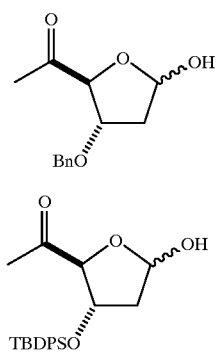

A50

A50.1

Compound A50 was prepared by treatment of A49 with a solution of 80% trifluoroacetic acid (0.1 M) for 2 hours. The reaction was poured into a saturated solution of sodium bicarbonate and extracted with ethyl acetate. Upon concentration the crude residue was chromatographed with 20% ethyl acetate in hexanes to provide A50. Compound A50.1 was prepared in an analogous fashion and obtained upon chromatography using a step gradient of 10% to 25% ethyl acetate in hexanes.

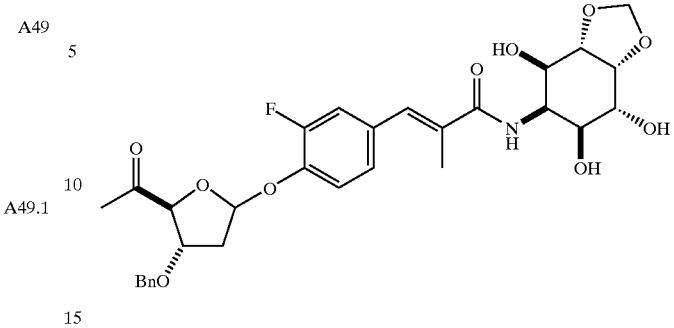

A51

Compound A51 was prepared by treatment of a mixture of A50 (1 eq.) and A46 (1.5 eq.) with diethylazodicarboxylate (1.6 eq.) and $PPh_3$ (1.6 eq.) in THF (0.15 M in substrate A50) and stirring overnight. The reaction mixture was concentrated and chromatographed on silica gel using a step gradient of 3% to 10% methanol in chloroform to provide A51 as a mixture of diastereomers.

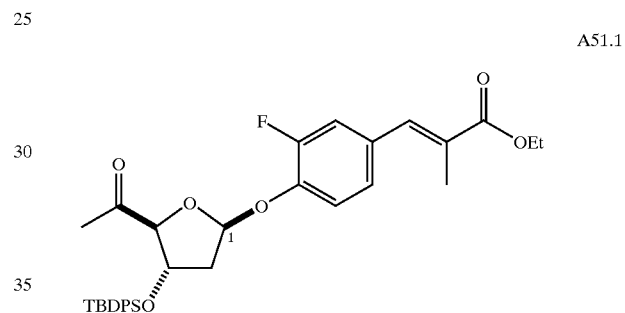

A51.1

Compound A51.1 was prepared in an analogous fashion and obtainedwith the advantage each C-1 isomer could be isolated upon chromatography using a step gradient of 5% to 20% ethyl acetate in hexanes. Each of the isomers was converted separately to the examples shown below but only the β isomer will be described.

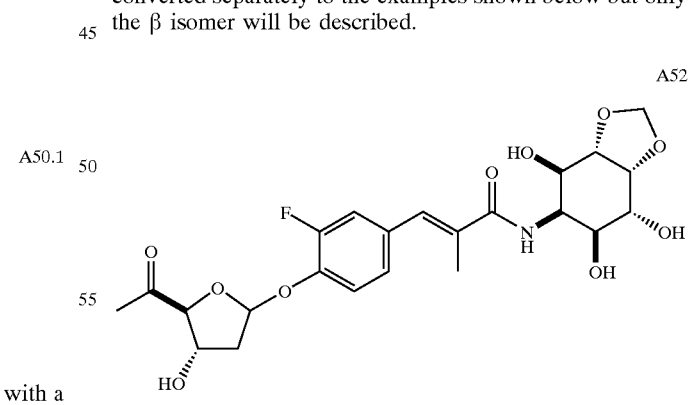

A52

Compound A52 was prepared by treatment of a solution of A51 in ethanol (0.05 M) with 10% Pd/C (1:1 wt:wt) and 1,4-cyclohexadiene (20 eq.) and stirring overnight. The reaction mixture was filtered through celite, concentrated and chromatographed on silica gel using a step gradient of 5% to 15% methanol in chloroform to provide A52.

A53

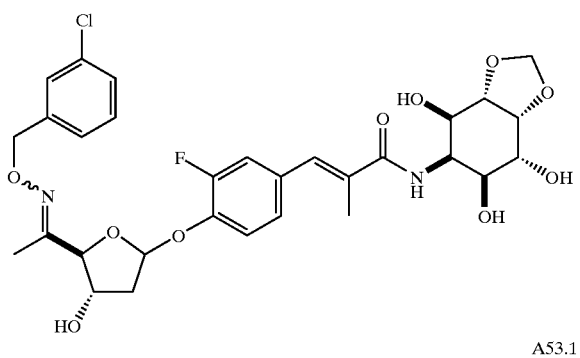

A53.1

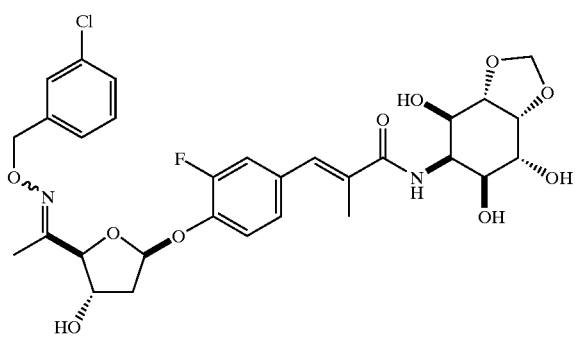

Compound A53 was prepared by treatment of a solution of A52 in methanol (0.1 M) with N-(3-chlorophenylmethyl)hydroxylamine (1.5 eq.) overnight. The reaction was concentrated and the residue was chromatographed on silica gel using a step gradient of 5% to 10% methanol in chloroform to provide A53, the compound of Example 62.

A53.2

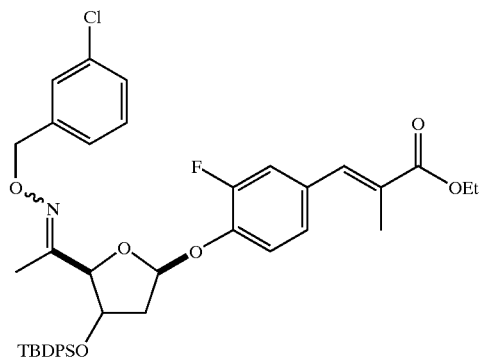

Compound A53.2 was prepared by treatment of a solution of A51.1 in methanol (0.1 M) with N-(3-chlorophenylmethyl)hydroxylamine (1.5 eq.) overnight. The reaction was concentrated and the residue was chromatographed on silica gel using a step gradient of 5% to 10% methanol in chloroform to provide A53.2.

Compound A53.1 was also prepared by treatment of A53.2 with 1 M sodium hydroxide (3 eq.) in a THF/methanol (1/1) solution at room temperature for 12–18 h whereupon the reaction was heated to 50° C. for 3 h. The reaction was quenched with dilute acetic acid and extracted with ethyl acetate. The combined organics were dried over $MgSO_4$ and concentrated to provide the crude acid, which was used without further purification. A solution of the acid, DCC (2 eq.) N-hydroxybenztriazole (2 eq) and 4-dimethyaminopyridine (1.5 eq.) was treated with inositol 2 (Scheme 1, Fragment A) (4 eq) at room temperature for 12–18 h. The reaction was concentrated and the residue was chromatographed using a step gradient of 3% to 10% methanol in chloroform to provide A53.1, the compound of example 66.

Preparation of Example 77

A54

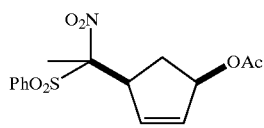

Compound A54 was prepared by treatment of the corresponding ethyl carbonate (Deardorff et. al. *J. Org. Chem.* 1996, 61, 3616) with $Pd(dba)_3$ (0.05 eq.), triphenylphosphine (0.2 eq.), $Et_3N$ (1.2 eq.), 1,1-phenylsulphonylnitroethane (1.2 eq.) in THF at OC for 2 h. The reaction was concentrated and the residue was chromatographed using a step gradient of 5% to 20% ethyl acetate in hexanes to provide A54

A55

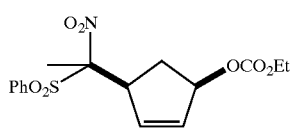

Compound A55 was prepared by treatment of A54 with $K_2CO_3$ (1.2 eq.) in THF, water, methanol (2:1:1) at room temperature for 2 h. The reaction was diluted with water and extracted with ether. The organic layer was washed with brine, dried over $MgSO_4$ and concentrated. The resulting material was used without purification and treated with ethylchloroformate (1.3 eq) and pyridine (8 eq.) in methylene chloride at rt for 12–18 h. The reaction was quenched with a saturated solution of ammonium chloride, acidified with 1 N HCl and extracted with methylene chloride. The combined organics were dried over $MgSO_4$ and concentrated. The residue was chromatographed using a step gradient of 10% to 30% ethyl acetate in hexanes to provide A55.

A56

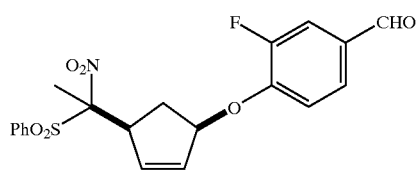

Compound A56 was prepared by treatment of A55 with $Pd(dba)_3$ (0.05 eq.), triisopropyl phosphite (0.25 eq.), $CeCO_3$ (2.2 eq.), 3-fluoro-4-hydroxy benzaldehyde (2 eq.) in THF at rt for 3 h. Water and ether were added and the reaction was extracted with ether and the organic extracts dried over $MgSO_4$. The reaction was concentrated and the residue was chromatographed using a step gradient of 10% to 30% ethyl acetate in hexanes to provide A56.

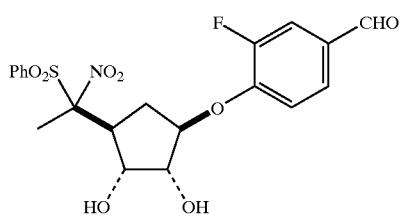
A57

Compound A57 was prepared by treatment of A56 with osmium tetroxide (0.05 eq.) N-methylmorpholine-N-oxide (1.5 eq.) in methylene chloride at rt for 12–18 h. The reaction was concentrated and the residue was chromatographed using a step gradient of 20% to 50% ethyl acetate in hexanes to provide A57.

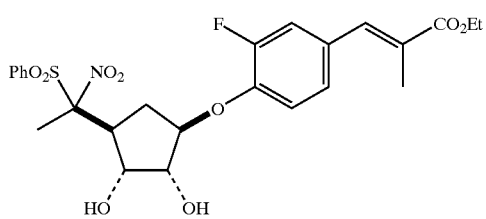
A58

Compound A58 was prepared by treatment of A57 with carbethoxyethylidenetriphenylphosphorane (1.2 eq.) in methylene chloride at rt for 2 h. The reaction was concentrated and the residue was chromatographed using a step gradient of 10% to 20% ethyl acetate in hexanes to provide A58.

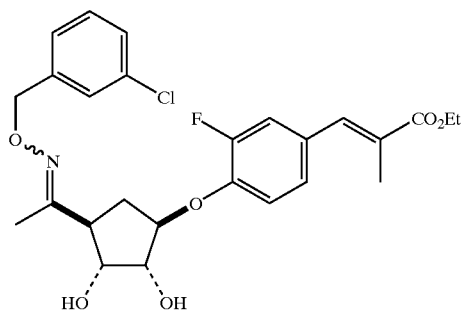
A59

Compound A59 was prepared by treatment of A58 with titanium trichloride (10 eq.) in a THF/water (5/13) solution buffered with ammonium acetate (78 eq) at rt for 2 h. The reaction was diluted with water and extracted with ethyl acetate. The combined extracts were washed with brine, dried over MgSO$_4$ and concentrated. The crude residue was chromatographed using a step gradient of 20% to 40% ethyl acetate in hexanes to provide the desired methyl ketone. The ketone was treated with O-3-chlorobenzylhydroxyl amine (1.5 eq.) in methanol at room temperature for 12–18 h. The reaction was concentrated and the residue was chromatographed using a step gradient of 10% to 40% ethyl acetate in hexanes to provide A59 as predominantly the E isomer.

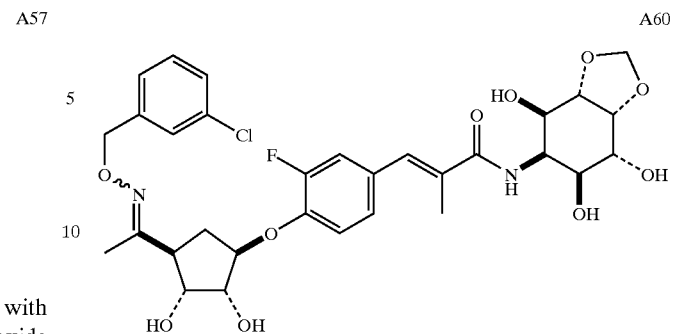
A60

Compound A60 was prepared by treatment of A59 with 1 M sodium hydroxide (2 eq.) in a THF/methanol (1/1) solution at room temperature for 12–18 h whereupon the reaction was heated to 50° C. for 3 h. The reaction was quenched with dilute acetic acid and extracted with ethyl acetate. The combined organics were dried over MgSO$_4$ and concentrated to provide the crude acid, which was used without further purification. The acid was treated with of inositol 2 (Scheme 1, Fragment A) (3 eq), DCC (2 eq.) N-hydroxybenztriazole (2 eq) and 4-dimethyaminopyridine (1.5 eq.) in DMF at rt for 12–18 h. The reaction was concentrated and the residue was chromatographed using preparative thin layer chromatography (prep TLC) using 15% methanol in chloroform to provide A60, the compound of example 77 (MW Calcd; found).

Preparation of Example 78

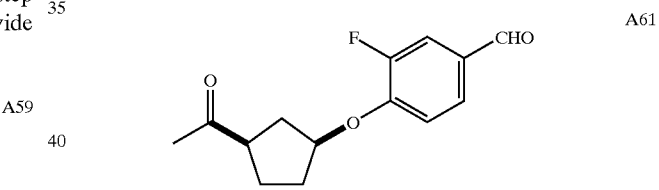
A61

Compound A61 was prepared by treatment of A57 with titanium trichloride as with compound A59. The resultant unsaturated ketone was treated with Pd on carbon (1 mg Pd to 4 mg substrate) in ethanol under an atmosphere of hydrogen at room temperature for 2–5 h. The reaction was filtered, concentrated and the residue chromatographed using a step gradient of 20% to 50% ethyl acetate in hexanes to provide A61.

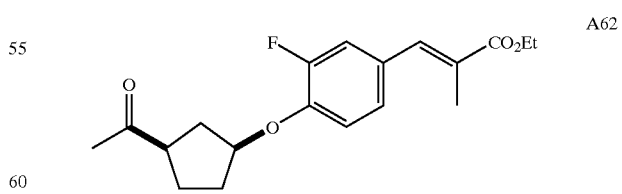
A62

Compound A62 was prepared by treatment of A57 with carbethoxyethylidenetriphenylphosphorane (1.2 eq.) in methylene chloride at rt for 2 h. The residue was chromatographed using a step gradient of 20% to 50% ethyl acetate in hexanes provided A62.

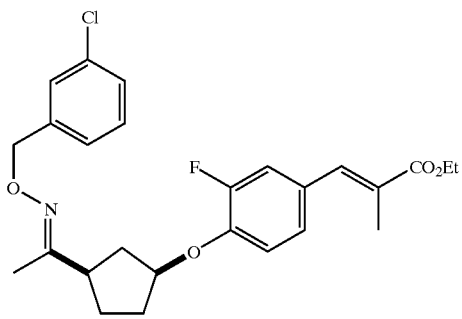

A63

Compound A63 was prepared by treatment of A62 with O-3-chlorobenzylhydroxyl amine (1.5 eq.) in methanol at room temperature for 12–18 h. The reaction was concentrated and the residue was chromatographed using a step gradient of 10% to 30% ethyl acetate in hexanes to provide A63 as predominantly the E isomer.

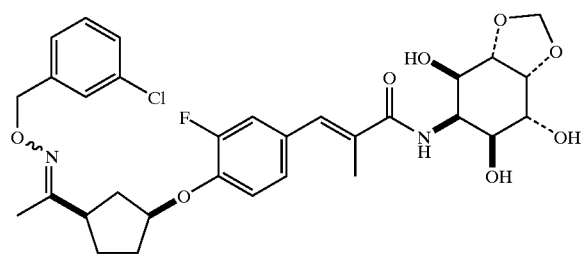

A64

Compound A64 was prepared the same methods used to prepare A60 from A59. The final product was purified by preparative thin layer chromatography (prep TLC) using 15% methanol in chloroform to provide A64, the compound of example 78 (MW Calcd found).

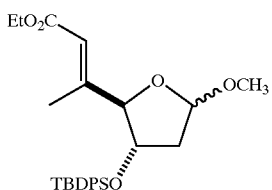

A65

Compound A65 was prepared by treating compound A49.1 with (carbethoxymethylene)-triphenylphosphorane (2eq.) in DMF at 50° C. for 12–18 h. The reaction mixture was diluted with 1:1 ether:hexanes and quenched with pH 7 buffer. The aqueous layer was extracted with 1:1 ether:hexanes and the combined organics were washed with water, brine, dried over $MgSO_4$ and concentrated. The crude residue was chromatographed using a step gradient of 3% to 12% ethyl acetate in hexanes to provide A65.

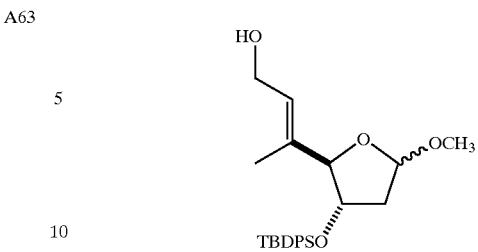

A66

Compound A66 was prepared by treating compound A65 with diisobutylaluminum hydride (5eq.) in methylene chloride at −78° C. for 30 min. The reaction was quenched at −78° C. with a saturated solution of Rochelle's salt (sodium potassium tartrate) and the reaction was allowed to warm to rt. A saturated solution of ammonium chloride was added and the reaction stirred for 1 h. The mixture was extracted with ethyl acetate and the combined organics were washed with brine, dried over $MgSO_4$ and concentrated. The crude residue, A66, was used without further purification.

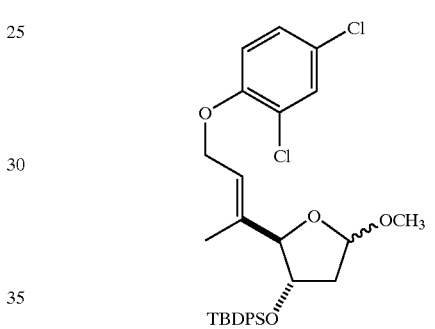

A67

Compound A67 was prepared by a dropwise addition of a THF solution of diethylazodicarboxylate (2.5 eq.) to a solution of compound 66, 2,4-diclorophenol (3 eq) (use extreme caution when handling this compound, Hogue, C. *Chemical and Engineering News* 2000, 18, p.49) and triphenylphosphine (2.5 eq.) in THF at rt. The reaction was stirred for 1 h and concentrated. The crude residue was chromatographed using a step gradient of 3% to 10% ethyl acetate in hexanes to provide A67.

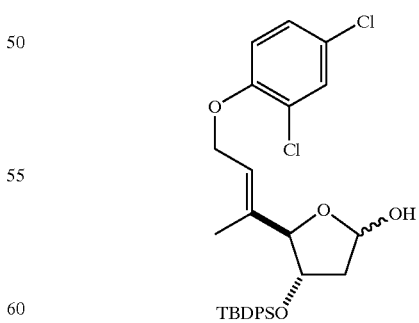

A68

Compound A68 was prepared treating compound 67 with 80% trifluoroacetic acid in THF at rt for 1.5 h. The reaction was quenched by addition of saturated sodium bicarbonate and extracted into ethyl acetate. The organics were washed with brine, dried over $MgSO_4$ and concentrated. The crude residue was chromatographed using a step gradient of 5% to 20% ethyl acetate in hexanes to provide A68.

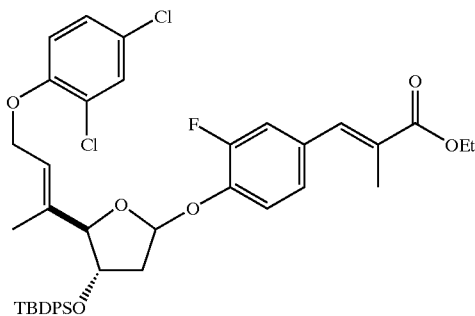

A69

Compound A69 was prepared from compound A68 using the methods described for the conversion of A50.1 to A51.1. Compound A69 was obtained after chromatography using a step gradient of 20% to 30% ethyl acetate in hexanes.

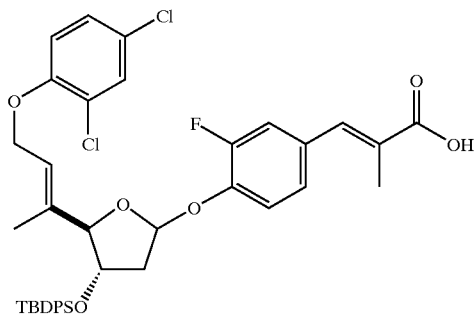

A70

Compound A70 was prepared by treating compound A69 with 1 M sodium hydroxide (2 eq.) in a THF/methanol (1/1) solution at 50° C. for 12–18 h. The reaction was quenched with dilute acetic acid (pH 4) and extracted with ethyl acetate. The combined organics were washed with brine, dried over $MgSO_4$ and concentrated. The crude acid was chromatographed using a step gradient of 40% to 66% ethyl acetate in hexanes to provide A70.

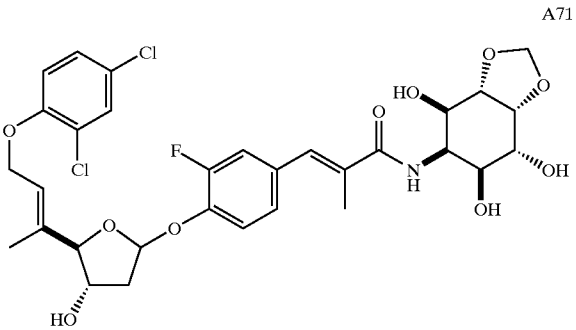

A71

The acid A70 was treated with of inositol 2 (Scheme 1, Fragment A) (3 eq), DCC (2 eq.) N-hydroxybenztriazole (2 eq) and 4-dimethylaminopyridine (1.5 eq.) in DMF at rt for 12–18 h. The reaction was concentrated and the residue was chromatographed using a step gradient of 3% to 5% metha-nol in chloroform to provide the desired amide. The silyl group was removed using the method described for the preparation of compound A14. Compound A71 was obtained after chromatography using prep TLC using 10% methanol in chloroform.

Preparation of Example 63

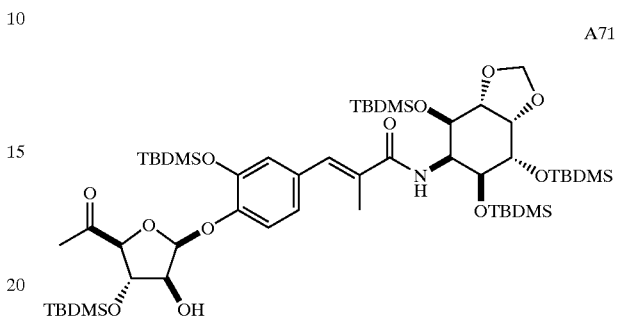

A71

Compound A71 was prepared when a solution of hygromycin A (1 eq.) in DMF (0.1 M) was treated with imidazole (10 eq) and tert-butyldimethylsilyl chloride (10 eq) at 35° C. for 14–16 h. The reaction was poured into water and extracted with ethyl acetate. The combined extracts were dried over $MgSO_4$ and concentrated. The product was obtained after chromatography using a step gradient of 5% to 15% ethyl acetate in hexanes to provide A71.

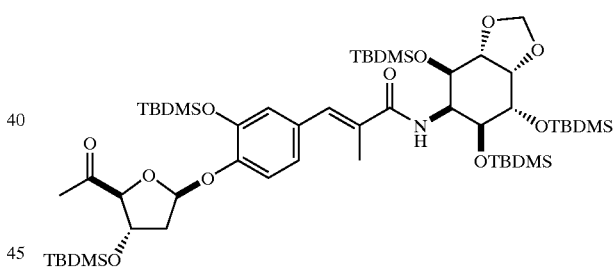

A72

Compound A72 was prepared when a solution of the compound A71 (1 eq.) in methylene chloride was treated with phenylthionochloroformate (3 eq.), pyridine (5 eq) and dimethylaminopyridine (0.05 eq.) at rt for 2–3 days. At the end of this time the reaction was diluted with methylene chloride, washed with 0.5 N HCl, saturated sodium bicarbonate and then Brine. The organics were dried over $MgSO_4$ and concentrated. The desired 2"-thionocarbonate was obtained after chromatography using a step gradient of 5% to 10% ethyl acetate in hexanes.

A solution of the above 2"-thionocarbonate (1 eq.) in toluene (0.1 M) was treated with AIBN (1 eq.) and tri-n-butyltinhydride (3 eq.) at 90° C. for 2 h. The reaction was concentrated and chromatographed using a step gradient of 5% to 10% ethyl acetate in hexanes. to provide the desired 2"-deoxy compound A72.

Preparation of Examples 64–66

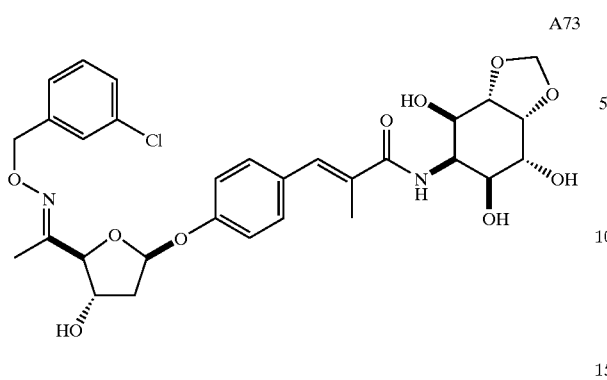

A73

A solution of the compound A72 (1 eq.) in methanol (0.1 M) was treated with the 3-chlorobenzyl hydroxylamine (1 eq.) at 60° C. for 30 min to 1 h. The reaction mixture was concentrated and the desired oxime was obtained after chromatography using a step gradient of 5% to 10% ethyl acetate in hexanes. The silyl protecting groups were removed by the method used to convert A18 to A19, thus providing A73.

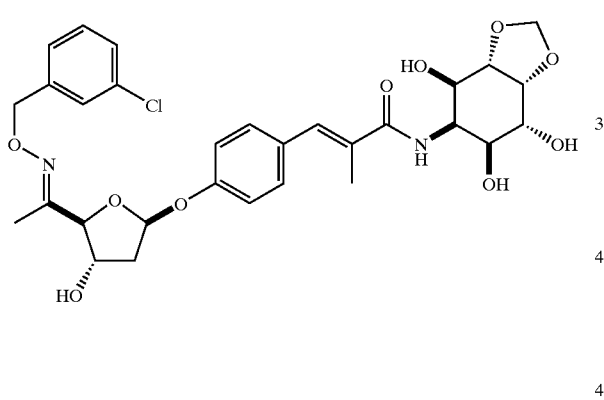

A74

The compound of formula A74 was prepared by treatment of A73 with N-phenyl-bis(trifluoromethanesulphonamide) (1.8 eq.) and triethylamine (2 eq.) in DMF at room temperature for 2 h. The reaction mixture was poured into brine and extracted with ethyl acetate. The combined organics were dried over MgSO$_4$ and concentrated. The crude residue was chromatographed using a step gradient of 5% to 15% methanol in chloroform. A solution of the resultant phenyl triflate, tris(dibenzylidineacetone)dipalladium(0)-chloroform adduct (0.04 eq.), 1,1'-bis(diphenylphosphino)ferrocene (0.08 eq.) and triethylamine (7.5 eq.) in DMF was treated with formic acid (5 eq.) and warmed to 60° C. for 5 h. The reaction mixture was poured into brine and extracted with ethyl acetate. The combined organics were dried over MgSO$_4$ and concentrated. The crude residue was chromatographed using a step gradient of 5% to 15% methanol in chloroform. The desired compound A74 (example 63) was further purified using reverse phase chromatography (C18) using a step gradient of 10% to 50% acetonitrile in water.

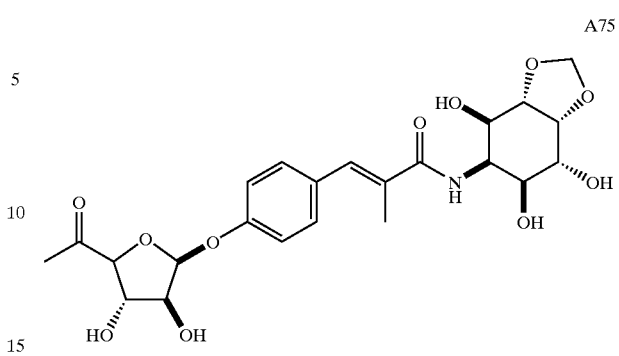

A75

The compound of formula A75 was prepared by treatment of hygromycin A with N-phenyl-bis(trifluoromethanesulphonamide) (1.8 eq.) and triethylamine (2 eq.) in DMF at room temperature for 2 h. The solvent was removed en vacuo and the crude residue was chromatographed using a step gradient of 3% to 15% methanol in chloroform. A solution of the resultant phenyl triflate, tris(dibenzylideneacetone)dipalladium(0)-chloroform adduct (0.04 eq.), 1,1'-bis(diphenylphosphino)ferrocene (0.08 eq.) and triethylamine (7.5 eq.) in DMF was treated with formic acid (5 eq.) and warmed to 60° C. for 5 h. The solvent was removed en vacuo and the crude residue was chromatographed using a step gradient of 3% to 15% methanol in chloroform to provide the desired compound A75.

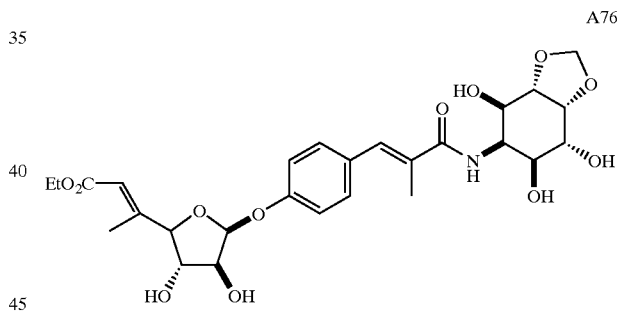

A76

Compound A76 was prepared by treating compound A75 with (carbethoxymethylene)-triphenylphosphorane (2eq.) in DMF at 70° C. for 12–18 h. The solvent was removed en vacuo and the crude residue was chromatographed using a step gradient of 5% to 10% methanol in chloroform to provide the desired compound A76.

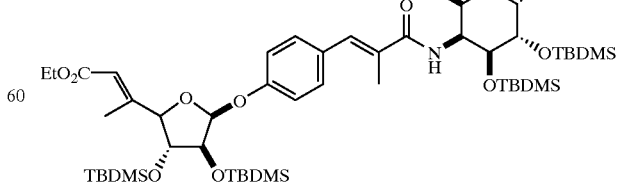

Compound A77 was prepared when a solution of A76 (1 eq.) in DMF was treated with imidazole (15 eq) and tert-butyldimethylsilyl chloride (15 eq) at 70° C. for 12–18 h. The reaction was poured into water and extracted with ethyl acetate/hexanes (1/1), washed with water and brine. The combined extracts were dried over MgSO$_4$ and concentrated. The product was obtained after chromatography using a step gradient of 3% to 20% ethyl acetate in hexanes to provide A77.

graphed using a step gradient of 3% to 20% ethyl acetate in hexanes to provide A78.

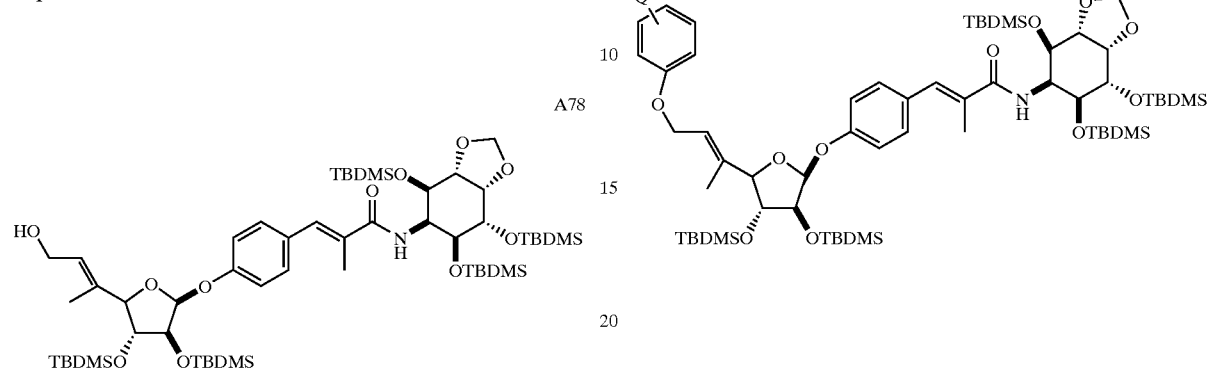

A78

Compound A78 was prepared by treating compound A77 with diisobutylaluminum hydride (6 eq.) in methylene chloride at −78° C. for 30 min. The reaction was quenched at −78° C. with a saturated solution of Rochelle's salt (sodium potassium tartrate) and the reaction was allowed to warm to rt. The mixture was extracted with chloroform and the combined organics were washed with brine, dried over MgSO$_4$ and concentrated. The residue was chromato- Compounds of the formula A79 were prepared by a dropwise addition of diethylazodicarboxylate (2.5 eq.) to a solution of compound A78, the appropriate phenol (5 eq) and triphenylphosphine (5 eq.) in toluene at 0° C. The reaction was stirred for 10 min and was diluted with ethyl acetate. The mixture was extracted with brine and the combined organics dried over MgSO$_4$ and concentrated. The crude residue was chromatographed using a step gradient of 3% to 20% ethyl acetate in hexanes to provide A67. The silyl protecting groups were removed by the method used to convert A18 to A19, thus providing A79.

TABLE 1

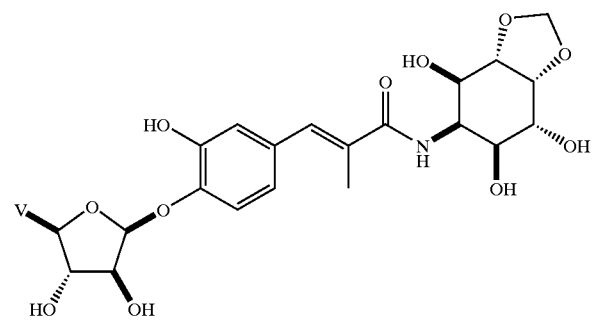

| Example | V | Stereo | Mol. Wt. | Mass Spec. |
|---------|---|--------|----------|------------|
| 1 | Cl-phenyl-isoxazolidinyl |  | 679.1 | 679.3 |

TABLE 1-continued

| Example | V | Stereo | Mol. Wt. | Mass Spec. |
|---|---|---|---|---|
| 2 | 3-Cl-phenyl isoxazolidine | | 679.1 | 679.0 |
| 3 | 4-F-phenyl isoxazolidine | | 662.7 | 662.9 |
| 4 | 4-F-phenyl isoxazolidine | | 662.7 | 663.1 |
| 5 | 3-O₂N-phenyl isoxazolidine | | 689.7 | 690.2 |

TABLE 1-continued
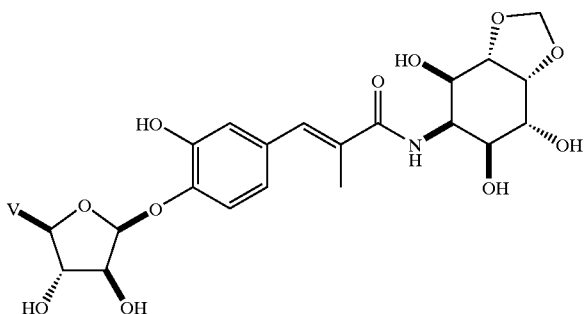
| Example | V | Stereo | Mol. Wt. | Mass Spec. |
|---|---|---|---|---|
| 6 | (4-cyanophenyl isoxazolidine structure) | | 669.7 | 669.9 |
| 7 | (3-chlorobenzyl oxime structure) | E,Z mix | 667.1 | 666.7 |
| 8 | (benzyl oxime structure) | E,Z mix | 632.6 | 633.6 |
| 9 | (3-fluorobenzyl oxime structure) | E,Z mix | 650.6 | 651.1 |

TABLE 1-continued

| Example | V | Stereo | Mol. Wt. | Mass Spec. |
|---|---|---|---|---|
| 10 | (methoxyimino group with HO-CH2- and methyl) | E,Z mix | 556.5 | 557.0 |
| 11 | (3,5-difluorobenzyloxyimino group with HO-CH2- and methyl) | E,Z mix | 668.6 | 669.0 |
| 12 | (benzyloxyimino group with MeO-CH2- and methyl) | E,Z mix | 646.7 | 647.4 |
| 13 | (methoxyimino group with 3-chlorophenoxymethyl and methyl) | E,Z mix | 667.1 | 667.3 |

TABLE 1-continued

| Example | V | Stereo | Mol. Wt. | Mass Spec. |
|---|---|---|---|---|
| 14 | (3-fluorophenoxymethyl)-(methoxyimino)-methyl group | E,Z mix | 650.6 | 651.3 |
| 15 | (phenoxymethyl)-(methoxyimino)-methyl group | E,Z mix | 632.6 | 633.3 |
| 16 | ((3-chlorobenzyloxy)aminocarbonyl)-dimethyl group | | 653.0 | 653.0 |
| 17 | (benzyloxyaminocarbonyl)-dimethyl group | | 618.6 | 619.6 |
| 18 | (phenylaminocarbonyl)-dimethyl group | | 588.6 | 589.2 |
| 19 | (benzylaminocarbonyl)-dimethyl group | | 602.6 | 602.9 |

TABLE 1-continued

| Example | V | Stereo | Mol. Wt. | Mass Spec. |
|---|---|---|---|---|
| 20 | | | 632.6 | 633.2 |
| 21 | | | 616.6 | 617.4 |
| 22 | | | 604.6 | 605.2 |
| 23 | | | 591.5 | 592.3 |
| 24 | | | 525.5 | 526.6 |
| 25 | | | 553.6 | 554.5 |
| 26 | | E | 696.7 | 697.9 |

TABLE 1-continued

| Example | V | Stereo | Mol. Wt. | Mass Spec. |
|---------|---|--------|----------|------------|
| 27 | (benzyl-O-N=C(Et)(C(CH3)-)) | Z | 630.7 | 631.5 |
| 28 | (benzyl-O-N=C(Et)(C(CH3)-)) | E | 630.7 | 631.5 |
| 29 | (3-Cl-benzyl-O-N=C(Et)(C(CH3)-)) | E | 665.1 | 665.4 |
| 30 | (3-Cl-benzyl-O-N=C(n-Bu)(C(CH3)-)) | Z | 693.2 | 693.5 |

TABLE 1-continued

| Example | V | Stereo | Mol. Wt. | Mass Spec. |
|---|---|---|---|---|
| 31 | 3-chlorobenzyl O-N=C(butyl)(methyl) | E | 693.2 | 693.5 |
| 32 | 3-fluorobenzyl O-N=CH-(methyl) | E,Z mix | 620.6 | 621.6 |
| 33 | 3,4-difluorobenzyl O-N=CH-(methyl) | E,Z mix | 638.6 | 638.7 |
| 34 | 3-chlorobenzyl O-N=CH-(methyl) | E,Z mix | 637.0 | 636.7 |

TABLE 1-continued
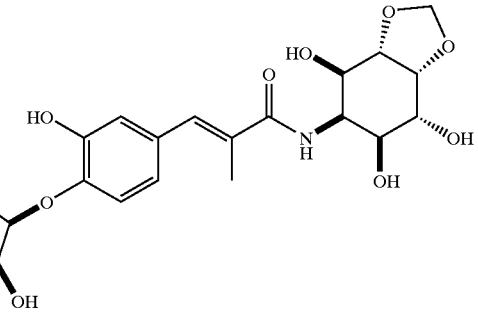
| Example | V | Stereo | Mol. Wt. | Mass Spec. |
|---|---|---|---|---|
| 35 | 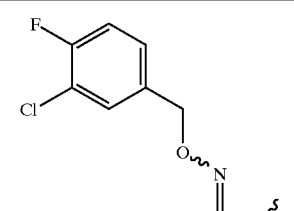 | E,Z mix | 655.0 | 655.4 |
| 36 | 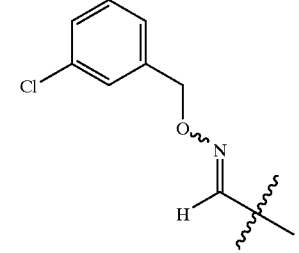 | E,Z mix | 655.0 | 654.5 |
TABLE 2
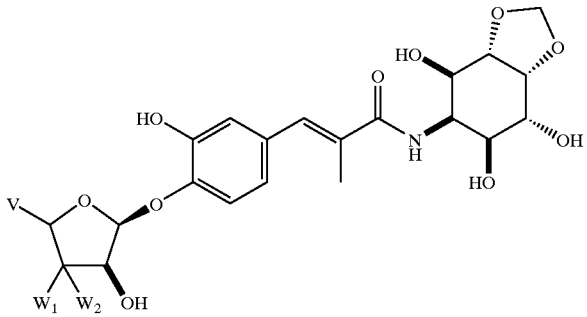
| Example | V | Stereo | W¹, W² | Mol. Wt. | Mass Spec. |
|---|---|---|---|---|---|
| 37 | 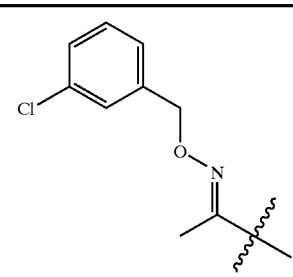 | E oxime | 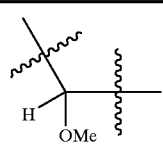 | 665.1 | 665.2 |

TABLE 2-continued
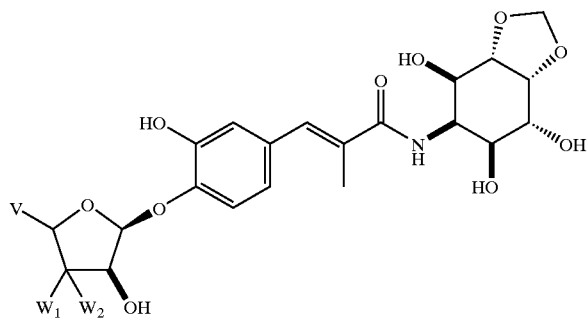
| Example | V | Stereo | W¹, W² | Mol. Wt. | Mass Spec. |
|---|---|---|---|---|---|
| 38 | (benzyloxyimino-isopropyl group) | E,Z mix; both isomers at C-4" | (CH₂ linker) | 600.6 | 601.3 |
| 39 | (3-chlorobenzyloxyimino-isopropyl group) | E,Z mix; both isomers at C-4" | (CH₂ linker) | 635.1 | 635.3 |
TABLE 3
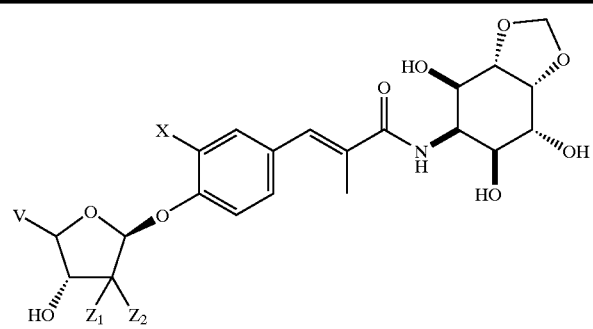
| Example | V | Stereo | Z¹, Z² | X | Mol Wt | Mass spec |
|---|---|---|---|---|---|---|
| 40 | (2,4-dichlorophenoxy-hydroxymethyl-butenyl group) | E | (OH, H) | OH | 700.5 | 700.3 |

TABLE 3-continued

| Example | V | Stereo | $Z^1, Z^2$ | X | Mol Wt | Mass spec |
|---|---|---|---|---|---|---|
| 41 | 4-F, 2-Cl phenoxy-allyl | E | -CH₃, -OH (with H) | OH | 654.1 | 654.4 |
| 42 | 3-Cl phenoxy-allyl | E | -CH₃, -OH (with H) | OH | 636.1 | 636.1 |
| 43 | 2,4-diCl phenoxy-allyl | E | -CH₃, -OH (with H) | OH | 670.5 | 671.8 |
| 44 | 2-amino-thiazol-4-yl methyl | | -CH₃, -OH (with H) | OH | 567.6 | 568.0 |
| 45 | 2-(4-F,2-Cl-benzylamino)-thiazol-4-yl methyl | | -CH₃, -OH (with H) | OH | 710.1 | 710.0 |

TABLE 3-continued

| Example | V | Stereo | Z¹, Z² | X | Mol Wt | Mass spec |
|---|---|---|---|---|---|---|
| 46 | 3-chlorobenzyl-NH-thiazole | | -C(OH)(H)(Me)- | OH | 692.1 | 692.1 |
| 47 | 2-chlorobenzyl-NH-thiazole | | -C(OH)(H)(Me)- | OH | 692.1 | 692.0 |
| 48 | benzimidazole-CH₂-C(O)- | | -C(OH)(H)(Me)- | OH | 627.6 | 628.1 |
| 49 | 3-chlorobenzyl-O-N=C(CH₂-imidazole)- | E | -C(OH)(H)(Me)- | OH | 717.1 | 717.1 |
| 50 | 3-chlorobenzyl-O-N=C(CH₂F)- | Z | -C(OH)(H)(Me)- | OH | 669.1 | 669.3 |
| 51 | 3-chlorophenyl-NH-thiazole | | -C(OH)(H)(Me)- | OH | 678.1 | 678.4 |

TABLE 3-continued

| Example | V | Stereo | $Z^1, Z^2$ | X | Mol Wt | Mass spec |
|---|---|---|---|---|---|---|
| 52 | 3-chlorobenzyl oxime | E | C=O (gem-dimethyl) | OH | 649.1 | 649.7 |
| 53 | 2,4-dichlorophenoxy prenyl | E | C=O (gem-dimethyl) | OH | 682.5 | 682.7 |
| 54 | 3-chlorobenzyl oxime | E | C(OH) (gem-dimethyl) | OH | 665.1 | 665.3 |
| 55 | 3-chlorobenzyl oxime | E | C(OH)(allyl) (gem-dimethyl) | OH | 691.1 | 691.5 |

TABLE 3-continued

| Example | V | Stereo | $Z^1, Z^2$ | X | Mol Wt | Mass spec |
|---|---|---|---|---|---|---|
| 56 | 3-chlorobenzyl oxime | E | C(OH)(vinyl)(methyl) | OH | 677.1 | 677.3 |
| 57 | 2,4-dichlorophenoxy prenyl | E | oxime (=N-OH) | OH | 697.5 | 697.5 |
| 58 | 3-chlorobenzyl oxime | E | oxime (=N-OH) | OH | 664.1 | 664.3 |
| 59 | 2,4-dichlorophenoxy prenyl | E | CH(NH₂) | OH | 683.5 | 684.4 |

TABLE 3-continued

| Example | V | Stereo | $Z^1$, $Z^2$ | X | Mol Wt | Mass spec |
|---|---|---|---|---|---|---|
| 60 | 2,4-dichlorophenoxy prenyl group | E | NH-CH2-(2,4-dimethoxyphenyl) | OH | 833.7 | 883.7 |
| 61 | 2,4-dichlorophenoxy prenyl group | E | NHMe | OH | 697.6 | 697.6 |
| 62 | 3-chlorobenzyl oxime isopropyl | E,Z mix | CH (H,H) | F | 637.1 | 637.4 |
| 63 | 3-chlorobenzyl oxime isopropyl | E | CH (H,H) | H | 618.2 | 619.0 |

TABLE 3-continued
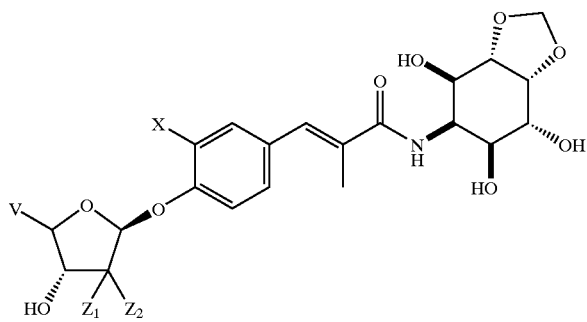
| Example | V | Stereo | $Z^1$, $Z^2$ | X | Mol Wt | Mass spec |
|---|---|---|---|---|---|---|
| 64 | [3-chlorobenzyl oxime of methyl ketone] | E,Z mix | [C(CH$_3$)$_2$OH] | H | 633.2 | 635.2 |
| 65 | [methyl 3-chloro-4-(3-methylbut-2-enyloxy)benzoate] | E | [C(CH$_3$)$_2$OH] | H | 691.2 | 692.1 |
| 66 | [4-(2-hydroxypropan-2-yl)-2-chloro-(3-methylbut-2-enyloxy)phenyl] | E | [C(CH$_3$)$_2$OH] | H | 691.2 | 690.3(M−1) |

TABLE 4

| Example | V | Stereo | C-1" stereochemistry | Mol Wt | Mass spec |
|---------|---|--------|----------------------|--------|-----------|
| 67 | 3-chlorobenzyl oxime | E,Z mix | β | 637.1 | 637.4 |
| 68 | 3-chlorobenzyl oxime | E,Z mix | α | 637.1 | 637.1 |
| 69 | benzyl oxime | E,Z mix | α | 602.2 | 602.7 |
| 70 | benzyl oxime | E,Z mix | β | 602.2 | 603.0 |

TABLE 4-continued

| Example | V | Stereo | C-1" stereochemistry | Mol Wt | Mass spec |
|---------|---|--------|----------------------|--------|-----------|
| 71 | | E,Z mix | β | 685.3 | 685.6 |
| 72 | | E,Z mix | β | 703.3 | 704.2 |
| 73 | | E,Z mix | β | 687.3 | 688.1 |

TABLE 4-continued

| Example | V | Stereo | C-1" stereochemistry | Mol Wt | Mass spec |
|---------|---|--------|----------------------|--------|-----------|
| 74 | | E,Z mix | β | 705.3 | 706.2 |
| 75 | | E,Z mix | β | 608.2 | 609.1 |
| 76 | | E,Z mix | β | 608.2 | 609.1 |
| Examples 77 and 78 are in the text | | | | | |
| 79 | | E | β | 669.2 | 669.7 |

TABLE 4-continued

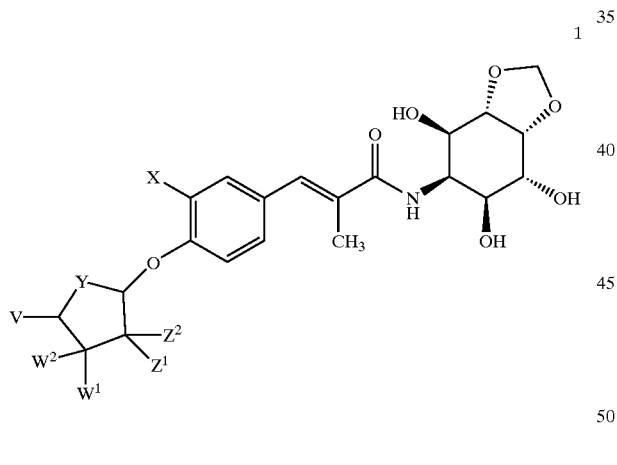

| Example | V | Stereo | C-1" stereochemistry | Mol Wt | Mass spec |
|---|---|---|---|---|---|
| 80 | 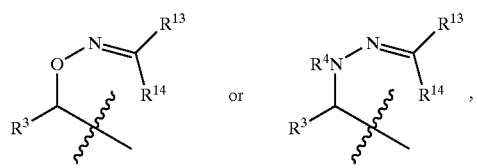 | E | α | 669.2 | 669.5 |

What is claimed is:

1. A compound of the formula

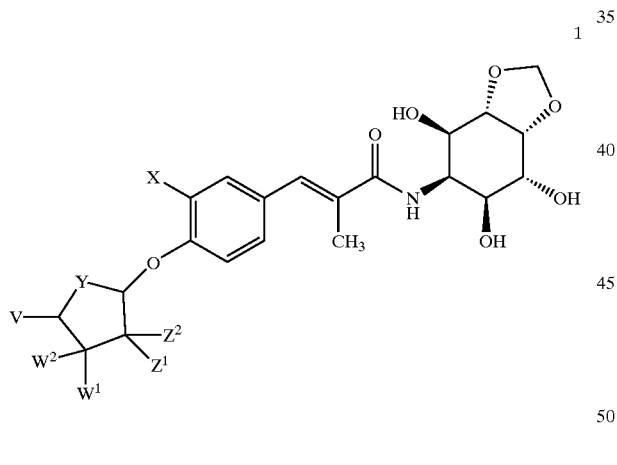

or a pharmaceutically acceptable salt, prodrug or solvate thereof, wherein:

X is H, F, OH, or $NH_2$;

Y is O or $CH_2$;

$Z^1$ is $R^3$ and $Z^2$ is $OR^{13}$; or $Z^1$ is H and $Z^2$ is $R^3$, $-NR^3R^4$, $-NR^3C(O)R^4$, or F; or $Z^1$ and $Z^2$ are taken together to form =O or $=NOR^3$;

$W^1$ is $R^3$ and $W^2$ is $OR^{13}$; or $W^1$ is H and $W^2$ is $R^3$, $-NR^3R^4$, $-NR^3C(O)R^4$, or F; or $W^1$ and $W^2$ are taken together to form =O or $=NOR^3$;

V is a group having the following structure

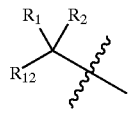

or V is $R^3OC(O)-$, $R^3R^4NC(O)-$ or $R^3O(R^4)NC(O)-$, in which groups $R^3$ and $R^4$ optionally can be taken together to form a 4 to 10 membered heterocyclic group which may be optionally substituted by 1 to 3 $R^6$ groups; or V is a group having the following structure:

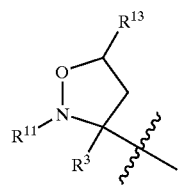

or V is a group of the structure

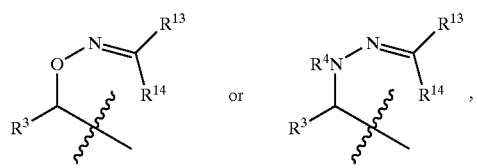

where both E and Z isomers are included;

or V is a carbon-linked 4 to 10 membered heterocyclic group, which may be optionally substituted by 1 to 3 $R^6$ groups;

$R^1$ is H and $R^2$ is —$NR^3R^4$, —$NR^4C(O)R^3$, —$OC(O)NR^3R^4$ or —$OR^3$; or $R^1$ and $R^2$ are taken together to form O, =N—$OR^3$, or =$C(R^5)$ $X^1$—$X^2$—$R^8$, wherein:

$X^1$ is —$CR^9R^{10}$—, and $X^2$ is selected from the group consisting of —$CR^9R^{10}$—, —$S(O)_n$— wherein n is an integer from 0 to 2, —$NR^9$—, and O; where $X^2$ is —$NR^9$—, then $R^8$ and $R^9$ may be taken together to form a 5 to 12 membered heterocyclic group, which is optionally substituted by 1 to 3 $R^6$ groups;

or $X^1$ and $X^2$ independently or together represent a bond with the proviso that if $X^1$ is a bond than $X^2$ is either a bond or —$CR^9R^{10}$—;

each $R^3$ is independently selected from the group consisting of H, $C_1$–$C_{10}$ alkyl, $C_2$–$C_{10}$ alkenyl, $C_2$–$C_{10}$ alkynyl, —$(CR^9R^{10})_t(C_3$–$C_{10}$ cycloalkyl), —$(CR^9R^{10})_t(C_6$–$C_{10}$ aryl), and —$(CR^9R^{10})_t$(4 to 10 membered heterocyclic), wherein each t is independently an integer from 0 to 5, said alkyl, alkenyl and alkynyl groups optionally contain 1 or 2 hetero moieties selected from the group consisting of O, —$S(O)_j$— wherein j is an integer from 0 to 2, and —$N(R^9)$— with the proviso that two O atoms, two S atoms, or an O and S atom are not attached directly to each other, and the proviso that an O atom, a S atom or a N atom are not attached directly to a triple bond or non-aromatic double bond; said cycloalkyl, aryl and heterocyclic $R^3$ groups are optionally fused to a benzene ring, a $C_5$–$C_8$ cycloalkyl group, or a 4 to 10 membered heterocyclic group; the —$(CR^9R^{10})_t$— moieties of the foregoing $R^3$ groups optionally include a carbon-carbon double or triple bond where t is an integer between 2 and 5; and the foregoing $R^3$ groups, except H but including any optional fused rings referred to above, are optionally substituted by 1 to 5 $R^6$ groups, and with the proviso that $R^3$ must be attached through a carbon atom unless $R^3$ is H; each $R^4$ is independently H or $C_1$–$C_{10}$ alkyl;

$R^5$ is H or $C_1$–$C_6$ alkyl, wherein the foregoing $R^5$ alkyl group is optionally substituted by 1 or 2 $R^6$ groups;

each $R^6$ is independently selected from the group consisting of $C_1$–$C_{10}$ alkyl, $C_2$–$C_{10}$ alkenyl, $C_2$–$C_{10}$ alkynyl, $C_3$–$C_{10}$ cycloalkyl, oxo, halo, cyano, nitro, trifluoromethyl, difluoromethoxy, trifluoromethoxy, azido, —$OR^7$, $C(O)R^7$, —$C(O)OR^7$, —$NR^9C(O)OR^{11}$, —$OC(O)R^7$, —$NR^9SO_2R^{11}$, —$SO_2NR^7R^9$, —$NR^9C(O)R^7$, —$C(O)NR^7R^9$, —$NR^7R^9$, $S(O)_j(CR^9R^{10})_m(C_6$–$C_{10}$ aryl), —$S(O)_j(C_1$–$C_6$ alkyl), wherein j is an integer from 0 to 2, —$(CR^9R^{10})_m(C_6$–$C_{10}$ aryl), —$O(CR^9R^{10})_m$ $(C_6$–$C_{10}$ aryl), —$NR^9(CR^9R^{10})_m$ $(C_6$–$C_{10}$ aryl), and —$(CR^9R^{10})_m$(4 to 10 membered heterocyclic), wherein each m is independently an integer from 0 to 4; said alkyl, alkenyl and alkynyl groups optionally contain 1 or 2 hetero moieties selected from the group consisting of O, —$S(O)_j$— wherein j is an integer from 0 to 2, and —$N(R^7)$— with the proviso that two O atoms, two S atoms, or an O and S atom are not attached directly to each other, and the proviso that an O atom, a S atom or a N atom are not attached directly to a triple bond or a non-aromatic double bond; said cycloalkyl, aryl and heterocyclic $R^6$ groups are optionally fused to a $C_6$–$C_{10}$ aryl group, a $C_5$–$C_8$ cycloalkyl group, or a 4 to 10 membered heterocyclic group; and said alkyl, cycloalkyl, aryl and heterocyclic $R^6$ groups are optionally substituted by 1 to 5 substituents independently selected from the group consisting of oxo, halo, cyano, nitro, trifluoromethyl, difluoromethoxy, trifluoromethoxy, azido, —$NR^9SO_2R^{11}$, —$SO_2NR^7R^9$, —$C(O)R^7$, —$C(O)OR^7$, —$OC(O)R^7$, —$NR^9C(O)OR^{11}$, —$NR^9C(O)R^7$, —$C(O)NR^7R^9$, —$NR^7R^9$, —$OR^7$, $C_1$–$C_{10}$ alkyl, —$(CR^9R^1)_m(C_6$–$C_{10}$ aryl), and —$(CR^9R^{10})_m$(4 to 10 membered heterocyclic), wherein each m is independently an integer ranging from 0 to 4;

each $R^7$ is independently selected from the group consisting of H, $C_1$–$C_{10}$ alkyl, $C_3$–$C_{10}$ cycloalkyl, —$(CR^9R^{10})_m(C_6$–$C_{10}$ aryl), and —$(CR^9R^{10})_m$(4 to 10 membered heterocyclic), wherein each m is independently an integer from 0 to 4; said alkyl group optionally includes 1 or 2 hetero moieties selected from the group consisting of O, —$S(O)_j$— wherein j is an integer ranging from 0 to 2, and —$N(R^9)$— with the proviso that two O atoms, two S atoms, or an O and S atom are not attached directly to each other; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^7$ substituents, except H, are optionally substituted by 1 to 5 substituents independently selected from the group consisting of oxo, halo, cyano, nitro, trifluoromethyl, difluoromethoxy, trifluoromethoxy, azido, —$C(O)R^9$, —$C(O)OR^9$, —$OC(O)R^9$, —$NR^9C(O)R^{10}$, —$C(O)NR^9R^{10}$, —$NR^9R^{10}$, hydroxy, $C_1$–$C_6$ alkyl, and $C_1$–$C_6$ alkoxy, and with the proviso that $R^7$ must be attached through a carbon atom unless $R^7$ is H;

each $R^8$ is independently selected from the group consisting of $R^3$, —$C(O)R^3$, or —$C(O)NR^9R^3$, wherein $R^3$ is as defined above;

each $R^9$ and $R^{10}$ is independently H or $C_1$–$C_6$ alkyl; and, $R^{11}$ is selected from the [substituents provided in the definition of $R^7$ except H] group consisting of $C_1$–$C_{10}$ alkyl, $C_3$–$C_{10}$ cycloalkyl, —$(CR^9R^{10})_m(C_6$–$C_{10}$ aryl), and —$(CR^9R^{10})_m$(4 to 10 membered heterocyclic), wherein each m is independently an integer from 0 to 4; said alkyl group optionally includes 1 or 2 hetero moieties selected from the group consisting of O, —$S(O)_j$— wherein j is an integer ranging from 0 to 2, and —$N(R^9)$— with the proviso that two O atoms, two S atoms, or an O and S atom are not attached directly to each other; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^{11}$ substituents are optionally substituted by 1 to 5 substituents independently selected from the group consisting of oxo, halo, cyano, nitro, trifluoromethyl, difluoromethoxy, trifluoromethoxy, azido, —$C(O)R^9$, —$C(O)OR^9$, —$OC(O)R^9$, —$NR^9C(O)R^{10}$, —$C(O)NR^9R^{10}$, —$NR^9R^{10}$, hydroxy, $C_1$–$C_6$ alkyl, and $C_1$–$C_6$ alkoxy, and with the proviso that $R^{11}$ must be attached through a carbon atom;

$R^{12}$ is selected from the [substituents provided in the definition of $R^3$,] group consisting of H, $C_1$–$C_{10}$ alkyl, $C_2$–$C_{10}$ alkenyl, $C_2$–$C_{10}$ alkynyl, —$(CR^9R^{10})_t(C_3$–$C_{10}$ cycloalkyl), —$(CR^9R^{10})_t(C_6$–$C_{10}$ aryl), and —$(CR^9R^{10})_t$(4 to 10 membered heterocyclic), wherein each t is independently an integer from 0 to 5, said alkyl, alkenyl and alkynyl groups optionally contain 1 or 2 hetero moieties selected from the group consisting of O, —$S(O)_j$— wherein j is an integer from 0 to 2, and —$N(R^9)$— with the proviso that two O atoms, two S atoms, or an O and S atom are not attached directly to each other, and with the proviso that an O atom, a S atom or a N atom are not attached directly to a triple bond or non-aromatic double bond; said cycloalkyl, aryl and heterocyclic $R^3$ groups are optionally fused to a benzene ring, a $C_5$–$C_8$ cycloalkyl group, or a 4 to 10 membered heterocyclic group; the —$(CR^9R^{10})_t$— moieties of the foregoing $R^{12}$ groups optionally include a carbon-carbon double or triple bond where t is an integer between 2 and 5; and the foregoing $R^{12}$ groups, except H but including any optional fused rings referred to above, are optionally substituted by 1 to 5 $R^6$ groups, and with the proviso that $R^{12}$ must be attached through a carbon atom unless $R^{12}$ is H, and wherein $R^{12}$ cannot be methyl if (a) X is OH, Y is O, $W^1$ is H, $W^2$ is α-OH, $Z^1$ is H, Z is β-OH; or (b) if X is OH, Y is O, $W^1$ is H, $W^2$ is α-OH, $Z^1$ and $Z^2$ are both H; and with the proviso that $R^{12}$ must be attached through a carbon atom unless $R^{12}$ is H;

$R^{13}$ is defined as described for $R^3$; and, $R^{14}$ is H or $C_1$–$C_{10}$ alkyl, except that $R^{14}$ cannot be H when $R^{13}$ is H.

2. A compound according to claim 1 wherein V equals

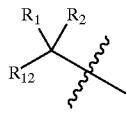

and $R^1$ and $R^2$ are taken together as =O or =NOR$^3$, and the configuration of the 1″ center is that of hygromycin A.

3. A compound according to claim 2 wherein:

$Z^1$ is $R^3$ and $Z^2$ is OR$^{13}$; or $Z^1$ is H and $Z^2$ is $R^3$, —NR$^3$R$^4$, —NR$^3$C(O)R$^4$, or F;

$W^1$ is $R^3$ and $W^2$ is OR$^{13}$; or $W^1$ is H and $W^2$ is $R^3$, —NR$^3$R$^4$, —NR$^3$C(O)R$^4$, or F; wherein each $R^3$ and $R^{13}$ are independently selected from the group consisting of H, $C_1$–$C_4$ alkyl, —$(CR^9R^{10})_t$($C_3$–$C_{10}$ cycloalkyl), —$(CR^9R^{10})_t$($C_6$–$C_{10}$ aryl), and —$(CR^9R^{10})_t$(4 to 10 membered heterocyclic), wherein each t is independently an integer from 0 to 3, said alkyl group optionally contains 1 hetero moiety selected from the group consisting of O, —S(O)$_j$— wherein j is an integer from 0 to 2, and —N(R$^9$)—, and the foregoing $R^3$ and $R^{13}$ groups, except H, are optionally substituted by 1 to 5 $R^6$ groups, and with the proviso that $R^3$ and $R^{13}$ must be attached through a carbon atom unless it is H; each $R^4$ is independently H or $C_1$–$C_4$ alkyl; each $R^6$ is independently selected from the group consisting of $C_1$–$C_4$ alkyl, oxo, halo, trifluoromethyl, difluoromethoxy, trifluoromethoxy, —OR$^1$, —C(O)R$^7$, —NR$^9$C(O)OR$^{11}$, —NR$^9$C(O)R$^7$, —C(O)NR$^7$R$^9$, NR$^7$R$^9$; wherein $R^7$ and $R^9$ are H, $C_1$–$C_4$ alkyl; $R^{11}$ is $C_1$–$C_4$ alkyl;

$R^1$ and $R^2$ are taken together as =O or =NOR$^3$, wherein each $R^3$ is independently selected from the group consisting of $C_1$–$C_4$ alkyl, $C_3$–$C_8$ alkenyl, —$(CR^9R^{10})_t$($C_6$–$C_{10}$ aryl), and —$(CR^9R^{10})_t$(4 to 10 membered heterocyclic), wherein each t is independently an integer ranging from 0 to 3, said alkyl and alkenyl groups optionally contain 1 or 2 hetero moieties selected from the group consisting of O, —S(O)$_j$— wherein j is an integer ranging from 0 to 2 and —N(R$^9$)—, with the proviso that two O atoms, two S atoms, or an O and S atom are not attached directly to each other, and the proviso that an O atom, a S atom or a N atom are not attached directly to a non-aromatic double bond; said aryl and heterocyclic $R^3$ groups are optionally fused to a benzene ring, a $C_5$–$C_8$ cycloalkyl group, or a 4 to 10 membered heterocyclic group; and the foregoing $R^3$ groups, including any optional fused rings referred to above, are optionally substituted by 1 to 5 $R^6$ groups, and with the proviso that $R^3$ must be attached through a carbon atom;

$R^{12}$ is $C_1$–$C_4$ alkyl, and said alkyl group is optionally substituted by 1 to 3 $R^6$ groups, except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H;

each $R^6$ is independently selected from the group consisting of $C_1$–$C_4$ alkyl, oxo, halo, trifluoromethyl, difluoromethoxy, trifluoromethoxy, —OR$^7$, —C(O)R$^7$, —NR$^9$C(O)OR$^{11}$, —NR$^9$SO$_2$R$^{11}$, —SO$_2$NR$^7$R$^9$, —NR$^9$C(O)R$^7$, —C(O)NR$^7$R$^9$, —NR$^7$R$^9$, —S(O)$_j$(CR$^9$R$^{10}$)$_m$(C$_6$–C$_{10}$ aryl), —S(O)$_j$(C$_1$–C$_6$ alkyl), wherein j is an integer ranging from 0 to 2, —(CR$^9$R$^{10}$)$_m$(C$_6$–C$_{10}$ aryl), —O(CR$^9$R$^{10}$)$_m$(C$_6$–C$_{10}$ aryl), —NR$^9$ (CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 2; and said alkyl, cycloalkyl, aryl and heterocyclic $R^6$ groups are optionally substituted by 1 to 5 substituents independently selected from the group consisting of oxo, halo, trifluoromethyl, difluoromethoxy, trifluoromethoxy, —NR$^9$SO$_2$R$^{11}$, —C(O)R$^7$, —NR$^9$C(O)OR$^{11}$, —NR$^9$C(O)R$^7$, —C(O)NR$^7$R$^9$, —NR$^7$R$^9$, —OR$^7$, $C_1$–$C_4$ alkyl, —(CR$^9$R$^{10}$)$_m$(C$_6$–C$_{10}$ aryl), and (CR$^9$R$^{10}$)$_m$(4 to 10 membered heterocyclic), wherein each m is independently an integer from 0 to 2;

$R^7$ is independently selected from the group consisting of H, $C_1$–$C_4$ alkyl, $C_3$–$C_6$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 2; said alkyl group optionally includes 1 hetero moiety selected from the group consisting of O, —S(O)$_j$— wherein j is an integer from 0 to 2, and —N (R$^9$)—; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^7$ substituents, except H, are optionally substituted by 1 to 5 substituents independently selected from the group consisting of oxo, halo, trifluoromethyl, difluoromethoxy, trifluoromethoxy, —C(O)R$^9$, —NR$^9$C(O)R$^{10}$, —C(O) NR$^9$R$^{10}$, —NR$^9$R$^{10}$, hydroxy, $C_1$–$C_4$ alkyl, and $C_1$–$C_4$ alkoxy, and with the proviso that $R^7$ must be attached through a carbon atom unless $R^7$ is H;

$R^9$ and $R^{10}$ are independently H, $C_1$–$C_4$ alkyl; $R^{11}$ is selected from the group consisting of $C_1$–$C_{10}$ alkyl, $C_3$–$C_{10}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom.

4. A compound according to claim 3 wherein:

X is F, H or OH;

Y is O;

W$^1$ is R$^3$, W$^2$ is OR$^{13}$; or W$^1$ is H, W$^2$ is R$^3$ or F;

Z$^1$ is R$^3$, Z$^2$ is OR$^{13}$; or Z$^1$ is H, Z$^2$ is R$^3$ or F; wherein R$^3$ and R$^{13}$ are independently H, C$_1$–C$_4$ alkyl, and said alkyl groups are optionally substituted by 1 to 3 R$^6$ groups; wherein each R$^6$ is independently oxo, halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, or —NR$^7$R$^9$; wherein R$^7$ and R$^9$ are H or C$_1$–C$_4$ alkyl; R$^{11}$ is C$_1$–C$_4$ alkyl;

R$^1$ and R$^2$ are taken together as =NOR$^3$;

R$^3$ is —(CR$^9$R$^{10}$)$_t$(C$_6$–C$_{10}$ aryl), and —(CR$^9$R$^{10}$)$_t$(4 to 10 membered heterocyclic), wherein each t is independently an integer from 0 to 3; the foregoing R$^3$ groups are optionally substituted by 1 to 5 R$^6$ groups, and with the proviso that R$^3$ must be attached through a carbon atom;

R$^{12}$ is C$_1$–C$_4$ alkyl, and said alkyl group is optionally substituted by 1 to 3 R$^6$ groups, except that R$^{12}$ cannot be methyl if (a) X is OH, Y is O, W$^1$ is H, W$^2$ is α-OH, Z$^1$ is H, Z$^2$ is β-OH, or if (b) X is OH, Y is O, W$^1$ is H, W$^2$ is α-OH, Z$^1$ is H, Z$^2$ is H; wherein R$^6$ is C$_1$–C$_4$ alkyl, oxo, halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, —NR$^7$R$^9$, —(CR$^9$R$^{10}$)$_m$(C$_6$–C$_{10}$ aryl), —O(CR$^9$R$^{10}$)$_m$(C$_6$–C$_{10}$ aryl), —NR$^9$(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 2; said alkyl, aryl and heterocyclic R$^6$ groups are optionally substituted by 1 to 5 substituents independently selected from the group consisting of oxo, halo, trifluoromethyl, difluoromethoxy, trifluoromethoxy, —NR$^9$SO$_2$R$^{11}$, —C(O)R$^7$, —NR$^9$C(C)OR$^{11}$, —NR$^9$(O)R$^7$—C(O)NR$^7$R$^9$, —NR$^7$R$^9$, —OR$^7$, and C$_1$–C$_4$ alkyl;

R$^7$ is independently selected from the group consisting of H, C$_1$–C$_4$ alkyl, C$_3$–C$_6$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; the foregoing R$^7$ substituents, except H, are optionally substituted by 1 to 5 substituents independently selected from the group consisting of oxo, halo, trifluoromethyl, difluoromethoxy, trifluoromethoxy, —C(O)R$^9$, —NR$^9$C(O)R$^{10}$, —C(O)NR$^9$R$^{10}$, —NR$^9$R$^{10}$, hydroxy, C$_1$–C$_4$ alkyl, and C$_1$–C$_4$ alkoxy;

each R$^9$ and R$^{10}$ are independently H or C$_1$–C$_4$ alkyl;

R$^{11}$ is selected from the group consisting of C$_1$–C$_{10}$ alkyl, C$_3$–C$_{11}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a C$_6$–C$_{10}$ aryl group, a C$_5$–C$_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$—C()OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom.

5. A compound according to claim 4 wherein:

Z$^1$ is H, Z$^2$ is OH; or Z$^1$ is methyl, Z$^2$ is OH; or both Z$^1$ and Z$^2$ are H; or Z$^1$ is H, Z$^2$ is F;

W$^1$ is H, W$^2$ is OH;

R$^1$ and R$^2$ are taken together as =NOR$^3$, wherein R$^3$ is —(CR$^9$R$^{10}$)$_t$(C$_6$–C$_{10}$ aryl), and —(CR$^9$R$^{10}$)$_t$(4 to 10 membered heterocyclic), wherein each t is independently an integer ranging from 0 to 2, and the foregoing R$^3$ groups are optionally substituted by 1 to 5 R$^6$ groups; wherein R$^6$ is C$_1$–C$_4$ alkyl, oxo, halo, trifluoromethyl, difluoromethoxy, trifluoromethoxy, —OR$^7$, —C(O)R$^7$, —(CR$^9$R$^{10}$)$_m$(C$_6$–C$_{10}$ aryl), —O(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; said alkyl, aryl and heterocyclic R$^6$ groups are optionally substituted by 1 to 5 substituents independently selected from the group consisting of oxo, halo, trifluoromethyl, difluoromethoxy, trifluoromethoxy, —C(O)R$^7$, —NR$^9$C(O)OR$^{11}$, —NR$^9$C(O)R$^7$, —C(O)NR$^7$R$^9$, —OR$^7$, and C$_1$–C$_4$ alkyl;

R$^7$ is independently selected from the group consisting of H, C$_1$–C$_4$ alkyl; the foregoing R$^7$ substituents, except H, are optionally substituted by 1 to 3 substituents independently selected from the group consisting of trifluoromethyl, —C(O)R$^9$, —NR$^9$C(O)R$^{10}$, —C(O)NR$^9$R$^{10}$, —NR$^9$R$^{10}$, hydroxy, and C$_1$–C$_4$ alkoxy; R$^9$ and R$^{10}$ are independently H, C$_1$–C$_4$ alkyl; R$^{11}$ is selected from the group consisting of C$_1$–C$_{10}$ alkyl, C$_3$–C$_{10}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a C$_6$–C$_{10}$ aryl group, a C$_5$–C$_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom; and R$^{12}$ is C$_1$–C$_4$ alkyl except that R$^{12}$ cannot be methyl if (a) X is OH, Y is O, W$^1$ is H, W$^2$ is α-OH, Z$^1$ is H, Z$^2$ is β-OH, or if (b) X is OH, Y is O, W$^1$ is H, W$^2$ is α-OH, Z$^1$ is H, Z$^2$ is H.

6. A compound according to claim 5 wherein:

R$^1$ and R$^2$ are taken together as =NOR$^3$, wherein R$^3$ is —(CR$^9$R$^{10}$)$_t$-phenyl, and —(CR$^9$R$^{10}$)$_t$(5 to 9 membered heterocyclic), where t is 0 or 1, and the foregoing $R^3$ groups are optionally substituted by 1 to 5 $R^6$ groups, wherein each $R^6$ is independently $C_1$–$C_4$ alkyl, halo, trifluoromethyl, and —$(CR^9R^{10})_m$(4 to 10 membered heterocyclic), wherein each m is independently an integer from 0 to 1; said heterocyclic $R^6$ groups are optionally substituted by 1 to 5 substituents independently selected from the group consisting of halo, trifluoromethyl, and $C_1$–$C_4$ alkyl; each $R^9$ and $R^{10}$ is independently H or $C_1$–$C_3$ alkyl.

7. A compound according to claim 1 wherein:
V equals

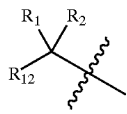

and $R^1$ and $R^2$ are taken together as =$C(R^5)X_1$—$X^2$—$R^8$ and the configuration of the 1" center is that of hygromycin A.

8. A compound according to claim 7 wherein:
$W^1$ is $R^3$, $W^2$ is $OR^{13}$; or $W^1$ is H, $W^2$ is $R^3$, $NR^3R^4$, $NR^3C(O)R^4$, or F;

$Z^1$ is $R^3$, $Z^2$ is $OR^{13}$; or $Z^1$ is H, $Z^2$ is $R^3$ $NR^3R^4$, $NR^3C(O)R^4$, or F; wherein $R^3$ and $R^{13}$ are independently selected from the group consisting of H, $C_1$–$C_4$ alkyl, —$(CR^9R^{10})_t(C_3$–$C_{10}$ cycloalkyl), —$(CR^9R^{10})_t$ $(C_6$–$C_{10}$ aryl), and —$(CR^9R^{10})_t$(4 to 10 membered heterocyclic), wherein each t is independently an integer ranging from 0 to 3, said alkyl group optionally contains 1 hetero moiety selected from the group consisting of O, —$S(O)_j$— wherein j is an integer ranging from 0 to 2, and —$N(R^9)$—, and the foregoing $R^3$ and $R^{13}$ groups, except H, are optionally substituted by 1 to 5 $R^6$ groups, and with the proviso that $R^3$ and $R^{13}$ must be attached through a carbon atom unless it is H; each $R^4$ is independently H or $C_1$–$C_4$ alkyl; each $R^6$ is independently selected from the group consisting of $C_1$–$C_4$ alkyl, oxo, halo, trifluoromethyl, difluoromethoxy, trifluoromethoxy, —$OR^7$, —$C(O)R^7$, —$NR^9C(O)OR^{11}$, —$NR^9C(O)R^7$, —$C(O)NR^7R^9$, and —$NR^7R^9$; wherein each $R^7$ and $R^9$ is independently H or $C_1$–$C_4$ alkyl; $R^{11}$ is $C_1$–$C_4$ alkyl;

$R^1$ and $R^2$ are taken together as =$C(R^5)X^1$—$X^2$—$R^8$; wherein $X^1$ is —$CR^9R^{10}$—, and $X^2$ is selected from the group consisting of —$CR^9R^{10}$—, $S(O)_n$— wherein n is 0 to 2, —$NR^9$—, and O; where $X^2$ is —$NR^9$—, then $R^8$ and $R^9$ may be taken together to form a 5 to 12 membered heterocyclic, which is optionally substituted by 1 to 3 $R^6$ groups; $X^1$ and $X^2$ can also independently or together represent a bond with the proviso that if $X^1$ is a bond than $X^2$ must be either a bond or —$CR^9R^{10}$—; and where $R^5$ is H or $C_1$–$C_6$ alkyl, wherein the foregoing $R^5$ alkyl group is optionally substituted by 1 or 2 $R^6$ groups;

and where each $R^8$ is independently selected from the group consisting of $R^3$, —$C(O)R^3$, or —$C(O)NR^9R^3$, with the additional proviso that an N and O atom, and an N and S atom are not attached directly to each other, wherein each $R^3$ is independently selected from the group consisting of $C_1$–$C_4$ alkyl, $C_3$–$C_8$ alkenyl, —$(CR^9R^{10})_t(C_6$–$C_{10}$ aryl), and —$(CR^9R^{10})_t$(4 to 10 membered heterocyclic), wherein each t is independently an integer ranging from 0 to 3, said alkyl or alkenyl group optionally contains 1 hetero moiety selected from the group consisting of O, —$S(O)_j$— wherein j is an integer ranging from 0 to 2, and —$N(R^9)$—, with the proviso that an O atom, a S atom or a N atom are not attached directly to a non-aromatic double bond; said aryl and heterocyclic $R^3$ groups are optionally fused to a benzene ring, a $C_5$–$C_8$ cycloalkyl group, or a 4 to 10 membered heterocyclic group; and the foregoing $R^3$ groups, including any optional fused rings referred to above, are optionally substituted by 1 to 5 $R^6$ groups, and with the proviso that $R^3$ must be attached through a carbon atom; $R^{12}$ is $C_1$–$C_4$ alkyl, and said alkyl group is optionally substituted by 1 to 3 $R^6$ groups, except that $R^{12}$ cannot be methyl if (a) X is OH, Y is O, $W^1$ is H, $W^2$ is α-OH, $Z^1$ is H, $Z^2$ is β-OH, or if (b) X is OH, Y is O, $W^1$ is H, $W^2$ is α-OH, $Z^1$ is H, $Z^2$ is H; each $R^6$ is independently selected from the group consisting of $C_1$–$C_4$ alkyl, oxo, halo, trifluoromethyl, difluoromethoxy, trifluoromethoxy, —$OR^7$, —$C(O)R^7$, —$NR^9C(O)OR^{11}$, —$NR^9SO_2R^{11}$, —$SO_2NR^7R^9$, —$NR^9C(O)R^7$, —$C(O)NR^7R^9$, —$NR^7R^9$, —$S(O)_j(CR^9R^{10})_m(C_6$–$C_{10}$ aryl), —$S(O)_j$ ($C_1$–$C_6$ alkyl), wherein j is an integer ranging from 0 to 2, —$(CR^9R^{10})_m(C_6$–$C_{10}$ aryl), —$O(CR^9R^{10})_m(C_6$–$C_{10}$ aryl) —$NR^9(CR^9R^{10})_m(C_6$–$C_{10}$ aryl), and —$(CR^9R^{10})_m$(4 to 10 membered heterocyclic), wherein each m is independently an integer ranging from 0 to 2; and said alkyl, cycloalkyl, aryl and heterocyclic $R^6$ groups are optionally substituted by 1 to 5 substituents independently selected from the group consisting of oxo, halo, trifluoromethyl, difluoromethoxy, trifluoromethoxy, —$NR^9SO_2R^{11}$, —$C(O)R^7$, —$NR^9C(O)OR^{11}$, —$NR^9C(O)R^7$, —$C(O)NR^7R^9$, —$NR^7R^9$, —$OR^7$, $C_1$–$C_4$ alkyl, —$(CR^9R^{10})_m(C_6$–$C_{10}$ aryl), and —$(CR^9R^{10})_m$(4 to 10 membered heterocyclic), wherein each m is independently an integer ranging from 0 to 2; $R^7$ is independently selected from the group consisting of H, $C_1$–$C_4$ alkyl, $C_3$–$C_6$ cycloalkyl, —$(CR^9R^{10})_m$ $(C_6$–$C_{10}$ aryl), and —$(CR^9R^{10})_m$(4 to 10 membered heterocyclic), wherein each m is independently an integer ranging from 0 to 2; said alkyl group optionally includes 1 hetero moiety selected from the group consisting of O, —$S(O)_j$— wherein j is an integer ranging from 0 to 2, and —$N(R^9)$—; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^7$ substituents, except H, are optionally substituted by 1 to 5 substituents independently selected from the group consisting of oxo, halo, trifluoromethyl, difluoromethoxy, trifluoromethoxy, —$C(O)R^9$, —$NR^9C(O)R^{10}$, —$C(O)NR^9R^{10}$, —$NR^9R^{10}$, hydroxy, $C_1$–$C_4$ alkyl, and $C_1$–$C_4$ alkoxy, and with the proviso that $R^7$ must be attached through a carbon atom unless $R^7$ is H;

each $R^9$ and $R^{10}$ are independently H or $C_1$–$C_4$ alkyl; and $R^{11}$ is selected from the group consisting of $C_1$–$C_{10}$ alkyl, $C_3$–$C_{10}$ cycloalkyl, —$(CR^9R^{10})_m(C_6$–$C_{10}$ aryl), and —$(CR^9R^{10})_m$(4 to 10 membered heterocyclic), wherein each m is independently an integer from 0 to 4; said alkyl group optionally includes 1 or 2 hetero moieties selected from the group consisting of O, —$S(O)_j$— wherein j is an integer ranging from 0 to 2, and —$N(R^9)$— with the proviso that two O atoms, two S atoms, or an O and S atom are not attached directly to each other; said cycloalkyl, aryl and heterocyclic $R^7$ groups are optionally fused to a $C_6$–$C_{10}$ aryl group, a $C_5$–$C_8$ cycloalkyl group, or a 4 to 10 membered heterocyclic group; and the foregoing $R^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom and the configuration of the 1" center is that of hygromycin A.

9. A compound according to claim 8 wherein:

X is F, H or OH;

Y is O;

W$^1$ is R$^3$, W$^2$ is OR$^{13}$; or W$^1$ is H, W$^2$ is R$^3$, NR$^3$R$^4$, or F;

Z$^1$ is R$^3$, Z$^2$ is OR$^{13}$; or Z$^1$ is H, Z$^2$ is R$^3$, NR$^3$R$^4$ or F; wherein each R$^3$ and R$^{13}$ are independently H or C$_1$–C$_4$ alkyl, and said alkyl groups are optionally substituted by 1 to 3 R$^6$ groups; wherein each R$^6$ is independently oxo, halo, trifluoromethyl, difluoromethoxy, trifluoromethoxy, —OR$^7$, —C(O)R$^7$—NR$^9$C(O)OR, —NR(O)R$^7$, —C(O)NR$^7$R$^9$, and —NR$^7$R$^9$; wherein each R$^7$ and R$^9$ is independently H or C$_1$–C$_4$ alkyl; R$^{11}$ is C$_1$–C$_4$ alkyl;

R$^1$ and R$^2$ are taken together as =C(R$^5$)X$^1$—X$^2$—R$^8$; wherein X$^1$ is —CR$^9$R$^{10}$—, and X$^2$ is selected from the group consisting of —CR$^9$R$^{10}$—, —S(O)$_n$— wherein n is 0 to 2, —NR$^9$—, and O; where X$^2$ is —NR$^9$—, then R$^8$ and R$^9$ may be taken together to form a 5 to 12 membered heterocyclic, which is optionally substituted by 1 to 3 R$^6$ groups; X$^1$ and X$^2$ can also independently or together represent a bond with the proviso that if X$^1$ is a bond than X$^2$ must be either a bond or —CR$^9$R$^{10}$; and where R$^5$ is H or C$_1$–C$_6$ alkyl, wherein the foregoing R$^5$ alkyl group is optionally substituted by 1 or 2 R$^6$ groups:

and where R$^8$ is R$^3$ wherein each R$^3$ is independently —(CR$^9$R$^{10}$)$_t$(C$_6$–C$_{10}$ aryl) or —(CR$^9$R$^{10}$)$_t$(4 to 10 membered heterocyclic), wherein each t is independently an integer ranging from 0 to 3; the foregoing R$^3$ groups are optionally substituted by 1 to 5 R$^6$ groups, and with the proviso that R$^3$ must be attached through a carbon atom; R$^{12}$ is C$_1$–C$_4$ alkyl, and said alkyl group is optionally substituted by 1 to 3 R$^6$ groups, except that R$^{12}$ cannot be methyl if (a) X is OH, Y is O, W$^1$ is H, W$^2$ is α-OH, Z$^1$ is H, Z$^2$ is β-OH, or if (b) X is OH, Y is O, W$^1$ is H, W$^2$ is α-OH, Z$^1$ is H, Z$^2$ is H; wherein each R$^6$ is independently C$_1$–C$_4$ alkyl, oxo, halo, trifluoromethyl, difluoromethoxy, trifluoromethoxy, —OR$^7$, —C(O)R$^7$, —NR$^9$C(O)OR$^{11}$, —NRC(O)R$^7$, —C(O)NR$^7$R$^9$, —NR$^7$R$^9$, —(CR$^9$R$^{10}$)$_m$(C$_6$–C$_{10}$ aryl), —O(CR$^9$R$^{10}$)$_m$(C$_6$–C$_{10}$ aryl), —NR$^9$(CR$^9$R$^{10}$)$_m$ (C$_6$–C$_{10}$ aryl), and —(CR$^9$R$^{10}$)$_m$(4 to 10 membered heterocyclic), wherein each m is independently an integer ranging from 0 to 2; said alkyl, aryl and heterocyclic R$^6$ groups are optionally substituted by 1 to 5 substituents independently selected from the group consisting of oxo, halo, trifluoromethyl, difluoromethoxy, trifluoromethoxy, —NR$^9$SO$_2$R$^{11}$, —C(O)R$^7$, —NR$^9$C(O)OR$^{11}$, —NR$^9$C(O)R$^7$, —C(O)NR$^7$R$^9$, —NR$^7$R$^9$, —OR$^7$, and C$_1$–C$_4$ alkyl;

each R$^7$ is independently selected from the group consisting of H, C$_1$–C$_4$ alkyl, C$_3$–C$_6$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; the foregoing R$^7$ substituents, except H, are optionally substituted by 1 to 5 substituents independently selected from the group consisting of oxo, halo, trifluoromethyl, difluoromethoxy, trifluoromethoxy, —C(O)R$^9$, —NR$^9$C(O)R$^{10}$, —C(O)NR$^9$R$^{10}$, —NR$^9$R$^{10}$, hydroxy, C$_1$–C$_4$ alkyl, and C$_1$–C$_4$ alkoxy; each R$^9$ and R$^{10}$ are independently H or C$_1$–C$_4$ alkyl;

R$^{11}$ is selected from the group consisting of C$_1$–C$_{10}$ alkyl, C$_3$–C$_{10}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a C$_6$–C$_{10}$ aryl group, a C$_5$–C$_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom.

10. A compound according to claim 9 wherein:

Z$^1$ is H, Z$^2$ is OH; or Z$^1$ is methyl, Z$^2$ is OH; or Z$^1$ is H, Z$^2$ is NH$_2$; or both Z$^1$ and Z$^2$ are H; or Z$^1$ is H, Z$^2$ is F;

W$^1$ is H, W$^2$ is OH;

R$^1$ and R$^2$ are taken together as =C(R$^5$)X$^1$—X$^2$—R$^8$; wherein X$^1$ is —CH$_2$—, and X$^2$ is selected from the group consisting of —S(O)$_n$— wherein n is 0 to 2, —NR$^9$—, and O; where X$^2$ is —NR$^9$—, then R$^8$ and R$^9$ may be taken together to form a 5 to 12 membered heterocyclic, which is optionally substituted by 1 to 3 R$^6$ groups; and where R$^5$ is H or C$_1$–C$_6$ alkyl, wherein the foregoing R$^5$ alkyl group is optionally substituted by 1 or 2 R$^6$ groups:

and where R$^8$ is R$^3$, wherein R$^3$ is —(CH$_2$)$_t$(C$_6$–C$_{10}$ aryl) or —(CH$_2$)$_t$(4 to 10 membered heterocyclic), wherein each t is independently an integer from 0 to 2, and the foregoing R$^3$ groups are optionally substituted by 1 to 5 R$^6$ groups; wherein each R$^6$ is independently C$_1$–C$_4$ alkyl, halo, trifluoromethyl, difluoromethoxy, trifluoromethoxy, —OR$^7$, —C(O)R$^7$, (CH$_2$)$_m$(C$_6$–C$_{10}$ aryl), —O(CH$_2$)$_m$(C$_6$–C$_{10}$ aryl), and —(CH$_2$)$_m$(4 to 10 membered heterocyclic), wherein each m is independently an integer from 0 to 2; said alkyl, aryl and heterocyclic R$^6$ groups are optionally substituted by 1 to 5 substituents independently selected from the group consisting of oxo, halo, trifluoromethyl, difluoromethoxy, trifluoromethoxy, —C(O)R$^7$, —NR$^9$C(O)OR$^{11}$, —NR$^9$C() R$^7$, —C(O)NR$^7$R$^9$, —OR$^7$, and C$_1$–C$_4$ alkyl;

each R$^7$ is independently selected from the group consisting of H and C$_1$–C$_4$ alkyl; the foregoing R$^7$ substituents, except H, are optionally substituted by 1 to 3 substituents independently selected from the group consisting of oxo, trifluoromethyl, —C(O)R$^9$, —NR$^9$C(O)R$^{10}$, —C(O)NR$^9$R$^{10}$, —NR$^9$R$^{10}$, hydroxy, and C$_1$–C$_4$ alkoxy;

each R$^9$ and R$^{10}$ are independently H, C$_1$–C$_4$ alkyl;

R$^{11}$ is selected from the group consisting of C$_1$–C$_{10}$ alkyl, C$_3$–C$_{10}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a C$_6$–C$_{10}$ aryl group, a C$_5$–C$_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom; R$^{12}$ is C$_1$–C$_4$ alkyl except that R$^{12}$ cannot be methyl if (a) X is OH, Y is O, W$^1$ is H, W$^2$ is α-OH, Z$^1$ is H, Z$^2$ is β-—OH, or if (b) X is OH, Y is O, W$^1$ is H, W$^2$ is α-OH, Z$^1$ is H, Z$^2$ is H.

11. A compound according to claim 10 wherein:
R$^1$ and R$^2$ are taken together as =C(R$^5$)X$^1$—X$^2$—R$^8$; wherein R$^5$ is H, X$^1$ is —CH$_2$—, and X$^2$ is O, and wherein R$^8$ is R$^3$, wherein R$^3$ is phenyl or (5 to 6 membered heterocyclic), and the foregoing R$^8$ groups are optionally substituted by 1 to 5 R$^6$ groups, wherein each R$^6$ is independently selected from the group consisting of C$_1$–C$_4$ alkyl, halo, trifluoromethyl, and —(CH$_2$)$_m$(4 to 10 membered heterocyclic), wherein each m is independently an integer ranging from 0 to 1; said heterocyclic R$^6$ groups are optionally substituted by 1 to 5 substituents independently selected from the group consisting of halo, trifluoromethyl, and C$_1$–C$_4$ alkyl.

12. A compound according to claim 1 wherein:
V equals

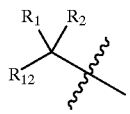

and R$^1$ is H and R$^2$ is —NR$^3$R$^4$, —NR$^4$C(O)R$^3$, —OC(O)NR$^3$R$^4$ or —OR$^3$;

X is F, H or OH;
Y is O;
W$^1$ is R$^3$, W$^2$ is OR$^{13}$; or W$^1$ is H, W$^2$ is R$^3$ or F;
Z$^1$ is R$^3$, Z$^2$ is OR$^{13}$; or Z$^1$ is H, Z$^2$ is R$^3$ or F; wherein each R$^3$ and R$^{13}$ are independently H or C$_1$–C$_4$ alkyl, and said alkyl groups are optionally substituted by 1 to 3 R$^6$ groups; wherein each R$^6$ is independently halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, or —NR$^7$R$^9$; wherein each R$^7$ and R$^9$ are independently H or C$_1$–C$_4$ alkyl; R$^{11}$ is C$_1$–C$_4$ alkyl;

and in the substituent R$^2$; R$^3$is independently selected from the group consisting of H, C$_1$–C$_{10}$ alkyl, —(CR$^9$R$^{10}$)$_t$(C$_3$–C$_{10}$ cycloalkyl), —(CR$^9$R$^{10}$)$_t$(C$_6$–C$_{10}$ aryl), and —(CR$^9$R$^{10}$)$_t$(4 to 10 membered heterocyclic), wherein each t is independently an integer from 0 to 3, said alkyl group optionally contains 1 hetero moiety selected from the group consisting of O, —S(O)$_j$— wherein j is an integer ranging from 0 to 2, and —N(R$^9$)—; said cycloalkyl, aryl and heterocyclic R$^3$ groups are optionally fused to a benzene ring, a C$_5$–C$_8$ cycloalkyl group, or a 4 to 10 membered heterocyclic group; and the foregoing R$^3$ groups, except H but including any optional fused rings referred to above, are optionally substituted by 1 to 5 R$^6$ groups, and with the proviso that R must be attached through a carbon atom unless R$^3$ is H;

each R$^4$ is independently H or C$_1$–C$_6$ alkyl; each R$^6$ is independently C$_1$–C$_4$ alkyl, halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, —NR$^7$R$^9$, —(CR$^9$R$^{10}$)$_m$(C$_6$–C$_{10}$ aryl), —O(CR$^9$R$^{10}$)$_m$(C$_6$–C$_{10}$ aryl), —NR$^9$(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; said alkyl, aryl and heterocyclic R$^6$ groups are optionally substituted by 1 to 5 substituents independently selected from the group consisting of halo, trifluoromethyl, difluoromethoxy, trifluoromethoxy, —NR$^9$SO$_2$R$^{11}$$_1$—C(O)R$^7$, —NR$^9$C(O)OR$^{11}$, —NR$^9$C(O)R$^7$, —C(O)NR$^7$R$^9$, —NR$^7$R$^9$, —OR$^7$, and C$_1$–C$_4$ alkyl;

each R$^7$ is independently selected from the group consisting of H, C$_1$–C$_4$ alkyl, C$_3$–C$_6$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; the foregoing R$^7$ substituents, except H, are optionally substituted by 1 to 5 substituents independently selected from the group consisting of halo, trifluoromethyl, difluoromethoxy, trifluoromethoxy, —C(O)R$^9$, —NR$^9$C(O)R$^{10}$, —C(O)NR$^9$R$^{10}$, —NR$^9$R$^{10}$, hydroxy, C$_1$–C$_4$ alkyl, and C$_1$–C$_4$ alkoxy; each R$^9$ and R$^{10}$ are independently H, C$_1$–C$_4$ alkyl;

R$^{11}$ is selected from the group consisting of C$_1$–C$_{10}$ alkyl, C$_3$–C$_{10}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a C$_6$–C$_{10}$ aryl group, a C$_5$–C$_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom;

R$^{12}$ is C$_1$–C$_4$ alkyl except that R$^{12}$ cannot be methyl if (a) X is OH, Y is O, W$^1$ is H, W is α-OH, Z$^1$ is H, Z$^2$ is β-OH, or if (b) X is OH, Y is O, W$^1$ is H, W$^2$ is α-OH, Z$^1$ is H, Z$^2$is H and the configuration of the 1" center is that of hygromycin A.

13. A compound according to claim 1 wherein:
V is R$^3$OC(O), R$^3$R$^4$NC(O) or R$^3$O(R$^4$)NC(O) and the configuration of the 1" center is that of hygromycin A
X is F, H or OH;

Y is O;

W$^1$ is R$^3$, W$^2$ is OR$^{13}$; or W$^1$ is H, W$^2$ is R$^3$ or F; Z$^1$ is R$^3$, Z$^2$ is OR$^{13}$; or Z$^1$ is H, Z$^2$ is R$^3$ or F; wherein each R$^3$ and R$^{13}$ are independently H or C$_1$–C$_4$ alkyl, and said alkyl groups are optionally substituted by 1 to 3 R$^6$ groups; wherein each R$^6$ is independently halo, trifluoromethyl, difluoromethoxy, trifluoromethoxy, —OR$^7$, —C(O)R$^7$—NR$^9$C(O)OR$^{11}$, —NR$^9$C(O)R$^7$, —C(O)NR$^7$R$^9$, or —NR$^7$R$^9$;

wherein each R$^7$ and R$^9$ are independently H or C$_1$–C$_4$ alkyl; R$^{11}$ is C$_1$–C$_4$ alkyl; within substituent V, R$^3$ is independently selected from the group consisting of H, C$_1$–C$_{10}$ alkyl, —(CR$^9$R$^{10}$)$_t$(C$_3$–C$_{10}$ cycloalkyl), —(CR$^9$R$^{10}$)$_t$(C$_6$–C$_{10}$ aryl), and —(CR$^9$R$^{10}$)$_t$(4 to 10 membered heterocyclic), wherein each t is independently an integer ranging from 0 to 3, said alkyl group optionally contains 1 hetero moiety selected from the group consisting of O, —S(O)$_j$— wherein j is an integer ranging from 0 to 2, and —N(R$^9$)—; said cycloalkyl, aryl and heterocyclic R$^3$ groups are optionally fused to a benzene ring, a C$_5$–C$_8$ cycloalkyl group, or a 4 to 10 membered heterocyclic group; and the foregoing R$^3$ groups, except H but including any optional fused rings referred to above, are optionally substituted by 1 to 5 R$^6$ groups, and with the proviso that R$^3$ must be attached through a carbon atom unless R$^3$is H; each R$^4$ is independently H or C$_1$–C$_6$ alkyl; each R$^6$ is independently C$_1$–C$_4$ alkyl, halo, trifluoromethyl, difluoromethoxy, trifluoromethoxy, —OR$_7$, —C(O)R$^7$, —NR$^9$C(O)OR$^{11}$, —NR$^9$C(O)R$^7$, —C(O)NR$^7$R$^9$, —NR$^7$R$^9$, —(CR$^9$R$^{10}$)$_m$(C$_6$–C$_{10}$ aryl), —O(CR$^9$R$^{10}$)$_m$(C$_6$–C$_{10}$ aryl), —NR$^9$(CR$^9$R$^{10}$)$_m$(C$_6$–C$_{10}$ aryl), and (CR$^9$R$^{10}$)$_m$(4 to 10 membered heterocyclic), wherein each m is independently an integer ranging from 0 to 2; said alkyl, aryl and heterocyclic R$^6$ groups are optionally substituted by 1 to 5 substituents independently selected from the group consisting of halo, trifluoromethyl, difluoromethoxy, trifluoromethoxy, —NR$^9$SO$_2$R$^{11}$, —C(O)R$^7$, —NR$^9$C(O)OR$^{11}$, —NR$^9$C (O)R$^7$, —C(O)NR$^7$R$^9$, —NR$^7$R$^9$, —OR$^7$, C$_1$–C$_4$ alkyl;

R$^7$ is independently selected from the group consisting of H, C$_1$–C$_4$ alkyl, C$_3$–C$_6$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; the foregoing R$^7$ substituents, except H, are optionally substituted by 1 to 5 substituents independently selected from the group consisting of halo, trifluoromethyl, difluoromethoxy, trifluoromethoxy, —C(O)R$^9$, —NR$^9$C(O)R$^{10}$, —C(O) NR$^9$R$^{10}$, —NR$^9$R$^{10}$, hydroxy, C$_1$–C$_4$ alkyl, and C$_1$–C$_4$ alkoxy; each R$^9$ and R$^{10}$ are independently H and C$_1$–C$_4$ alkyl;

R$^{11}$ is selected from the group consisting of C$_1$–C$_{10}$ alkyl, C$_3$–C$_{10}$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a C$_6$–C$_{10}$ aryl group, a C$_5$–C$_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, C$_1$–C$_6$ alkyl, and C$_1$–C$_6$ alkoxy, and with the proviso that R$^{11}$ must be attached through a carbon atom.

14. A compound according to claim 1 wherein:

V is a moiety of the structure

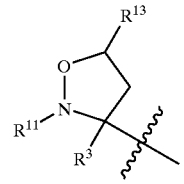

and the configuration of the 1″ center is that of hygromycin A,

X is F, H or OH;

Y is O;

W$^1$ is R$^3$, W$^2$ is OR$^{13}$; or W$^1$ is H, W$^2$ is R$^3$ or F;

Z$^1$ is R$^3$, Z$^2$ is OR$^{13}$; or Z$^1$ is H, Z$^2$ is R$^3$ or F; wherein each R$^3$ and R$^{13}$ are independently H or C$_1$–C$_4$ alkyl, and said alkyl groups are optionally substituted by 1 to 3 R$^6$ groups; wherein each R$^6$ is independently halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, or —NR$^7$R$^9$; wherein each R$^7$ and R$^9$ is H or C$_1$–C$_4$ alkyl; R$^{11}$ is C$_1$–C$_4$ alkyl; within the substituent V, R$^3$ is C$_1$–C$_6$ alkyl; each R$^{13}$ is independently selected from the group consisting of H, C$_1$–C$_{10}$ alkyl, —(CR$^9$R$^{10}$)$_t$(C$_3$–C$_{10}$ cycloalkyl), —(CR$^9$R$^{10}$)$_t$(C$_6$–C$_{10}$ aryl), and —(CR$^9$R$^{10}$)$_t$(4 to 10 membered heterocyclic), wherein each t is independently an integer ranging from 0 to 3, said alkyl group optionally contains 1 hetero moiety selected from the group consisting of O, —S(O)$_j$— wherein j is an integer ranging from 0 to 2, and —N(R$^9$)—; said cycloalkyl, aryl and heterocyclic R$^3$ groups are optionally fused to a benzene ring, a C$_5$–C$_8$ cycloalkyl group, or a 4 to 10 membered heterocyclic group; and the foregoing R$^3$ groups, except H but including any optional fused rings referred to above, are optionally substituted by 1 to 5 R$^6$ groups, and with the proviso that R$^3$ must be attached through a carbon atom unless R$^3$ is H; each R$^6$ is independently C$_1$–C$_4$ alkyl, halo, trifluoromethyl, difluoromethoxy, trifluoromethoxy, —OR$^7$, —C(O)R$^7$, —NR$^9$C(O)OR$^{11}$, —NR$^9$C(O)R$^7$, —C(O)NR$^7$R$^9$, —NR$^7$R$^9$, —(CR$^9$R$^{10}$)$_m$(C$_6$–C$_{10}$ aryl), —O(CR$^9$R$^{10}$)$_m$(C$_6$–C$_{10}$ aryl), —NR$^9$(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; said alkyl, aryl and heterocyclic R$^6$ groups are optionally substituted by 1 to 5 substituents independently selected from the group consisting of halo, trifluoromethyl, difluoromethoxy, trifluoromethoxy, —NR$^9$SO$_2$R$^{11}$, —C(O)R$^7$, —NR$^9$C(O)OR$^{11}$, —NR$^9$C (O)R$^7$, —C(O)NR$^7$R$^9$, —NR$^7$R$^9$, —OR$^7$, and C$_1$–C$_4$ alkyl;

each R$^7$ is independently selected from the group consisting of H, C$_1$–C$_4$ alkyl, C$_3$–C$_6$ cycloalkyl, —(CR$^9$R$^{10}$)$_m$(C$_6$–C$_{10}$ aryl), and —(CR$^9$R$^{10}$)$_m$(4 to 10 membered heterocyclic), wherein each m is independently an integer ranging from 0 to 2; the foregoing R$^7$ substituents, except H, are optionally substituted by 1 to 5 substituents independently selected from the group consisting of halo, trifluoromethyl, difluoromethoxy, trifluoromethoxy, —C(O)R$^9$, —NR$^9$C(O)R$^{10}$, —C(O)NR$^9$R$^{10}$, —NR$^9$R$^{10}$, hydroxy, $C_1$–$C_4$ alkyl, and $C_1$–$C_4$ alkoxy; each R$^9$ and R$^{10}$ are independently H or $C_1$–$C_4$ alkyl;

R$^{11}$ is selected from the group consisting of $C_1$–$C_{10}$ alkyl, $C_3$–$C_{10}$ cycloalkyl, —(CR$^9$R$^{10}$)$_m$($C_6$–$C_{10}$ aryl), and —(CR$^9$R$^{10}$)$_m$(4 to 10 membered heterocyclic), wherein each m is independently an integer from 0 to 4; said alkyl group optionally includes 1 or 2 hetero moieties selected from the group consisting of O, —S(O)$_j$— wherein j is an integer ranging from 0 to 2, and —N(R$^9$)— with the proviso that two O atoms, two S atoms, or an O and S atom are not attached directly to each other; said cycloalkyl, aryl and heterocyclic R$^7$ groups are optionally fused to a $C_6$–$C_{10}$ aryl group, a $C_5$–$C_8$ cycloalkyl group, or a 4 to 10 membered heterocyclic group; and the foregoing R$^{11}$ substituents are optionally substituted by 1 to 5 substituents independently selected from the group consisting of oxo, halo, cyano, nitro, trifluoromethyl, difluoromethoxy, trifluoromethoxy, azido, —C(O)R$^9$, —C(O)OR$^9$, —OC(O)R$^9$, —NR$^9$C(O)R$^{10}$, —C(O)NR$^9$R$^{10}$, —NR$^9$R$^{10}$, hydroxy, $C_1$–$C_6$ alkyl, and $C_1$–$C_6$ alkoxy, and with the proviso that R$^{11}$ must be attached through a carbon atom.

15. A compound according to claim 1 wherein:
V is a group of the structure

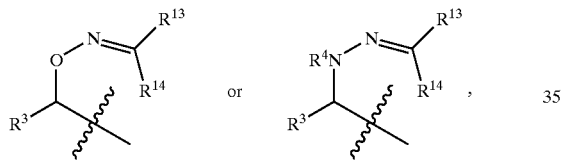

where both E and Z isomers are included or V is a carbon-linked 4 to 10 membered heterocyclic group, which may be optionally substituted by 1 to 3 R$^6$, and the configuration of the 1" center is that of hygromycin A;

X is F, H or OH;
Y is O;
R$^{13}$ is —(CR$^9$R$^{10}$)$_t$($C_6$–$C_{10}$ aryl) or —(CR$^9$R$^{10}$)$_t$(4 to 10 membered heterocyclic), wherein each t is independently an integer ranging from 0 to 2, and the foregoing R$^3$ groups are optionally substituted by 1 to 5 R$^6$ groups; wherein each R$^6$ is independently $C_1$–$C_4$ alkyl, oxo, halo, trifluoromethyl, difluoromethoxy, trifluoromethoxy, —OR$^7$, —C(O)R$^7$, —(CR$^9$R$^{10}$)$_m$ ($C_6$–$C_{10}$ aryl), —O(CR$^9$R$^{10}$)$_m$($C_6$–$C_{10}$ aryl), or —(CR$^9$R$^{10}$)$_m$(4 to 10 membered heterocyclic), wherein each m is independently an integer ranging from 0 to 2; said alkyl, aryl and heterocyclic R$^6$ groups are optionally substituted by 1 to 5 substituents independently selected from the group consisting of oxo, halo, trifluoromethyl, difluoromethoxy, trifluoromethoxy, —C(O)R$^7$, —NR$^9$C(O)OR$^{11}$, —NR$^9$C(O)R$^7$, —C(O)NR$^7$R$^9$, —OR$^7$, and $C_1$–$C_4$ alkyl;

each R$^7$ is independently selected from the group consisting of H and $C_1$–$C_4$ alkyl; the foregoing R$^7$ substituents, except H, are optionally substituted by 1 to 3 substituents independently selected from the group consisting of trifluoromethyl, —C(O)R$^9$, —NR$^9$C(O)R$^{10}$, —C(O)NR$^9$R$^{10}$, —NR$^9$R$^{10}$, hydroxy, and $C_1$–$C_4$ alkoxy; each R$^9$ and R$^{10}$ are independently H or $C_1$–$C_4$ alkyl;

each R$^4$ and R$^{14}$ are independently selected from the group consisting of H and $C_1$–$C_4$ alkyl;

R$^3$ is $C_1$–$C_4$ alkyl, and said alkyl group is optionally substituted by 1 to 3 R$^6$ groups; each R$^6$ is independently selected from the group consisting of $C_1$–$C_4$ alkyl, oxo, halo, trifluoromethyl, difluoromethoxy, trifluoromethoxy, —OR$^7$, —C(O)R$^7$, —NR$^9$C(O)OR$^{11}$, —NR$^9$SO$_2$R$^{11}$, —SO$_2$NR$^7$R$^9$, —NR$^9$C(O)R$^7$, —C(O)NR$^7$R$^9$, —NR$^7$R$^9$, —S(O)$_j$(CR$^9$R$^{10}$)$_m$($C_6$–$C_{10}$ aryl), —S(O)$_j$($C_1$–$C_6$ alkyl), wherein j is an integer ranging from 0 to 2, —(CR$^9$R$^{10}$)$_m$($C_{6-10}$ aryl), —O(CR$^9$R$^{10}$)$_m$($C_6$–$C_{10}$ aryl) —NR$^9$(CR$^9$R$^{10}$)$_m$ ($C_6$–$C_{10}$ aryl), and —(CR$^9$R$^{10}$)$_m$(4 to 10 membered heterocyclic), wherein each m is independently an integer ranging from 0 to 2; and said alkyl, cycloalkyl, aryl and heterocyclic R$^6$ groups are optionally substituted by 1 to 5 substituents independently selected from the group consisting of oxo, halo, trifluoromethyl, difluoromethoxy, trifluoromethoxy, —NR$^9$SO$_2$R$^{11}$, —C(O)R$^7$, —NR$^9$C(O)OR$^{12}$, —NR$^9$C(O)R$^7$, —C(O)NR$^7$R$^9$, —NR$^7$R$^9$, —OR$^7$, $C_1$–$C_4$ alkyl, —(CR$^9$R$^{10}$)$_m$ ($C_6$–$C_{10}$ aryl), and —(CR$^9$R$^{10}$)$_m$(4 to 10 membered heterocyclic), wherein each m is independently an integer ranging from 0 to 2;

each R$^7$ is independently selected from the group consisting of H, $C_1$–$C_4$ alkyl, $C_3$–$C_6$ cycloalkyl, —(CR$^9$R$^{10}$)$_m$($C_6$–$C_{10}$ aryl), and —(CR$^9$R$^{10}$)$_m$(4 to 10 membered heterocyclic), wherein each m is independently an integer ranging from 0 to 2; said alkyl group optionally includes 1 hetero moiety selected from the group consisting of O, —S(O)$_j$— wherein j is an integer ranging from 0 to 2, and —N(R$^9$)—; said cycloalkyl, aryl and heterocyclic R$^7$ groups are optionally fused to a $C_6$–$C_{10}$ aryl group, a $C_5$–$C_8$ cycloalkyl group, or a 4 to 10 membered heterocyclic group; and the foregoing R$^7$ substituents, except H, are optionally substituted by 1 to 5 substituents independently selected from the group consisting of oxo, halo, trifluoromethyl, difluoromethoxy, trifluoromethoxy, —C(O)R$^9$, —NR$^9$C(O)R$^{10}$, —C(O)NR$^9$R$^{10}$— NR$^9$R$^{10}$, hydroxy, $C_1$–$C_4$ alkyl, and $C_1$–$C_4$ alkoxy, and with the proviso that R$^7$ must be attached through a carbon atom unless R$^7$ is H; each R$^9$ and R$^{10}$ are independently H or $C_1$–$C_4$ alkyl.

16. A pharmaceutical composition for the treatment of a bacterial infection or a protozoal infection in a mammal, fish, or bird which comprises a therapeutically effective amount of a compound according to claim 1 and a pharmaceutically acceptable carrier.

17. A method of treating a bacterial infection or a protozoal infection in a mammal, fish, or bird which comprises administering to said mammal, fish or bird a therapeutically effective amount of a compound according to claim 1.

18. A pharmaceutical composition for the treatment of a bacterial infection or a protozoal infection in a mammal, fish, or bird which comprises a therapeutically effective amount of a compound according to claim 1 in combination with a beta-lactam, quinolone, tetracycline, streptogramin, aminoglycoside, glycopeptide, macrolide or oxazolidinone antibiotic; or in combination with a compound which inhibits bacterial or protozoal efflux or degradation of a compound according to claim 1.

19. A method of treating a bacterial infection or a protozoal infection in a mammal, fish, or bird which comprises administering to said mammal, fish or bird a therapeutically effective amount of a compound according to claim 1 in combination or co-administered with a beta-lactam, quinolone, tetracycline, streptogramin, aminoglycoside, glycopeptide, macrolide or oxazolidinone antibiotic; or in combination with a compound which inhibits bacterial or protozoal efflux or degradation of a compound according to claim 1.

20. A compound according to claim 1 selected from the group consisting of:

(2S,3S,4S,5S)-3,4-Dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-propenyl)-phenoxy)-tetrahydro-furan-2-carboxylic acid benzyloxy-amide;

3-(4-((2S,3S,5S)-5-(1-((E)-3,4-Difluoro-benzyloxyimino)-ethyl)-3-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-3-Amino-5-(1-((E)-3-chloro-benzyloxyimino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(1-((E)-Benzo(1,3)dioxol-5-ylmethoxyimino)-ethyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((1R,3R,4R)-3-(1-((E)-Benzo(1,3)dioxol-5-ylmethoxyimino)-ethyl)-4-hydroxy-cyclopentyloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(1-((E)-Benzo(1,3)dioxol-5-ylmethoxyimino)-ethyl)-4-hydroxy-tetrahydro-furan-2-yloxy)-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(((E)-Benzo(1,3)dioxol-5-ylmethoxyimino)-methyl)-4-hydroxy-tetrahydro-furan-2-yloxy)-3-hydroxy-phenyl)-2-methyl-N-((3aS,4R, 5R,6S,7R,7aR)-4,6,7-trihydroxy-hexahydro-benzo(1,3)dioxol-5-yl)-(2E)-acrylamide;

3-(4-((1R,2S,3R,4R)-4-(((E)-2,4-Dichloro-benzyloxyimino)-methyl)-2,3-dihydroxy-cyclopentyloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((1R,2S,3R,4R)-4-(1-((E)-2-Fluoro-benzyloxyimino)-ethyl)-2,3-dihydroxy-cyclopentyloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-hydroxymethyl-(E)-propenyl)-3,4-dihydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Dichloro-phenoxy)-1-hydroxymethyl-(E)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((1R,2S,3R,4S)-4-(3-(2,4-Dichloro-phenoxy)-(E)-propenyl)-2,3-dihydroxy-cyclopentyloxy)-3-hydroxy-phenyl)-2-methyl-N-((3aS,4R,5R,6S,7R, 7aR)-4,6,7-trihydroxy-hexahydro-benzo(1,3)dioxol-5-yl)-(2E)-acrylamide;

3-(4-((2S,3S,4R,5R)-5-(1-((E)-3,4-Difluoro-benzyloxyimino)-ethyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3R,4R,5R)-5-(1-((E)-3-Chloro-benzyloxyimino)-ethyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3R,4R,5R)-5-(3-(3,4-Difluoro-phenoxy)-1-methyl-(E)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(1-((E)-4-Fluoro-benzyloxyimino)-propyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Chloro-phenoxy)-1-ethyl-(E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4R,5R)-5-(1-((E)-2-Fluoro-benzyloxyimino)-ethyl)-3,4-dihydroxy-3-methyl-tetrahydro-furan-2-yloxy)-3-hydroxy-phenyl)-2-methyl-N-((3aS,4R, 5R ,6S,7 R,7aR)-4,6,7-trihydroxy-hexahydro-benzo(1,3)dioxol-5-yl)-(2E)-acrylamide;

3-(4-((2S,3S,4R,5R)-5-(3-(3-Chloro-phenoxy)-1-methyl-(E)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Chloro-phenoxy)-1-methyl-(Z)-propenyl)-4-hydroxy-tetrahydro-furan-2-yloxy)-3-fluoro-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,3-Dichloro-5-fluoro-phenoxy)-1-ethyl-(Z)-propenyl)-4-hydroxy-tetrahydro-furan-2-yloxy)-3-hydroxy-phenyl)-2-methyl-N-((3aS,4R,5R,6S,7R, 7aR)-4,6,7-trihydroxy-hexahydro-benzo(1,3)dioxol-5-yl)-(2E)-acrylamide;

3-(4-((2S,3S,4R,5R)-5-(3-(3,4-Difluoro-phenoxy)-1-ethyl-(Z)-propenyl)-3-fluoro-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3R,4S,5R)-3-Amino-5-(1-((E)-3,4-difluoro-benzyloxyimino)-ethyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4R,5R)-5-(3-(3-Chloro-phenoxy)-1-methyl-(Z)-propenyl)-3,4-dihydroxy-3-methyl-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(5S-(3-Chloro-phenyl)-2,3-dimethyl-isoxazolidin-3-yl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

and the pharmaceutically acceptable salts, prodrugs and solvates of the foregoing compounds.

* * * * *